(12) United States Patent
Andou et al.

(10) Patent No.: US 6,190,576 B1
(45) Date of Patent: Feb. 20, 2001

(54) LIQUID CRYSTAL COMPOUNDS, LIQUID CRYSTAL COMPOSTIONS CONTAINING THE COMPOUNDS, AND LIQUID CRYSTAL DISPLAY DEVICES MADE BY USING THE COMPOSITIONS

(75) Inventors: Tugumiti Andou; Shuichi Matsui; Kazutoshi Miyazawa; Hiroyuki Takeuchi, all of Chiba; Yasuyuki Koizumi, Kanagawa; Yasuko Sekiguchi, Chiba; Etsuo Nakagawa, Chiba; Fusayuki Takeshita, Chiba, all of (JP)

(73) Assignee: Chisso Corporation, Osaka (JP)

( * ) Notice: Under 35 U.S.C. 154(b), the term of this patent shall be extended for 0 days.

(21) Appl. No.: 09/155,595

(22) PCT Filed: Mar. 27, 1997

(86) PCT No.: PCT/JP97/01048

§ 371 Date: Sep. 30, 1998

§ 102(e) Date: Sep. 30, 1998

(87) PCT Pub. No.: WO97/36847

PCT Pub. Date: Oct. 9, 1997

(30) Foreign Application Priority Data

Apr. 2, 1996 (JP) .................................................... 8-079946
Aug. 22, 1996 (JP) .................................................... 8-239751

(51) Int. Cl.$^7$ .......................... C09K 19/34; C09K 19/30; C09K 19/12; C09K 19/06; C09K 19/20
(52) U.S. Cl. .............................. 252/299.63; 252/299.61; 252/299.66; 252/299.6; 252/299.67; 570/144
(58) Field of Search ............................. 252/299.6, 299.63, 252/299.67, 299.61, 299.66; 570/144

(56) References Cited

U.S. PATENT DOCUMENTS

| | | | |
|---|---|---|---|
| 4,855,076 | * 8/1989 | Goto et al. ........................ | 252/299.63 |
| 4,895,986 | * 1/1990 | Vauchier et al. ...................... | 568/643 |
| 4,897,216 | * 1/1990 | Reiffenrath et al. ............. | 252/299.63 |
| 4,952,337 | * 8/1990 | Bradshaw et al. ................ | 252/299.63 |
| 5,032,313 | 7/1991 | Goto et al. ........................ | 252/299.63 |
| 5,045,229 | * 9/1991 | Bartmann et al. ............... | 252/299.01 |
| 5,174,920 | * 12/1992 | Iijima et al. ...................... | 252/299.01 |
| 5,204,019 | * 4/1993 | Reiffenrath et al. ............. | 252/299.66 |
| 5,248,447 | * 9/1993 | Reiffenrath et al. ............. | 252/299.63 |
| 5,279,764 | * 1/1994 | Reiffenrath et al. ............. | 252/299.66 |
| 5,534,189 | * 7/1996 | Nakagawa et al. ............... | 252/299.63 |
| 5,589,102 | * 12/1996 | Bartmann et al. ............... | 252/299.01 |
| 5,611,957 | * 3/1997 | McDonnell et al. ............. | 252/299.01 |
| 5,772,914 | * 6/1998 | Pauluth et al. ..................... | 252/299.6 |
| 5,792,386 | * 8/1998 | Matsui et al. ..................... | 252/299.01 |
| 5,798,058 | * 8/1998 | Goodby et al. ................... | 252/299.61 |
| 5,876,626 | * 3/1999 | Weber et al. ..................... | 252/299.01 |

FOREIGN PATENT DOCUMENTS

| | | |
|---|---|---|
| 3906058 | 9/1989 | (DE) . |
| 4027840 | 3/1991 | (DE) . |
| 4023106 | 1/1992 | (DE) . |
| 19531165 | 3/1996 | (DE) . |
| 0640578 | 3/1995 | (EP) . |
| 0735015 | 10/1996 | (EP) . |
| 2229438 | 9/1990 | (GB) . |
| 2278841 | 12/1994 | (GB) . |
| 61-26899 | 6/1986 | (JP) . |
| 62-39136 | 8/1987 | (JP) . |
| 62-46527 | 10/1987 | (JP) . |
| 1-275549 | 11/1989 | (JP) . |
| 2-4725 | 1/1990 | (JP) . |
| 2-503431 | 10/1990 | (JP) . |
| 2-503441 | 10/1990 | (JP) . |
| 2-503443 | 10/1990 | (JP) . |
| 4-28693 | 5/1992 | (JP) . |
| 89/06678 | 7/1989 | (WO) . |
| 89/08632 | 9/1989 | (WO) . |
| 96/11897 | 4/1996 | (WO) . |

OTHER PUBLICATIONS

Chambers et al., "Low Birefringence Esters Exhibiting a Wide SMECTIC C Phase", Ferroelectrics, 1991, vol. 114, pp.201–205.

Kelly, "Smectic liquid crystals VIII. Some new laterally subsituted smectic C compounds", Liquid Crystals, 1989, vol. 5, No. 1, 171–175.

* cited by examiner

Primary Examiner—C. H. Kelly
(74) Attorney, Agent, or Firm—Wenderoth, Lind & Ponack, L.L.P.

(57) ABSTRACT

The invention is to provide liquid crystalline compounds which have a low viscosity, high negative dielectric anisotropy, high resistivity, and high voltage holding ratio, and are stable against heat and ultraviolet light; to provide liquid crystal compositions comprising the liquid crystalline compound; and to provide liquid crystal display devices using the liquid crystal composition therein;

the liquid crystalline compound is expressed by the general formula (1)

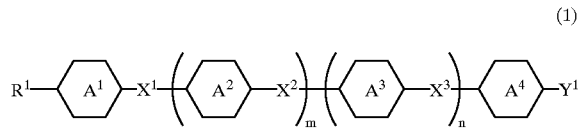

(1)

wherein $R^1$ and $Y^1$ represent an alkyl group having 1 to 20 carbon atoms; $X^1$, $X^2$, and $X^3$ independently represent single bond, 1,2-ethylene group, vinylene group, —COO—, —$CF_2O$—, or —$OCF_2$—; ring $A^1$, ring $A^2$, ring $A^3$, and ring $A^4$ independently represent trans-1,4-cyclohexylene, or 1,4-phenylene hydrogen atom on the ring may be replaced by fluorine atom or chlorine atom provided that at least one of ring $A^2$, ring $A^3$, and ring $A^4$ represents 2,3-difluoro-1,4-phenylene; m and n are 0 or 1, and each element which constitutes this compound may be replaced by its isotope.

21 Claims, No Drawings

LIQUID CRYSTAL COMPOUNDS, LIQUID CRYSTAL COMPOSTIONS CONTAINING THE COMPOUNDS, AND LIQUID CRYSTAL DISPLAY DEVICES MADE BY USING THE COMPOSITIONS

This application is a 371 of PCT/JP97/01048, filed Feb. 27, 1997.

TECHNICAL FIELD

The present invention relates to novel liquid crystalline compounds which make liquid crystal compositions principally for it twist nematic (TN) display mode, super twist nematic (STN) display mode, or thin film transistor (TFT) display mode develop preferable physical properties, to liquid crystal compositions comprising the liquid crystalline compound and having preferable physical properties, and to liquid crystal display devices using the liquid crystal composition therein.

BACKGROUND ART

Liquid crystal display devices utilize optical anisotropy and dielectric anisotropy of liquid crystal substances. The liquid crystal display devices are widely used in tabletop calculators, word processors, and television sets, including watches, and demand for the display devices is in a trend to increase year by year. Liquid crystal phase exists between solid phase and liquid phase, and is divided broadly into nematic phase, smectic phase, and cholesteric phase. Among them, nematic phase is most widely employed for display devices at present. On the other hand, while many display modes were devised up to date, three types of twist nematic (TN) mode, super twist nematic (STN) mode, and thin film transistor (TFT) mode have now become main currents. Properties required of liquid crystal substances (liquid crystalline compounds) for these various liquid crystal display devices are different depending on their uses, but any of the liquid crystal substances is required to be stable against outside environmental factors such as moisture, air, heat, and light; to exhibit liquid crystal phase at a temperature range as wide as possible with room temperature being its center; to be in a low viscosity; and to have a low driving voltage. However, no liquid crystal substances which satisfy such requirements at the same time by a single compound have been found.

With respect to liquid crystal substances used for liquid crystal display devices, it is an actual circumstance that several kind or several tens kind of liquid crystalline compounds, and further several kind of liquid non-crystalline compounds when necessary, are usually mixed to produce liquid crystal compositions and used for display devices, in order to adjust such physical properties as dielectric anisotropy (Δε), optical anisotropy (Δn), viscosity, and elastic constant ratio $K_{33}/K_{11}$ ($K_{33}$: bend elastic constant, $K_{11}$: splay elastic constant) of liquid crystal compositions to most suitable ones required of each display device. Accordingly, liquid crystalline compounds are required to be excellent in miscibility with other liquid crystal compounds, and recently in particular required to be excellent in the miscibility even at low temperatures from the requirement of being used in various environments.

Meanwhile, active matrix mode, especially thin film transistor (TFT) mode is extensively adopted in recent years as display mode, for example, for television sets and viewfinders from the aspect of display performances such as contrast, display capacity, and response time. Also, STN mode which has a large display capacity and display devices of which can be produced by comparatively simpler methods and at a lower cost than those of active matrix mode from the structural factor of display devices is largely adopted in displays, for example, for personal computers.

Recent development in these fields is being progressed while placing stress on (a) downsizing of liquid crystal display devices into a portable size as shown by the development of small size TV sets and notebook size personal computers both of which are characterized by being in small size, light, and thus portable; and (b) production of liquid crystalline compounds and liquid crystal compositions having a low driving voltage, that is, a low threshold voltage from the viewpoint of withstand voltage of IC, in the aspect of liquid crystal material.

It is known that threshold voltage ($V_{th}$) can be expressed by the following equation (H. J. Deuling et al., Mol. Cryst. Liq. Cryst., 27 (1975) 81):

$$V_{th}=\pi(K/\epsilon_0\Delta\epsilon)^{1/2}$$

In the equation described above, K is an elastic constant and $\epsilon_0$ is a dielectric constant in vacuum. As will be seen from this equation, two methods, that is, a method of increasing dielectric anisotropy (Δε) and a method of lowering elastic constant can be considered to lower the threshold voltage. However, since actual control of elastic constant is very difficult, it is an actual situation that liquid crystal materials having a high dielectric anisotropy (Δε) are ordinarily used to cope with the requirements. With the facts described above for a background, development of liquid crystalline compounds having a high dielectric anisotropy (Δε) has actively been conducted.

Almost all liquid crystal compositions currently used in display devices for TFT mode are composed of fluorine type liquid crystal materials. This is because (i) a high voltage holding ratio (V.H.R.) is required in TFT mode from the viewpoint of construction of the devices, (ii) the materials have to be small in the temperature dependency, and (iii) materials other than fluorine type can not meet these requirements. As fluorine type materials for low voltage, the following compounds are heretofore disclosed:

(a) DE-4027840A1

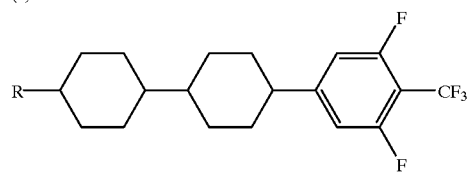

(b) USP-5,032,313

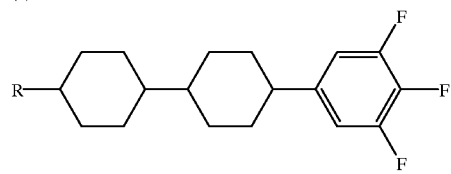

in the structural formula described above, R represents an alkyl group.

Whereas it is reported that either compounds (a) and (b) have several fluorine atoms at a terminal of the molecule and exhibit a high dielectric anisotropy, it is known that their clearing point (NI point) is low and viscosity is a comparatively high. Among the persons skilled in the art, it is empirically known that there are inversely proportional and direct proportional relations between the number of substituted fluorine atom and the clearing point, and between the number of substituted fluorine atom and the viscosity, respectively, although it is not simple. Accordingly, it is difficult to attain the required clearing point and viscosity (response speed) when liquid crystal compositions are produced only a series of these compounds. With the object of offsetting this defect, a viscosity decreasing agent represented by the following compounds is usually added in liquid crystal compositions.

(c) Japanese Patent Publication No. Sho 62-39136

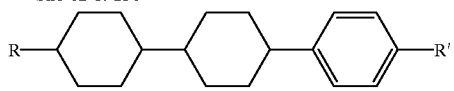

(d) Japanese Patent Publication No. Sho 62-46527

Japanese Patent Publication No. Hei 4-28693

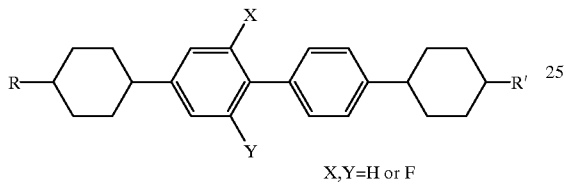

X,Y=H or F in the structural formula described above, R and R' represent an alkyl group.

Whereas compounds (c) have a comparatively low viscosity, their clearing point is not sufficiently high to offsetting the low clearing point of liquid crystal compositions comprising the liquid crystalline compounds for low voltage described above. In order to meet the requirement, a comparatively large amount is necessary to be added, but characteristics of liquid crystal compositions are lost in this case. Accordingly, compounds (c) are unsuitable as material to solve the problems described above. Whereas compounds (d) have a sufficiently high clearing point, their viscosity is remarkably high since they have a four ring structure. Thus, the increase in the viscosity is unavoidable when the compounds (d) are added in liquid crystal compositions. Besides, since compounds (d) themselves have smectic phase, when liquid crystal compositions prepared by adding the compounds were left at a low temperature, smectic phase some times develops in the liquid crystal compositions. Accordingly, compounds (d) are unsuitable to solve the problems described above, either. Further, since any one of compounds (c) and (d) has an extremely low dielectric anisotropy value, when it is added to liquid crystal compositions for low voltage having a large dielectric anisotropy value as described above, the compound considerably lower the dielectric anisotropy of the liquid crystal compositions. As the result, the threshold voltage of the compositions raise, and thus, the compound is not preferable to solve the problems.

In the meantime, researches to overcome narrow viewing angle which is only one defect of liquid crystal panel of TFT display mode were actively conducted recent years, and many results of the researches are reported at lectures in academic society and disclosed in patent publications. As an example of the step for the improvement, the following method is disclosed. For instance, in Laid-open Japanese Patent Publication Nos. Hei 4-229828 and Hei 4-258923, a method is disclosed in which the viewing angle is improved by disposing a phase difference film between a pair of polarizing plates and a TN type liquid crystal cell. In Laid-open Japanese Patent Publication Nos. Hei 4-366808 and Hei 4-366809, a method is disclosed in which two layers liquid crystal system using a layer of chiral nematic liquid crystal as phase difference film is adopted. However, either methods described above are insufficient in improvement of the viewing angle and also had such problems that production cost is high and liquid crystal panels become heavy.

As a new method to solve the problems, In-Plane Switching (IPS) driving has recently come to attract public attention (R. Kiefer et al., JAPAN DISPLAY '92, 547 (1992); G. Baur, Freiburger Arbeitstagung Flussigkristalle, Abstract No. 22 (1993)). As characteristics in the structure of liquid crystal panels of the IPS drive, the fact that whereas an electrode is disposed on both upper and lower substrates, respectively, in conventional liquid crystal panels, a comb-shape electrode is disposed on the substrate only at one side in the IPS drive, and the fact that the direction of major axis of liquid crystal molecules is all the time in parallel to the substrates in the IPS drive can be mentioned. As advantages of the IPS drive, ① cell thickness can be reduced since the electrode exists on the substrate only at one side, ② By reduction of production cost can be expected since cell thickness can be reduced, and ③ By distance between electrodes is maintained constant, can be mentioned in addition to the fact that the viewing angle is expanded.

In order to actualize high speed response and low voltage drive in the IPS drive, the liquid crystalline compounds to be used are required to have a low viscosity and a high negative dielectric anisotropy. Also, as another example of attempts to improve the narrow viewing angle, a method which utilizes a vertical orientation of liquid crystal molecules and is disclosed in Laid-open Japanese Patent Publication No. Hei 2-176625 can be mentioned. One of the characteristics of this method is the use of liquid crystal compositions having a negative dielectric anisotropy. Meantime, as a conventional compound having a high negative dielectric anisotropy, the following compounds are disclosed in the patent publication shown below:

(e) Japanese Patent Publication No. Sho 61-26899

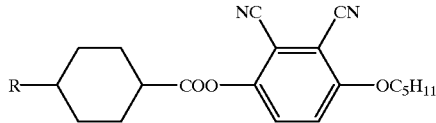

in the structural formula described above, R represents an alkyl group.

Compounds (e) (Japanese Patent Publication No. Sho 61-26899) are reported to have 2,3-dicyano—1,4-phenylene group in their partial structure and exhibit a high negative anisotropy. However, since they have cyano groups, their dependency of voltage holding ratio on temperature is large and viscosity is remarkably high, and thus the compounds can not be used as liquid crystal material for IPS drive utilizing TFT display mode. As described above, compounds having characteristics which are necessary for actualizing the high speed response and low voltage driving in the IPS driving, in a well balanced condition with each other, have not yet been known.

DISCLOSURE OF THE INVENTION

An object of the present invention is to provide liquid crystalline compounds which have such a high resistivity and high voltage holding ratio as can be used even for TFT display mode, are stable against heat and UV irradiation, have an effect as viscosity reducing agent, that is, 1) effect of raising clearing point of liquid crystal compositions,
2) effect of reducing viscosity of the compositions, and
3) effect of preventing the dielectric anisotropy of the compositions from lowering (or preventing the threshold voltage of the compositions from raising), in a comprehensively well balanced condition, and further have a low viscosity and high negative dielectric anisotropy which can cope with the IPS driving or with such display devices of vertically oriented mode as described in Laid-open Japanese Patent Publication No. Hei 2-176625; to provide liquid crystal compositions comprising the liquid crystalline compound; and to provide liquid crystal display devices fabricated by using the liquid crystal composition.

Heretofore, as for the compounds which have a partial structure in which two phenylene groups are cross-linked with bonding group —$CF_2O$— and have an alkyl group as both terminal groups of the molecule, structural formula is disclosed in Laid-open Japanese Patent Publication No. Hei 2-289529 only with reference to two rings compound (f). It is true that structural formula is described in the patent publication mentioned above.

However, physical data of the compound and specific value of physical properties of the compound necessary for evaluating the utility as liquid crystalline compound are not disclosed at all, and thus the characteristics of the compound were not known in the least.

(f) Laid-open Japanese Patent Publication No. Hei 2-289529

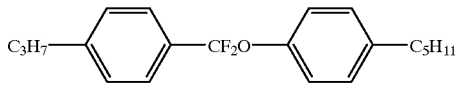

Then, specific two rings, three rings, or four rings compounds which have a partial structure in which two ring structures are cross-linked with bonding group —$CF_2O$— and have a group selected from an alkyl group, alkenyl group, alkoxy group, alkoxyalkyl group, and alkynyl group as both terminal groups of the molecule were devised and their physical properties were diligently investigated by the present inventors to find out that the compounds have not only a high clearing point but also an extremely low viscosity lower than expected at first, that the compounds exhibit a medium extent of dielectric anisotropy value ($\Delta\epsilon$=~4.0), and further that the compounds having a partial structure of 2,3-difluoro-1,4-phenylene group and a bonding group of —COO—, —$CF_2O$—, or —$OCF_2$— at the same time not only exhibit a large negative dielectric anisotropy value but also are excellent in miscibility with other liquid crystal compounds, have a high resistivity and high voltage holding ratio, and are stable physically and chemically, leading to the accomplishment of the present invention.

Thus, the present invention is summarized as shown in the following paragraphs [1] to [29]:

[1] A liquid crystalline compound expressed by the general formula (1)

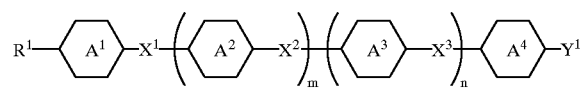

(1)

wherein $R^1$ and $Y^1$ represent an alkyl group having 1 to 20 carbon atoms one or more non-adjacent methylene groups in the alkyl group may be replaced by oxygen atom, sulfur atom, or vinylene group, and one or more hydrogen atoms in the alkyl group may be replaced by fluorine atom or chlorine atom;

$X^1$, $X^2$, and $X^3$ independently represent single bond, 1,2-ethylene group, vinylene group, —COO—, —$CF_2O$—, or —$OCF_2$— provided that at least one of $X^1$, $X^2$, and $X^3$ represents —COO—, —$CF_2O$—, or —$OCF_2$—;

ring $A^1$, ring $A^2$, ring $A^3$, and ring $A^4$ independently represent trans-1,4-cyclohexylene group $CH_2$ group on which ring may be replaced by oxygen atom, or 1,4-phenylene group one or more hydrogen atoms of which may be replaced by fluorine atom or chlorine atom; and m and n are 0 or 1 provided that when $X^1$, $X^2$, or $X^3$ represents —COO—, then at least one of ring $A^2$, ring $A^3$, and ring $A^4$ represents 2,3-difluoro-1,4-phenylene group, and $Y^1$ represents an alkoxy group;

when m=n=0 and $X^1$ represents —COO—, then ring $A^1$ represents 1,4-phenylene group at least one hydrogen atom in which group is replaced by fluorine atom;

when m=1, n=0, $X^1$ represents single bond or 1,2-ethylene group, and $X^2$ represents —COO—, then ring $A^2$ represents 1,4-phenylene group at least one hydrogen atom in which group is replaced by fluorine atom;

when m=n=1, $X^2$ represents —COO—, and $X^1$ represents single bond or 1,2-ethylene group, then ring $A^2$ represents 1,4-phenylene group at least one hydrogen atom in which group is replaced by fluorine atom;

when m=n=1, $X^3$ represents —COO—, and $X^1$ and $X^2$ independently represent single bond or 1,2-ethylene group, then ring $A^3$ represents 1,4-phenylene group at least one hydrogen atom in which group is replaced by fluorine atom; and when m=n=0 and $X^1$ represents —$CF_2O$— or —$OCF_2$—, then ring $A^1$ or ring $A^4$ represents trans-1, 4cyclohexylene group, or 1,4-phenylene group at least one hydrogen atom in which group is replaced by chlorine atom or fluorine atom;

when m+n=1, $X^2$ or $X^3$ represents —$CF_2O$—, ring $A^2$ or ring $A^3$ represents 1,4-phenylene group, and $A^4$ represents 1,4-phenylene group at least one hydrogen atom in which group may be replaced by a halogen atom, then $Y^1$ represents an alkyl or alkoxy group, and each element which constitutes this compound may be replaced by its isotope.

[2] The liquid crystalline compound recited in paragraph [1] above wherein m=n=0, $X^1$ is —$CF_2O$—, and ring $A^1$ or ring $A^4$ is 1,4-phenylene group at least one hydrogen atom in which group is replaced by fluorine atom or chlorine atom in the general formula (1).

[3] The liquid crystalline compound recited in paragraph [1] above wherein m=1, n=0, and $X^2$ is —COO— in the general formula (1).

[4] The liquid crystalline compound recited in [1] above wherein m=n=1 and $X^2$ is —COO— in the general formula (1).

[5] The liquid crystalline compound recited in paragraph [1] above wherein m=n=1 and $X^3$ is —COO— in the general formula (1).

[6] The liquid crystalline compound recited in paragraph [3] above wherein ring $A^1$ is trans-1,4-cyclohexylene group and ring $A^2$ is 1,4-phenylene group in the general formula (1).

[7] The liquid crystalline compound recited in paragraph [3] above wherein both ring $A^1$ and ring $A^2$ are trans-1,4-cyclohexylene group in the general formula (1).

[8] The liquid crystalline compound recited in paragraph [6] above wherein $X^1$ is 1,2-ethylene group, $X^2$ is —COO—, and ring $A^2$ is 3-fluoro-1,4-phenylene group in the general formula (1).

[9] The liquid crystalline compound recited in paragraph [6] above wherein $X^1$ is vinylene group and $X^2$ is —COO— in the general formula (1).

[10] The liquid crystalline compound recited in paragraph [7] wherein $X^1$ is vinylene group and $X^2$ is —COO— in the general formula (1).

[11] The liquid crystalline compound recited in paragraph [1] above wherein m=1, n=0, and $X^1$ or $X^2$ is —CF$_2$O— or —OCF$_2$— in the general formula (1).

[12] The liquid crystalline compound recited in paragraph [1] above wherein both $R^1$ and $Y^1$ are an alkyl group in the general formula (1).

[13] The liquid crystalline compound recited in paragraph [11] above wherein at least one of $R^1$ and $Y^1$ is an alkenyl group in the general formula (1).

[14] The liquid crystalline compound recited in paragraph [11] above wherein $X^1$ is single bond, $X^2$ is —CF$_2$O— or —OCF$_2$—, both ring $A^1$ and ring $A^2$ are 1,4-cyclohexylene group, and ring $A^4$ is 1,4-phenylene group at least one hydrogen atom of which may be replaced by fluorine atom or chlorine atom in the general formula (1).

[15] The liquid crystalline compound recited in paragraph [1] above wherein m=n=1, and $X^1$, $X^2$, or $X^3$ is —CF$_2$O— or OCF$_2$— in the general formula (1).

[16] The liquid crystalline compound recited in paragraph [15] above wherein $R^1$ and $Y^1$ are an alkyl group, both ring $A^1$ and ring $A^4$ are 1,4-cyclohexylene group, both ring $A^2$ and ring $A^3$ are 1,4-phenylene group at least one hydrogen atom of which may be replaced by fluorine atom or chlorine atom, $X^2$ is —CF$_2$O— or —OCF$_2$—, and both $X^1$ and $X^3$ are single bond in the general formula (1).

[17] The liquid crystalline compound recited in paragraph [15] above wherein $R^1$ and $Y^1$ are an alkyl group, both ring $A^1$ and ring $A^4$ are 1,4-cyclohexylene group, both ring $A^2$ and ring $A^3$ are 1,4-phenylene group at least one hydrogen atom of which may be replaced by fluorine atom or chlorine atom, $X^2$ is —CF$_2$O— or —OCF$_2$—, and any one of $X^1$ and $X^3$ is single bond and the other is 1,2-ethylene group in the general formula (1).

[18] The liquid crystalline compound recited in paragraph [15] above wherein at least one of $R^1$ and $Y^1$ is an alkenyl group in the general formula (1).

[19] A liquid crystal composition comprising at least two components and comprising at least one liquid crystalline compound expressed by the general formula (1).

[20] A liquid crystal composition comprising, as a first component, at least one liquid crystalline compound recited in any one of paragraphs [1] to [18] above, and comprising, as a second component, at least one compound selected from the group consisting of the compounds expressed by any one of the general formulas (2), (3), and (4)

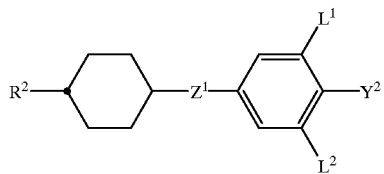

(2)

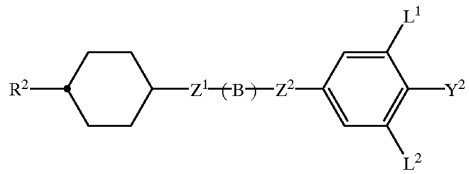

(3)

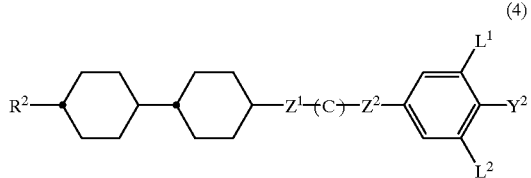

(4)

wherein $R^2$ represents an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

$Y^2$ represents fluorine atom, chlorine atom, —OCF$_3$, —OCF$_2$H, —CF$_3$, —CF$_2$H, —CFH$_2$OCF$_2$CF$_2$H, or —OCF$_2$CFHCF$_3$;

$L^1$ and $L^2$ independently represent hydrogen atom or fluorine atom;

$Z^1$ and $Z^2$ independently represent 1,2-ethylene group, vinylene group, 1,4-butylene group, —COO—, —CF$_2$O—, —OC$_2$—, or single bond;

ring B represents trans-1,4-cyclohexylene, 1,3-dioxane-2,5-diyl, or 1,4-phenylene group hydrogen atom of which may be replaced by fluorine atom;

ring C represents trans-1,4-cyclohexylene, or 1,4-phenylene group hydrogen atom of which may be replaced by fluorine atom; and each atom which constitutes these compounds may be replaced by its isotope.

[21] A liquid crystal composition comprising, as a first component, at least one liquid crystalline compound recited in any one of paragraphs [1] to [18] above, and comprising, as a second component, at least one compound selected from the group consisting of the compounds expressed by the general formula (5) or (6)

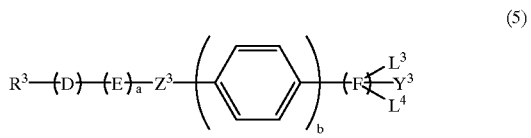

(5)

-continued (6)

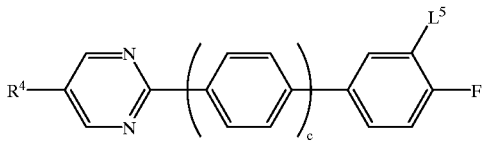

wherein R³ and R⁴ independently represent an alkyl group having 1 to 10 carbon atoms one or more non-adjacent methylene groups in the alkyl group may be replaced by oxygen atom or vinylene group, and any hydrogen atom in the alkyl group may be replaced by fluorine atom;

Y³ represents CN group or —C≡C—CN;

ring D represents trans-1,4-cyclohexylene, 1,4-phenylene, pyrimidine-2,5-diyl, or 1,3-dioxane-2,5-diyl group;

ring E represents trans-1,4-cyclohexylene, 1,4-phenylene group hydrogen atom of which may be replaced by fluorine atom, or pyrimidine-2,5-diyl group;

ring F represents trans-1,4-cyclohexylene or 1,4-phenylene group;

Z³ represents 1,2-ethylene group, —COO—, or single bond;

L³, L⁴, and L⁵ independently represent hydrogen atom or fluorine atom;

a, b, and c are independently 0 or 1; and each atom which constitutes these compounds may be replaced by its isotope.

[22] A liquid crystal composition comprising, as a first component, at least one liquid crystalline compound recited in any one of paragraphs [1] to [18] above, and comprising, as a second compound, at least one compound selected from the group consisting of the compounds expressed by any one of the general formulas (7), (8), and (9)

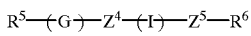 (7)

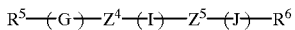 (8)

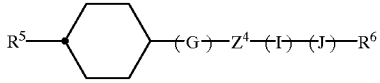 (9)

wherein R⁵ and R⁶ independently represent an alkyl group having 1 to 10 carbon atoms one or more non-adjacent methylene groups in the alkyl group may be replaced by oxygen atom or —CH═CH—, and any hydrogen atom in the alkyl group may be replaced by fluorine atom;

ring G, ring I, and ring J independently represent trans-1,4-cyclohexylene, pyrimidine-2,5-diyl, or 1,4-phenylene group at least one hydrogen atom of which may be replaced by fluorine atom;

Z⁴ and Z⁵ independently represent —C≡C—, —COO—, —CH₂CH₂—, —CH═CH—, or single bond; and each atom which constitutes these compounds may be replaced by its isotope.

[23] A liquid crystal composition comprising, as a first component, at least one liquid crystalline compound recited in any one of paragraphs [1] to [18] above, and comprising, as a second component, at least one compound selected from the group consisting of the compounds expressed by any one of the general formulas (10), (11), and (12)

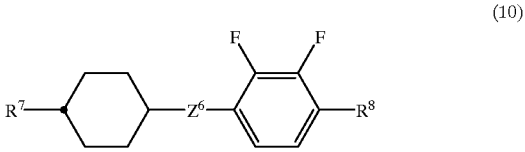 (10)

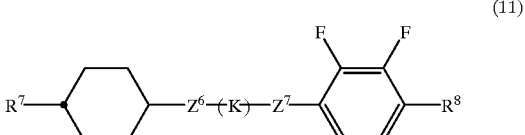 (11)

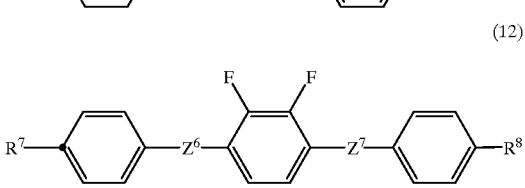 (12)

wherein R⁷ and R⁸ independently represent an alkyl group having 1 to 10 carbon atoms one or more non-adjacent methylene groups in the alkyl group may be replaced by oxygen atom or —CH═CH—, and any hydrogen atom in the alkyl group may be replaced by fluorine atom;

ring K represents trans-1,4-cyclohexylene or 1,4-phenylene group;

Z⁶ and Z independently represent —CH₂CH₂-—, —CH₂O—, or single bond; and each atom which constitutes these compounds may be replaced by its isotope.

[24] A liquid crystal composition comprising, as a first component, at least one liquid crystalline compound recited in any one of paragraphs [1] to [18] above, comprising, as a second component, at least one compound selected from the group consisting of the compounds expressed by any one of the general formulas (7), (8), and (9), and comprising, as a third component, at least one compound selected from the group consisting of the compounds expressed by any one of the general formulas (10), (11), and (12).

[25] A liquid crystal composition comprising, as a first component, at least one liquid crystalline compound recited in any one of paragraphs [1] to [18] above, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (7), (8), and (9).

[26] A liquid crystal composition comprising, as a first component, at least one liquid crystalline compound recited in any one of paragraphs [1] to [18] above, comprising, as a second component, at least one compound selected from the group consisting of the compounds expressed by the general formula (5) or (6), and comprising, as a third component, at least one compounds selected from the group consisting of the compounds expressed by any one of the general formulas (7), (8), and (9).

[27] A liquid crystal composition comprising, as a first component, at least one liquid crystalline compound recited in any one of paragraphs [1] to [18] above, comprising, as a second component, at least one compound selected from the group consisting of the compounds expressed by any one of the general formulas (2), (3), and (4), comprising, as a third component, at least one compound selected from the group consisting of the compounds expressed by the general formula (5) or (6), and comprising, as a fourth component, at least one compound selected from the group consisting of the compounds expressed by any one of the general formulas (7), (8), and (9).

[28] A liquid crystal composition comprising one or more optically active compounds in addition to the liquid crystal composition recited in any one of paragraphs [19] to [27] above.

[29] A liquid crystal display device using therein the liquid crystal composition recited in any one of paragraphs [19] to [28] above.

Any compounds of the present invention have a high clearing point and are low in viscosity. Among them, the compounds in which 2,3-difluoro-1,4-phenylene group is not selected as ring structure exhibit a medium extent of dielectric anisotropy value ($\Delta\epsilon$=~-4.0). On the other hand, the compounds in which 2,3-difluoro-1,4-phenylene group is selected as ring structure exhibit a large negative dielectric anisotropy value. Any type of these compounds are excellent in miscibility with other liquid crystal compounds, have a high resistivity and high voltage holding ratio, and are stable physically and chemically.

More specifically, the compounds in which an alkyl group is selected as terminal substituents of the molecule exhibit an extremely high voltage holding ratio and are very effective as viscosity reducing agent for display devices of TFT mode. The compounds in which an alkenyl group or another one is selected as terminal group of the molecule exhibit a comparatively large elastic constant ratio and are very useful as viscosity reducing agent for display devices of STN mode.

Since the compounds in which 2,3-difluoro-1,4-phenylene group is not selected as ring structure have a medium extent of dielectric anisotropy value compared with the compounds (c) or (d) described in the section of BACKGROUND ART, when the compounds are added to liquid crystal compositions having a high dielectric anisotropy and used for low voltage, it is possible to raise clearing point and further to maintain or reducing viscosity while suppressing the lowering of dielectric anisotropy (raising of threshold voltage).

On the other hand, since the compounds in which 2,3-difluoro-1,4-phenylene group is selected as ring structure are low in viscosity as described above and exhibit a large negative dielectric anisotropy value, it is possible to provide liquid crystal compositions and liquid crystal display devices which can be driven at a low voltage and can respond at a high speed in display devices of the IPS driving or the devices of such vertically oriented mode as described in Laid-open Japanese Patent Publication No. Hei 2-176625 by using the compounds of the present invention.

As a matter of course, while any compounds of the present invention exhibit preferable physical properties, liquid crystal compositions which meet their own purposes can be produced by using compounds in which proper $R^1$, $Y^1$, rings $A^1$, $A^2$, $A^3$, and $A^4$, $X^1$, $X^2$, $X^3$, m, and n in the general formula (1) are selected.

That is, when the compounds are used for liquid crystal compositions of which temperature range of liquid crystal phase has to be at as high a temperature as possible, it is sufficient to use four rings compounds in which m=n=1, and when the circumstance is not so, it is sufficient to use two rings or three rings compounds.

When a particularly high voltage holding ratio is necessary, for example, for liquid crystal compositions used in active matrix, it is sufficient to select an alkyl group or alkoxy group as side chains $R^1$ and $Y^1$. When a large elastic constant ratio is necessary, for example, for STN liquid crystal compositions, it is sufficient to select a substituent having such an unsaturated bonding group as an alkenyl group and alkynyl group as side chains $R^1$ and $Y^1$.

In order to obtain compounds having a positive comparatively large dielectric anisotropy value, it is sufficient to select compounds having a partial structure in which two 1,4-phenylene groups are cross-linked with —$CF_2O$—, and substitute one or two fluorine atoms at the ortho position of phenyl ring at the side of difluoromethylene. In order to answer a still larger dielectric anisotropy value, it is sufficient to additionally substitute one or two fluorine atoms at the meta position on the phenyl ring at the side of oxygen atom in the fluorine atom substituted partial structure described above, and the purpose can be achieved by introducing fluorine atom so that the dipoles face the same direction.

In order to obtain compounds having a large negative dielectric anisotropy value, it is sufficient to select —$CF_2O$— or —COO— for one of bonding groups, $X^1$, $X^2$, and $X^3$. Further, the compounds in which 2,3-difluoro-4-alkoxyphenyl group is selected instead of 2,3-difluoro-1,4-phenylene group exhibit a higher negative dielectric anisotropy.

Optical anisotropy value can also be optionally adjusted by selecting proper $R^1$, $Y^1$, rings $A^1$, $A^2$, $A^3$, and $A^4$, $X^1$, $X^2$, $X^3$, m and n. That is, when a large optical anisotropy value is necessary, it is sufficient to select compounds having many 1,4-phenylene rings and having single bond as bonding group. When a small optical anisotropy value is necessary, it is sufficient to select compounds having many trans-1,4-cyclohexylene groups.

For the purpose of the present invention, the term "alkyl group" means a straight chain or branched alkyl group having 1 to 15 carbon atoms, and an alkyl group having 1 to 5 carbon atoms is preferable particularly from the viewpoint of low viscosity. Specifically, methyl group, ethyl group, propyl group, butyl group, pentyl group, hexyl group, heptyl group, octyl group, nonyl group, isopropyl group, isobutyl group, isoamyl group, isohexyl group, 2-methylbutyl group, 2-methylpentyl group, and 3-methylpentyl group are preferable, and racemic modifications, S isomers, and R isomers are comprehended.

For the purpose of the present invention, the term "alkenyl group" means a straight chain alkenyl group having 2 to 15 carbon atoms. The alkenyl group preferably includes 1E-alkenyl, 2Z-alkenyl, 3E-alkenyl, and 4-alkenyl, and more specifically, 1-ethenyl, 1E-propenyl, 1E-butenyl, 1E-hexenyl, 2-propenyl, 2Z-butenyl, 2Z-pentenyl, 2Z-hexenyl, 3-butenyl, 3E-pentenyl, and 3E-hexenyl can be mentioned.

As rings $A^1$, $A^2$, $A^3$, and $A^4$, while benzene ring, cyclohexane ring, pyrimidine ring, pyridine ring, pyrazine ring, pyridazine ring, dioxane ring, dithian ring, and their halogen substituted ring can be mentioned, cyclohexane ring, benzene ring, and their halogen substituted ring are especially preferable.

Preferable embodiments of the compounds of the present invention expressed by the general formula (1) are compounds expressed by one of the following general formulas (1-1) to (1-217):

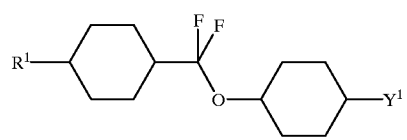 (1-1)
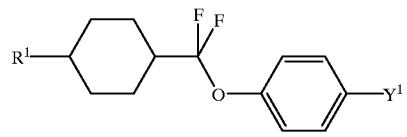 (1-2)
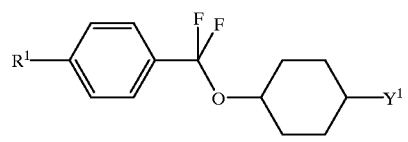 (1-3)
 (1-4)
 (1-5)
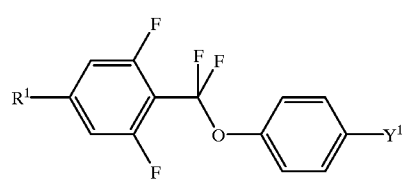 (1-6)
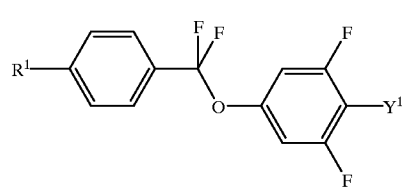 (1-7)
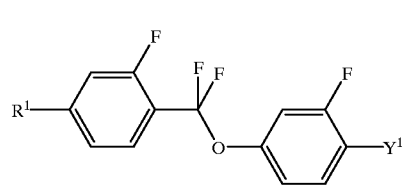 (1-8)
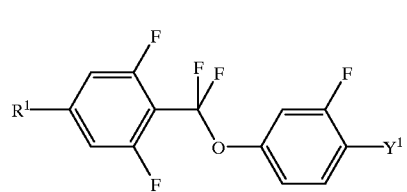 (1-9)
-continued
 (1-10)
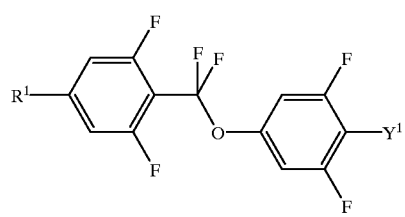 (1-11)
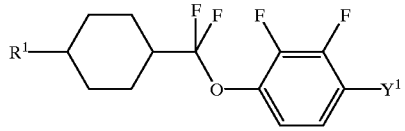 (1-12)
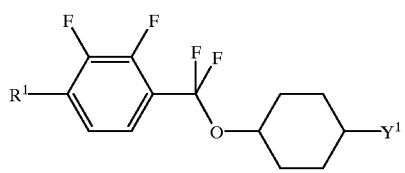 (1-13)
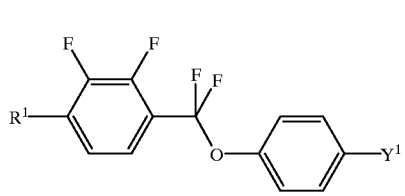 (1-14)
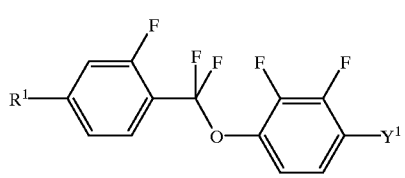 (1-15)
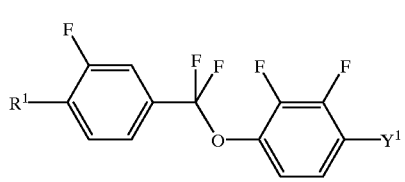 (1-15)
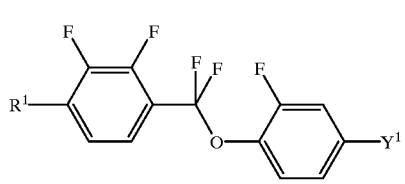 (1-16)

-continued
(1-17)
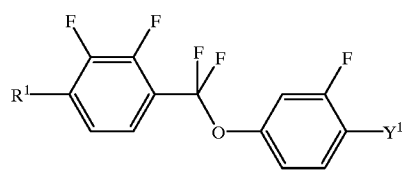
(1-18)
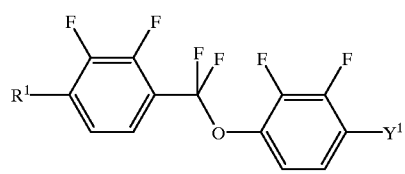
(1-19)
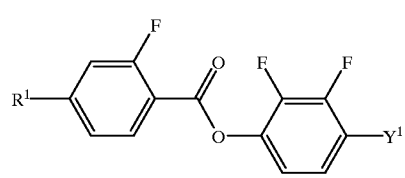
(1-20)
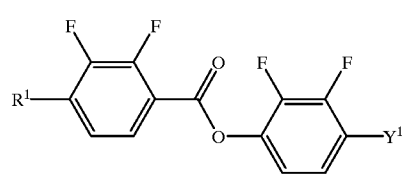
(1-21)
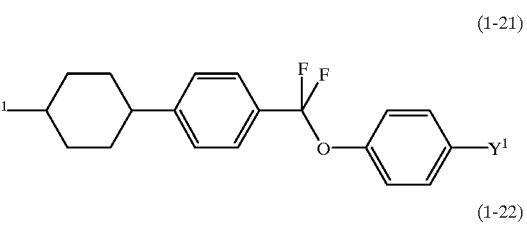
(1-22)
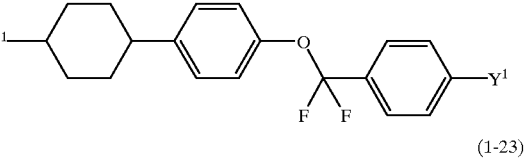
(1-23)
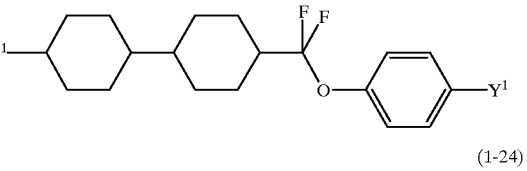
(1-24)
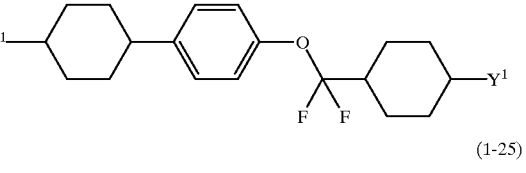
(1-25)
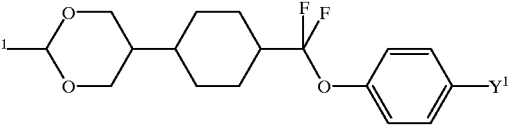
(1-26)
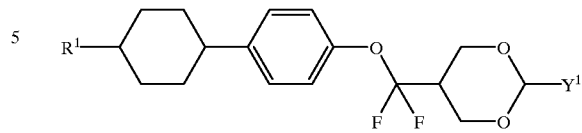
(1-27)
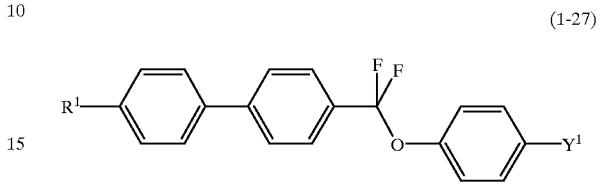
(1-28)
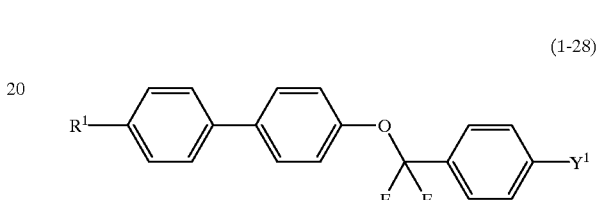
(1-29)
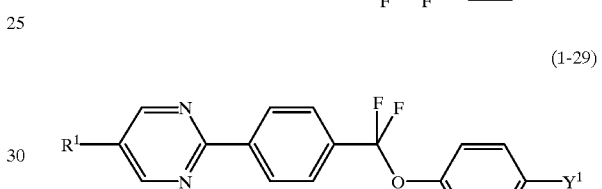
(1-30)
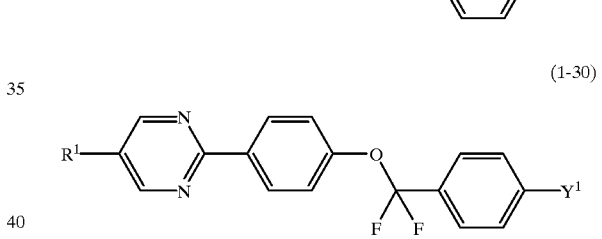
(1-31)
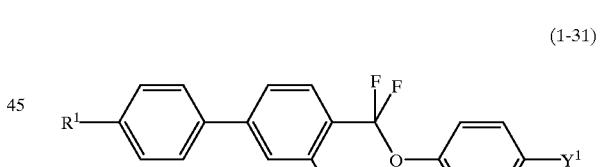
(1-32)
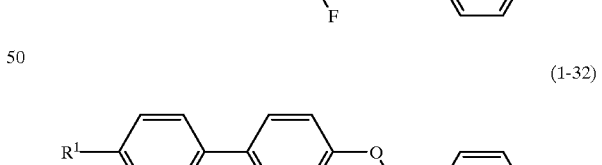
(1-33)
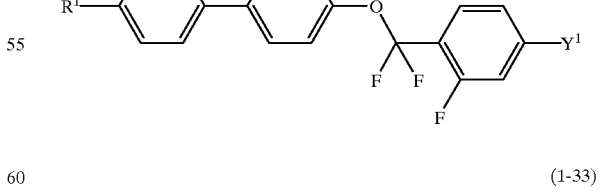
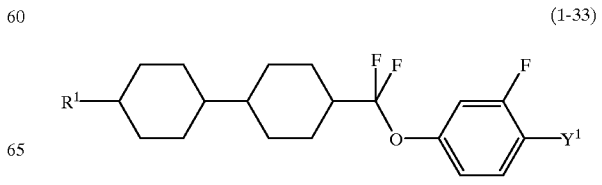

(1-34) 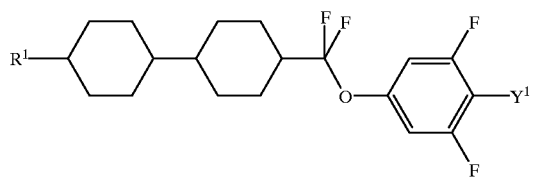
(1-35) 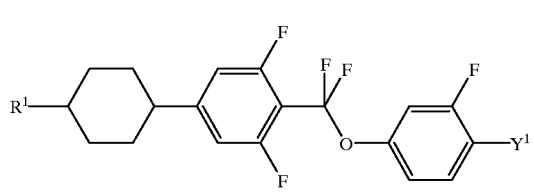
(1-36) 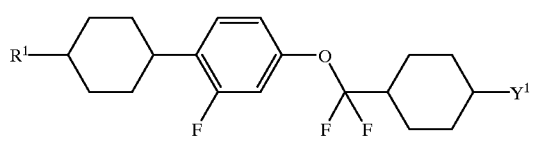
(1-37) 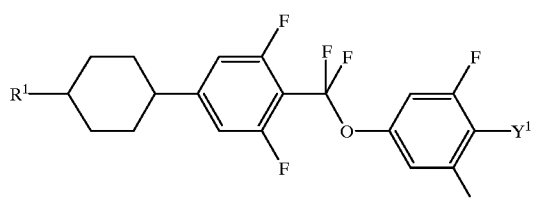
(1-38) 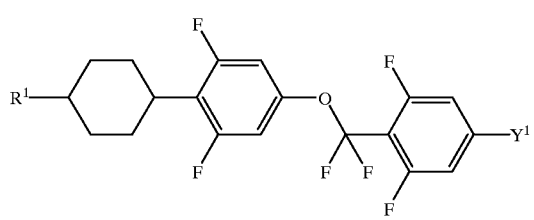
(1-39) 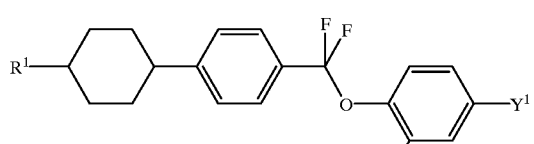
(1-40) 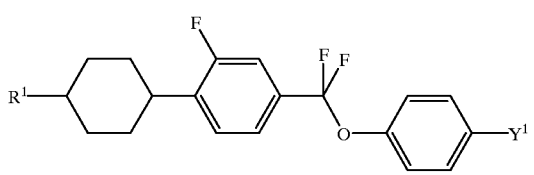
(1-41) 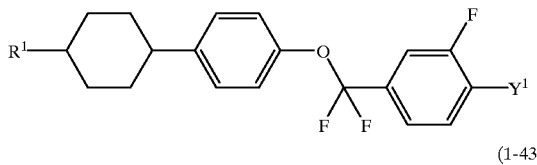
(1-42) 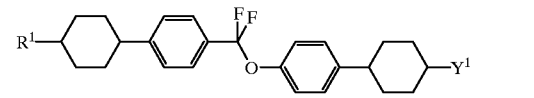
(1-43) 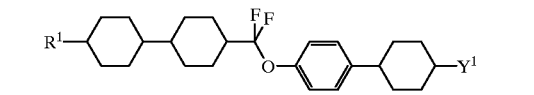
(1-44) 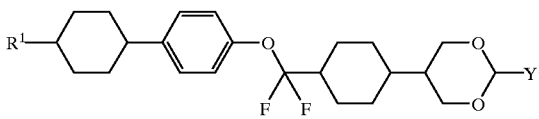
(1-45) 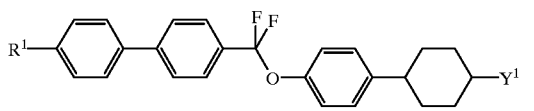
(1-46) 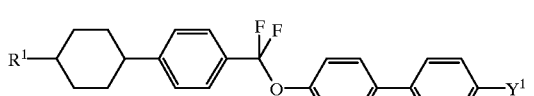
(1-47) 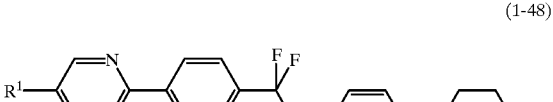
(1-48) 
(1-49)
(1-50)

-continued
(1-51)
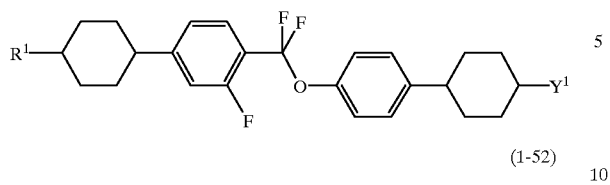
(1-52)
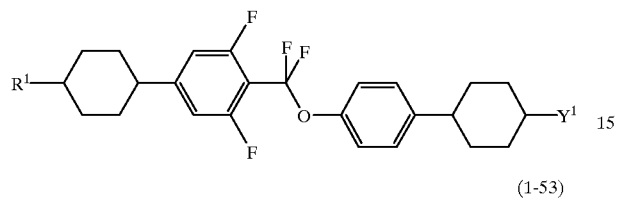
(1-53)
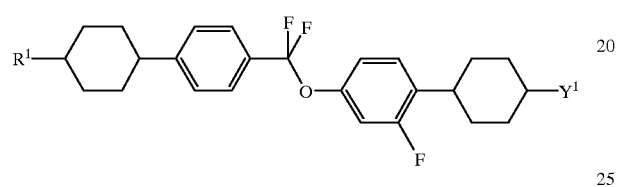
(1-54)
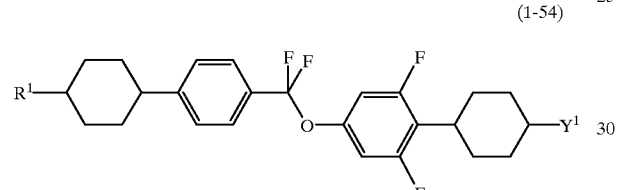
(1-55)
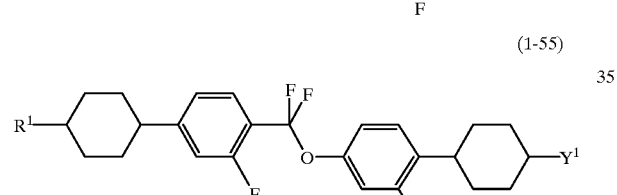
(1-56)
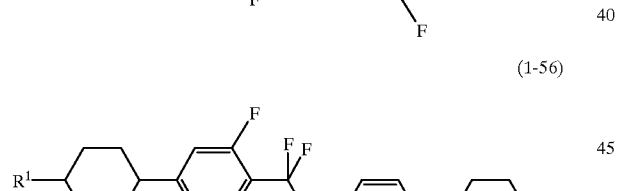
(1-57)
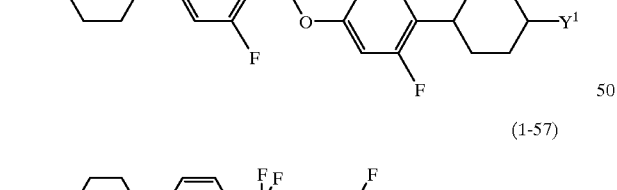
(1-58)
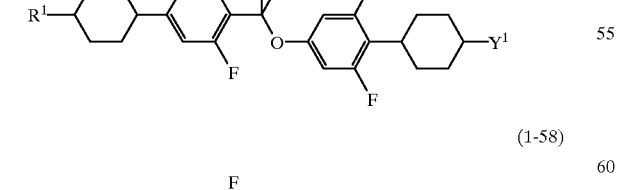
-continued
(1-59)
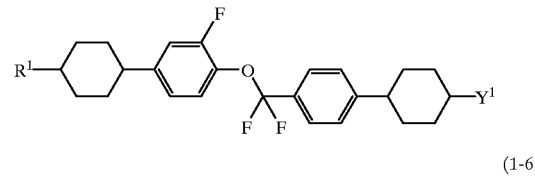
(1-61)
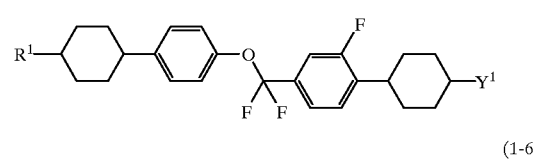
(1-62)
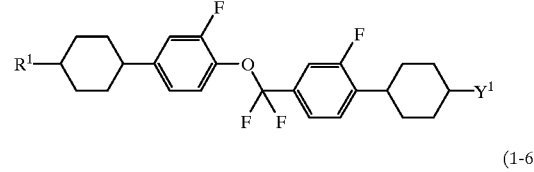
(1-63)
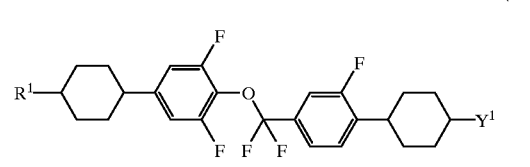
(1-64)
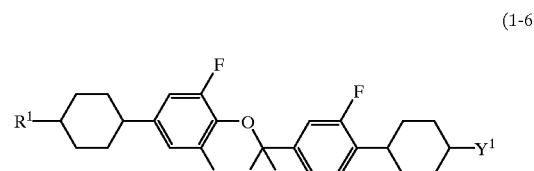
(1-65)
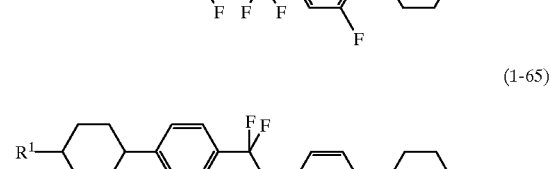
(1-66)
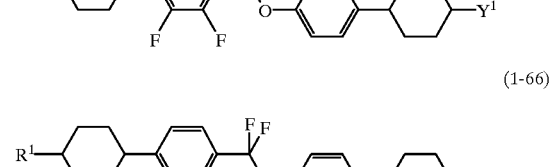
(1-67)
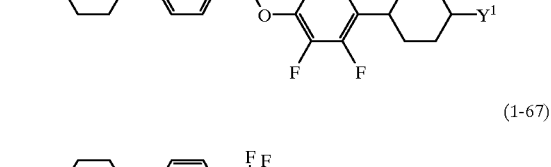
(1-68)
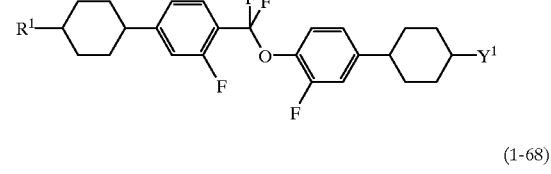

-continued
(1-69)
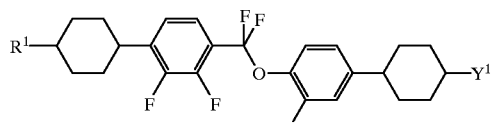
(1-70)
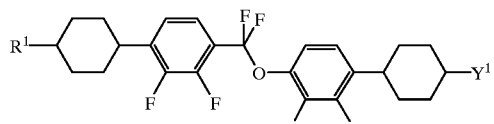
(1-71)
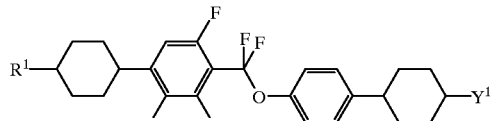
(1-72)
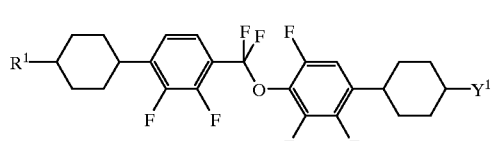
(1-73)
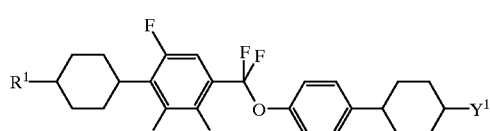
(1-74)
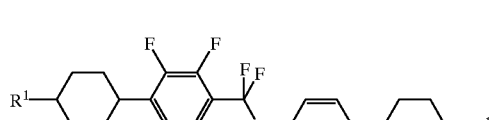
(1-75)
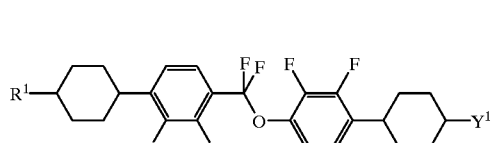
(1-76)
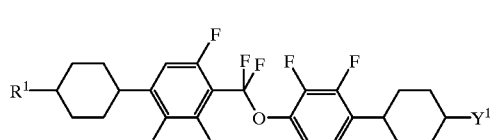
-continued
(1-77)
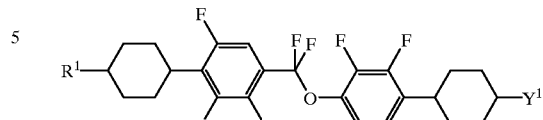
(1-78)
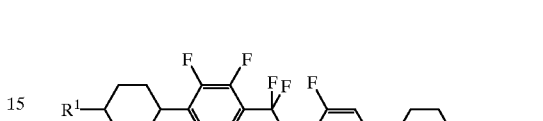
(1-79)
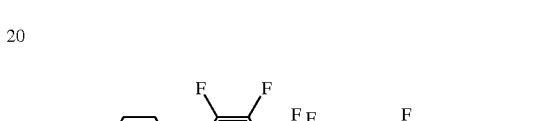
(1-80)
(1-81)
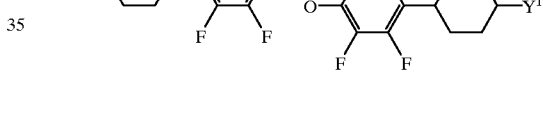
(1-82)
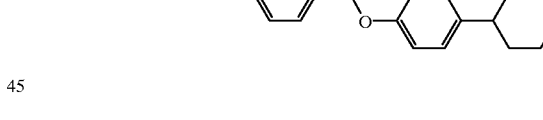
(1-83)
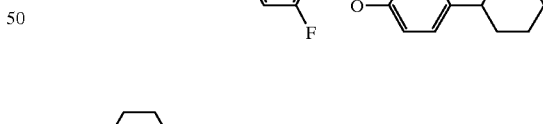
(1-84)
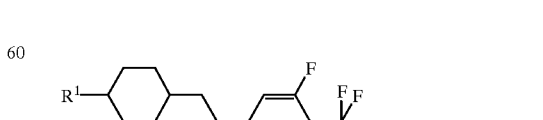

(1-85)
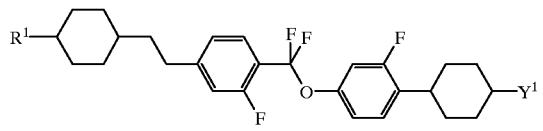
(1-86)
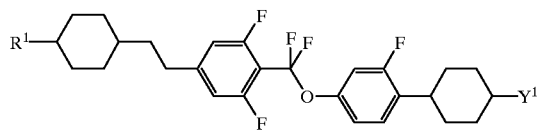
(1-87)
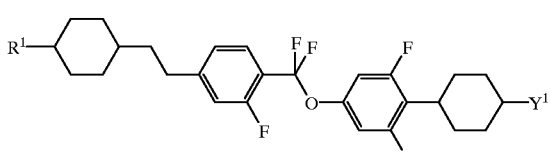
(1-88)
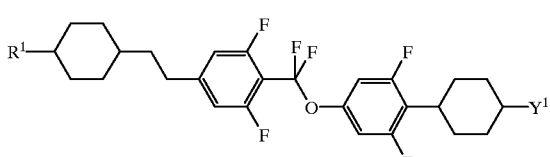
(1-89)
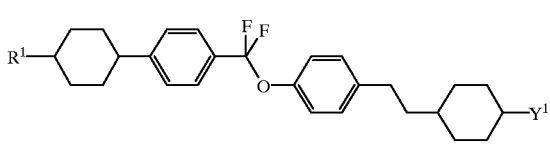
(1-90)
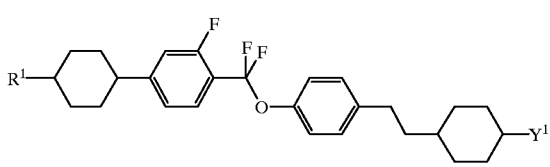
(1-91)
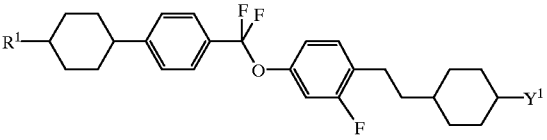
(1-92)
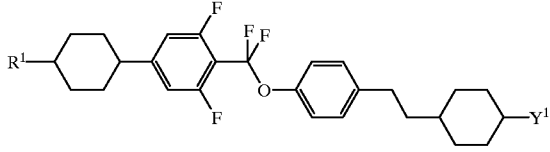
(1-93)
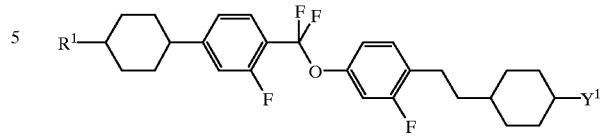
(1-94)
(1-95)
(1-96)
(1-97)
(1-98)
(1-99)
(1-100)
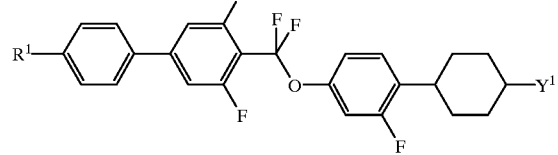

-continued
(1-101)
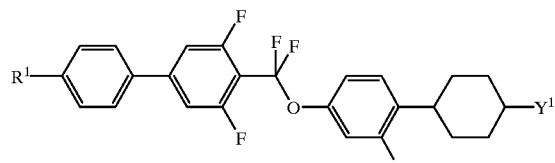
(1-102)
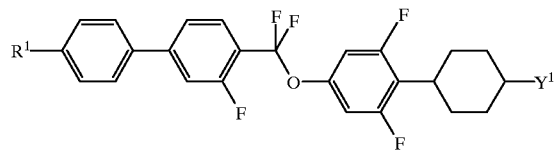
(1-103)
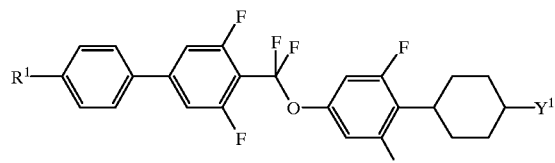
(1-104)
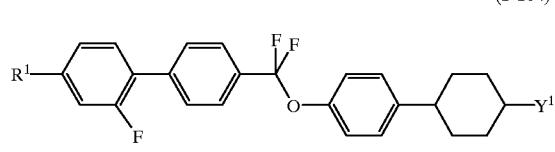
(1-105)
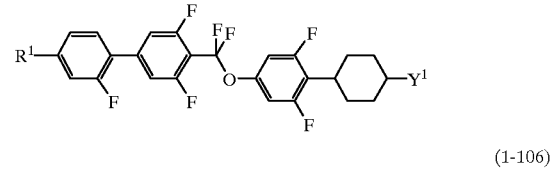
(1-106)
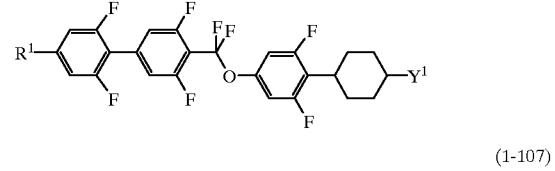
(1-107)
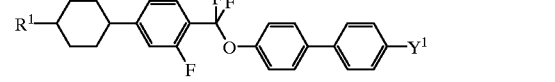
(1-108)
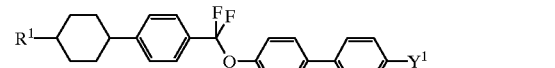
(1-109)
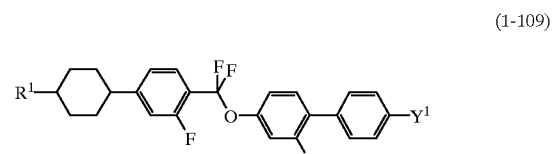
-continued
(1-110)
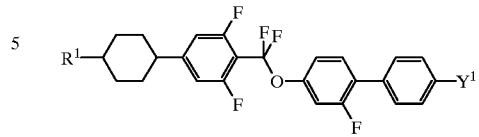
(1-111)
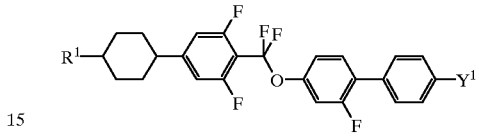
(1-112)
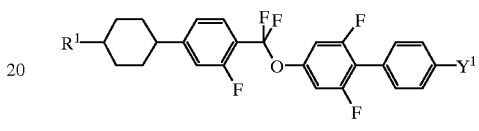
(1-113)
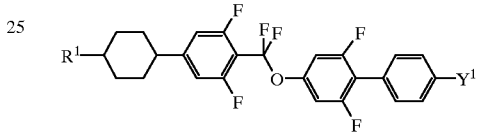
(1-114)
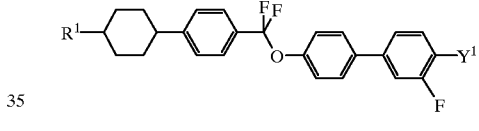
(1-115)
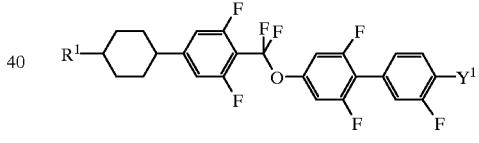
(1-116)
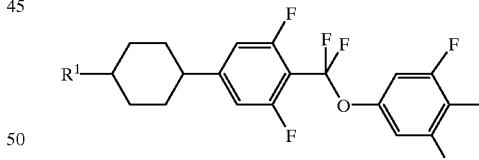
(1-117)
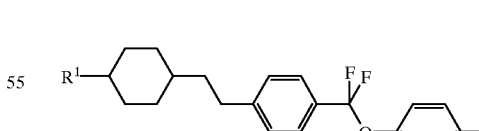
(1-118)
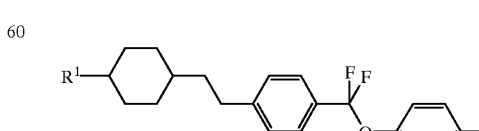

(1-119)
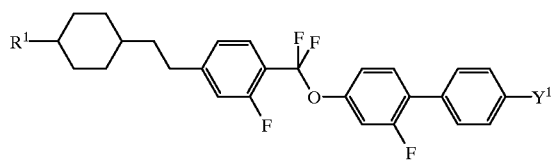
(1-120)
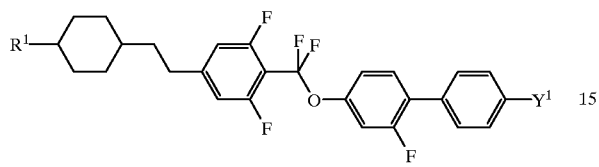
(1-121)
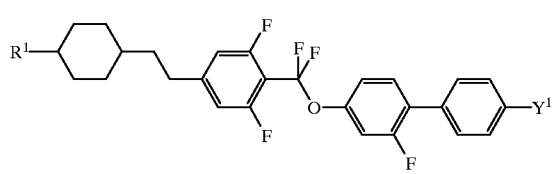
(1-122)
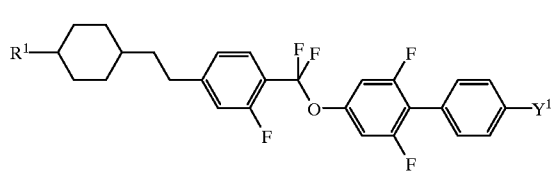
(1-123)
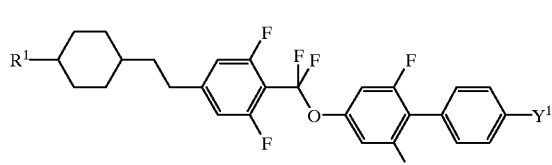
(1-124)
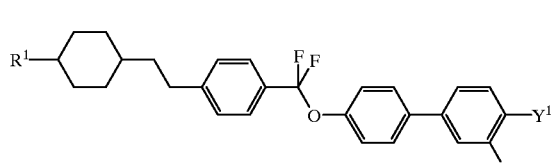
(1-125)
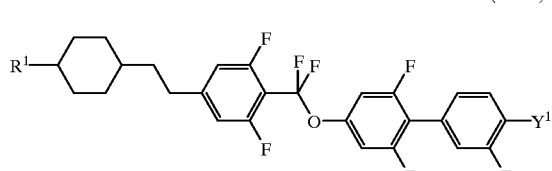
(1-126)
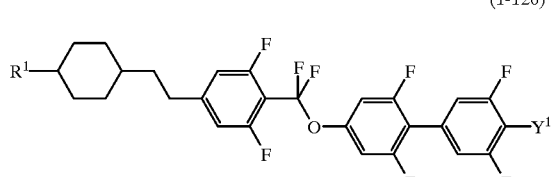
(1-127)
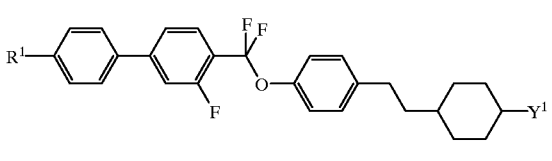
(1-128)
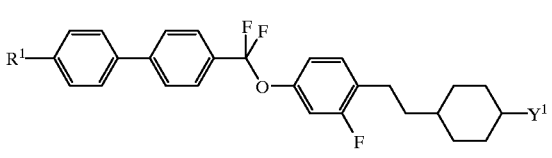
(1-129)
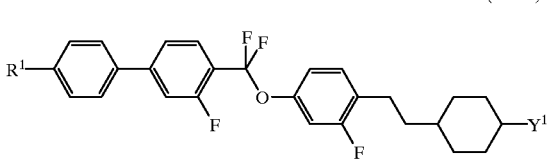
(1-130)
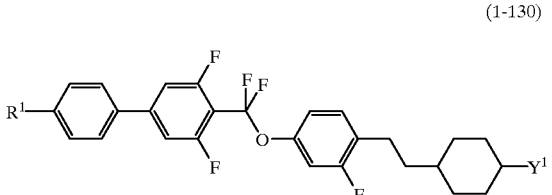
(1-131)
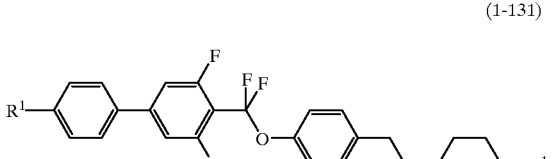
(1-132)
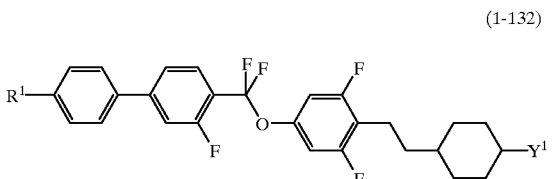
(1-133)
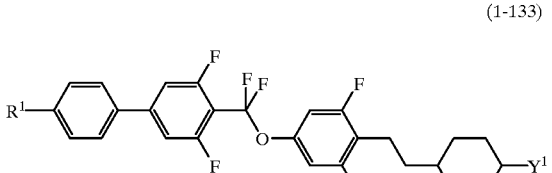
(1-134)
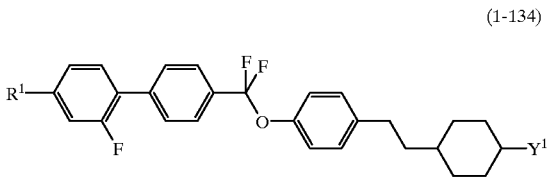

(1-135)
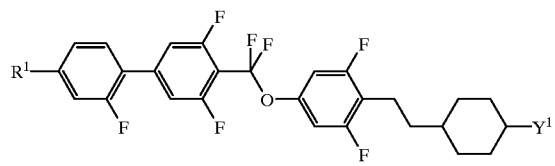
(1-136)
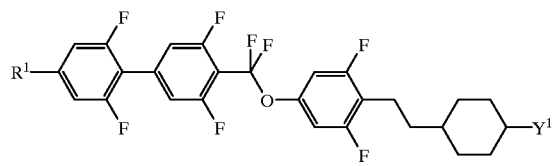
(1-138)
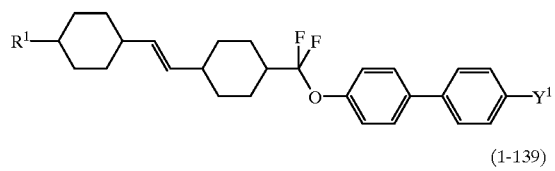
(1-139)
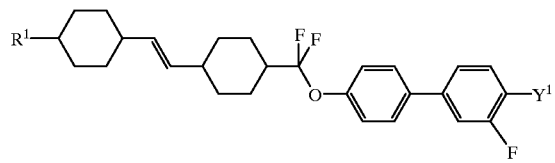
(1-140)
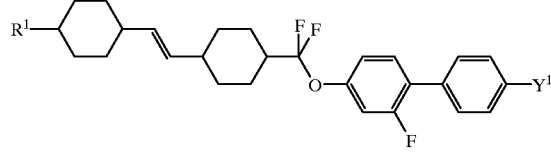
(1-141)
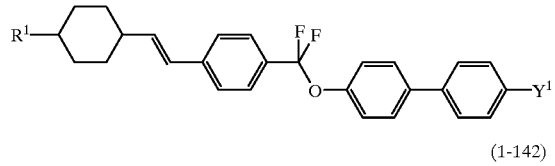
(1-142)
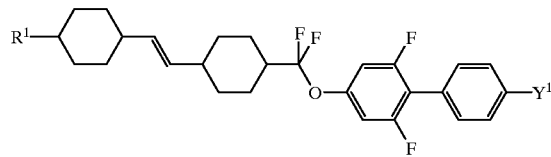
(1-143)
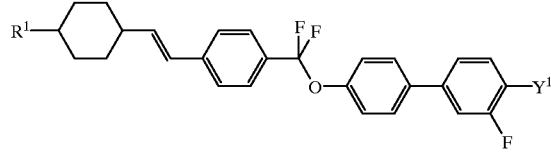
(1-144)
(1-145)
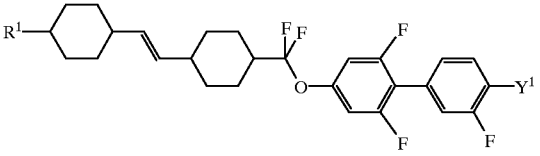
(1-146)
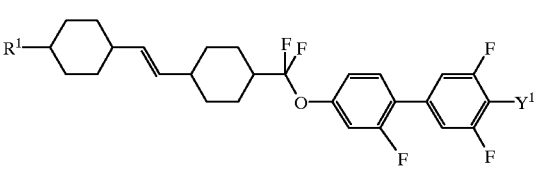
(1-147)
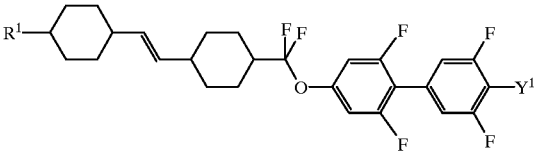
(1-148)
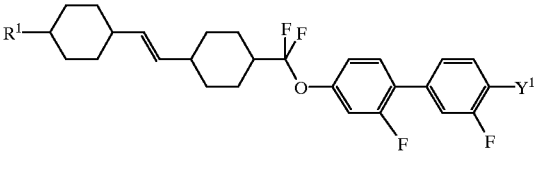
(1-149)
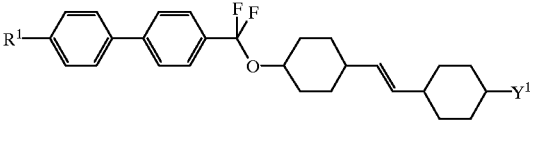
(1-150)
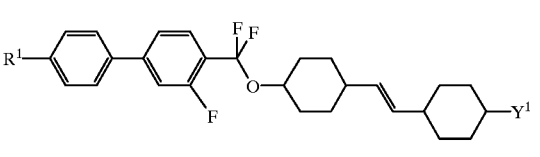
(1-151)
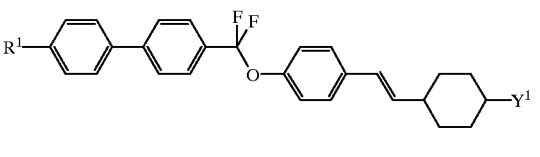

(1-152)
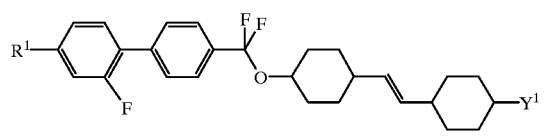
(1-153)
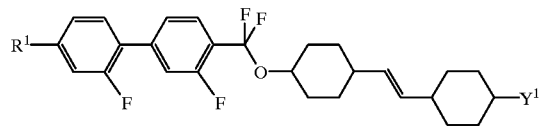
(1-154)
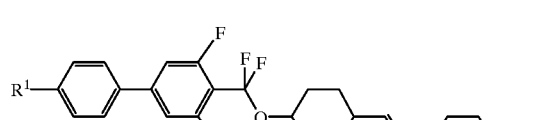
(1-155)
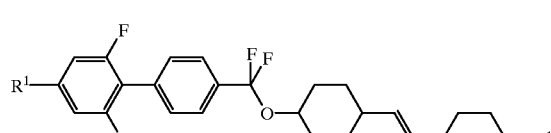
(1-156)
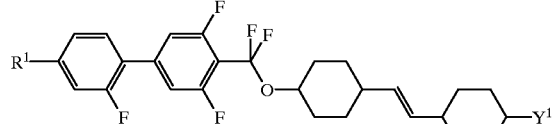
(1-157)
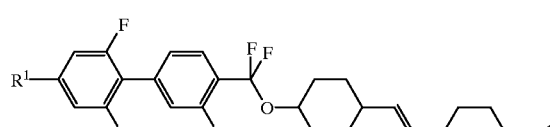
(1-158)
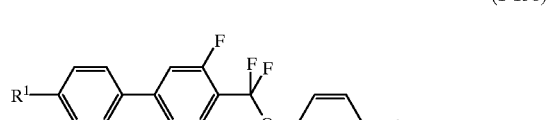
(1-159)
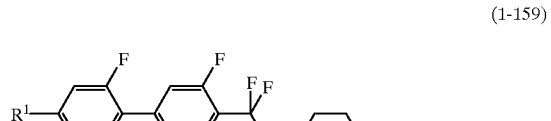
(1-160)
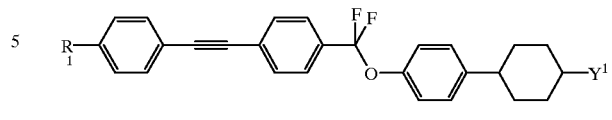
(1-161)
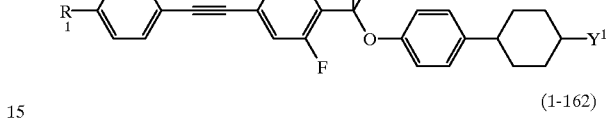
(1-162)
(1-163)
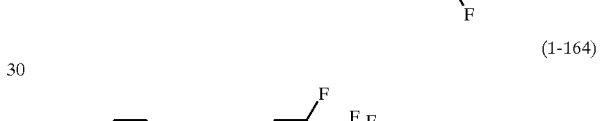
(1-164)
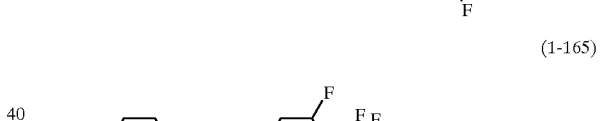
(1-165)
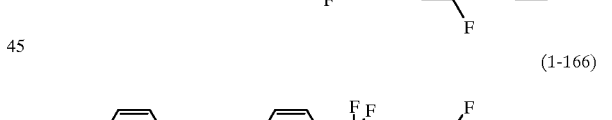
(1-166)
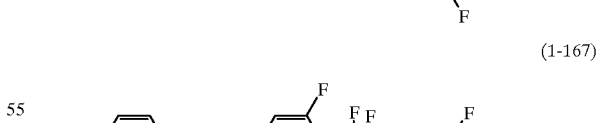
(1-167)
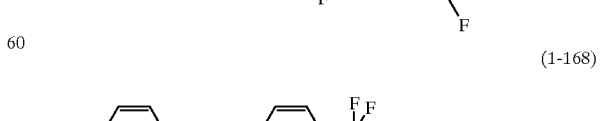
(1-168)
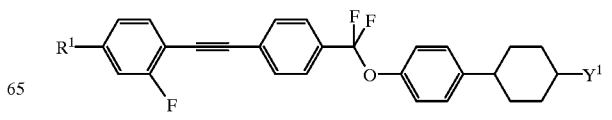

(1-169)
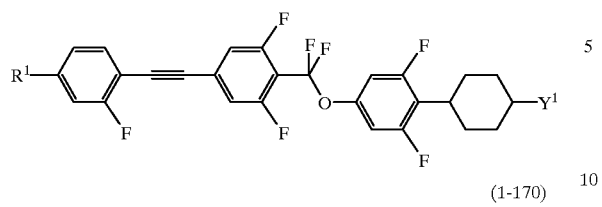
(1-170)
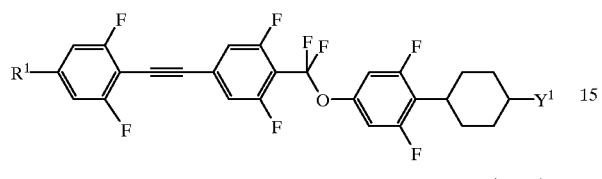
(1-171)
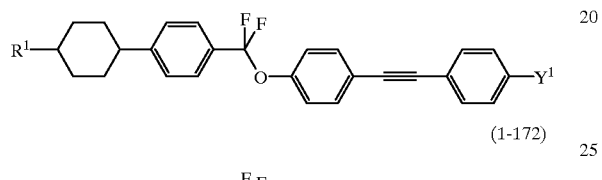
(1-172)
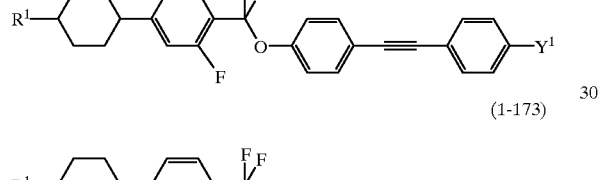
(1-173)
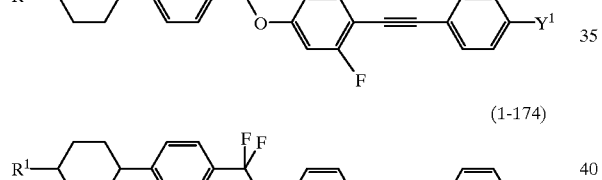
(1-174)
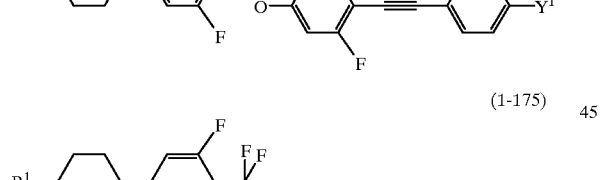
(1-175)
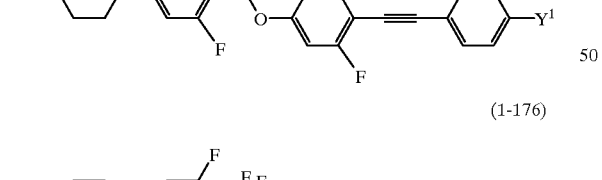
(1-176)
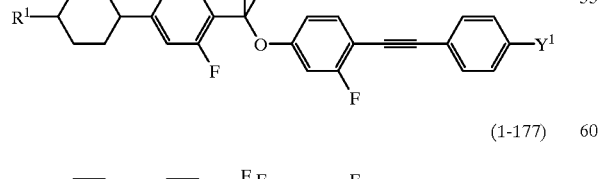
(1-177)
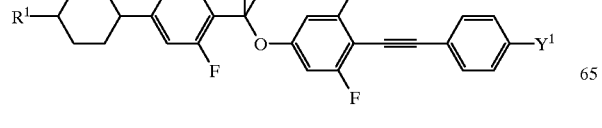
(1-178)
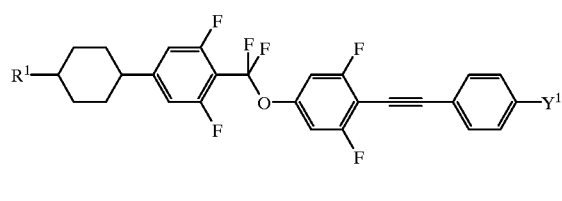
(1-179)
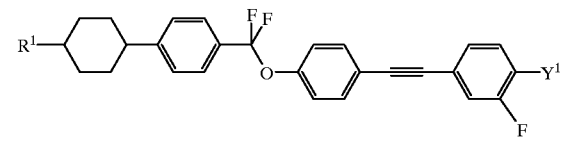
(1-180)
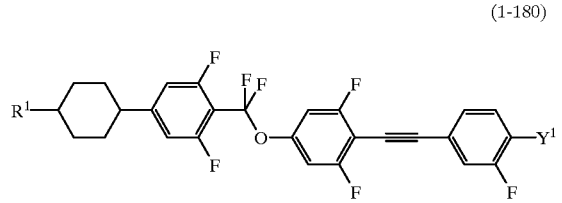
(1-181)
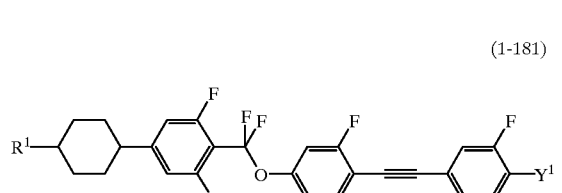
(1-182)
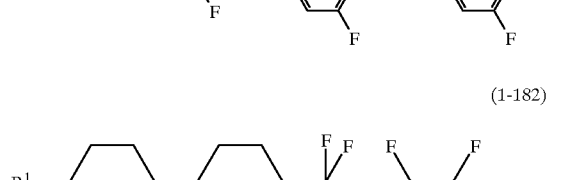
(1-183)
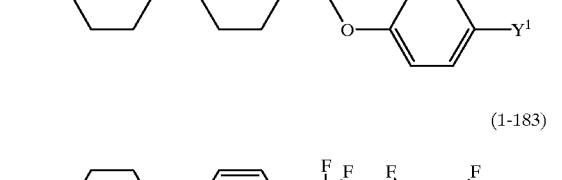
(1-184)
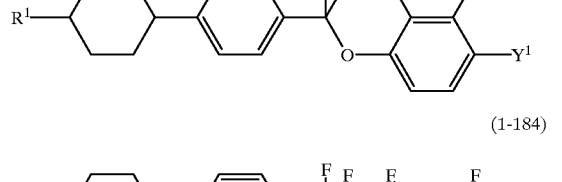
(1-185)
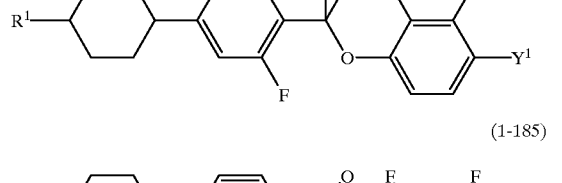

(1-186)
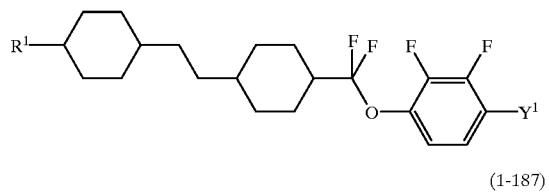
(1-187)
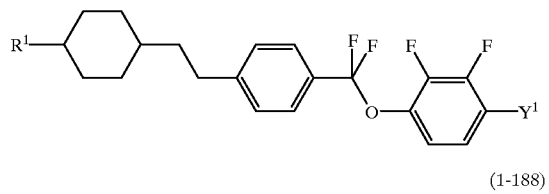
(1-188)
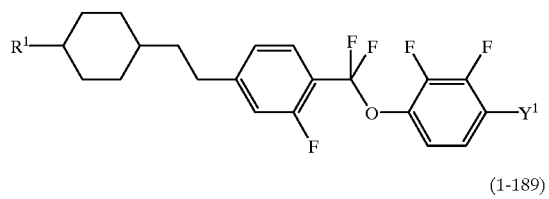
(1-189)
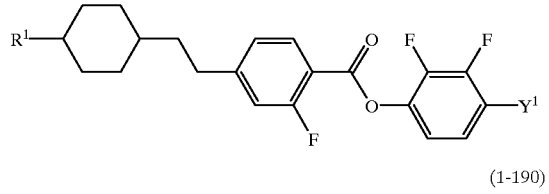
(1-190)
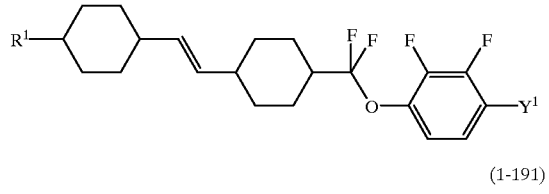
(1-191)
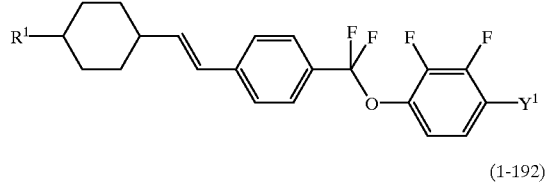
(1-192)
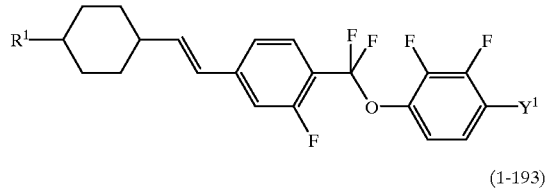
(1-193)
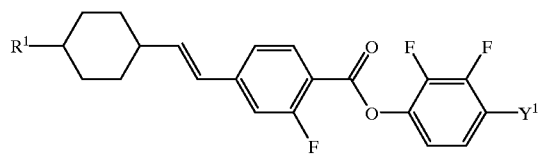
(1-194)
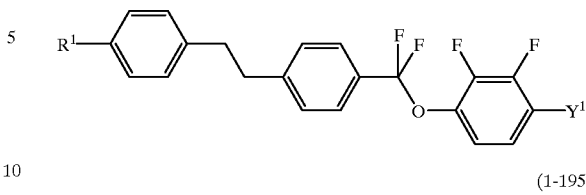
(1-195)
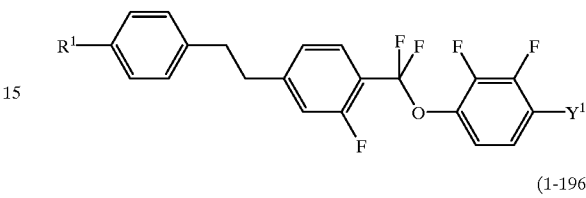
(1-196)
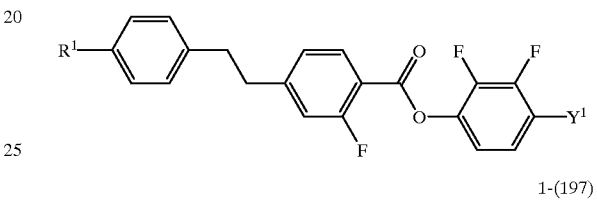
1-(197)
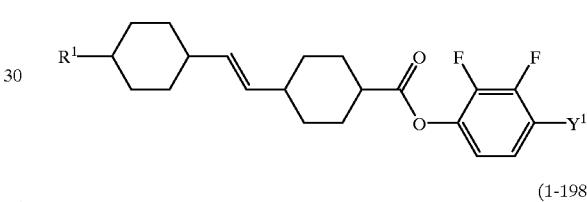
(1-198)
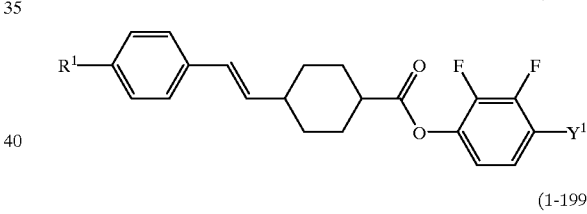
(1-199)
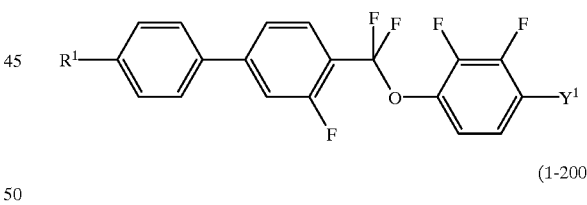
(1-200)
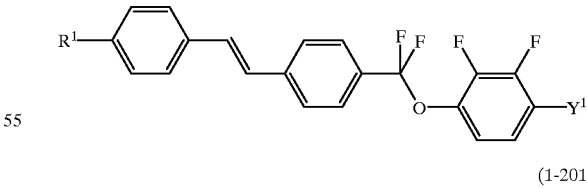
(1-201)
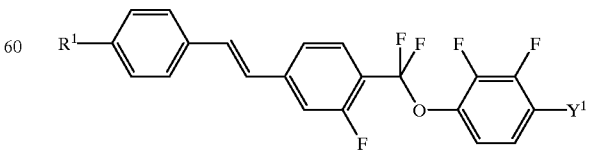

(1-202)
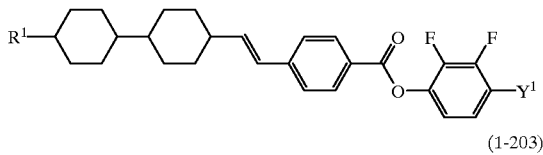
(1-203)
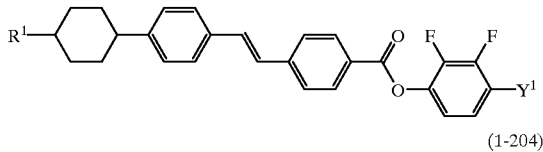
(1-204)
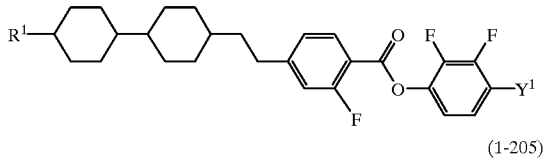
(1-205)
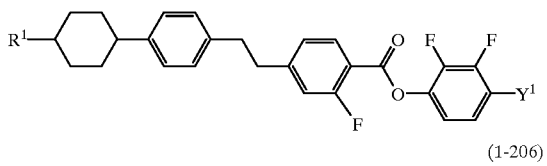
(1-206)
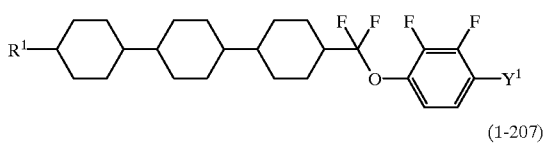
(1-207)
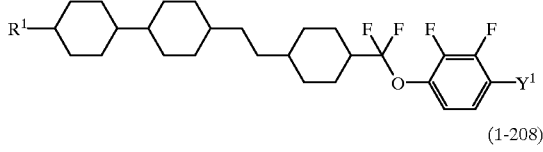
(1-208)
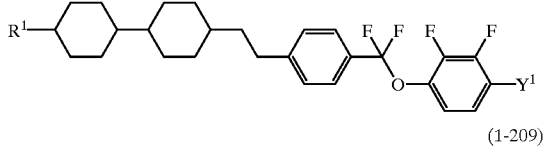
(1-209)
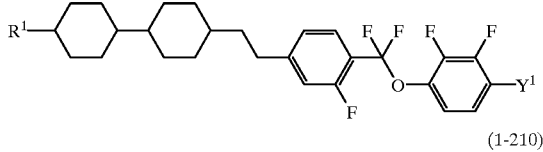
(1-210)
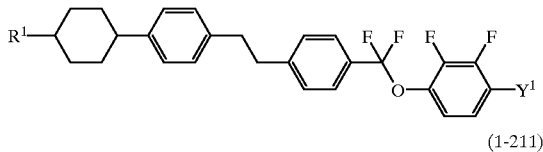

(1-212)
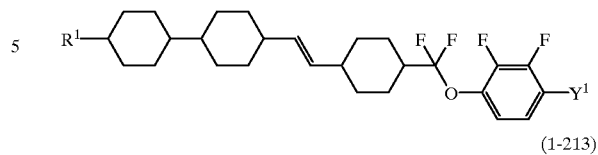
(1-213)
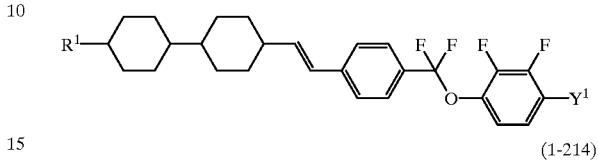
(1-214)
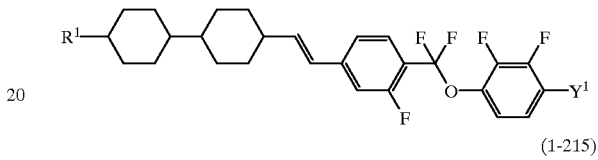
(1-215)
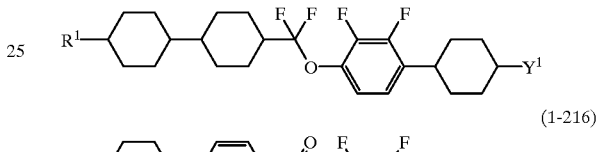
(1-216)
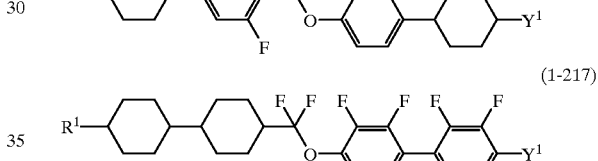
(1-217)

wherein $R^1$ and $Y^1$ have the same meaning as described above.

Any compounds expressed by one of the general formulas (1-1) to (1-11), (1-21) to (1-64), and (1-81) to (1-181) are low in viscosity and exhibit a medium extent of dielectric anisotropy. Among them, two rings or three rings compounds expressed by one of the general formulas (1-1) to (1-11) and (1-21) to (1-42) can remarkably lower only viscosity of liquid crystal compositions without lowering clearing point when added to the compositions as their component since the compounds are particularly low in viscosity and excellent in miscibility at low temperatures. Four rings compounds expressed by one of the general formulas (1-43) to (1-64) and (1-81) to (1-181) can raise only clearing point without raising viscosity when added to liquid crystal compositions as their component since the compounds have a wide temperature range of nematic phase and are low in viscosity.

Compounds expressed by one of the general formulas (1-97) to (1-136) and (1-160) to (1-181) have a characteristic that their optical anisotropy is high, in addition to the characteristic of the four rings compounds described above. Among them, tolan derivatives expressed by one of the general formulas (1-160) to (1-181) are low in viscosity and have an extremely high optical anisotropy, and thus they exhibit excellent characteristics as liquid crystal materials for STN.

Any compounds expressed by one of the general formulas (1-12) to (1-20), (1-65) to (1-70), and (1-182) to (1-217) can increase only dielectric anisotropy in negative numeral without raising viscosity of liquid crystal compositions when added to the compositions as their component since the compounds are extremely low in viscosity and exhibit such a characteristics that they have a high negative dielectric anisotropy, and thus the compounds can provide liquid crystal compositions which achieve both low voltage driving and high speed response in the display devices of IPS driving or such a vertical orientation mode as disclosed in Laid-open Japanese Patent Publication No. Hei 2-176625.

Further, any derivatives expressed by one of the general formulas (1-1) to (1-217) wherein one or more of $R^1$ and $Y^1$ are an alkenyl group exhibit an extremely large elastic constant ratio K33/K11. The derivatives are low in viscosity and exhibit a high clearing point compared with saturated compounds having the same skeleton. As described above, the compounds of the present invention have excellent characteristics, and thus liquid crystal compositions and liquid crystal display devices having improved characteristics can be provided by using the compounds.

Liquid crystal compositions of the present invention are described in more detail below. Liquid crystal compositions of the present invention preferably comprise at least one compound expressed by the general formula (1) in the ratio of 0.1 to 99.9% by weight to develop excellent characteristics.

More specifically, liquid crystal compositions provided according to the present invention are accomplished by mixing a compound optionally selected from the group of compounds expressed by one of the general formulas (2) to (4) depending on the purposes of liquid crystal compositions in addition to a first component comprising at least one compound expressed by the general formula (1).

As the compound expressed by one of the general formulas (2) to (4), the following compounds can preferably be mentioned:

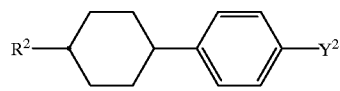
(2-1)

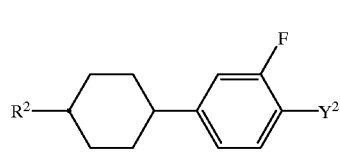
(2-2)

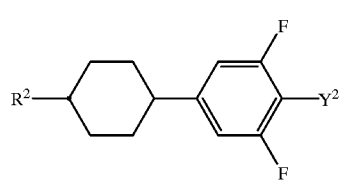
(2-3)

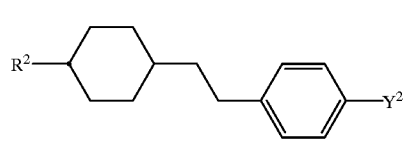
(2-4)

-continued

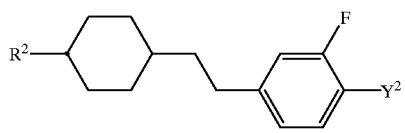
(2-5)

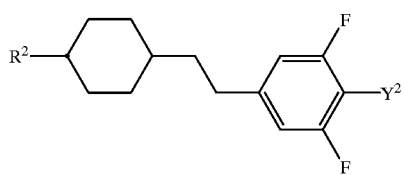
(2-6)

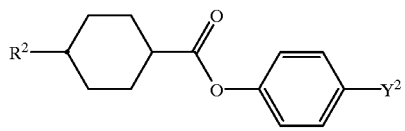
(2-7)

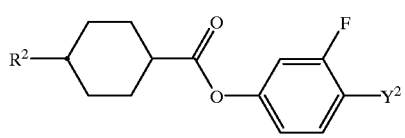
(2-8)

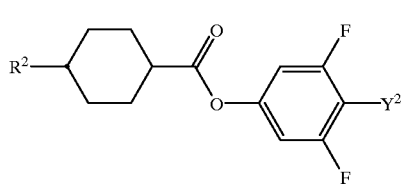
(2-9)

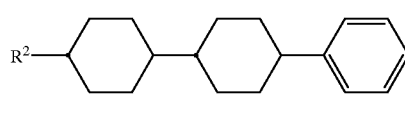
(3-1)

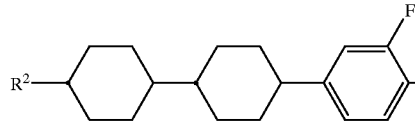
(3-2)

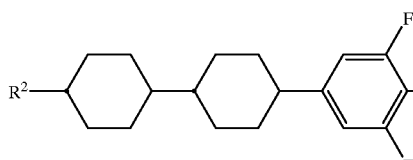
(3-3)

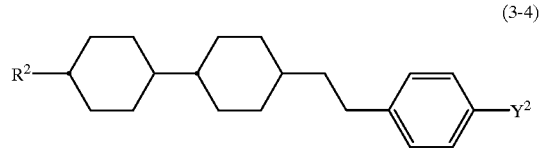
(3-4)

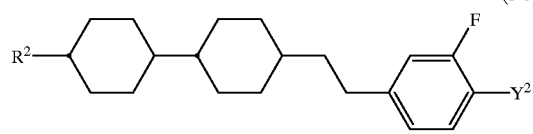
(3-5)

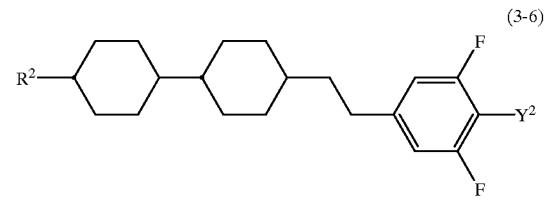
(3-6)
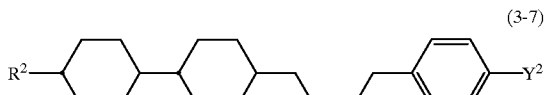
(3-7)
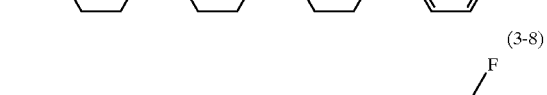
(3-8)
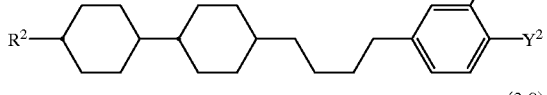
(3-9)
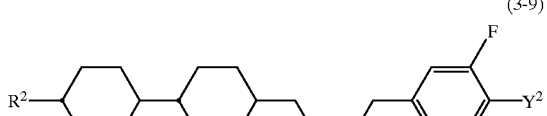
(3-10)
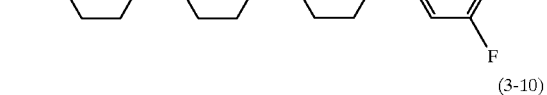
(3-11)
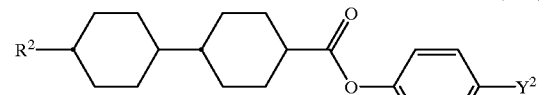
(3-12)
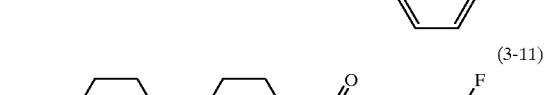
(3-13)
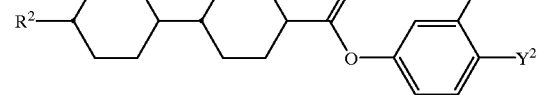
(3-14)
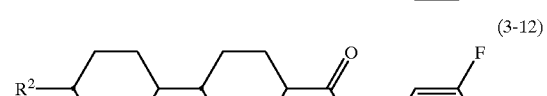
(3-15)
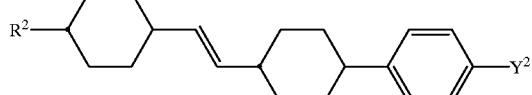
(3-16)
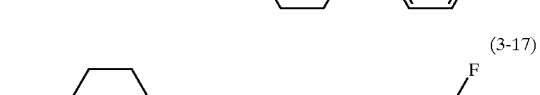
(3-17)
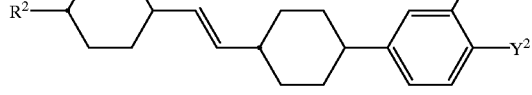
(3-18)
(3-19)
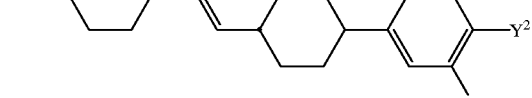
(3-20)
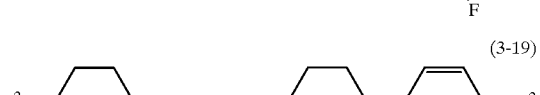
(3-21)
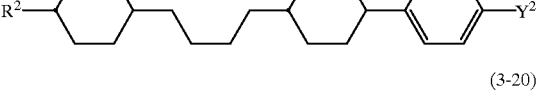
(3-22)
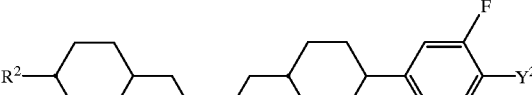
(3-23)
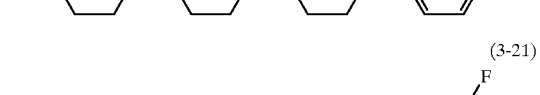
(3-24)
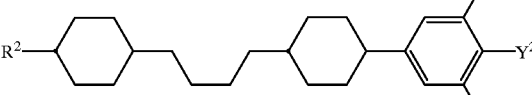
(3-25)

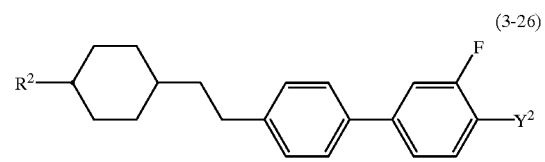
(3-26)
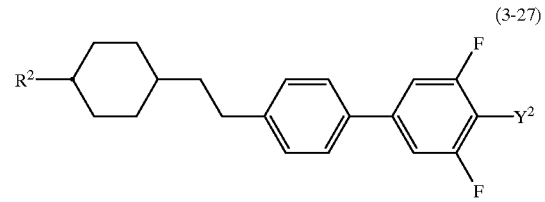
(3-27)
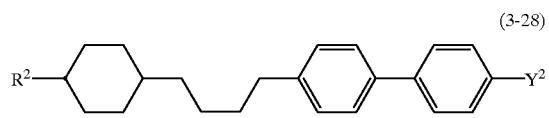
(3-28)
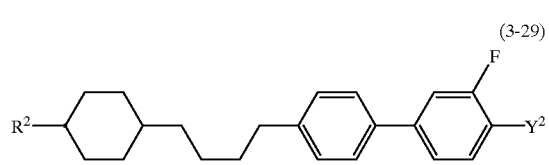
(3-29)
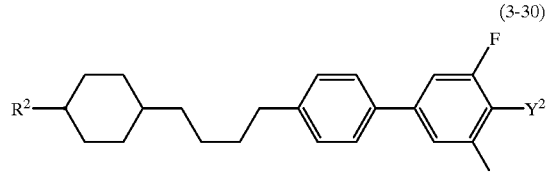
(3-30)
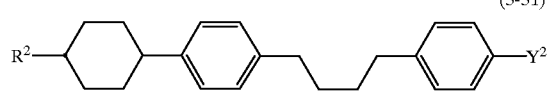
(3-31)
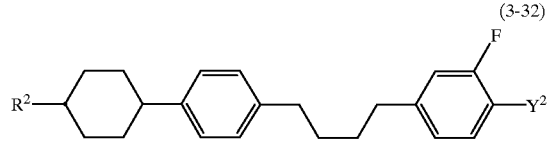
(3-32)
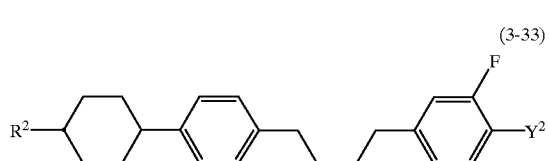
(3-33)
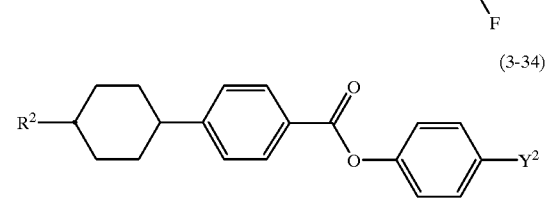
(3-34)
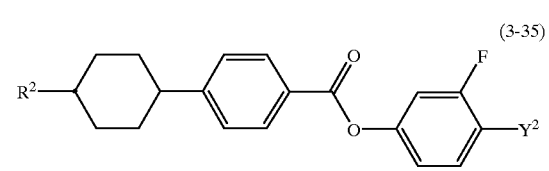
(3-35)
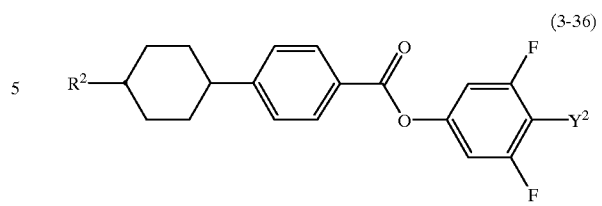
(3-36)
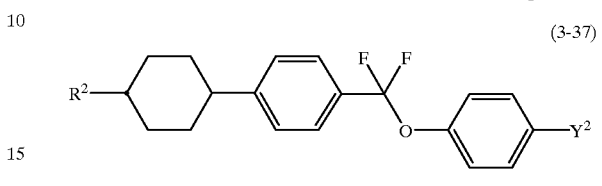
(3-37)
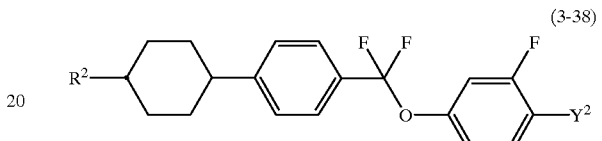
(3-38)
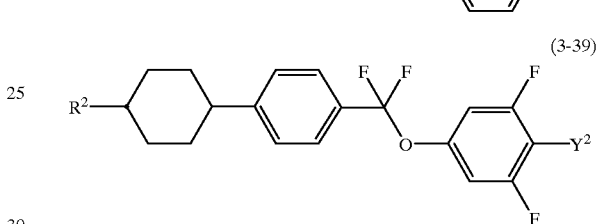
(3-39)
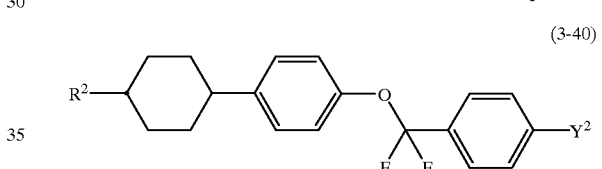
(3-40)
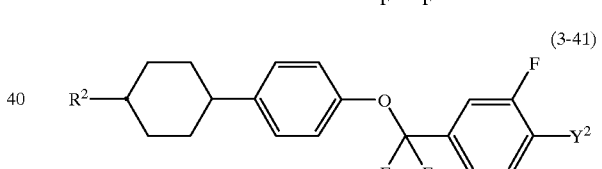
(3-41)
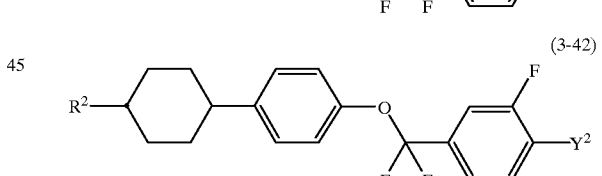
(3-42)
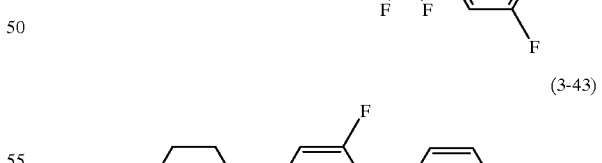
(3-43)
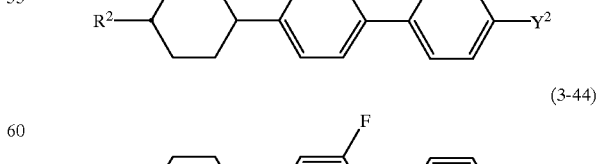
(3-44)

(3-45) 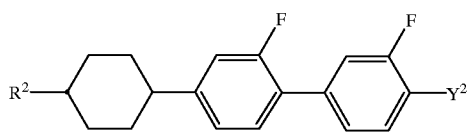
(3-46) 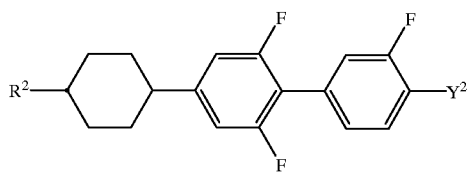
(3-47) 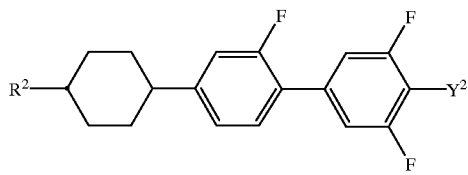
(3-48) 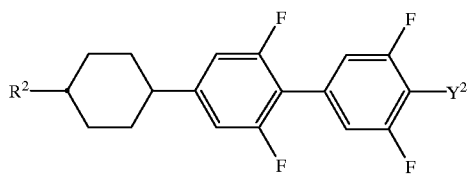
(3-49) 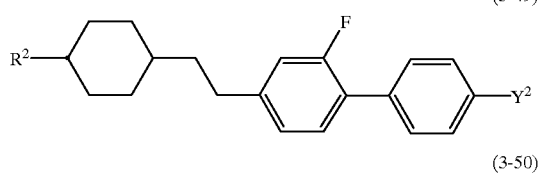
(3-50) 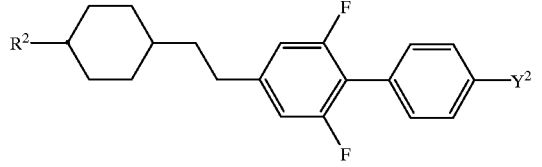
(3-51) 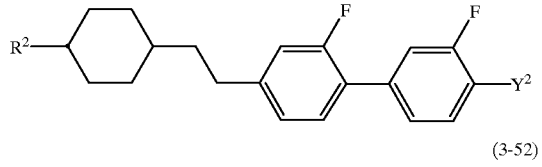
(3-52) 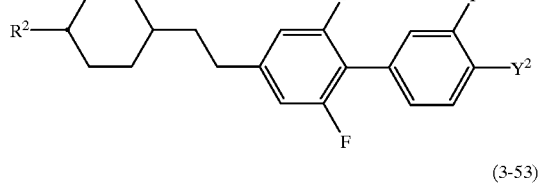
(3-53) 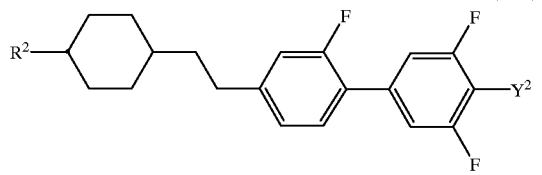
(3-54) 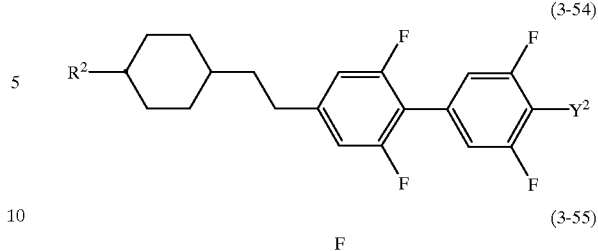
(3-55) 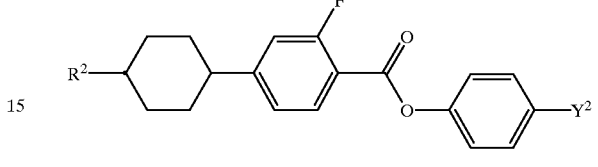
(3-56) 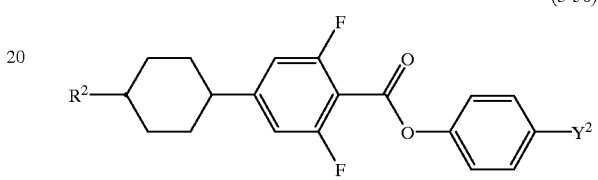
(3-57) 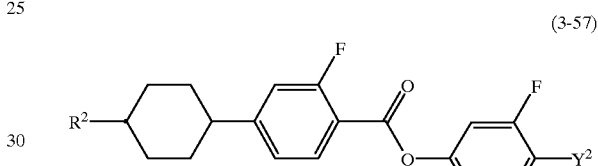
(3-58) 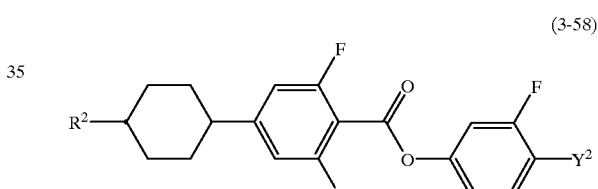
(3-59) 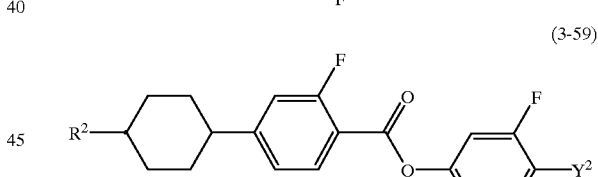
(3-60) 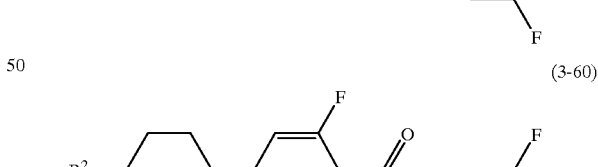
(3-61) 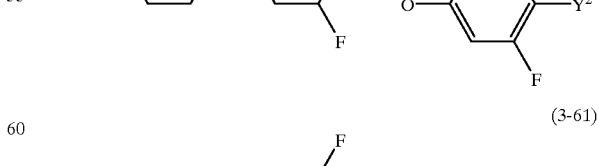
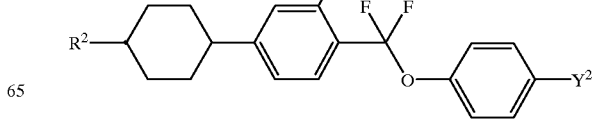

(3-62) 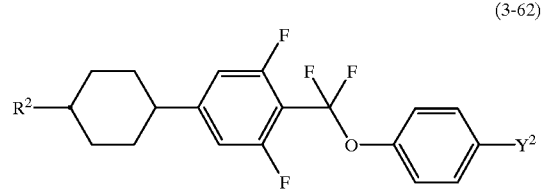
(3-63) 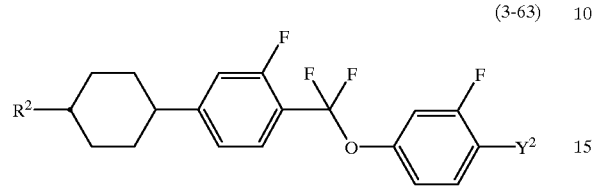
(3-64) 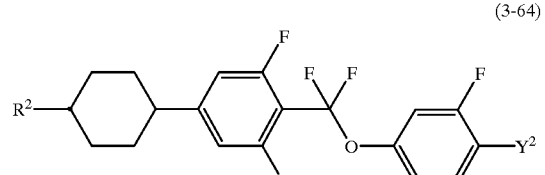
(3-65) 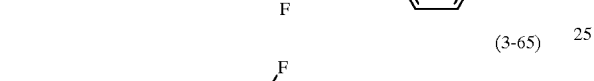
(3-66) 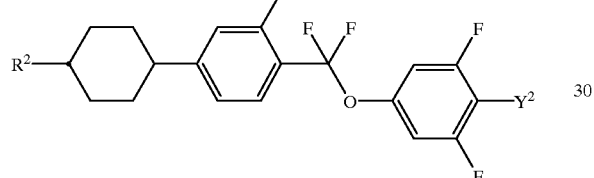
(3-67) 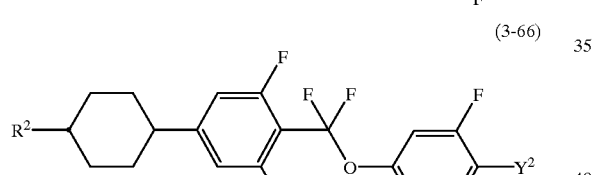
(3-68) 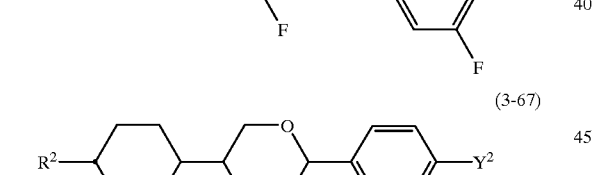
(3-69) 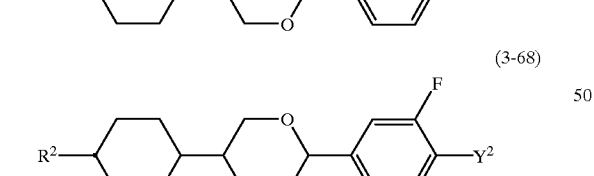
(4-1) 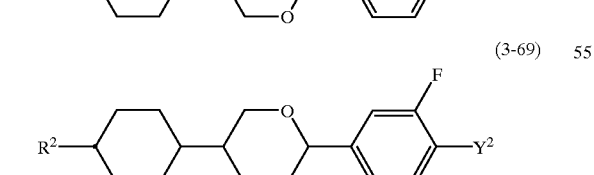
(4-2) 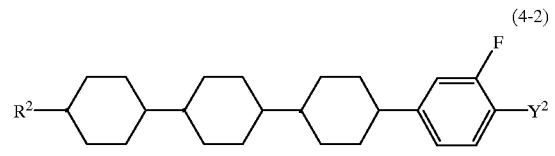
(4-3) 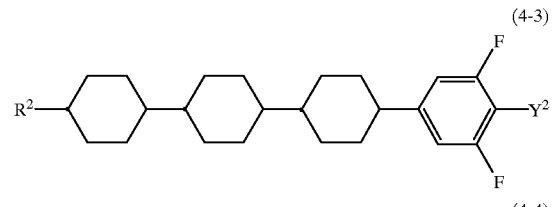
(4-4) 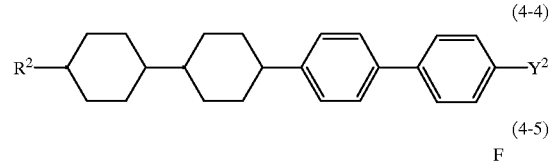
(4-5) 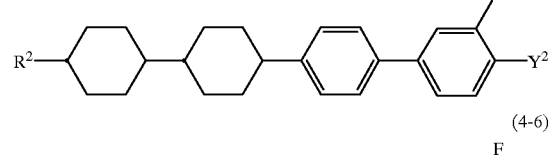
(4-6) 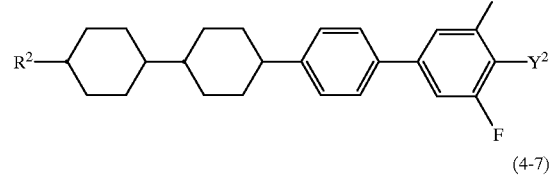
(4-7) 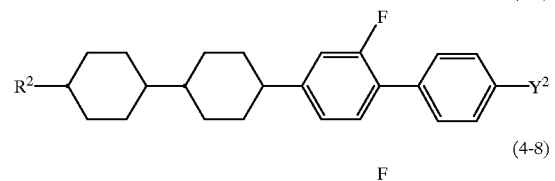
(4-8) 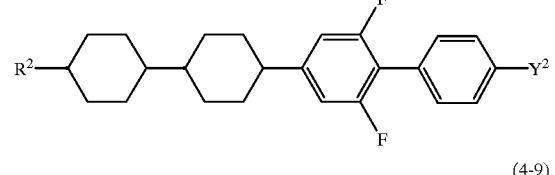
(4-9) 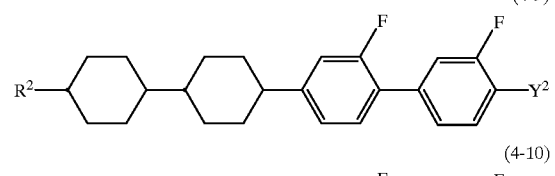
(4-10) 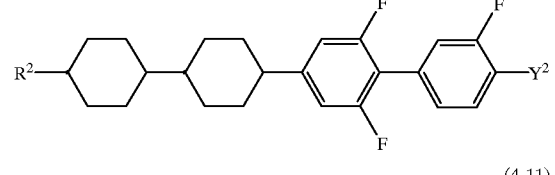
(4-11) 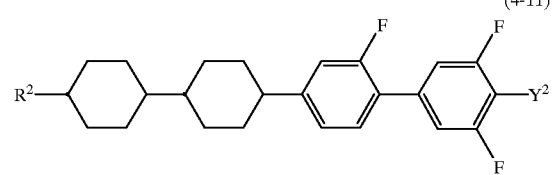

-continued (4-12)
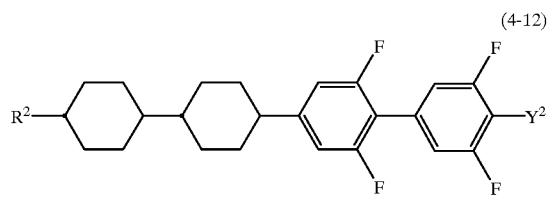

(4-13)
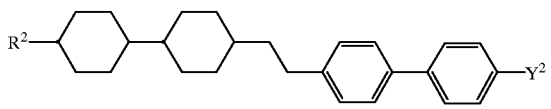

(4-14)
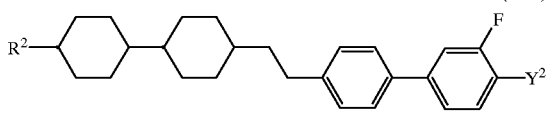

(4-15)
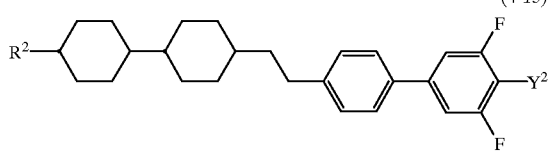

(4-16)
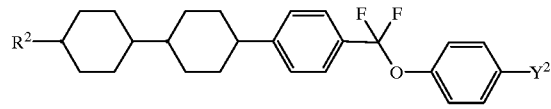

(4-17)
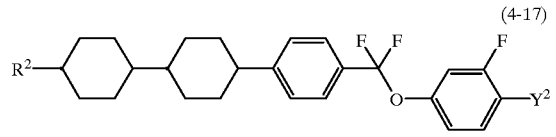

(4-18)
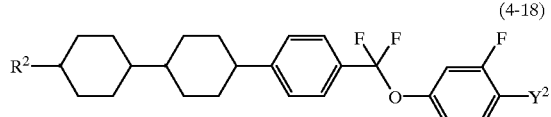

(4-19)
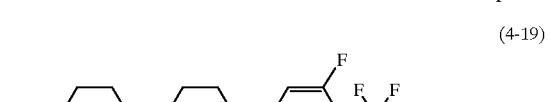

(4-20)

(4-21)
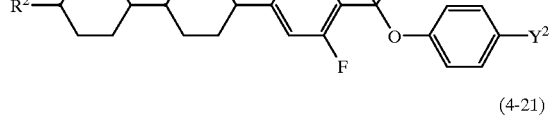

-continued (4-22)
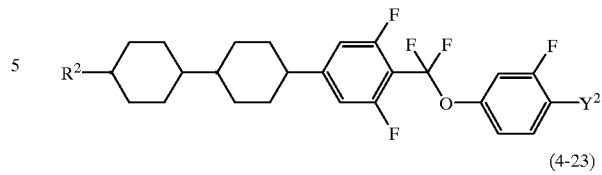

(4-23)
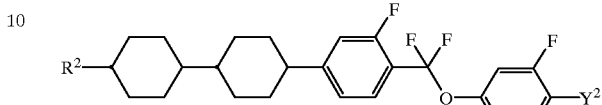

(4-24)

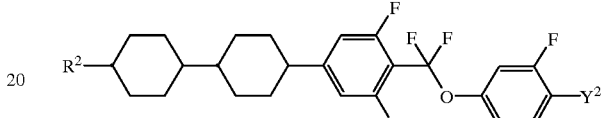

wherein $R^2$ and $Y^2$ have the same meaning as described above.

Compounds expressed by one of the general formulas (2) to (4) have a positive dielectric anisotropy value and are remarkably excellent in thermal stability and chemical stability, and thus the compounds are particularly useful when liquid crystal compositions for TFT display mode, of which a high reliability represented by a high voltage holding ratio and a large resistivity is required, are produced.

When liquid crystal compositions for TFT display mode are produced, while a compound expressed by one of the general formulas (2) to (4) can optionally be used in the range of 0.1 to 99.9% by weight based on the total amount of liquid crystal composition in addition to a first component comprising at least one compound expressed by the general formula (1), the amount of the compound of the general formula (2) to (4) is preferably 10 to 97% by weight and more desirably 40 to 95% by weight.

Also, when liquid crystal compositions for STN display mode or TN display mode are produced, a compound expressed by one of the general formulas (2) to (4) can be used in addition to the first component comprising at least one compound expressed by the general formula (1), but the amount of the compound of the general formula (2) to (4) is preferably less than 50% by weight in this case.

To the liquid crystal compositions thus obtained comprising a compound expressed by the general formula (1) and a compound expressed by one of the general formulas (2) to (4), the compound selected from a group of the compounds expressed by one of the general formulas (5) to (12) may further be added for the. purpose of adjusting viscosity of the liquid crystal compositions.

As the compound expressed by the general formula (5) or (6), the following compounds can preferably be mentioned:

(5-1)
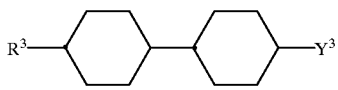

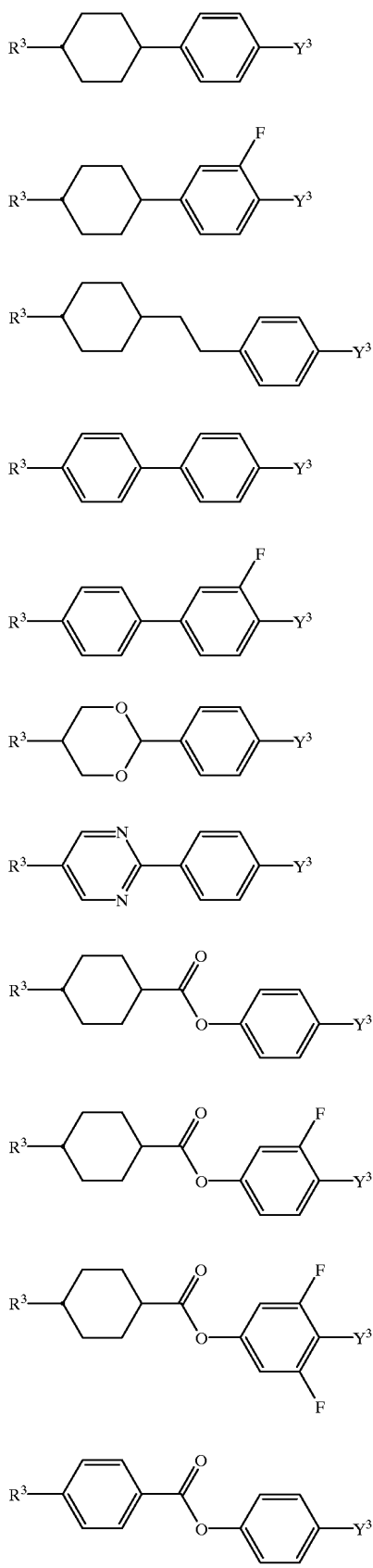

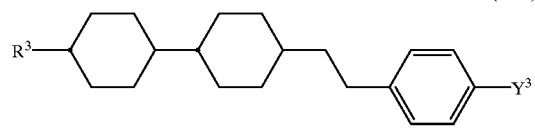 (5-23)
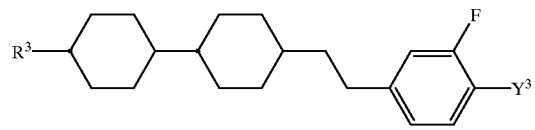 (5-24)
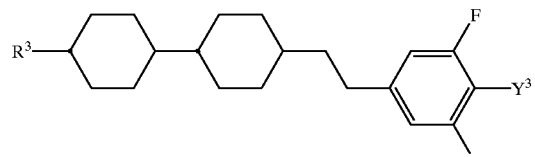 (5-25)
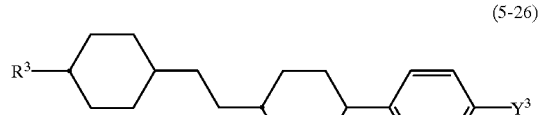 (5-26)
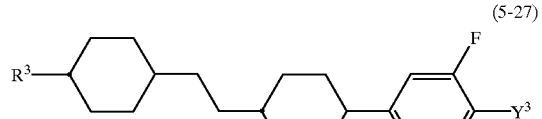 (5-27)
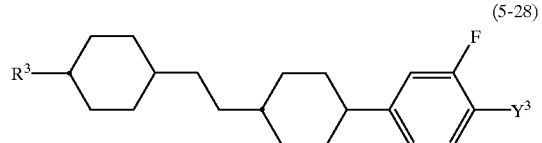 (5-28)
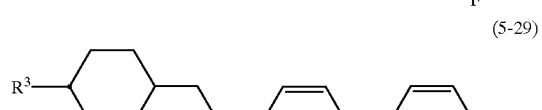 (5-29)
 (5-30)
 (5-31)
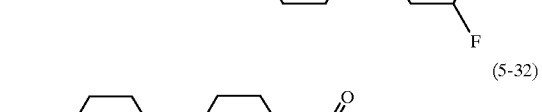 (5-32)
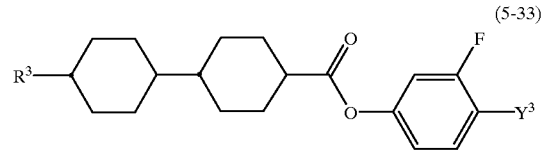 (5-33)
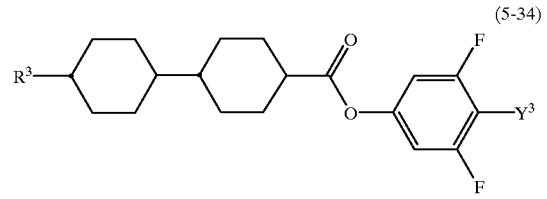 (5-34)
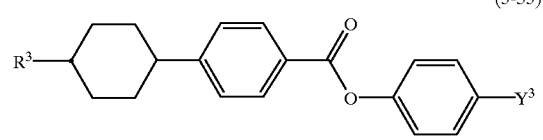 (5-35)
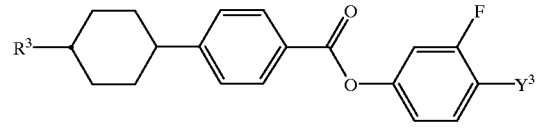 (5-36)
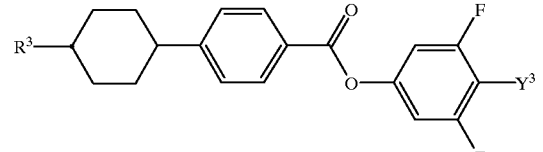 (5-37)
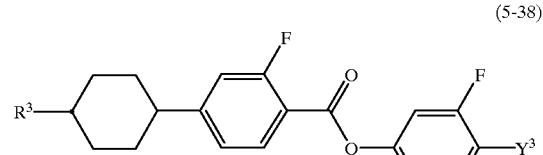 (5-38)
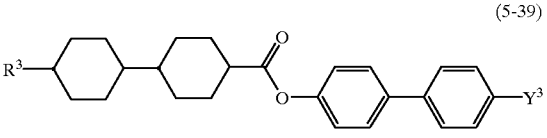 (5-39)
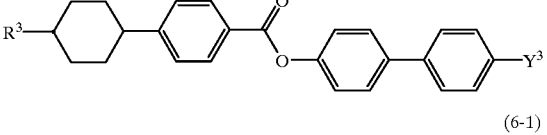 (5-40)
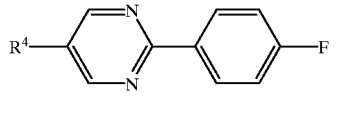 (6-1)
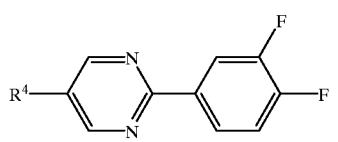 (6-2)

(6-3)

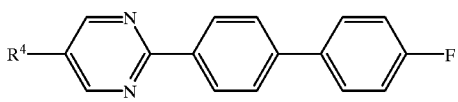

wherein $R^3$, $R^4$, and $Y^3$ have the same meaning as described above.

Compounds expressed by the general formula (5) or (6) have a large positive dielectric anisotropy value and thus are used particularly for the purpose of lowering threshold voltage of liquid crystal compositions. They are used also for the purpose of adjusting optical anisotropy value and widening the temperature range of nematic phase such as raising clearing point. Further, the compounds are used for the purpose of improving the steepness of voltage-transmittance curve of liquid crystal compositions for STN display mode or TN display mode.

When the amount of the compound expressed by the general formula (5) or (6) is increased, threshold voltage of liquid crystal compositions lowers and viscosity increases. Accordingly, it is advantageous to use the compound in a large quantity so far as the viscosity of liquid crystal compositions satisfies required characteristics, since the compositions can be driven at a low voltage. While the compound expressed by the general formula (5) or (6) can be used in any amount in the range of 0.1 to 99.9% by weight when liquid crystal compositions for STN display mode or TN display mode are produced, the amount is preferably 10 to 97% by weight and more desirably 40 to 95% by weight.

As the compound used in the present invention and expressed by one of the general formula (7) to (9), the following compounds can preferably be mentioned:

(7-1)

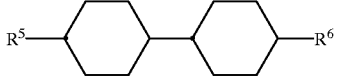

(7-2)

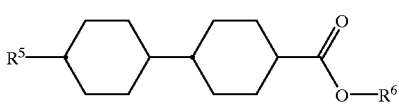

(7-3)

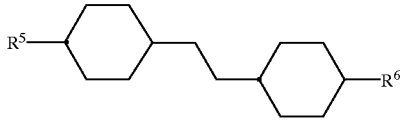

(7-4)

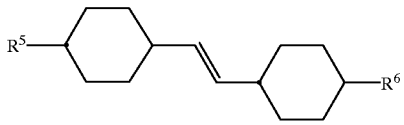

(7-5)

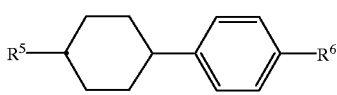

(7-6)

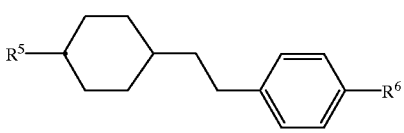

(7-7)

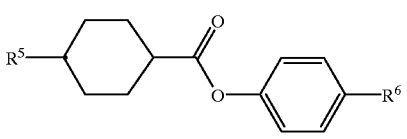

(7-8)

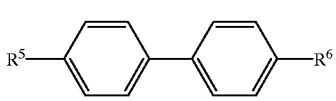

(7-9)

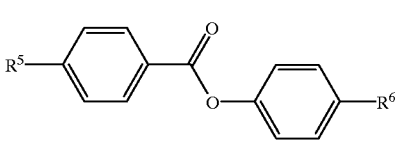

(7-10)

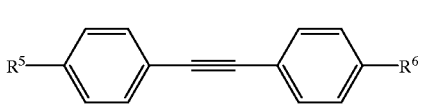

(7-11)

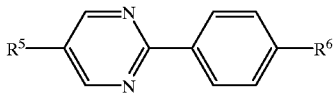

(8-1)

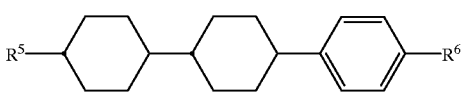

(8-2)

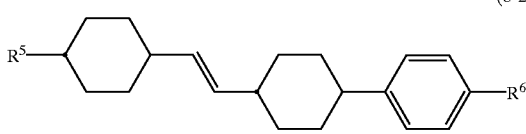

(8-3)

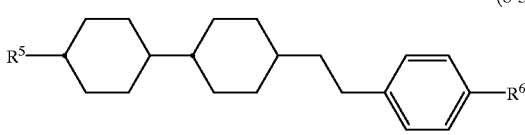

(8-4)

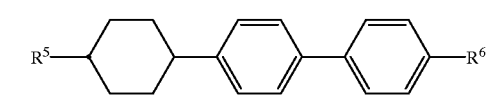

(8-5)

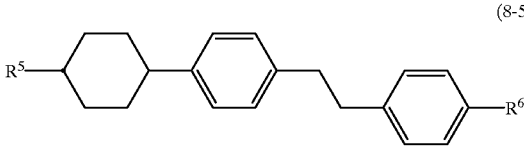

(8-6)

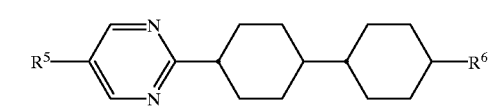

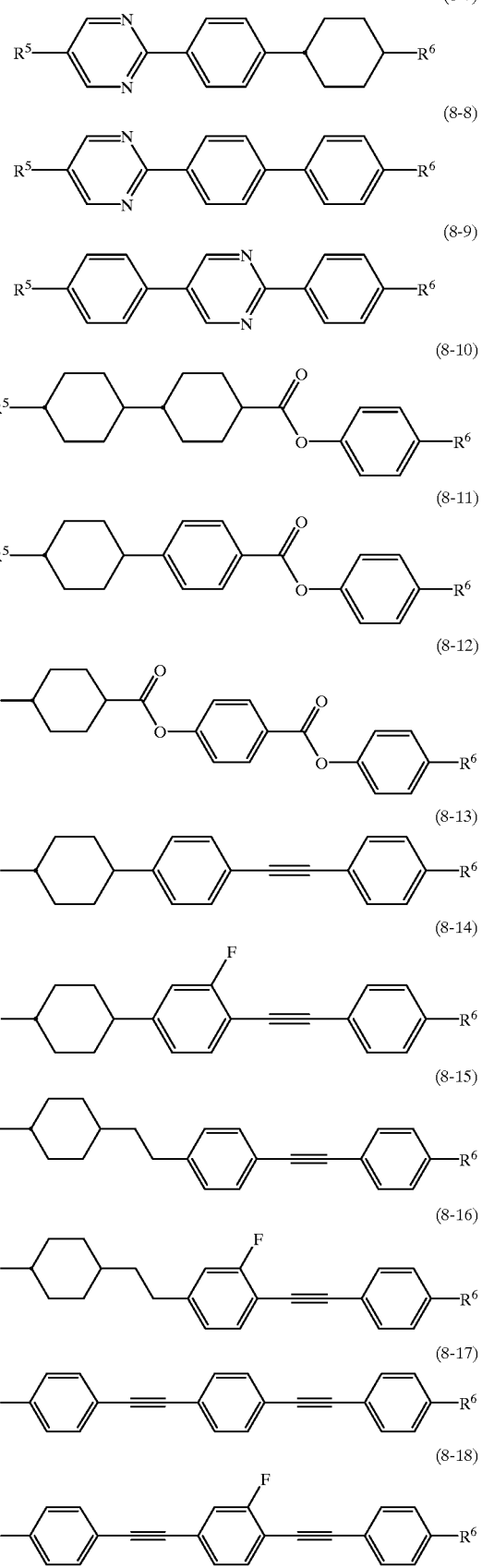
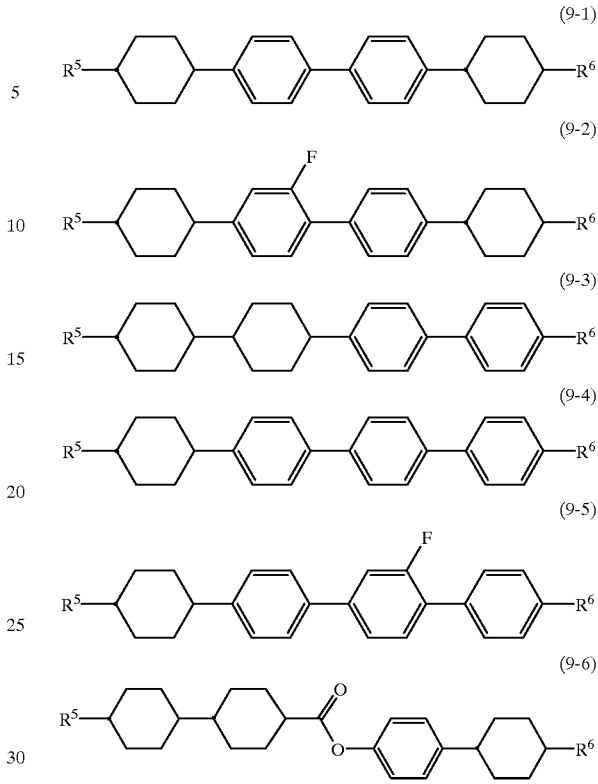

wherein $R^5$ and $R^6$ have the same meaning as described above.

Compounds expressed by one of the general formulas (7) to (9) are small in absolute value of dielectric anisotropy and are close to neutral. Compounds expressed by the general formula (7) are used principally for the purpose of adjusting viscosity and adjusting optical anisotropy value of liquid crystal compositions. Compounds expressed by the general formula (8) or (9) are used for the purpose of widening the temperature range of nematic phase such as raising clearing point of liquid crystal compositions or for the purpose of adjusting the optical anisotropy value.

When the amount of the compound expressed by one of the general formulas (7) to (9) to be used is increased, threshold voltage of liquid crystal compositions rises and their viscosity lowers. Accordingly, it is desirable to use a large quantity of the compound so far as the threshold voltage of liquid crystal compositions is satisfied. Amount of the compound expressed by 0 one of the general formulas (7) to (9) to be used is 40% by weight or less and more desirably less than 35% by weight when liquid crystal compositions for TFT display mode are produced. Further, the amount is 70% by weight or less and more desirably less than 60% by weight when liquid crystal compositions for STN display mode or TN display mode are produced.

As the compounds used in the present invention and expressed by one of the general formulas (10) to (12), the following compounds can preferably be mentioned:

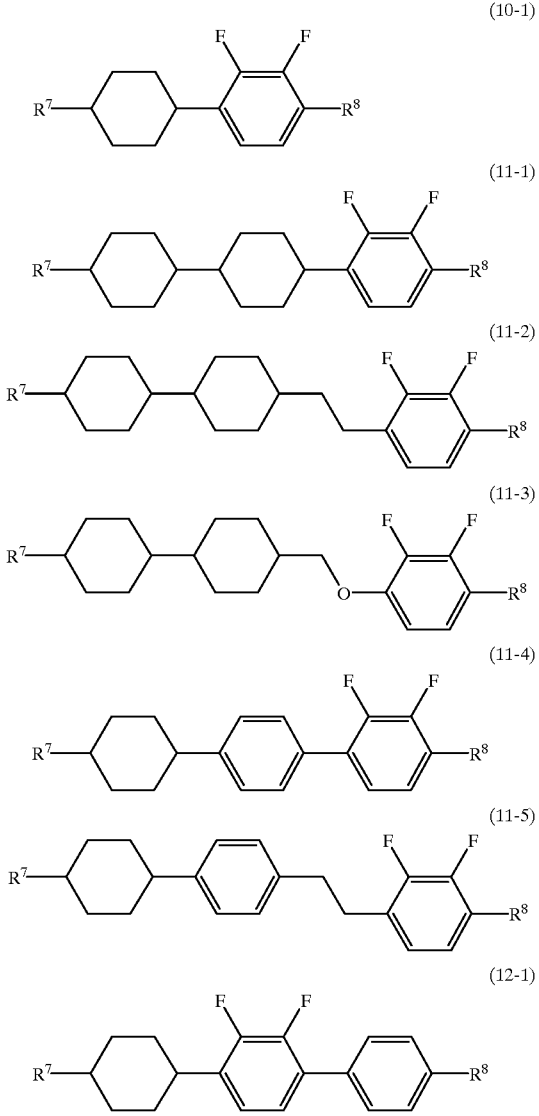

(10-1)
(11-1)
(11-2)
(11-3)
(11-4)
(11-5)
(12-1)

wherein $R^7$ and $R^8$ have the same meaning as described above.

Compounds expressed by one of the general formulas (10) to (12) have a negative dielectric anisotropy value. Accordingly, the compounds can control the elastic constant of liquid crystal compositions, which is a function of dielectric anisotropy value, by mixing with a compound having a positive dielectric anisotropy value, and thereby the steepness of voltage-transmittance curve of liquid crystal compositions can be controlled. Accordingly, the compounds can be used for various driving modes.

Compounds expressed by one of the general formulas (10) to (12) can optionally be used in the range of 0.1 to 99.9% by weight, preferably 10 to 97% by weight, and more desirably 10 to 60% by weight when liquid crystal compositions for TFT display mode, STN display mode, or TN display mode are produced.

Except such specific cases as liquid crystal compositions for OCB (Optically Compensated Birefringence) mode, an optically active compound is sometimes added to liquid crystal compositions generally for the purpose of inducing helical structure of liquid crystals to adjust required twisting angle and to prevent the reverse twist, and the optically active compound can be added in the same way even in the liquid crystal compositions of the present invention. While any known optically active compounds can be used for such purposes, preferable optically active compounds can be mentioned as follows:

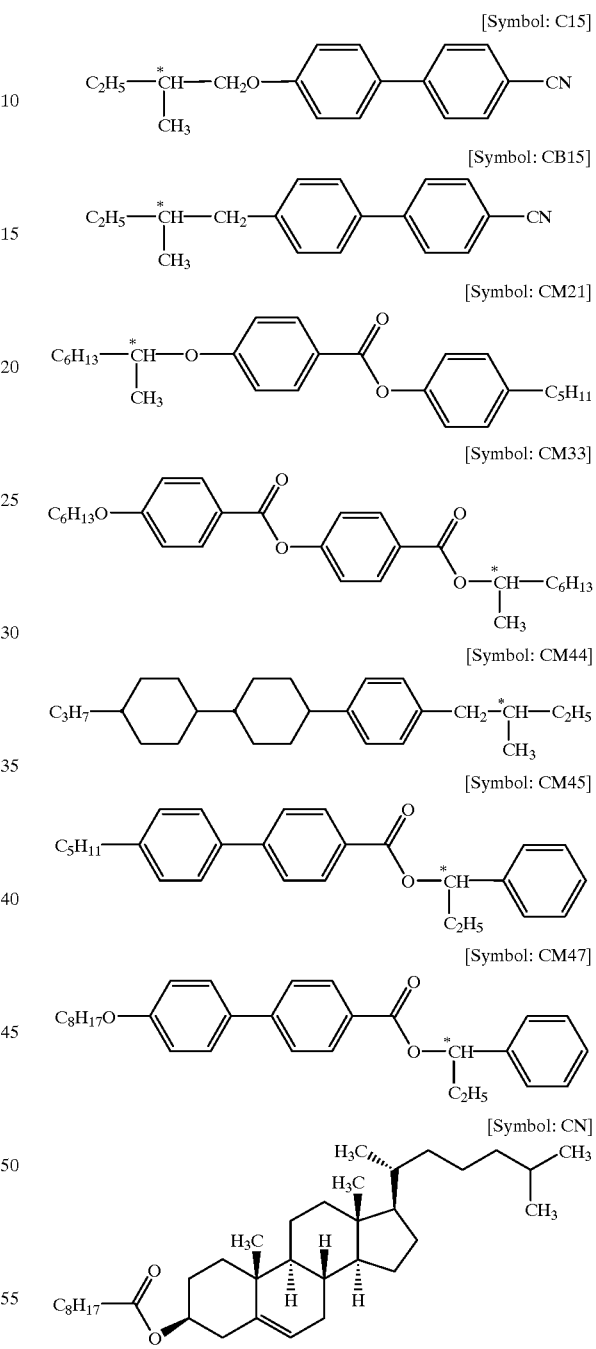

[Symbol: C15]
[Symbol: CB15]
[Symbol: CM21]
[Symbol: CM33]
[Symbol: CM44]
[Symbol: CM45]
[Symbol: CM47]
[Symbol: CN]

Usually, one of these optically active compounds is added to the liquid crystal compositions of the present invention to adjust the pitch of the twist of liquid crystals. The twist pitch is preferably adjusted in the range of 10 to 200 pm in the case of liquid crystal compositions for TFT display mode or TN display mode. In the case of liquid crystal compositions for STN display mode, the pitch is preferably adjusted in the range of 6 to 20 $\mu$m. In the case of bistable TN mode, the pitch is preferably adjusted in the range of 1.5 to 4 $\mu$m.

Further, two or more kind of optically active compounds may be added for the purpose of adjusting the dependency of the pitch on temperature.

Liquid crystal compositions of the present invention can be produced by methods which are known in public by themselves. Generally, a method wherein various components are dissolved in each other at a high temperature is adopted.

Liquid crystal compositions of the present invention can be used as ones for guest-host (GH) mode by adding a dichroic dye such as merocyanine type, styryl type, azo type, azomethine type, azoxy type, quinophthalone type, anthraquinone type, or tetrazine type dye. Liquid crystal compositions of the present invention can also be used as ones for NCAP which is prepared by the microencapsulation of a nematic liquid crystal, or for a polymer dispersed liquid crystal display device (PDLCD) represented by polymer network liquid crystal display device (PNLCD) prepared by forming polymers of three-dimensional reticulated structure in a liquid crystal. In addition, the liquid crystal compositions of the present invention can be used as ones for electrically controlled birefringence (ECB) mode or dynamic scattering (DS) mode.

As nematic liquid crystal compositions comprising the liquid crystalline compound of the present invention, the following composition examples can be mentioned. In the composition examples, compounds are designated by using symbols according to the definitions shown in Table 1 below.

Further, in the case where hydrogen atoms of trans-1,4-cyclohexylene are replaced by deuterium atom at positions $Q^1$, $Q^2$, and $Q^3$, it is designated as symbol H [1D, 2D, 3D]. In the case where the hydrogen atom is replaced at positions $Q^5$, $Q^6$, and $Q^7$, it is designated as symbol H [5D, 6D, 7D]. Thus, the position where deuterium atom substituted is indicated by the number in the parenthesis.

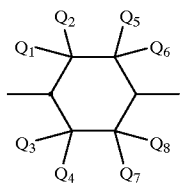

TABLE 1

Method for designating compounds by using symbols
R—(A$_1$)—Z$_1$— ... —Z$_n$—(A$_n$)—X

| 1) Left side terminal group R— | Symbol |
|---|---|
| C$_n$H$_{2n+1}$— | n— |
| C$_n$H$_{2n+1}$O— | nO— |
| C$_n$H$_{2n+1}$OC$_m$H$_{2m}$— | nOm— |
| CH$_2$=CH— | V— |
| CH$_2$=CHC$_n$H$_{2n}$— | Vn— |
| C$_n$H$_{2n+1}$CH=CHC$_m$H$_{2m}$— | nVm— |
| C$_n$H$_{2n+1}$CH=CHC$_m$H$_{2m}$CH=CHC$_k$H$_{2k}$— | nVmVk— |

| 2) Ring structure —(A$_1$)—, —(A$_n$)— | Symbol |
|---|---|
| benzene | B |
| fluorobenzene (F) | B(F) |
| difluorobenzene (2F,3F) | B(2F,3F) |
| difluorobenzene (F,F) | B(F,F) |
| cyclohexane | H |
| pyridine | Py |
| dioxane | D |
| cyclohexene | Ch |

| 3) Bonding group —Z$_1$—, —Z$_n$— | Symbol |
|---|---|
| —C$_2$H$_4$— | 2 |
| —C$_4$H$_8$— | 4 |
| —COO— | E |
| —C≡C— | T |
| —CH=CH— | V |
| —CF$_2$O— | CF2O |
| —OCF$_2$— | OCF2 |

| 4) Right side terminal group —X | Symbol |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —C$_n$H$_{2n+1}$ | —n |
| —OC$_n$H$_{2n+1}$ | —On |
| —COOCH$_3$ | —EMe |
| —C$_n$H$_{2n}$CH=CH$_2$ | —nV |
| —C$_m$H$_{2m}$CH=CHC$_n$H$_{2n+1}$ | —mVn |
| —C$_m$H$_{2m}$CH=CHC$_n$H$_{2n}$F | —mVnF |
| —CH=CF$_2$ | —VFF |
| —C$_n$H$_{2n}$CH=CF$_2$ | —nVFF |
| —C≡C—CN | —TC |

TABLE 1-continued

Method for designating compounds by using symbols
R—(A$_1$)—Z$_1$— . . . —Z$_n$—(A$_n$)—X 5) Example of designation Example 1    3-H2B(F,F)B(F)—F

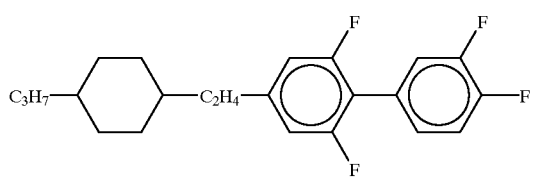

Example 2    3-HB(F)TB-2

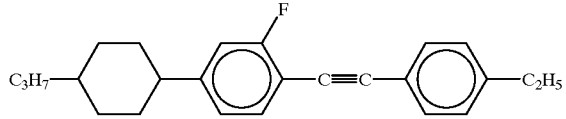

Example 3    1V2—BEB(F,F)—C

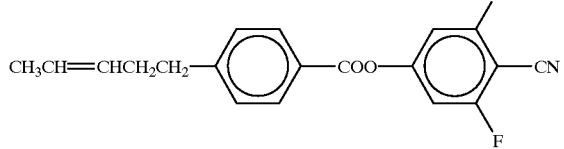

COMPOSITION EXAMPLE 1

| | |
|---|---|
| 3-H2B(F)EB(2F,3F)—O2 | 15.0% |
| 1V2-BEB(F,F)—C | 5.0% |
| 3-HB—C | 25.0% |
| 2-BTB-1 | 11.0% |
| 3-HH-4 | 10.0% |
| 3-HHB-1 | 10.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |
| CM33 | 0.8 part |

COMPOSITION EXAMPLE 2

| | |
|---|---|
| 5-HVHEB(2F,3F)—O2 | 7.0% |
| V2-HB—C | 12.0% |
| 1V2-HB—C | 12.0% |
| 3-HB—C | 15.0% |
| 3-H [1D,2D,3D]—C | 9.0% |
| 3-HB(F)—C | 5.0% |
| 2-BTB-1 | 2.0% |
| 3-HH-4 | 6.0% |
| 3-HH—VFF | 6.0% |
| 2-H [1D,2D,3D] HB—C | 3.0% |
| 3-HHB—C | 3.0% |
| 3-HB(F)TB-2 | 6.0% |
| 3-H2BTB-2 | 5.0% |
| 3-H2BTB-3 | 5.0% |
| 3-H2BTB-4 | 4.0% |

COMPOSITION EXAMPLE 3

| | |
|---|---|
| 3-H2B(F)EB(2F,3F)—O2 | 10.0% |
| 2O1-BEB(F)—C | 5.0% |
| 3O1-BEB(F)—C | 15.0% |
| 4O1-BEB(F)—C | 13.0% |
| 5O1-BEB(F)—C | 11.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HB(F)TB-4 | 4.0% |
| 3-HHB—O1 | 4.0% |

COMPOSITION EXAMPLE 4

| | |
|---|---|
| 3-H2B(F)EB(2F,3F)—O2 | 6.0% |
| 5-HVHEB(2F,3F)—O2 | 6.0% |
| 5-PyB—F | 4.0% |
| 3-PyB(F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 3-PyBB—F | 6.0% |
| 4-PyBB—F | 6.0% |
| 5-PyBB—F | 6.0% |
| 3-HHB-1 | 5.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

COMPOSITION EXAMPLE 5

| | |
|---|---|
| 5-HVHEB(2F,3F)—O2 | 7.0% |
| 5-HBCF2OB(2F,3F)—O2 | 13.0% |
| 3-HB—C | 18.0% |
| 7-HB—C | 3.0% |
| 1O1-HB—C | 10.0% |
| 3-HB(F)—C | 10.0% |
| 2-PyB-2 | 2.0% |
| 3-PyB-2 | 2.0% |
| 4-PyB-2 | 2.0% |
| 1O1-HH-3 | 4.0% |
| 2-BTB—O1 | 5.0% |
| 3-HHB—F | 4.0% |
| 3-HHB—O1 | 4.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

COMPOSITION EXAMPLE 6

| | |
|---|---|
| 3-H2B(F)EB(2F,3F)—O2 | 4.0% |
| 5-HVHEB(2F,3F)—O2 | 4.0% |

-continued

| | |
|---|---|
| 5-HBCF2OB(2F,3F)—O2 | 4.0% |
| 5-BEB(F)—C | 5.0% |
| V—HB—C | 11.0% |
| 5-PyB—C | 6.0% |
| 4-BB-3 | 11.0% |
| 3-HH-2V | 6.0% |
| 5-HH—V | 11.0% |
| V—HHB-1 | 7.0% |
| V2-HHB-1 | 11.0% |
| 3-HHB-1 | 5.0% |
| 1V2-HBB-2 | 10.0% |
| 3-HHEBH-3 | 5.0% |

COMPOSITION EXAMPLE 7

| | |
|---|---|
| 3-H2B(F)EB(2F,3F)—O2 | 7.0% |
| 2O1-BEB(F)—C | 5.0% |
| 3O1-BEB(F)—C | 12.0% |
| 5O1-BEB(F)—C | 4.0% |
| 1V2-BEB(F,F)—C | 16.0% |
| 3-HB—O2 | 10.0% |
| 3-HH-4 | 3.0% |
| 3-HHB—F | 3.0% |
| 3-HHB-1 | 3.0% |
| 3-HHB—O1 | 2.0% |
| 3-HBEB—F | 4.0% |
| 3-HHEB—F | 7.0% |
| 5-HHEB—F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

COMPOSITION EXAMPLE 8

| | |
|---|---|
| 5-HBCF2OB(2F,3F)—O2 | 10.0% |
| 2-BEB—C | 12.0% |
| 3-BEB—C | 4.0% |
| 4-BEB—C | 6.0% |
| 3-HB—C | 28.0% |
| 3-HEB—O4 | 12.0% |
| 4-HEB—O2 | 8.0% |
| 5-HEB—O1 | 8.0% |
| 3-HEB—O2 | 6.0% |
| 3-HHB-1 | 2.0% |
| 3-HHB—O1 | 4.0% |

COMPOSITION EXAMPLE 9

| | |
|---|---|
| 3-H2B(F)EB(2F,3F)—O2 | 5.0% |
| 5-HVHEB(2F,3F) | 5.0% |
| 5-HBCF2OB(2F,3F)—O2 | 5.0% |
| 2-BEB—C | 10.0% |
| 5-BB—C | 12.0% |
| 7-BB—C | 7.0% |
| 1-BTB-3 | 7.0% |
| 2-BTB-1 | 10.0% |
| 1O—BEB-2 | 10.0% |
| 1O—BEB-5 | 10.0% |
| 2-HHB-1 | 4.0% |
| 3-HHB—F | 4.0% |
| 3-HHB-1 | 7.0% |
| 3-HHB—O1 | 4.0% |

COMPOSITION EXAMPLE 10

| | |
|---|---|
| 5-HVHEB(2F,3F)—O2 | 7.0% |
| 5-HBCF2OB(2F,3F)—O2 | 8.0% |
| 1V2-BEB(F,F)—C | 8.0% |
| 3-HB—C | 10.0% |
| V2V—HB—C | 14.0% |
| V2V—HH-3 | 16.0% |
| 3-HB—O2 | 4.0% |
| 3-HHB-1 | 10.0% |
| 3-HHB-3 | 3.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |

COMPOSITION EXAMPLE 11

| | |
|---|---|
| 5-HVHEB(2F,3F)—O2 | 5.0% |
| 5-HBCF2OB(2F,3F)—O2 | 6.0% |
| 5-BTB(F)TB-3 | 10.0% |
| V2-HB—TC | 10.0% |
| 3-HB—TC | 10.0% |
| 3-HB—C | 10.0% |
| 5-HB—C | 7.0% |
| 5-BB—C | 3.0% |
| 2-BTB-1 | 10.0% |
| 2-BTB—O1 | 5.0% |
| 3-HH-4 | 5.0% |
| 3-HHB-1 | 10.0% |
| 3-H2BTB-2 | 3.0% |
| 3-H2BTB-3 | 3.0% |
| 3-HB(F)TB-2 | 3.0% |

COMPOSITION EXAMPLE 12

| | |
|---|---|
| 5-HVHEB(2F,3F)—O2 | 3.0% |
| 5-HBCF2OB(2F,3F)—O2 | 4.0% |
| 1V2-BEB(F,F)—C | 6.0% |
| 3-HB—C | 18.0% |
| 2-BTB-1 | 10.0% |
| 5-HH—VFF | 30.0% |
| 1-BHH—VFF | 8.0% |
| 1-BHH-2VFF | 4.0% |
| 3-H2BTB-2 | 5.0% |
| 3-H2BTB-3 | 4.0% |
| 3-H2BTB-4 | 4.0% |
| 3-HHB-1 | 4.0% |

COMPOSITION EXAMPLE 13

| | |
|---|---|
| 3-H2B(F)EB(2F,3F)—O2 | 5.0% |
| 5-HVHEB(2F,3F)—O2 | 10.0% |
| 5-HBCF2OB(2F,3F)—O2 | 10.0% |
| 2-HB—C | 5.0% |
| 3-HB—C | 12.0% |
| 3-HB—O2 | 12.0% |
| 2-BTB-1 | 3.0% |
| 3-HHB-1 | 3.0% |
| 3-HHB—F | 4.0% |
| 3-HHB—O1 | 2.0% |
| 3-HHEB—F | 4.0% |
| 5-HHEB—F | 4.0% |
| 2-HHB(F)—F | 7.0% |

-continued

| | |
|---|---|
| 3-HHB(F)—F | 7.0% |
| 5-HHB(F)—F | 7.0% |
| 3-HHB(F,F)—F | 5.0% |

COMPOSITION EXAMPLE 14

| | |
|---|---|
| 5-HBCF2OB(2F,3F)—O2 | 10.0% |
| 2-HHB(F)—F | 17.0% |
| 3-HHB(F)—F | 17.0% |
| 5-HHB(F)—F | 16.0% |
| 2-H2HB(F)—F | 10.0% |
| 3-H2HB(F)—F | 5.0% |
| 2-HBB(F)—F | 6.0% |
| 3-HBB(F)—F | 6.0% |
| 5-HBB(F)—F | 13.0% |
| CN | 0.3 part |

COMPOSITION EXAMPLE 15

| | |
|---|---|
| 5-HVHEB(2F,3F)—O2 | 8.0% |
| 5-HBCF2OB(2F,3F)—O2 | 5.0% |
| 7-HB(F)—F | 5.0% |
| 5-H2B(F)—F | 5.0% |
| 3-HB—O2 | 10.0% |
| 3-HH-4 | 2.0% |
| 3-HH [5D,6D,7D]-4 | 3.0% |
| 2-HHB(F)—F | 10.0% |
| 3-HHB(F)—F | 5.0% |
| 5-HH [5D,6D,7D] B(F)—F | 10.0% |
| 3-H2HB(F)—F | 5.0% |
| 2-HBB(F)—F | 3.0% |
| 3-HBB(F)—F | 3.0% |
| 5-HBB(F)—F | 6.0% |
| 2-H2BB(F)—F | 5.0% |
| 3-H2BB(F)—F | 6.0% |
| 3-HHB—O1 | 5.0% |
| 3-HHB-3 | 4.0% |

COMPOSITION EXAMPLE 16

| | |
|---|---|
| 3-H2B(F)EB(2F,3F)—O2 | 3.0% |
| 5-HVHEB(2F,3F)—O2 | 3.0% |
| 5-HBCF2OB(2F,3F)—O2 | 4.0% |
| 7-HB(F,F)—F | 3.0% |
| 3-HB—O2 | 7.0% |
| 2-HHB(F)—F | 10.0% |
| 3-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |

COMPOSITION EXAMPLE 17

| | |
|---|---|
| 5-HBCF2OB(2F,3F)—O2 | 15.0% |
| 7-HB(F,F)—F | 3.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 5.0% |
| 4-HHB(F,F)—F | 5.0% |
| 3-HH2B(F,F)—F | 15.0% |
| 3-HBB(F,F)—F | 12.0% |
| 5-HBB(F,F)—F | 7.0% |
| 3-HBCF2OB(F,F)—F | 6.0% |

COMPOSITION EXAMPLE 18

| | |
|---|---|
| 3-H2B(F)EB(2F,3F)—O2 | 10.0% |
| 7-HB(F,F)—F | 5.0% |
| 3-H2HB(F,F)—F | 12.0% |
| 3-HHB(F,F)—F | 10.0% |
| 4-HHB(F,F)—F | 5.0% |
| 3-HBB(F,F)—F | 10.0% |
| 3-HHEB(F,F)—F | 10.0% |
| 4-HHEB(F,F)—F | 3.0% |
| 5-HHEB(F,F)—F | 3.0% |
| 2-HBEB(F,F) | 3.0% |
| 3-HBEB(F,F) | 5.0% |
| 5-HBEB(F,F) | 3.0% |
| 3-HDB(F,F) | 15.0% |
| 3-HHBB(F,F)—F | 6.0% |

COMPOSITION EXAMPLE 19

| | |
|---|---|
| 5-HBCF2OB(2F,3F)—O2 | 10.0% |
| 3-BCF2OB(2F,3F)—O2 | 10.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 11.0% |
| 5-HBB(F,F)—F | 10.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-4 | 4.0% |
| 1O1-HBBH-5 | 4.0% |

COMPOSITION EXAMPLE 20

| | |
|---|---|
| 5-HBCF2OB(2F,3F)—O2 | 4.0% |
| 5-B2BCF2OB(2F,3F)—O2 | 4.0% |
| 3-BCF2OB(2F,3F)—O2 | 4.0% |
| 5-HB—F | 12.0% |
| 6-HB—F | 9.0% |
| 7-HB—F | 7.0% |
| 2-HHB—OCF3 | 7.0% |
| 3-HHB—OCF3 | 7.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB(F,F)—OCF3 | 5.0% |
| 3-HBB(F)—F | 8.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |

COMPOSITION EXAMPLE 21

| | |
|---|---|
| 3-H2B(F)EB(2F,3F)—O2 | 15.0% |
| 3-HEB—O4 | 23.0% |
| 4-HEB—O2 | 18.0% |
| 5-HEB—O1 | 18.0% |
| 3-HEB—O2 | 14.0% |
| 5-HEB—O2 | 12.0% |

COMPOSITION EXAMPLE 22

| | |
|---|---|
| 5-HBCF2OB(2F,3F)—O2 | 15.0% |
| 5-HVHEB(2F,3F)—O2 | 5.0% |
| 3-HB—O2 | 10.0% |
| 3-HB—O4 | 10.0% |
| 3-HEB—O4 | 16.0% |
| 4-HEB—O2 | 13.0% |
| 5-HEB—O1 | 13.0% |
| 3-HEB—O2 | 10.0% |
| 5-HEB—O2 | 8.0% |

COMPOSITION EXAMPLE 23

| | |
|---|---|
| 5-HBCF2OB(2F,3F)—O2 | 15.0% |
| 3-HB—O2 | 15.0% |
| 3-HB—O4 | 10.0% |
| 3-HEB—O4 | 10.0% |
| 4-HEB—O2 | 7.0% |
| 5-HEB—O1 | 7.0% |
| 3-HEB—O2 | 6.0% |
| 5-HEB—O2 | 5.0% |
| 3-HB(2F,3F)—O2 | 7.0% |
| 5-HHB(2F,3F)—O2 | 5.0% |
| 5-HBB(2F,3F)-2 | 5.0% |
| 5-HBB(2F,3F)—O2 | 4.0% |
| 5-BB(2F,3F)B-3 | 4.0% |

COMPOSITION EXAMPLE 24

| | |
|---|---|
| 3-BCF2OB(2F,3F)—O2 | 20.0% |
| 3-H2B(F)EB(2F,3F)—O2 | 15.0% |
| 5-HBCF2OB(2F,3F)—O2 | 15.0% |
| 3-HB(2F,3F)—O2 | 20.0% |
| 5-HHB(2F,3F)—O2 | 10.0% |
| 5-HHB(2F,3F)-1O1 | 5.0% |
| 5-HBB(2F,3F)-2 | 10.0% |
| 5-HBB(2F,3F)-1O1 | 5.0% |

COMPOSITION EXAMPLE 25

| | |
|---|---|
| 3-BCF2OB(2F,3F)—O2 | 10.0% |
| 3-H2B(F)EB(2F,3F)—O2 | 5.0% |
| 5-HVHEB(2F,3F)—O2 | 5.0% |
| 5-BBCF2OB(2F,3F)—O2 | 5.0% |
| 3-DB—C | 10.0% |
| 4-DB—C | 10.0% |
| 2-BEB—C | 12.0% |
| 3-BEB—C | 4.0% |
| 3-PyB(F)—F | 6.0% |
| 3-HEB—O2 | 3.0% |
| 5-HEB—O2 | 4.0% |

-continued

| | |
|---|---|
| 5-HEB-5 | 5.0% |
| 4-HEB-5 | 5.0% |
| 1O—BEB-2 | 4.0% |
| 3-HHB-1 | 3.0% |
| 3-HHEBB—C | 3.0% |
| 3-HBEBB—C | 3.0% |
| 5-HBEBB—C | 3.0% |

COMPOSITION EXAMPLE 26

| | |
|---|---|
| 3-H2HCF2OB(2F,3F)—O2 | 10.0% |
| 3-HVBCF2OB(2F,3F)—O2 | 5.0% |
| 5-H2BCF2OB(2F,3F)—O2 | 5.0% |
| 3-HHBCF2OB(2F,3F)—O2 | 3.0% |
| 2O1-BEB(F)—C | 5.0% |
| 3O1-BEB(F)—C | 12.0% |
| 5O1-BEB(F)—C | 4.0% |
| 1V2-BEB(F,F)—C | 10.0% |
| 3-HH—EMe | 5.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F,F)—C | 2.0% |
| 3-HHB—F | 2.0% |
| 3-HHB-3 | 1.0% |
| 3-HEBEB—F | 2.0% |
| 3-HEBEB-1 | 2.0% |

COMPOSITION EXAMPLE 27

| | |
|---|---|
| 3-B(F)EB(2F,3F)—O2 | 5.0% |
| 3-BCF2OB(2F,3F)—O2 | 5.0% |
| 5-HBCF2OB(2F,3F)—O2 | 5.0% |
| 5-H2BCF2OB(2F,3F)—O2 | 10.0% |
| 5-B2BCF2OB(2F,3F)—O2 | 15.0% |
| 5-HB—CL | 4.0% |
| 7-HB—CL | 4.0% |
| 1O1-HH-5 | 3.0% |
| 2-HBB(F)—F | 8.0% |
| 3-HBB(F)—F | 8.0.% |
| 4-HHB—CL | 4.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |

COMPOSITION EXAMPLE 28

| | |
|---|---|
| 3-B(F)EB(2F,3F)—O2 | 5.0% |
| 5-HVBEB(2F,3F)—O3 | 5.0% |
| 5-H2B(F)EB(2F,3F)—O2 | 5.0% |
| 5-H4HB(F,F)—F | 7.0% |
| 5-H4HB—OCF3 | 15.0% |
| 3-H4HB(F,F)—CF3 | 3.0% |
| 3-HB—CL | 6.0% |
| 5-HB—CL | 4.0% |
| 2-H2BB(F)—F | 5.0% |
| 3-H2BB(F)—F | 10.0% |
| 5-HVHB(F,F)—F | 5.0% |

-continued

| | |
|---|---|
| 3-HHB—OCF3 | 5.0% |
| 3-H2HB—OCF3 | 5.0%. |
| V—HHB(F)—F | 5.0% |
| 3-HHB(F)—F | 5.0% |
| 5-HHEB—OCF3 | 2.0% |
| 3-HBEB(F,F)—F | 5.0% |
| 5-HH—V2F | 3.0% |

COMPOSITION EXAMPLE 29

| | |
|---|---|
| 5-B(F)CF2OB(2F,3F)—O1 | 5.0% |
| 3-H2HB(F)EB(2F,3F)—O2 | 3.0% |
| 3-HH2BCF2OB(2F,3F)—O2 | 3.0% |
| 5-HBCF2OB(2F,3F)—O2 | 5.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 15.0% |
| 5-HBB(F,F)—F | 19.0% |
| 1O1-HBBH-4 | 4.0% |

COMPOSITION EXAMPLE 30

| | |
|---|---|
| 5-B(F)CF2OB(2F,3F)—O1 | 5.0% |
| 5-HBCF2OB(2F,3F)—O2 | 5.0% |
| 5-HB—CL | 12.0% |
| 3-HH-4 | 2.0% |
| 3-HB—O2 | 20.0% |
| 3-H2HB(F,F)—F | 5.0% |
| 3-HHB(F,F)—F | 8.0% |
| 3-HBB(F,F)—F | 6.0% |
| 2-HHB(F)—F | 5.0% |
| 3-HHB(F)—F | 5.0% |
| 5-HHB(F)—F | 5.0% |
| 2-H2HB(F)—F | 2.0% |
| 3-H2HB(F)—F | 1.0% |
| 5-H2HB(F)—F | 2.0% |
| 3-HHBB(F,F)—F | 4.0% |
| 3-HBCF2OB—OCF3 | 4.0% |
| 5-HBCF2OB(F,F)—OCF3 | 4.0% |
| 3-HHB-1 | 3.0% |
| 3-HHB—O1 | 2.0% |

COMPOSITION EXAMPLE 31

| | |
|---|---|
| 5-HBCF2OB-3 | 8.0% |
| 5-HBCF2OBH-3 | 7.0% |
| 7-HB(F)—F | 14.0% |
| 2-HHB(F)—F | 11.0% |
| 3-HHB(F)—F | 11.0% |
| 5-HHB(F)—F | 11.0% |
| 2-H2HB(F)—F | 5.3% |
| 3-H2HB(F)—F | 2.6% |
| 5-H2HB(F)—F | 5.3% |
| 2-HBB(F)—F | 6.2% |
| 2-HBB(F)—F | 6.2% |
| 2-HBB(F)—F | 12.4% |

COMPOSITION EXAMPLE 32

| | |
|---|---|
| 5-HBCF2OBH-3 | 7.0% |
| 3-H2BCF2OBH-3 | 7.0% |
| 3-H2BCF2OBH-5 | 6.0% |
| 7-HB(F,F)—F | 4.0% |
| 3-HHB(F,F)—F | 6.0% |
| 3-H2HB(F,F)—F | 5.0% |
| 3-HBB(F,F)—F | 12.0% |
| 5-HBB(F,F)—F | 12.0% |
| 3-H2BB(F,F)—F | 5.0% |
| 4-H2BB(F,F)—F | 5.0% |
| 5-H2BB(F,F)—F | 5.0% |
| 3-HBEB(F,F)—F | 2.0% |
| 4-HBEB(F,F)—F | 2.0% |
| 5-HBEB(F,F)—F | 2.0% |
| 3-HHEB(F,F)—F | 12.0% |
| 4-HHEB(F,F)—F | 4.0% |
| 5-HHEB(F,F)—F | 4.0% |

COMPOSITION EXAMPLE 33

| | |
|---|---|
| 3-HBCF2OB-3 | 5.0% |
| 3-BCF2OB-5 | 5.0% |
| 3-H2HB(F,F)—F | 9.0% |
| 5-H2HB(F,F)—F | 8.0% |
| 3-HHB(F,F)—F | 9.0% |
| 4-HHB(F,F)—F | 5.0% |
| 3-HH2B(F,F)—F | 11.0% |
| 5-HH2B(F,F)—F | 7.0% |
| 3-HBB(F,F)—F | 14.0% |
| 5-HBB(F,F)—F | 14.0% |
| 3-HHEB(F,F)—F | 9.0% |
| 3-HHBB(F,F)—F | 2.0% |
| 3-HH2BB(F,F)—F | 2.0% |

COMPOSITION EXAMPLE 34

| | |
|---|---|
| 3-HBCF2OBH-3 | 6.0% |
| 3-HBCF2OBH-5 | 4.0% |
| 3-H2BCF2OBH-2 | 5.0% |
| 7-HB(F,F)—F | 4.0% |
| 7-HB(F)—F | 6.0% |
| 2-HHB(F)—F | 11.5% |
| 3-HHB(F)—F | 11.5% |
| 5-HHB(F)—F | 11.5% |
| 2-H2HB(F)—F | 3.0% |
| 3-H2HB(F)—F | 1.5% |
| 5-H2HB(F)—F | 3.0% |
| 3-H2HB(F,F)—F | 5.0% |
| 4-H2HB(F,F)—F | 4.0% |
| 5-H2HB(F,F)—F | 4.0% |
| 3-HHB(F,F)—F | 7.0% |
| 3-HH2B(F,F)—F | 7.0% |
| 5-HH2B(F,F)—F | 6.0% |

COMPOSITION EXAMPLE 35

| | |
|---|---|
| 3-HB(F)CF2OB-3 | 8.0% |
| 3-HB(F,F)CF2OB-5 | 5.0% |
| 2-HBCF2OBH-2 | 7.0% |
| 7-HB(F,F)—F | 4.0% |
| 2-HHB(F)—F | 11.1% |
| 3-HHB(F)—F | 11.2% |
| 5-HHB(F)—F | 11.2% |

-continued

| | |
|---|---|
| 2-H2HB(F)—F | 3.0% |
| 3-H2HB(F)—F | 1.5% |
| 5-H2HB(F)—F | 3.0% |
| 3-H2HB(F,F)—F | 5.0% |
| 4-H2HB(F,F)—F | 3.0% |
| 5-H2HB(F,F)—F | 3.0% |
| 3-HHB(F,F)—F | 8.0% |
| 4-HHB(F,F)—F | 4.0% |
| 3-HH2B(F,F)—F | 6.0% |
| 5-HH2B(F,F)—F | 6.0% |

COMPOSITION EXAMPLE 36

| | |
|---|---|
| 3-HBCF2OB-5 | 7.0% |
| 3-HB(F)CF2OBH-3 | 5.0% |
| 3-HB(F)CF2OBTB-3 | 3.0% |
| 3-HB—Cl | 7.0% |
| 7-HB(F,F)—F | 10.0% |
| 2-HBB(F)—F | 6.5% |
| 3-HBB(F)—F | 6.5% |
| 5-HBB(F)—F | 13.0% |
| 2-HHB—CL | 5.0% |
| 4-HHB—CL | 8.0% |
| 5-HHB—CL | 5.0% |
| 3-HBB(F,F)—F | 10.0% |
| 5-HBB(F,F)—F | 8.0% |
| 3-HB(F)VB-2 | 3.0% |
| 3-HB(F)VB-3 | 3.0% |

COMPOSITION EXAMPLE 37

| | |
|---|---|
| 3-BCF2OBH—V | 5.0% |
| 5-HB(F,F)CF2OBH-3 | 3.0% |
| 2-BTBCF2OBH-2 | 3.0% |
| 3-BTB(F)CF2OBH-3 | 3.0% |
| 5-HB—CL | 5.0% |
| 7-HB—CL | 6.0% |
| 2-HBB(F)—F | 7.0% |
| 3-HBB(F)—F | 7.0% |
| 5-HBB(F)—F | 14.0% |
| 2-HHB—CL | 5.0% |
| 4-HHB—CL | 5.0% |
| 5-HHB—CL | 4.0% |
| 3-HBB(F,F)—F | 16.0% |
| 5-HBB(F,F)—F | 14.0% |
| 3-HB(F)TB-2 | 3.0% |

COMPOSITION EXAMPLE 38

| | |
|---|---|
| 5-HBCF2OBH-3 | 6.0% |
| 3-HBCF2OBH-3 | 6.0% |
| 5-HBCF2OBTB-3 | 3.0% |
| 2-HHB(F)—F | 8.0% |
| 3-HHB(F)—F | 8.0% |
| 5-HHB(F)—F | 8.0% |
| 3-HHB(F,F)—F | 6.0% |
| 5-HHB(F,F)—F | 5.0% |
| 3-H2HB(F,F)—F | 7.0% |
| 4-H2HB(F,F)—F | 7.0% |
| 5-H2HB(F,F)—F | 7.0% |
| 3-HH2B(F,F)—F | 12.0% |
| 5-HH2B(F,F)—F | 8.0% |
| 2-HBB—F | 3.0% |

-continued

| | |
|---|---|
| 3-HBB—F | 3.0% |
| 3-HHB-1 | 3.0% |

COMPOSITION EXAMPLE 39

| | |
|---|---|
| 5-HBCF2OB-3 | 5.0% |
| 2-HB(F)CF2OB-3 | 5.0% |
| 3-HB(F)CF2OB-3 | 5.0% |
| 7-HB(F)—F | 4.0% |
| 2-HHB(F)—F | 13.0% |
| 3-HHB(F)—F | 13.0% |
| 5-HHB(F)—F | 13.0% |
| 2-H2HB(F)—F | 6.0% |
| 3-H2HB(F)—F | 3.0% |
| 5-H2HB(F)—F | 6.0% |
| 2-HBB(F)—F | 3.0% |
| 3-HBB(F)—F | 3.0% |
| 5-HBB(F)—F | 6.0% |
| 3-HBB—F | 2.0% |
| 3-HHB—F | 3.0% |
| 3-HB—O2 | 5.0% |
| 3-HHB-1 | 3.0% |
| 1O1-HBBH-3 | 2.0% |

COMPOSITION EXAMPLE 40

| | |
|---|---|
| 5-HBCF2OB-3 | 8.0% |
| 3-BCF2OBH—V | 8.0% |
| 2-BCF2OBH-2V | 8.0% |
| 3-HB(F)CF2OBH-3 | 6.0% |
| 7-HB(F,F)—F | 5.0% |
| 5-H2B(F)—F | 5.0% |
| 2-HHB(F)—F | 4.0% |
| 3-HHB(F)—F | 4.0% |
| 5-HHB(F)—F | 4.0% |
| 2-HBB(F)—F | 8.0% |
| 3-HBB(F)—F | 8.0% |
| 5-HBB(F)—F | 16.0% |
| 2-HBB—F | 4.0% |
| 3-HB(F)TB-2 | 4.0% |
| 3-HB(F)TB-3 | 4.0% |
| 3-HB(F)TB-4 | 4.0% |

COMPOSITION EXAMPLE 41

| | |
|---|---|
| 3-HB(F,F)CF2OB-1 | 4.0% |
| 3-HB(F,F)CF2OBH-3 | 4.0% |
| 2-BTB(F,F)CF2OBH-2 | 2.0% |
| 2-HHB(F)—F | 10.0% |
| 3-HHB(F)—F | 10.0% |
| 5-HHB(F)—F | 10.0% |
| 2-HBB(F)—F | 5.0% |
| 3-HBB(F)—F | 5.0% |
| 5-HBB(F)—F | 10.0% |
| 3-HHB(F,F)—F | 7.0% |
| 5-HHB(F,F)—F | 4.0% |
| 3-HH2B(F,F)—F | 8.0% |
| 5-HH2B(F,F)—F | 8.0% |
| 5-H2HB(F,F)—F | 5.0% |
| 5-HHEBB—F | 2.0% |
| 3-HB—O2 | 4.0% |
| 3-HHB—O1 | 2.0% |

COMPOSITION EXAMPLE 42

| | |
|---|---|
| 5-HBCF2OB-3 | 5.0% |
| 3-BCF2OBH—V | 4.0% |
| 5-HBCF2OBH-3 | 5.0% |
| 3-H2BCF2OBH-3 | 5.0% |
| 2-HHB(F)—F | 4.0% |
| 3-HHB(F)—F | 4.0% |
| 5-HHB(F)—F | 4.0% |
| 2-HBB(F)—F | 4.0% |
| 3-HBB(F)—F | 4.0% |
| 5-HBB(F)—F | 8.0% |
| 4-H2BB(F)—F | 6.0% |
| 5-H2BB(F)—F | 6.0% |
| 3-H2BB(F,F)—F | 4.0% |
| 4-H2BB(F,F)—F | 5.0% |
| 5-H2BB(F,F)—F | 4.0% |
| 3-HBB(F,F)—F | 12.0% |
| 5-HBB(F,F)—F | 8.0% |
| 3-HH2B(F,F)—F | 4.0% |
| 5-HH2B(F,F)—F | 4.0% |

COMPOSITION EXAMPLE 43

| | |
|---|---|
| 5-HBCF2OB-3 | 6.0% |
| 3-BCF2OBH—V | 4.0% |
| 5-HBCF2OBH-3 | 5.0% |
| 3O1-BEB(F)—C | 12.0% |
| V2-HB—C | 10.0% |
| 3-HB—O2 | 4.0% |
| 2-BTB—O1 | 5.0% |
| 3-BTB—O1 | 5.0% |
| 4-BTB—O1 | 5.0% |
| 4-BTB—O2 | 5.0% |
| 5-BTB—O1 | 5.0% |
| 3-HHB—O1 | 3.0% |
| 3-H2BTB-2 | 2.0% |
| 3-H2BTB-3 | 3.0% |
| 3-H2BTB-4 | 3.0% |
| 3-HB(F)TB-2 | 3.0% |
| 3-HB(F)TB-3 | 3.0% |
| 3-HB(F)TB-4 | 5.0% |
| 2-PyBH-3 | 4.0% |
| 2-PyBH-3 | 4.0% |
| 3-PyBB-2 | 4.0% |

COMPOSITION EXAMPLE 44

| | |
|---|---|
| 5-HBCF2OBH-3 | 6.0% |
| 3-H2BCF2OBH-3 | 6.0% |
| 3-H2BCF2OBH-5 | 5.0% |
| V2-HB—C | 9.0% |
| 1V2-HB—C | 9.0% |
| 3-HB—C | 14.0% |
| 1O1-HB—C | 8.0% |
| 2O1-HB—C | 4.0% |
| 2-HHB—C | 5.0% |
| 3-HHB—C | 5.0% |
| 3-HH-4 | 8.0% |
| 1O1-HH-5 | 5.0% |
| 2-BTB—O1 | 8.0% |
| 3-HHB-1 | 4.0% |
| 3-HHB-3 | 4.0% |

COMPOSITION EXAMPLE 45

| | |
|---|---|
| 3-BCF2OBH—V | 3.0% |
| 5-BCF2OBH-2V | 4.0% |
| 3-BCF2OBH-2V1 | 4.0% |
| 3-H2BCF2OBH-5 | 4.0% |
| 1V2-BEB(F,F)—C | 12.0% |
| 3O1-BEB(F)—C | 12.0% |
| 2-HB—C | 12.0% |
| 3-HB—C | 19.0% |
| 2-HHB—C | 4.0% |
| 3-HHB—C | 5.0% |
| 4-HHB—C | 4.0% |
| 5-HHB—C | 4.0% |
| 3-HB—O2 | 5.0% |
| 3-H2BTB-3 | 4.0% |
| 3-H2BTB-4 | 4.0% |

COMPOSITION EXAMPLE 46

| | |
|---|---|
| 5-HBCF2OB-3 | 10.0% |
| 3-HB(F)CF2OB-3 | 10.0% |
| 2-HB(F)CF2OBH—V | 4.0% |
| 3-HB(F)CF2OBH—V1 | 3.0% |
| 3-BTBCF2OBH-3 | 3.0% |
| V2-HB—C | 12.0% |
| 1V2-HB—C | 11.0% |
| 1V2-BEB(F,F)—C | 11.0% |
| 2-BTB-1 | 5.0% |
| 4-BTB—O2 | 5.0% |
| 5-BTB—O1 | 5.0% |
| 3-HH—EMe | 4.0% |
| 2-H2BTB-3 | 4.0% |
| 2-H2BTB-2 | 4.0% |
| 3-HB(F)TB-2 | 3.0% |
| 3-HB(F)TB-3 | 3.0% |
| 3-HB(F)TB-4 | 3.0% |

COMPOSITION EXAMPLE 47

| | |
|---|---|
| 2-HBCF2OBH-2 | 6.0% |
| 3-HBCF2OBH-3 | 6.0% |
| 3-HB(F,F)CF2OBH—V | 3.0% |
| 3-HB(F,F)CF2OBH-2V1 | 3.0% |
| 2O1-BEB(F)—C | 4.0% |
| 3O1-BEB(F)—C | 12.0% |
| 5O1-BEB(F)—C | 4.0% |
| 1V2-BEB(F,F)—C | 15.0% |
| 3-HHEB—F | 5.0% |
| 5-HHEB—F | 5.0% |
| 3-HBEB—F | 6.0% |
| 3-HHB—F | 3.0% |
| 3-HB—O2 | 10.0% |
| 3-HH-4 | 5.0% |
| 3-H2BTB-2 | 4.0% |
| 3-H2BTB-3 | 4.0% |
| 3-HB(F)VB-2 | 5.0% |

COMPOSITION EXAMPLE 48

| | |
|---|---|
| 3-HBCF2OB-3 | 7.0% |
| 2-HB(F)CF2OBH-2V | 3.0% |
| 3-HB(F)CF2OBH-2V1 | 3.0% |
| 3-HB(F,F)CF2OBTB-3 | 3.0% |
| 2-HB(F)—C | 15.0% |

-continued

| | |
|---|---|
| 2-HEB—F | 2.4 % |
| 3-HEB—F | 2.3 % |
| 4-HEB—F | 2.3 % |
| 3-HHEB—F | 4.0% |
| 5-HHEB—F | 4.0% |
| 2-HHB(F)—C | 12.0% |
| 3-HHB(F)—C | 12.0% |
| 2-HHB(F)—F | 10.0% |
| 3-HHB(F)—F | 10.0% |
| 5-HHB(F)—F | 10.0% |

COMPOSITION EXAMPLE 49

| | |
|---|---|
| 3-BCF2OBH-3 | 7.0% |
| 2-BCF2OBH—V | 7.0% |
| 3-HB(F,F)CF2OBH—V1 | 3.0% |
| 3-HB(F,F)CF2OBH-2V | 3.0% |
| 3-HB(F)—C | 3.0% |
| 3-HB—C | 21.0% |
| 3-HHB—C | 5.0% |
| 5-PyB—F | 10.0% |
| 3-HB—O2 | 4.0% |
| 2-BTB-1 | 6.0% |
| 3-HH-4 | 6.0% |
| 3-HH-5 | 6.0% |
| 3-HHB-1 | 5.0% |
| 3-HHB-3 | 7.0% |
| 3-HHB—O1 | 3.0% |
| 3-HEBEB-2 | 2.0% |
| 3-HEBEB—F | 2.0% |

COMPOSITION EXAMPLE 50

| | |
|---|---|
| 3-HBCF2OBH-3 | 8.0% |
| 3-HBCF2OBH-5 | 8.0% |
| 3-HB(F)CF2OBTB-3 | 4.0% |
| 2-BB—C | 8.0% |
| 4-BB—C | 6.0% |
| 2-HB—C | 10.0% |
| 3-HB—C | 13.0% |
| 3-HHB—F | 5.0% |
| 2-HHB—C | 4.0% |
| 3-HHB—C | 6.0% |
| 5-PyB—F | 6.0% |
| 3-PyBB—F | 6.0% |
| 2-HHB-1 | 6.0% |
| 3-HHB-3 | 5.0% |
| 3-HHB—O1 | 5.0% |

COMPOSITION EXAMPLE 51

| | |
|---|---|
| 5-HBCF2OB-3 | 8.0% |
| 3-BCF2OBH—V | 8.0% |
| 3-HB(F)CF2OBH-3 | 6.0% |
| 5-BB—C | 8.0% |
| 3-HHB—F | 4.0% |
| 3-HB—O2 | 12.0% |
| 3-HB—O4 | 10.0% |
| 3-PyB-4 | 2.5% |
| 4-PyB-4 | 2.5% |
| 6-PyB-4 | 2.5% |
| 3-PyB-5 | 2.5% |
| 4-PyB-5 | 2.5% |
| 6-PyB-5 | 2.5% |
| 6-PyB—O5 | 3.0% |

-continued

| | |
|---|---|
| 6-PyB—O6 | 3.0% |
| 6-PyB—O7 | 3.0% |
| 6-PyB—O8 | 3.0% |
| 2-HHB-1 | 4.0% |
| 3-HHB-1 | 8.0% |
| 3-HHB—O1 | 5.0% |

COMPOSITION EXAMPLE 52

| | |
|---|---|
| 5-HBCF2OB-3 | 8.0% |
| 5-HBCF2OBH-3 | 6.0% |
| 3-H2BCF2OBH-3 | 6.0% |
| 3-DB—C | 10.0% |
| 4-DB—C | 12.0% |
| 5-DB—C | 8.0% |
| 2-BEB—C | 10.0% |
| 5-PyB(F)—F | 10.0% |
| 2-PyB-2 | 1.4% |
| 3-PyB-2 | 1.3% |
| 4-PyB-2 | 1.3% |
| 3-HEB—O4 | 2.2% |
| 4-HEB—O2 | 1.6% |
| 3-HEB—O2 | 1.3% |
| 1O—BEB-2 | 1.1% |
| 5-HEB-1 | 1.6% |
| 4-HEB-4 | 2.2% |
| 3-HHB-3 | 6.0% |
| 3-HHB—O1 | 4.0% |
| 2-PyBH-3 | 6.0% |

COMPOSITION EXAMPLE 53

| | |
|---|---|
| 2-HBCF2OB-2 | 6.0% |
| 3-HBCF2OB-3 | 4.0% |
| 5-HBCF2OBH-3 | 6.0% |
| 3-DB—C | 10.0% |
| 4-DB—C | 10.0% |
| 2-BEB—C | 12.0% |
| 3-BEB—C | 4.0% |
| 3-HHEBB—C | 3.0% |
| 3-HBEBB—C | 3.0% |
| 5-HBEBB—C | 3.0% |
| 3-PyB(F)—F | 6.0% |
| 3-HEB—O4 | 8.3% |
| 4-HEB—O2 | 6.2% |
| 5-HEB—O1 | 6.2% |
| 3-HEB—O2 | 5.2% |
| 5-HEB—O2 | 4.1% |
| 3-HHB-1 | 3.0% |

COMPOSITION EXAMPLE 54

| | |
|---|---|
| 3-H2BCF2OBH-3 | 5.0% |
| 3-H2BCF2OBH-5 | 5.0% |
| 5-HB—F | 4.0% |
| 7-HB—F | 7.0% |
| 3-HHB—OCF3 | 10.0% |
| 5-HHB—OCF3 | 8.0% |
| 3-H2HB—OCF3 | 6.0% |
| 5-H2HB—OCF3 | 5.0% |
| 2-HHB(F)—F | 5.0.% |
| 3-HHB(F)—F | 5.0% |
| 5-HHB(F)—F | 5.0% |
| 3-H2HB(F,F)—F | 6.0% |
| 4-H2HB(F,F)—F | 5.0% |

-continued

| | |
|---|---|
| 5-H2HB(F,F)—F | 5.0% |
| 3-HHB(F,F)—F | 8.0% |
| 3-HH2B(F,F)—F | 6.0% |

COMPOSITION EXAMPLE 55

| | |
|---|---|
| 5-HBCF2OB-3 | 8.0% |
| 5-HBCF2OBH-3 | 6.0% |
| 3-H2BCF2OBH-3 | 6.0% |
| 7-HB—F | 5.0% |
| 3-HB—O2 | 4.0% |
| 3-HHB—OCF3 | 10.0% |
| 5-HHB—OCF3 | 5.0% |
| 3-H2HB—OCF3 | 5.0% |
| 5-H2HB—OCF3 | 5.0% |
| 2-HHB(F)—F | 7.0% |
| 3-HHB(F)—F | 7.0% |
| 5-HHB(F)—F | 7.0% |
| 2-H2HB(F)—F | 4.0% |
| 3-H2HB(F)—F | 2.0% |
| 5-H2HB(F)—F | 4.0% |
| 2-HBB(F)—F | 3.0% |
| 3-HBB(F)—F | 3.0% |
| 5-HBB(F)—F | 6.0% |
| 3-HHB-1 | 3.0% |

COMPOSITION EXAMPLE 56

| | |
|---|---|
| 3-BCF2OBH—V | 6.0% |
| 5-HBCF2OBH-3 | 4.0% |
| V2-HB—C | 9.0% |
| 1V2-HB—C | 9.0% |
| 3-HB—C | 14.0% |
| 1O1-HB—C | 8.0% |
| 2O1-HB—C | 4.0% |
| 2-HHB—C | 5.0% |
| 3-HHB—C | 5.0% |
| V2-HH-3 | 10.0% |
| 1O1-HH-5 | 4.0% |
| 2-BTB—O1 | 8.0% |
| V—HHB-1 | 5.0% |
| V—HBB-2 | 5.0% |
| 1V2-HBB-2 | 4.0% |

COMPOSITION EXAMPLE 57

| | |
|---|---|
| 3-BCF2OBH—V | 6.0% |
| 3-H2BCF2OBH-3 | 7.0% |
| 3-H2BCF2OBH-5 | 7.0% |
| 2O1-BEB(F)—C | 4.0% |
| 3O1-BEB(F)—C | 10.0% |
| 5O1-BEB(F)—C | 4.0% |
| V—HB—C | 10.0% |
| 1V—HB—C | 10.0% |
| 3-HB—C | 8.0% |
| 2-HHB—C | 4.0% |
| 3-HHB—C | 4.0% |
| 4-HHB—C | 4.0% |
| 5-HHB—C | 4.0% |
| 3-HB—O2 | 5.0% |
| V—HHB-1 | 5.0% |
| V—HBB-2 | 4.0% |
| 3-H2BTB-2 | 4.0% |

COMPOSITION EXAMPLE 58

| | |
|---|---|
| 3-BCF2OBH-3 | 6.0% |
| 5-HB(F,F)CF2OB-3 | 4.0% |
| 3-HB(F)CF2OBH-3 | 5.0% |
| 5-HB—F | 6.0% |
| 6-HB—F | 4.0% |
| 7-HB—F | 7.0% |
| 5-HB-3 | 3.0% |
| 3-HB—O1 | 3.0% |
| 2-HHB—OCF3 | 5.0% |
| 3-HHB—OCF3 | 5.0% |
| 4-HHB—OCF3 | 5.0% |
| 5-HHB—OCF3 | 7.0% |
| 3-HH2B—OCF3 | 2.0% |
| 5-HH2B—OCF3 | 3.0% |
| 3-HH2B—F | 3.0% |
| 5-HH2B—F | 3.0% |
| 3-HBB(F)—F | 6.0% |
| 5-HBB(F)—F | 5.0% |
| 3-HH2B(F)—F | 7.0% |
| 5-HH2B(F)—F | 9.0% |
| 5-HB(F)BH-3 | 2.0% |

COMPOSITION EXAMPLE 59

| | |
|---|---|
| 3HB(F,F)CF2OBH-3 | 4.0% |
| 2-BTB(F,F)CF2OBH-2 | 4.0% |
| 2-HBCF2OBTB-2 | 8.0% |
| 5-HB—F | 7.0% |
| 3-HH—O1 | 4.0% |
| 3-HH—O3 | 4.0% |
| 5-HH—O1 | 3.0% |
| 3-HHB—OCF2 | 5.0% |
| 5-HHB—OCF2 | 5.0% |
| 3-HHB(F,F)—OCF2 | 8.0% |
| 5-HHB(F,F)—OCF2 | 8.0% |
| 2-HHB—OCHF3 | 5.0% |
| 3-HHB—OCHF3 | 5.0% |
| 4-HHB—OCHF3 | 5.0% |
| 5-HHB—OCHF3 | 5.0% |
| 3-HH2B(F)—F | 7.0% |
| 5-HH2B(F)—F | 8.0% |
| 3-HHEB(F)—F | 5.0% |

COMPOSITION EXAMPLE 60

| | |
|---|---|
| 2-BCF2OBH-2V | 8.0% |
| 3-HB(F)CF2OBH—V | 6.0% |
| 2-HB(F)CF2OBH-2V | 6.0% |
| V—HB—C | 10.0% |
| 1V-HB—C | 5.0% |
| 3-BB—C | 5.0% |
| 5-BB—C | 5.0% |
| 2-HB)F)—C | 4.0% |
| 4-BB-3 | 3.0% |
| 3-H2B—O2 | 3.0% |
| 5-H2B—O2 | 6.0% |
| 3-BEB—C | 5.0% |
| 5-HEB—O1 | 6.0% |
| 5-HEB—O3 | 6.0% |
| 5-BBB—C | 3.0% |
| 4-BPyB—C | 4.0% |
| 4-BPyB-5 | 4.0% |
| 5-HB2B-4 | 3.0% |
| 5-HBB2B-3 | 2.0% |
| 1V—HH-1O1 | 3.0% |
| 1V2-HBB-3 | 3.0% |

COMPOSITION EXAMPLE 61

| | |
|---|---|
| 3-BCF2OBH-2V1 | 6.0% |
| 3-HB(F,F)CF2OBH-3 | 3.0% |
| 2-BTB(F)CF2OBH-2 | 6.0% |
| 4-HEB(F)—F | 8.0% |
| 5-HEB(F)—F | 8.0% |
| 2-BEB(F)—C | 5.0% |
| 3-BEB(F)—C | 5.0% |
| 4-BEB(F)—C | 6.0% |
| 5-BEB(F)—C | 6.0% |
| 1O3-HB(F)—C | 6.0% |
| 3-HHEB(F)—F | 5.0% |
| 5-HHEB(F)—F | 5.0% |
| 2-HBEB(F)—C | 5.0% |
| 3-HBEB(F)—C | 5.0% |
| 4-HBEB(F)—C | 5.0% |
| 5-HBEB(F)—C | 5.0% |
| 3-HBTB-2 | 5.0% |
| V2-HH-3 | 3.0% |
| V2-HHB-1 | 3.0% |

Liquid crystalline compounds of the present invention expressed by the general formula (1) can readily produced by ordinary procedures in organic synthetic chemistry. For instance, the compounds can easily be produced by selecting proper procedures described in Organic Synthesis, Organic Reactions, Jikken Kagaku Kouza (Course of Chemical Experiment), or others and using them in combination.

For instance, compounds (1-A) expressed by the general formula (1) wherein m is 1, n is 0, and $X^2$ is —COO— can preferably be produced by the following method. That is, the compounds (1-A) can be produced by reacting carboxylic acid derivatives (13) with alcohol or phenol derivatives (14) in a solvent such as dichloromethane and chloroform in the presence of a dehydrating agent such as dicyclohexylcarbodiimide (DCC), and 4-dimethylaminopyridine (DMAP) (B. Neises et al., Organic Synthesis, 63, 183 (1985)).

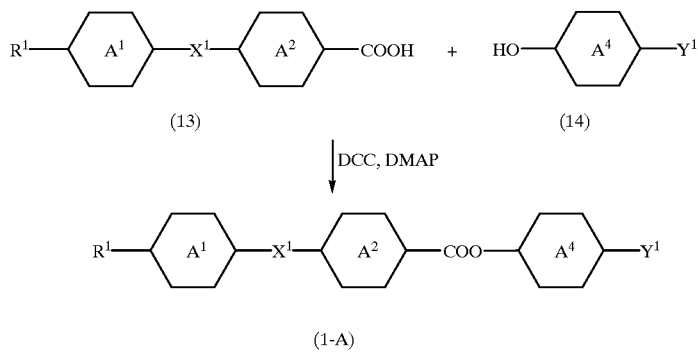

wherein $R^1$, $X^1$, $Y^1$, and rings $A^1$, $A^2$, and $A^4$ have the same meaning as described above.

Compounds (1-B) expressed by the general formula (1) wherein m is 1, n is 0, and $X^2$ is —CF$_2$O— can preferably be produced by the following method. That is, halides (15) are converted into Grignard reagents or lithiated compounds by using magnesium and lithium reagent, and then the reagents or lithiated compounds are reacted with carbon disulfide to produce dithiocarboxylic acid —derivatives (16). Subsequently, the derivatives (16) are reacted with thionyl chloride to convert into thioncarboxylic acid chloride, reacted with an alcohol or phenol to produce thion-O-ester derivatives (17), and then the derivatives (17) is reacted with diethylaminosulfur trifluoride (hereinafter abbreviated to DAST) or reacted with tetrabutylammonium dihydrogen trifluoride or HF-pyridine in the presence of an oxidizing agent such as N-bromosuccinimide (hereinafter abbreviated to NBS) and 1,3-dibromo-5,5-dimethylhidantoin (hereinafter abbreviated to DBH) according to a method described in Laid-open Japanese Patent Publication No. Hei 5-255165 to produce the objective compounds (1-B).

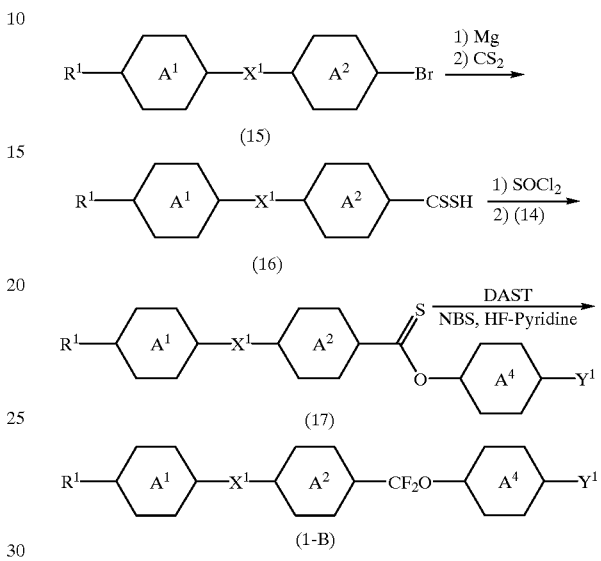

wherein $R^1$, $X^1$, $Y^1$, and rings $A^1$, $A^2$, and $A^4$ have the same meaning as described above.

The thion-O-ester derivatives (17) can also be produced by deriving dithiocarboxylic acid derivatives (16) into alkali metal salts and then reacting with an alcolate or phenolate in the presence of iodine. Further, the ester derivatives (17) can be produced by reacting the ester derivatives (1-A) obtained by the production method described above with 2,4-bis(4-methoxyphenyl)-1,3-dithia-2,4-diphosphetane-2,4-disulfide (hereinafter abbreviated to Lawesson's reagent).

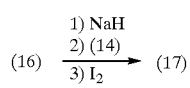

Compounds expressed by the general formula (1) wherein $X^1$, $X^2$, or $X^3$ is an ethenylene group, for example, compounds (1-C) expressed by the general formula (1) wherein m is 1, n is 0, $X^1$ is —CH=CH—, and $X^2$ is —CF$_2$O—, and compounds (1-D) wherein $X^2$ is —COO— can preferably be produced by the following method. That is, first, E,Z-olefin mixtures (22) are obtained by reacting ylides prepared by reacting the Wittig reagent (19), which can be prepared from bromomethane derivatives (18) and triphenylphosphine according to a method described in Organic Reactions, Vol. 14, Chapter 3, with a base such as a sodium alkoxide and an alkyl lithium in tetrahydrofuran (hereinafter abbreviated as THF) with aldehyde derivatives (21). Next, the E,Z-olefin mixtures are reacted with benzene sulfinic acid or p-toluenesulfinic acid according to a method described in Japanese patent publication No. Hei 4-30382 to isomerize. Alternatively, E,Z-olefin mixtures are reacted with m-chloroperbenzoic acid according to a method described in Japanese patent Publication No. Hei 6-62462 to convert into oxylane derivatives (23). The oxylane derivatives are then reacted with dibromotriphenyl phosphorane to derive into dibromo derivatives (24). Subsequently, the derivatives (24) are subjected to recrystallization to purify only erithro isomer and then reduced with metal zinc to produce E-olefin derivatives (25). The objective compounds (1-C) can be produced by treating the derivatives (25) in the same manner as in the compounds (I-B) described above.

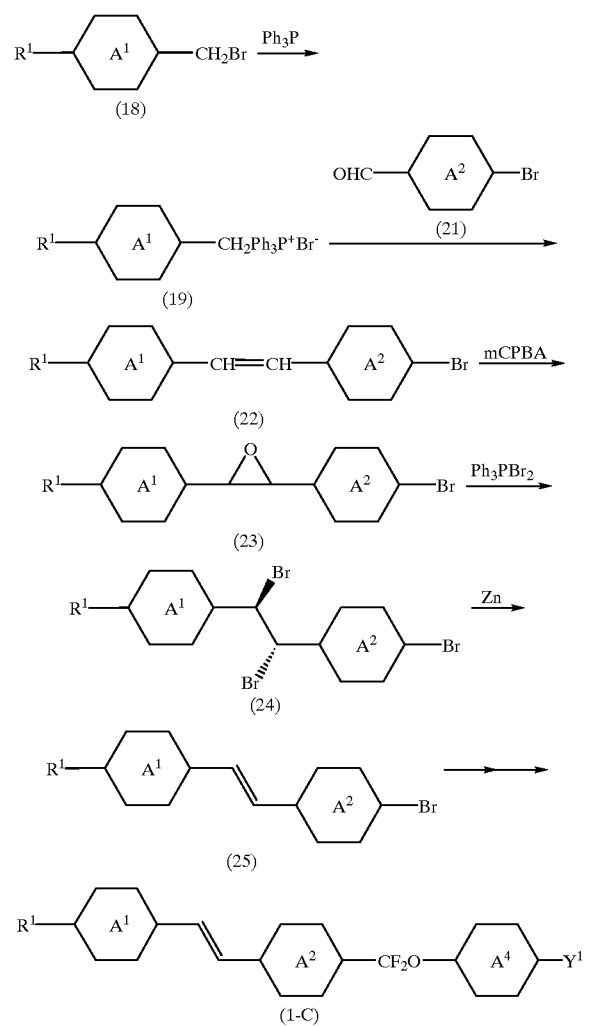

wherein $R^1$, $Y^1$, and rings $A^1$, $A^2$, and $A^4$ have the same meaning as described above.

On the other hand, carboxylic acid derivatives (26) can be produced by lithiating the compounds (25) obtained by the procedures described above with butyl lithium or the like, and then reacting with carbon dioxide. The objective compounds (1-D) can be produced by treating the compounds (26) in the same manner as in the case of producing compounds (1-C).

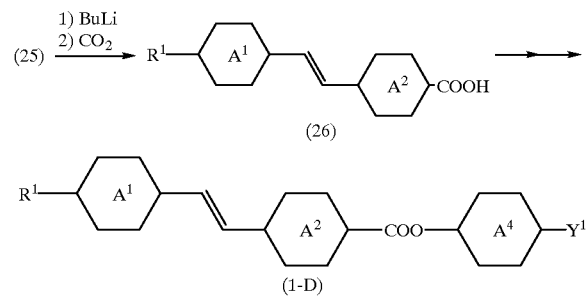

wherein $R^1$, $Y^1$, and rings $A^1$, $A^2$, and $A^4$ have the same meaning as described above.

Compounds expressed by the general formula (1) wherein $X^1$, $X^2$, or $X^3$ is ethynylene group, for examples, compounds (I-E) expressed by the general formula (1) wherein m is 1, n is 0, XI is —C≡C—, and $X^2$ is —CF$_2$O—, and compounds (1-F) wherein $X^2$ is —COO— can preferably be produced by the following methods. That 15 is, acetylene derivatives (27) are reacted with compounds (28) in the presence of a catalyst according to a method described in J. Org. Chem., 28, 2163, 3313 (1963) to produce compounds (29). The objective compounds (1-E) can be produced by treating the compounds (29) thus obtained in the same manner as in the case of producing the compounds (1-B) described above.

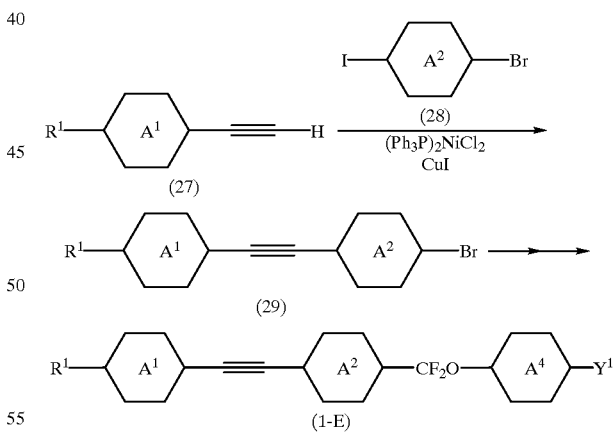

wherein $R^1$, $Y^1$, and rings $A^1$, $A^2$, and $A^4$ have the same meaning as described above.

On the other hand, carboxylic acid derivatives (30) can be produced by lithiating the compounds (29) obtained by the procedures described above with butyl lithium or the like, and then reacting with carbon dioxide. The objective compounds (1-F) can be produced by treating the compounds (30) in the same manner as in the case of producing the compounds (1-C) described above.

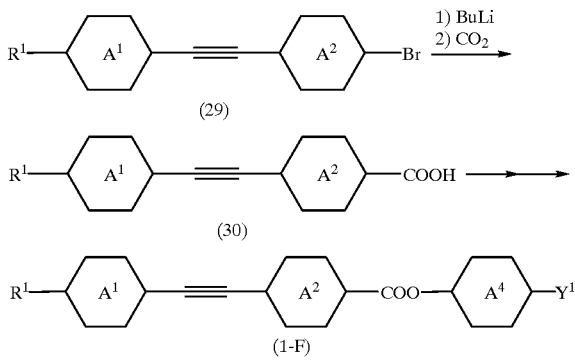

wherein $R^1$, $X^1$, $Y^1$, and rings $A^1$, $A^2$, and $A^4$ have the same meaning as described above.

Acetylene derivatives (27) can readily be produced by treating dibromides (31), which can easily be produced by adding bromine to corresponding vinyl derivatives, with a base according to a method described in J. Org. Chem., 38, 1367 (1963).

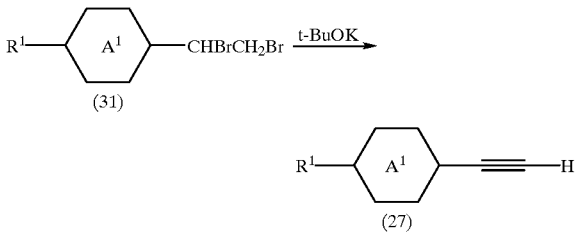

wherein $R^1$ and ring $A^1$ have the same meaning as described above.

Besides, other compounds which are not described above can preferably be produced by properly selecting various methods described in well known reference books on organic synthesis or patent publications and combining the methods.

BEST MODE FOR CARRYING OUT THE INVENTION

Now, the methods for producing the compounds of the present invention and the methods for using the compounds are described in more detail with reference to Examples. In each of the Examples, Cr indicates crystal; N, nematic phase; Sm, smectic phase; and Iso, isotropic liquid, and the unit of all phase transition temperatures is ° C. In $^1$H-NMR, s indicates singlet; d, doublet; t, triplet; and m, multiplet; and J indicates coupling constant (Hz). Further, in mass spectrum (GC-MS), $M^+$ indicates molecular ion peak.

EXAMPLE 1

Preparation of 2,3-difluoro-4-ethoxyphenyl 2-fluoro-4-(2-(trans-4-propylcyclohexyl)ethyl)benzoate (Compound expressed by the general formula (1) wherein m is 1, n is 0, ring $A^1$ represents trans-1,4-cyclohexylene group, ring $A^2$ represents 2fluoro-1,4-phenylene group, ring $A^4$ represents 2,3-difluoro-1,4-phenylene group, $X^1$ represents —CH$_2$CH$_2$-, $R^1$ represents n—C$_3$H$_7$, and $Y^1$ represents OC$_2$H$_5$; Compound No. 15)

(First step)

First, 100 g (0.77 mol) of 2,3-difluorophenol, 100 g (0.92 mol) of ethyl bromide, 127 g (0.92 mol) of potassium carbonate, 1.0 g (6.0 mmol) of potassium iodide, and 1.3 l of dimethyl-formamide (DMF) were mixed and heated to reflux for 7 hours. After finishing of the reaction, 1.0 l of water was added to the reaction solution and then extracted with 2.0 l of toluene. The organic layer thus obtained was washed with water once and then dried over anhydrous magnesium sulfate. The solvent was distilled off under a reduced pressure and the residue was distilled under a reduced pressure to obtain 87.5 g of 2,3-difluoroethoxybenzene (yield 71.4%).

(Second step)

To a solution prepared by dissolving 19.0 g (0.12 mol) of the 2,3-difluoroethoxybenzene obtained by the first step, in 250 ml of tetrahydrofuran (THF) was added dropwise 100 ml of solution of 1.56 M of n-butyl lithium in hexane at −78° C. in 30 min and stirred as it was for 30 min. To this solution was added dropwise solution of 25 g (0.24 mol) of trimethyl borate in 50 ml of THF at the same temperature in 10 min, stirred at the same temperature for 3 hours, and then gradually warmed up to room temperature. To this solution was added 55.2 g (1.2 mol) of formic acid, further 108.8 g of 30% by weight of hydrogen peroxide was added in 30 min, and then the solution was heated up to 50° C. and stirred as it was for 30 min. After the reaction solution was allowed to stand to cool down to room temperature, the solution was poured into 5% by weight of aqueous sodium thiosulfate solution and extracted with 400 ml of toluene. The organic layer was dried over anhydrous magnesium sulfate, the solvent was distilled off under a reduced pressure, and the residue was recrystallized from heptane to obtain 9.1 g of 2,3-difluoro-4-ethoxyphenol (yield 43.4%).

(Third step)

First, 1.7 g (10 mmol) of the 2,3-difluoro-4-ethoxyphenol obtained by the second step, 2.9 g (10 mmol) of 2-fluoro-4-(2-(trans-4-propylcyclohexyl)ethyl)benzoic acid, 1.3 g (11 mmol) of DMAP, and 100 ml of dichloromethane were mixed. To this mixture was added dropwise solution of 2.27 g (11 mmol) of DCC in 15 ml of dichloromethane under a condition cooled with ice in 10 min, and then the mixture was warmed up to room temperature and stirred as it was overnight. Separated crystals were filtered off and the solvent was distilled off under a reduced pressure from the filtrate. The residue was purified by silica gel column chromatography (eluent: ethyl acetate) and further recrystallized from heptane to obtain 2.48 g of the subject compound (yield 55.3%).

This compound exhibited liquid crystal phase and its phase transition temperatures were as follows:

C-N point: 65.4, N-I point: 141.3

Data of various kind of spectrums supported the structure of the compound described above.

$^1$H-NMR (CDCl$_3$) δ (ppm): 8.09–7.92 (t, 1H, J=15.7 Hz), 7.11–6.75 (m, 4H), 4.25–4.02 (q, 2H, J=21.2 Hz), 2.78–2.61 (t, 2H, J=15.7 Hz), 1.81–0.88 (m, 22H)

Mass spectrum: 448 ($M^+$)

EXAMPLE 2

Preparation of (2,3-difluoro-4-ethoxyphenyl)oxy(4-(trans-4-n-pentylcyclohexyl)phenyl)difluoromethane (Compound expressed by the general formula (1) wherein m is 1, n is 0, ring $A^1$ represents trans-1,4-cyclohexylene group, ring $A^2$ represents 1,4-phenylene group, ring $A^4$ represents 2,3-difluoro-1,4-phenylene group, $X^1$ represents single bond, $X^2$ represents —CF$_2$O—, $R^1$ represents n-C$_5$H$_{11}$, and $Y^1$ represents OC$_2$H$_5$; Compound No. 152)

(First step)

To a suspension prepared by suspending 0.95 g (39 mmol) of magnesium in 200 ml of THF was added dropwise a solution prepared by dissolving 9.28 g (30 mmol) of 4-(trans-4-n-pentylcyclohexyl)bromobenzene in 80 ml of THF, at room temperature while being stirred in 1 hour, and then heated to reflux for 2 hours to prepare a Grignard reagent. To this solution was added dropwise 5.7 g (75 mmol) of carbon disulfide at room temperature in 30 min and stirred as it was overnight. To this reaction solution was added 150 ml of 1M hydrochloric acid to terminate the reaction and extracted with 350 ml of toluene. The organic layer was dried over anhydrous magnesium sulfate, the solvent was distilled off under a reduced pressure, and the residue was recrystallized from heptane to obtain 4.74 g of 4-(trans-4-n-pentylcyclohexyl)phenyldithiocarboxylic acid (yield 51.5%).

(Second step)

To a suspension prepared by suspending 1.52 g (38.0 mmol) of 60% sodium hydride in 15 ml of THF was added dropwise solution of 5.29 g (17.3 mmol) of the 4-(transs-4-n-pentylcyclohexyl)phenyldithiocarboxylic acid obtained by the first step, in 20 ml of THF under a condition cooled with ice in 15 min, and stirred as it was for 30 min. To this reaction solution was added dropwise solution of 2.50 g (14.4 mmol) of 2,3-difluoro-4-ethoxyphenol in 20 ml of THF in 15 min and stirred as it was for 30 min. To this reaction solution was added dropwise solution of 9.64 g (38.0 mmol) of iodine in 20 ml of THF in 15 min, stirred as it was for 1 hour, warmed up to room temperature, and then stirred at the same temperature overnight. This reaction solution was poured into 10% aqueous sodium thiosulfate solution and extracted with 100 ml of diethyl ether. The organic layer was dried over anhydrous magnesium sulfate, the solvent was distilled off under a reduced pressure, and the residue was purified by silica gel column chromatography (eluent: heptane) and further recrystallized from heptane to obtain 2.0 g of 2,3-difluoro-4-ethoxyphenyl 4-(trans-4-n-pentylcyclohexyl)thiobenzoate (yield 31.2%).

(Third step)

To a suspension prepared by suspending 1.59 g (8.93 mmol) of N-bromosuccinimide in 20 ml of methylene chloride was added dropwise 1.78 g of hydrogen fluoride-pyridine at −78° C. in 15 min and stirred as it was for 10 min. To this reaction solution was added dropwise solution of 2.0 g (4.48 mmol) of 2,3-difluoro-4-ethoxyphenyl 4-(trans-4-n-pentylcyclohexyl)thiobenzoate in 30 ml of methylene chloride in 30 min and stirred as it was for 2 hours. This reaction solution was poured into saturated aqueous sodium carbonate solution to terminate the reaction. The methylene chloride layer was separated, and washed with 10% aqueous sodium bisulfite solution and water in turn, and dried over anhydrous magnesium sulfate. The solvent was distilled off under a reduced pressure and the residue was purified by silica gel column chromatography (eluent: heptane) to obtain 0.72 g of the subject compound (yield 35.5%).

This compound exhibited liquid crystal phase and its phase transition temperatures were as follows:

C-N point: 61.4, N-I point: 131.4

Data of various kind of spectrums supported the structure of the compound described above.

$^1$H-NMR (CDCl$_3$) δ (ppm): 7.71–6.57 (m, 6H), 4.26–4.00 (q, 2H, J=21.0 Hz), 2.53–2.83 (m, 24H)

$^{19}$F-NMR (CDCl$_3$) δ (ppm): −66.5 (s, —CF$_2$O—)

Mass spectrum: 452 (M$^+$)

EXAMPLE 3

Preparation of difluoro-(4-pentylphenyloxy) (4-(trans-4-propylcyclohexyl)phenyl)methane (Compound expressed by the general formula (1) wherein m is 1, n is 0, ring A$^1$ represents trans-1,4-cyclohexylene group, ring A$^2$ represents 1,4-phenylene group, ring A$^4$ represents 1,4-phenylene group, X$^1$ represents single bond, X$^2$ represents —CF$_2$O—, R$^1$ represents n—C$_3$H$_7$, and Y$^1$ represents C$_5$H$_{11}$; Compound No. 331)

(First step)

In a 500 ml three-necked flask provided with a stirrer, thermometer, and nitrogen gas inlet tube, 2.7 g (112.1 mmol) of turnings of magnesium were suspended in 50 ml of THF while being stirred under nitrogen gas atmosphere, and 70 ml of solution of 30 g (106.8 mmol) of 4-(trans-4-propylcyclohexyl)bromobenzene in THF was added dropwise in 40 min so that the internal temperature did not exceed 50° C. The reaction solution was stirred while being heated at 50° C. with a hot water bath for 2 hours to age. After the solution was cooled with an ice bath to lower the internal temperature down to 5° C., 24.4 g (320.4 mmol) of carbon disulfide was added dropwise in 25 min so that the internal temperature did not exceed 10° C. The reaction solution was stirred while being maintained at a temperature lower than 10° C. for 30 min, warmed up to room temperature, and then stirred for 1 hour. The reaction solution was cooled down to a temperature lower than 5° C. again, 25 ml of 6N hydrochloric acid was added thereto to terminate the reaction, and then extracted with 400 ml of diethyl ether. The organic layer was washed with 300 ml of an ice water and dried over anhydrous magnesium sulfate. Diethyl ether was distilled off and the residue was concentrated to obtain 23.7 g of a deep purplish red (murex) solid. This product was 4-(trans-4-propylcyclohexyl)phenyldithiocarboxylic acid.

(Second step)

In a 500 ml eggplant type flask, 23.7 g of the 4-(trans-4-propylcyclohexyl)phenyldithiocarboxylic acid obtained by the procedures described above was dissolved in 200 ml of diethyl ether, 50.8 g of thionyl chloride was added thereto, and then the solution was heated on a hot water bath to reflux for 8 hours. The diethyl ether and unreacted thionyl chloride were distilled off under a reduced pressure produced with an aspirator, and the residue was concentrated to obtain 25 g of a deep murex oily substance. This substance was thioncarboxylic acid chloride derivative. Subsequently, in a 500 ml three-necked flask provided with a stirrer, thermometer, and nitrogen gas inlet tube, 21.0 g (128.2 mmol) of 4-pentylphenol and 10.1 g (128.1 mmol) of pyridine were dissolved in 30 ml of toluene under nitrogen gas atmosphere, and 70 ml of solution of 25.0 g of the thioncarboxylic acid chloride derivative obtained by the procedures described above in toluene was added thereto while being stirred the solution at room temperature in 20 min. After finishing of the dropping, the reaction solution was heated on a hot water bath so that the internal temperature rose up to 60° C. and then stirred for 3 hours to age. After the reaction solution was cooled down to room temperature, 100 ml of water and 30 ml of 6N hydrochloric acid were added to the reaction solution, the toluene layer was separated, and then the water layer was extracted with 200 ml of toluene. The toluene layers were coalesced, washed with 200 ml of water, 80 ml of 2N aqueous sodium hydroxide solution, and 300 ml of water in turn, and then dried over anhydrous magnesium sulfate. The toluene was distilled off under a reduced pressure to obtain 28.3 g of a deep murex past like residue. The residue was purified by silica gel column chromatography (eluent: heptane) and further recrystallized from heptane to obtain 12.7 g of pale yellow needle-shaped crystals of 4-pentylphenyl 4-(trans-4-n-propylcyclohexyl)thiobenzoate.

(Third step)

In a 300 ml eggplant type flask, 5.0 g (12.3 mmol) of the 4-pentylphenyl 4-(trans-4-n-propylcyclohexyl)thiobenzoate obtained by the procedures described above was dissolved in 60 ml of dichloromethane under nitrogen gas stream, 7.9 g (49.0 mmol) of DAST was added thereto at room temperature, and then the solution was stirred for 25 hours. The reaction solution was added to 200 ml of an ice water to terminate the reaction, the dichloromethane layer was separated, and further the water layer was extracted with 100 ml of dichloromethane. The dichloromethane layers were coalesced, washed with 200 ml of water, 50 ml of 2N aqueous sodium hydroxide solution, and 200 ml of water in turn, and then dried over anhydrous magnesium sulfate. The dichloromethane was distilled off and the residue was concentrated to obtain 3.8 g of a pale yellow crystalline crude product. This crude product was purified by silica gel column chromatography (eluent: heptane) and then recrystallized from heptane to obtain 1.7 g of colorless needle-shaped crystals of difluoro-(4-pentylphenyloxy) (4-(trans-4-propylcyclohexyl)phenyl)methane. Data of various kind of spectrums supported the structure of the compound described above.

Mass spectrum: 414 (M$^+$)

EXAMPLE 4

Preparation of difluoro-(4-(trans-4-ethenylcyclohexyl) phenyloxy) (4-propylphenyl)methane (Compound expressed by the general formula (1) wherein m is 1, n is 0, both ring A$^1$ and ring A$^2$ represent 1,4-phenylene group, ring A$^4$ represents trans-1,4 -cyclohexylene group, X$^1$ represents —CF$_2$O—, X$^2$ represents single bond, R$^1$ represents n—C$_3$H$_7$, and Y$^1$ represents vinyl group; Compound No. 441)

Preparation process can broadly be divided into three stages of 1) synthesis of 4-(4-hydroxyphenyl) cyclohexanone, 2) synthesis of cyclohexanone intermediate (32), and 3) preparation of difluoro-(4-(trans-4-ethenylcyclohexyl)phenyloxy) (4-propylphenyl)methane. The process is described in detail below with each preparation stage being separated.

1) [Synthesis of 4-(hydroxyphenyl)cyclohexanone]
(First step)

In a 1 l three-necked flask provided with a stirrer, thermometer, and nitrogen gas inlet tube, 5.8 g (239.0 mmol) of turnings of magnesium were suspended in 100 ml of THF while being stirred under nitrogen atmosphere, and 200 ml of solution of 60 g (228.1 mmol) of 4-bromophenoxybenzyl ether in THF was added dropwise thereto in 80 min so that the internal temperature did not exceed 50° C. The reaction solution was stirred while being heated at 50° C. with a hot water bath for 2 hours to age. Subsequently, 42.7 g (274.3 mmol) of 1,4-cyclohexanedionemonoethyleneketal was added dropwise at room temperature to the reaction solution in 40 min so that the internal temperature did not exceed 60° C. The reaction solution was stirred on a hot water bath while being maintained at 50° C. for 2 hours and then cooled with an ice water, and 100 ml of saturated aqueous ammonium chloride solution was added thereto to terminate the reaction. The reaction solution was extracted with 400 ml of toluene. The toluene extract was washed with 900 ml of water and then dried over anhydrous magnesium sulfate. The toluene was distilled off under a reduced pressure to obtain 73.6 g of a brown solid product. This product was dissolved in 340 ml of toluene in a 1 l eggplant type flask provided with a Dean and Stark dehydrating tube, 5.9 g of non-aqueous acidic ion exchange resin (Amberlist) was added as acid catalyst thereto, and the solution was heated to reflux for 3 hours while being stirred. After the catalyst was removed by filtration, the toluene was distilled off under a reduced pressure, and the residue was purified by silica gel column chromatography (eluent: toluene), and then recrystallized from toluene to obtain 41.8 g of colorless needle-shaped crystals of cyclohexene derivative (33).

(33)

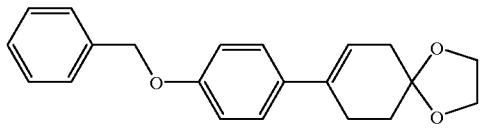

(Second step)

The cyclohexene derivative (33) obtained in the first step was dissolved in 200 ml of mixed solvent of toluene/ethanol of 1/1 in a 1 l eggplant type flask, 2.5 g of 5% palladium-carbon catalyst was added thereto, and the solution was subjected to a hydrogenation reaction at room temperature under a hydrogen gas pressure of 1 to 2 kg/cm$^2$ for 6 hours. After the catalyst was removed by filtration, the reaction solution was concentrated to obtain 30.2 g of a reaction product. This reaction product was dissolved in 100 ml of toluene in a 300 ml three-necked flack provided with a stirrer and thermometer, 29.9 g of 99% formic acid was added to the solution, and then the solution was heated to reflux while being stirred for 2 hours. Water in an amount of 300 ml was added to the reaction solution, the toluene layer was separated, and further the water layer was extracted with 200 ml of toluene. The toluene layers were coalesced, washed with 800 ml of water, and then dried over anhydrous magnesium sulfate. The toluene was distilled off under a reduced pressure to obtain 18.0 g of 4-(4-hydroxyphenyl) cyclohexanone.

2) [Synthesis of cyclohexanone intermediate (32)]
(Third step)

In a 300 ml three-necked flask provided with a stirrer, thermometer, and nitrogen gas inlet tube, 18.0 g (94.8 mmol) of 4-(4-hydroxyphenyl)cyclohexanone was dissolved in 30 ml of toluene under nitrogen gas atmosphere, 9.7 g (123.0 mmol) of pyridine was added thereto, and then 50 ml of solution of 24.4 g (123.0 mmol) of the 4-propylphenylthioncarboxylic acid chloride synthesized by the same procedures as in the first and second steps in Example 1, in toluene was added dropwise in 15 min. After finishing of the dropping, the reaction solution was heated up to 60° C. on a hot water bath and stirred for 3 hours to age. After the reaction solution was cooled down to room temperature, 100 ml of water and 50 ml of 6N hydrochloric acid were added thereto, the toluene layer was separated, and then the water layer was extracted with 200 ml of toluene. The toluene layers were coalesced, washed with 200 ml of water, 50 ml of 2N aqueous sodium hydroxide solution, and 300 ml of water in turn, and then dried over anhydrous magnesium sulfate. The toluene was distilled off under a reduced pressure to obtain 33.2 g of a deep murex paste like product. This product was purified by silica gel column chromatography (eluent: mixed solvent of heptane/toluene=1/1) and further recrystallized from heptane to obtain 18.4 g of pale yellow needle-shaped crystals. These crystals were thioncarboxylic acid—O—ester derivative (34).

(34)

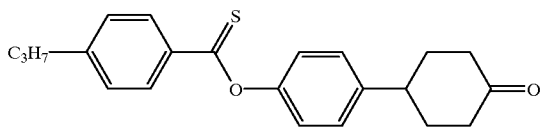

(Fourth step)
In a 300 ml eggplant type flask provided with a nitrogen gas inlet tube, 18.4 g (52.0 mmol) of the thioncarboxylic acid—O— ester derivative (34) obtained by the procedures described above was dissolved in 250 ml of dichloromethane under nitrogen gas atmosphere, 33.5 g (208.0 mmol) of DAST was added thereto at room temperature, and then the solution was stirred for 25 hours. The reaction solution was added to 200 ml of an ice water to terminate the reaction, the dichloromethane layer was separated, and further the water layer was extracted with 100 ml of dichloromethane. The dichloromethane layers were coalesced, washed with 200 ml of water, 50 ml of 2N aqueous sodium hydroxide solution, and 200 ml of water in turn, and then dried over anhydrous magnesium sulfate. The dichloromethane was distilled off to obtain 13,6 g of a pale yellow crystalline crude product. This crude product was purified by silica gel column chromatography (eluent: mixed solvent of heptane/toluene=1/1) and further recrystallized from heptane to obtain 8.0 g of colorless needle-shaped crystals. These crystals were cyclohexanone intermediate (32).

(32)

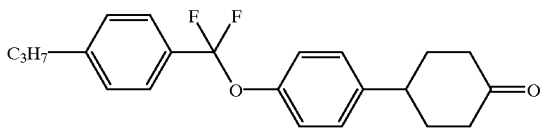

3) [Synthesis of difluoro-(4-(trans-4-ethenylcyclohexyl) phenyloxy) (4-propylphenyl)methane]
(Fifth step)
In a 300 ml three-necked flask provided with a stirrer, thermometer, and nitrogen gas inlet tube, 9.8 g (28.6 mmol) of methoxymethyltriphenylphosphonium chloride was dissolved in 80 ml of THF under nitrogen gas atmosphere and cooled down to a temperature lower than −50° C. with a dry ice-acetone bath, 3.4 g (30.0 mmol) of potassium-t-butoxide was added thereto, and then the solution was stirred while being maintained at a temperature lower than −50° C. for 2 hours to prepare an ylide. Then, 20 ml of solution of 8.0 g (22.0 mmol) of the cyclohexanone intermediate (32) obtained by the fourth step described above, in THF was added thereto at the same temperature in 10 min, and stirred at the same temperature for 1 hour. Subsequently, the solution was warmed up to room temperature and further stirred at room temperature for 8 hours. After 200 ml of water was added to the reaction solution to terminate the reaction, the THF layer was separated, and further the water layer was extracted with 100 ml of toluene. The toluene layers were coalesced, washed with 500 ml of water, and then dried over anhydrous magnesium sulfate. The solvent was distilled off under a reduced pressure to obtain 18.5 g of a crude product. This crude product was purified by silica gel column chromatography (eluent: toluene) to obtain 7.6 g of a yellowish brown product. The product thus obtained was dissolved in 50 ml of toluene in a 200 ml eggplant type flask, 5.3 g (114.0 mmol) of 99% formic acid was added thereto, and the solution was heated to reflux for 2 hours. Water in an amount of 50 ml was added to the reaction solution and extracted with 50 ml of toluene. The toluene layer was washed with 100 ml of water, 30 ml of 2N aqueous sodium hydroxide solution, and 100 ml of water in turn, and then dried over anhydrous magnesium sulfate. The solvent was distilled off under a reduced pressure and 7.3 g of the residue thus obtained was purified by silica gel column chromatography (eluent: toluene) to obtain 5.6 g of colorless crystalline cyclohexanecarbaldehyde derivative (35).

(35)

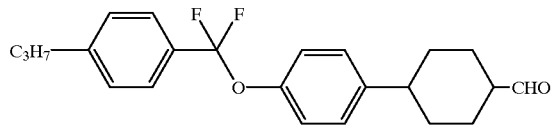

(Sixth step)
In a 200 ml three-necked flask provided with a stirrer, thermometer, and nitrogen gas inlet tube, 7.0 g (17.4 mmol) of methyltriphenylphosphonium iodide was suspended in 30 ml of THF under nitrogen gas atmosphere and cooled down to a temperature lower than −50° C. with a dry ice-acetone bath, and 2.1 g (18.3 mmol) of potassium-t-butoxide was added thereto, and then the suspension was stirred while being maintained at a temperature lower than −50° C. for 2 hours to prepare a ylide. Then, 15 ml of solution of 5.0 g (13.4 mmol) of the cyclohexanecarboaldehyde derivative (35) obtained by the fifth step, in THF was added dropwise thereto at the same temperature in 5 min, stirred at the same temperature for 1 hour, warmed up to room temperature, and further stirred for 8 hours. Water in an amount of 50 ml was added to the reaction solution to terminate the reaction, the THF layer was separated, and further the water layer was extracted with 50 ml of toluene. The THF layer and the toluene layer were coalesced, washed with 80 ml of water, and then dried over anhydrous magnesium sulfate. The solvent was distilled off under a reduced pressure, and 4.8 g of the product thus obtained was purified by silica gel column chromatography (eluent: heptane) and further recrystallized from heptane to obtain 2.4 g of a colorless needle-shaped compound. This compound was the objective difluoro-(4-(trans-4-ethenylcyclohexyl)phenyloxy) (4-propylphenyl)methane. Data of various kind of spectrums supported the structure of the compound described above.
Mass spectrum: 370 (M+)

EXAMPLE 5

Preparation of difluoro-(4-(trans-4-(3-butenyl) cyclohexyl)phenyloxy) (4-propylphenyl)methane (Compound expressed by the general formula (1) wherein m is 1, n is 0, both ring $A^1$ and ring $A^2$ represent 1,4-phenylene group, ring $A^4$ represents trans-1,4-cyclohexylene group, $X^1$ represents —$CF_2O$—, $X^2$ represents single bond, $R^1$ represents n—$C_3H_7$, and $Y^1$ represents 3-butenyl; Compound No. 442)
(First step)
In a 100 ml three-necked flask provided with a stirrer, thermometer, and nitrogen gas inlet tube, 12.8 g (29.1 mmol) of 2-(1,3-dioxane-2-yl)ethyltriphenylphosphonium bromide was suspended in 40 ml THF under nitrogen gas atmosphere and cooled down to a temperature lower than -50° C. with a dry ice-acetone bath, 3.4 g (30.5 mmol) of potassium-t-butoxide was added to the suspension, and then the suspension was stirred while being maintained at a temperature lower than −50° C. for 2 hours to prepare a ylide. Then, 30 ml of solution of 8.0 g (22.4 mmol) of the cyclohexanone intermediate (32) described in Example 4, in THF was added dropwise thereto at the same temperature in 20 min, stirred at the same temperature for 1 hour, warmed up to room temperature, and further stirred for 8 hours. Water in an amount of 50 ml was added to the reaction solution to terminate the reaction, the THF layer was separated, and the water layer was extracted with 100 ml of toluene. The THF layer and the toluene layer were coalesced, washed with 200 ml of water, and then dried over anhydrous magnesium sulfate. The solvent was distilled off under a reduced pressure, and 15.5 g of the residue thus obtained was purified by silica gel column chromatography (eluent: mixed solvent of toluene/ethyl acetate) to obtain 8.2 g of yellowish brown crystals. Subsequently, these yellowish brown crystals were dissolved in 60 ml of mixed solvent of toluene/ethanol of 1/1 in a 200 ml eggplant type flask, 0.4 g of 5% palladium-carbon catalyst was added thereto, and then the solution was subjected to a catalytic hydrogen reduction at room temperature under a condition of hydrogen gas pressure of 1 to 2 kg/cm$^2$ until the time when absorption of hydrogen ceased. The catalyst was removed from the reaction solution by filtration and then the solvent was distilled off under a reduced pressure to obtain 7.4 g of a product. This product was dissolved in 30 ml of toluene in a 100 ml of eggplant type flask, 3.9 g (83.5 mmol) of 99% formic acid was added thereto, and then the solution was heated to reflux for 2 hours. Water in an amount of 50 ml was added to the reaction solution, the toluene layer was separated, and further the water layer was extracted with 60 ml of toluene. The toluene layers were coalesced, washed with 100 ml of water, 30 ml of 2N aqueous sodium hydroxide solution, and 100 ml of water in turn, and then dried over anhydrous magnesium sulfate. The toluene was distilled off under a reduced pressure, and 7.0 g of the residue thus obtained was purified by silica gel column chromatography (eluent: toluene) to obtain 5.9 g of yellowish brown crystalline aldehyde derivative (36).

(36)

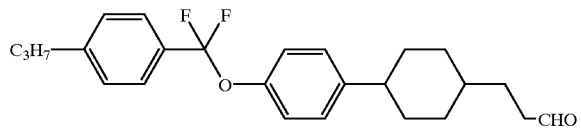

(Second step)

In a 100 ml three-necked flask provided with a stirrer, thermometer, and nitrogen gas inlet tube, 7.8 g (19.3 mmol) of methyltriphenylphosphonium iodide was suspended in 30 ml of THF under nitrogen gas atmosphere and cooled down to a temperature lower than −50° C. with a dry ice-acetone bath, 2.2 g (20.3 mmol) of potassium-t-butoxide was added thereto, and then the suspension was stirred while being maintained at a temperature lower than −50° C. for 2 hours to prepare a ylide. Then, 20 ml of solution of 5.9 g (14.9 mmol) of the aldehyde derivative (36) obtained by the first step, in THF was added dropwise at the same temperature thereto in 5 min, stirred at the same temperature for 1 hour, warmed up to room temperature, and further stirred for 8 hours. Water in an amount of 50 ml was added to the reaction solution to terminate the reaction, the THF layer was separated, and the water layer was extracted with 100 ml of toluene. The THF layer and the toluene layer were coalesced, washed with 200 ml of water, and then dried over anhydrous magnesium sulfate. The solvent was distilled off under a reduced pressure, and 5.6 g of the product thus obtained was purified by silica gel column chromatography (eluent: heptane) and further recrystallized from heptane to obtain 2.4 g of colorless needle-shaped crystals. These crystals were the objective difluoro-(4-(trans-4-(3-butenyl)cyclohexyl)phenyloxy) (4-propylphenyl)methane. Data of various kind of spectrums supported the structure of the compound described above.

Mass spectrum: 398 (M$^+$)

EXAMPLE 6

Preparation of difluoro-(4-(trans-4-propylcyclohexyl) phenyloxy) (4-(trans-4-pentylcyclohexyl)phenyl)methane (Compound expressed by the general formula (1) wherein m and n are 1, both ring A$^1$ and ring A$^4$ represent trans-1,4-cyclohexylene group, both A$^2$ and ring A$^3$ represent 1,4-phenylene group, both X$^1$ and X$^3$ represent single bond, X$^2$ represents —CF$_2$O—, R$^1$ represents n— C$_5$H$_{11}$, and Y$^1$ represents n—C$_3$H$_7$; Compound No. 572)

(First step)

In a 500 ml three-necked flask provided with a stirrer, thermometer, and nitrogen gas inlet tube, 4.2 g (172.7 mmol) of turnings of magnesium were suspended in 50 ml of THF under nitrogen gas atmosphere, and 120 ml of solution of 50 g (161.7 mmol) of 4-(trans-4-pentylcyclohexyl) bromobenzene in THF was added dropwise thereto while the internal temperature being maintained at 50° C. on a hot water bath in 40 min. The reaction solution was stirred while being heated at 50° C. with a hot water bath for 2 hours to age. Then, the contents of the flask were cooled with an ice bath so that the internal temperature lowered down to 5° C., and 61.6 g (809.0 mmol) of carbon disulfide was added dropwise in 35 min so that the internal temperature did not exceed 10° C. The reaction solution was stirred while being maintained at a temperature lower than 10° C. for 30 min, warmed up to room temperature, and then stirred for 2 hours. The reaction solution was cooled down again to a temperature lower than 5° C., 100 ml of 6N hydrochloric acid was added thereto to terminate the reaction, and then extracted with 800 ml of diethyl ether. The diethyl ether layer was washed with 800 ml of an ice water and then dried over anhydrous magnesium sulfate. The diethyl ether was distilled off to obtain 50.8 g of a deep murex solid. This solid was 4-(trans-4-pentylcyclohexyl)phenyl-dithiocarboxylic acid.

(Second step)

In a 500 ml eggplant type flask, 50.8 g of the 4-(trans-4-pentylcyclohexyl)phenyldithiocarboxylic acid obtained by the procedures described above was dissolved in 300 ml of diethyl ether, 115.6 g (971.6 mmol) of thionyl chloride was added thereto at room temperature, and then the solution was heated on a hot water bath to reflux for 8 hours. The diethyl ether and unreacted thionyl chloride were distilled off under a reduced pressure produced with an aspirator to obtain 66.8 g of a deep murex paste like substance. This substance was thioncarboxylic acid chloride derivative.

Subsequently, in a 500 ml three-necked flask provided with a stirrer, thermometer, and nitrogen gas inlet tube, 17.2 g (78.8 mmol) of 4-(trans-4-propylcyclohexyl)phenol and 5.7 g (72.2 mmol) of pyridine were dissolved in 80 ml of toluene under nitrogen gas atmosphere, and 60 ml of solution of 20.3 g of the thioncarboxylic acid chloride derivative obtained by the procedures described above, in toluene was added dropwise thereto in 20 min. After finishing of the dropping, the reaction solution was heated up to 60° C. on a hot water bath and stirred for 3 hours to age. After the reaction solution was cooled down to room temperature, 200 ml of water and 80 ml of 6N hydrochloric acid were added to the reaction solution, the toluene layer was separated, and further the water layer was extracted with 300 ml of toluene. The toluene layers were coalesced, washed with 400 ml of water, 80 ml of 2N aqueous sodium hydroxide solution, and 400 ml of water in turn, and then dried over anhydrous magnesium sulfate. The toluene was distilled off under a reduced pressure, and 31.9 of a deep murex paste like product thus obtained was purified by silica gel column chromatography (eluent: mixed solvent of heptane/toluene) and recrystallized from heptane to obtain 5.8 g of pale yellow needle-shaped crystals. These crystals were thioncarboxylic acid—O—ester derivative (37).

Phase transition temperatures: Cr 136.2 N 263.6 Iso $^1$H-NMR δ (ppm): 0.8–2.1 (36H, m), 2.3–2.7 (2H, m), 7.0 (2H, d, J=8.6 Hz), 7.2–7.3 (4H, bd), and 8.3 (2H, d, J=8.3 Hz)

(37)

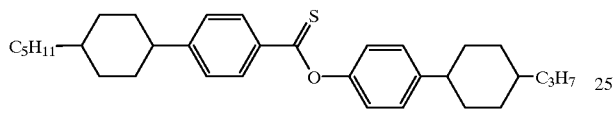

(Third step)

In a 100 ml eggplant type flask, 5.8 g (11.9 mmol) of the thioncarboxylic acid—O—ester derivative (37) obtained by the procedures described above was dissolved in 60 ml of dichloromethane under nitrogen gas stream, and 9.6 g (59.5 mmol) of DAST was added thereto at room temperature and stirred for 25 hours. The reaction solution was added to 200 ml of an ice water to terminate the reaction, the dichloromethane layer was separated, and further the water layer was extracted with 100 ml of dichloromethane. The dichloromethane layers were coalesced, washed with 200 ml of water, 50 ml of 2N aqueous sodium hydroxide solution, and 200 ml of water in turn, and then dried over anhydrous magnesium sulfate. The dichloromethane was distilled off, and 7.6 g of a pale yellow crystalline mixture thus obtained was purified by silica gel column chromatography (eluent: heptane) and further recrystallized from heptane to obtain 1.9 g of colorless needle-shaped crystals. These crystals were the objective difluoro-(4-(trans-4-propylcyclohexyl) phenyloxy) (4-(trans-4-pentylcyclohexyl)phenyl)methane. Data of various kind of spectrums supported the structure of the compound described above.

Phase transition temperatures: $S_A$ 106.3 N~170.0 Iso (decomposed)

$^1$H-NMR δ (ppm): 0.8–2.1 (36H, m), 2.3–2.8 (2H, m), 7.2 (4H, S), 7.2–7.3 (2H, bd), and 7.6 (2H, d, J=8.3 Hz)

Mass spectrum: 496 (M$^+$)

EXAMPLE 7

Preparation of difluoro-(4-(trans-4-ethenylcyclohexyl) phenyloxy) (4-(trans-4-propylcyclohexyl)phenyl)methane (Compound expressed by the general formula (1) wherein m and n are 1, both ring $A^1$ and ring $A^4$ represent trans-1,4-cyclohexylene group, both ring $A^2$ and ring $A^3$ represent 1,4-phenylene group, both $X^1$ and $X^3$ represent single bond, $X^2$ represents —CF$_2$O—, $R^1$ represents n—C$_3$H$_7$, and $Y^1$ represents vinyl group; Compound No. 573)

(First step)

In a 500 ml three-necked flask provided with a stirrer, thermometer, and nitrogen gas inlet tube, 14.1 g (74.3 mmol) of the 4-(4-hydroxyphenyl)cyclohexanone prepared by Example 4 (first and second steps) and 7.4 g (93.7 mmol) of pyridine were dissolved in 50 ml of toluene under nitrogen gas atmosphere, and 60 ml of solution of 25.0 g (89.2 mmol) of the thioncarboxylic acid chloride derivative prepared by Example 3 (first and second steps), in toluene was added dropwise while being stirred at room temperature in 20 min. After finishing of the dropping, the reaction solution was heated up to 60° C. on a hot water bath and stirred for 3 hours to age. The reaction solution was cooled down to room temperature, 200 ml of water and 80 ml of 6N hydrochloric acid were added to the solution, the toluene layer was separated, and further the water layer was extracted with 300 ml of toluene. The toluene layers were coalesced, washed with 400 ml of water, 80 ml of 2N aqueous sodium hydroxide solution, and 400 ml of water in turn, and then dried over anhydrous magnesium sulfate. The toluene was distilled off under a reduced pressure, and 38.2 g of the deep murex paste like product thus obtained was purified by silica gel column chromatography (eluent: mixed solvent of heptane/toluene) and further recrystallized from heptane to obtain 14.3 g of pale yellow needle-shaped crystals. These crystals were thioncarboxylic acid—O—ester derivative (38).

(38)

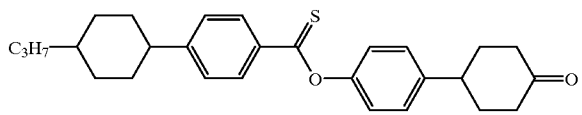

(Second step)

In a 100 ml eggplant type flask, 14.3 g (32.9 mmol) of the thioncarboxylic acid-O-ester derivative (38) obtained by the procedures described above was dissolved in 100 ml of dichloromethane under nitrogen gas atmosphere, and 26.5 g (164.7 mmol) of DAST was added thereto at room temperature and stirred for 25 hours. The reaction solution was added to 300 ml of an ice water to terminate the reaction, the dichloromethane layer was separated, and further the water layer was extracted with 200 ml of dichloromethane. The dichloromethane layers were coalesced, washed with 500 ml of water, 80 ml of 2N aqueous sodium hydroxide solution, and 500 ml of water in turn, and then dried over anhydrous magnesium sulfate. The dichloromethane was distilled off, and 14.1 g of a pale yellow crystalline mixture thus obtained was purified by silica gel column chromatography (eluent: toluene) and further recrystallized from heptane to obtain 7.1 g of colorless needle-shaped crystals. These crystals were cyclohexanone derivative (39).

(39)

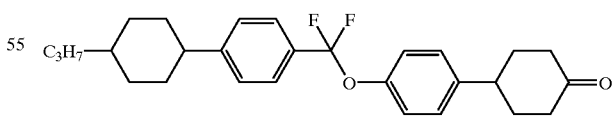

(Third step)

In a 300 ml three-necked flask provided with a stirrer, thermometer, and nitrogen gas inlet tube, 6.9 g (20.1 mmol) of methoxymethyl-triphenylphosphonium chloride was suspended in 50 ml of THF under nitrogen gas atmosphere and cooled down to a temperature lower than −50° C. with a dry ice-acetone bath, 2.4 g (21.1 mmol) of potassium-t-butoxide was added thereto, and then the suspension was stirred while being maintained at a temperature lower than −50° C. for 2 hours to prepare a ylide. Then, 20 ml of solution of 7.1 g (16.1 mmol) of the cyclohexanone derivative (39) obtained by the second step, in THF was added dropwise thereto in 10 min at the same temperature, stirred at the same temperature for 1 hour, warmed up to room temperature, and then further stirred for 8 hours. Water in an amount of 100 ml was added to the reaction solution to terminate the reaction, the THF layer was separated, and further the water layer was extracted with 100 ml of toluene. The THF layer and the toluene layer were coalesced, washed with 200 ml of water, and then dried over anhydrous magnesium sulfate. The solvent was distilled off, and 14.1 g of the product thus obtained was purified by silica gel column chromatography (eluent: toluene) to obtain 6.8 g of a yellowish brown reaction product.

Subsequently, in a 200 ml eggplant type flask, the reaction product was dissolved in 40 ml of toluene, 4.1 g (88.2 mmol) of 99% formic acid was added thereto, and the solution was heated to reflux for 2 hours. Water in an amount of 50 ml was added to the reaction solution and extracted with 50 ml of toluene, the extract layer was washed with 100 ml of water, 30 ml of 2N aqueous sodium hydroxide solution, and 100 ml of water in turn, and then dried over anhydrous magnesium sulfate. The solvent was distilled off under a reduced pressure, and 9.8 g of the product thus obtained was purified by silica gel column chromatography (eluent: toluene) to obtain 4.7 g of colorless crystals. These crystals were cyclohexanecarbaldehyde derivative (40).

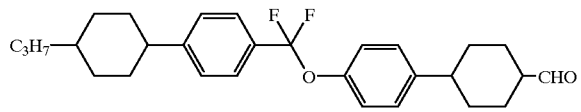

(40)

(Fourth step)

In a 200 ml three-necked flask provided with a stirrer, thermometer, and nitrogen gas inlet tube, 5.2 g (12.9 mmol) of methyltriphenylphosphonium iodide was suspended in 30 ml of THF under nitrogen gas atmosphere and cooled down to a temperature lower than −50° C. with a dry ice-acetone bath, 1.5 g (13.5 mmol) of potassium-t-butoxide was added thereto, and then the suspension was stirred while being maintained at a temperature lower than −50° C. for 2 hours to prepare a ylide. Then, 15 ml of solution of 4.7 g (10.4 mmol) of the cyclohexanecarbaldehyde derivative (40) obtained by the procedures described above in THF was added dropwise thereto at the same temperature in 5 min, stirred for 1 hour at the same temperature, warmed up to room temperature, and further stirred for 8 hours. Water in an amount of 50 ml was added to the reaction solution to terminate the reaction, the THF layer was separated, and the water layer was extracted with 50 ml of toluene. The THF layer and the toluene layer were coalesced, washed with 80 ml of water, and then dried over anhydrous magnesium sulfate. The solvent was distilled off under a reduced pressure, and 6.4 g of the product thus obtained was purified by silica gel column chromatography (eluent: heptane) and further recrystallized from heptane to obtain 1.5 g of a colorless needle-shaped compound. This compound was the objective difluoro-(4-(trans-4-ethenylcyclohexyl) phenyloxy) (4-(trans-4-propylcyclohexyl)phenyl)methane. Data of various kind of spectrums supported the structure of the compound described above.

Mass spectrum: 452 (M$^+$)

EXAMPLE 8

Preparation of (2,3-difluoro-4-ethoxyphenyl)oxy(trans-4-(trans-4-n-propylcyclohexyl)cyclohexyl)difluoromethane (Compound expressed by the general formula (1) wherein m is 1, n is 0, both rings A$^1$ and ring A$^2$ represent trans-1,4-cyclohexylene group, ring A$^4$ represents 2,3-difluoro-1,4-phenylene group, X$^1$ represents single bond, X$^2$ represents —CF$_2$O—, R$^1$ represents n—C$_3$H$_7$, and Y$^1$ represents OC$_2$H$_5$; Compound No. 144)

(First step)

First, 10.0 g (57.5 mmol) of the 2,3-difluoro-4-ethoxyphenol obtained by the method described in the second step of Example 1, 17.4 g (68.9 mmol) of trans-4-(trans-4-propylcyclohexyl)cyclohexanecarboxylic acid, 0.2 g (1.8 mmol) of DMAP, and 300 ml of dichloromethane were mixed. To this mixture was added dropwise 80 ml of solution of 12.3 g (60.0 mmol) of DCC in dichloromethane under a condition cooled with ice in 10 min, warmed up to room temperature, and then stirred as it was overnight. Separated crystals were removed by filtration, the solvent was distilled of under a reduced pressure from the filtrate, and the residue thus obtained was purified by silica gel column chromatography (eluent: toluene) and further recrystallized from heptane to obtain 20.8 g of 2,3-difluoro-4-ethoxyphenyl trans-4-(trans-4-propylcyclohexyl) benzoate.

(Second step)

In a 300 ml sealed glass tube, 20.8 g (50.9 mmol) of the 2,3-difluoro-4-ethoxyphenyl trans-4-(trans-4-propylcyclohexyl)benzoate was dissolved in 150 ml of toluene, 24.7 g (61.1 mmol) of Lawesson's reagent was added thereto, and then the solution was heated at 140° C. on an oil bath for 8 hours. Water in an amount of 200 ml was added to the reaction solution and then the toluene layer was separated. The toluene layer was washed with 150 ml of water thrice and then dried over anhydrous magnesium sulfate. The solvent was distilled off under a reduced pressure, and the brown residue thus obtained was purified by silica gel column chromatography (eluent: mixed solvent of heptane/toluene) and then recrystallized from heptane to obtain -6.7 g of yellow needle-shaped crystalline 2,3-difluoro-4-ethoxyphenyl trans-4-(trans-4-n-propylcyclohexyl)cyclohexane-thiocarboxylate.

(Third step)

To a suspension prepared by suspending 8.5 g (47.4 mmol) of N-bromosuccinimide in 50 ml of methylene chloride was added dropwise 6.9 g of hydrogen fluoride-pyridine at -78° C. in 20 min and stirred as it was for 10 min. To this reaction solution was added dropwise 40 ml of solution of 6.7 g (15.8 mmol) of 2,3-difluoro-4-ethoxyphenyl trans-4-(trans-4-n-propylcyclohexyl) cyclohexane-thiocarboxylate in methylene chloride in 40 min and stirred as it was for 2 hours. The reaction solution was poured into saturated aqueous sodium carbonate solution to terminate the reaction and then the methylene chloride layer was separated. The methylene chloride layer was washed with 10% aqueous sodium bisulfite solution and water in turn, and then dried over anhydrous magnesium sulfate. The solvent was distilled off under a reduced pressure, and the residue thus obtained was purified by silica gel column chromatography (eluent: heptane) and further recrystallized from heptane to obtain 4.4 g of the subjective compound. Data of various kind of spectrums supported the structure of the compound described above.

$^{19}$F-NMR (CDCl3) δ (ppm): −79.4 (s, —CF$_2$O—)

Mass spectrum: 452 (M$^+$)

Compounds shown below can be prepared by selecting known procedures of organic synthesis and using them in combination with reference to the procedures described in Examples described above.

m = 1, n = 0
| No. | R¹ | A¹ | X¹ | A² | X² | A⁴ | Y¹ |
|---|---|---|---|---|---|---|---|
| 1 | $C_3H_7$ |  |  |  | $CO_2$ | 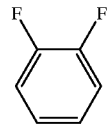 | $OC_2H_5$ |
| 2 | $C_3H_7$ |  | 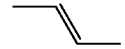 |  | $CO_2$ | 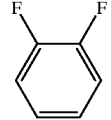 | $OC_2H_5$ |
| 3 | $C_3H_7$ |  | 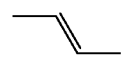 |  | $CO_2$ | 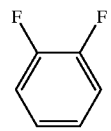 | $OC_2H_5$ |
| 4 | $C_3H_7$ |  | 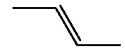 |  | $CO_2$ | 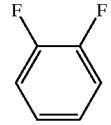 | $OCH_3$ |
| 5 | $C_3H_7$ |  | 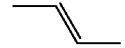 |  | $CO_2$ | 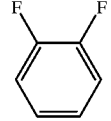 | $OC_2H_5$ |
| 6 | $C_3H_7$ |  | 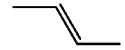 |  | $CO_2$ | 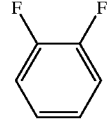 | $OC_3H_7$ |
| 7 | $C_5H_{11}$ |  | 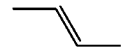 |  | $CO_2$ | 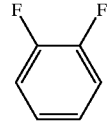 | $OC_2H_5$ |
| 8 | $C_5H_{11}$ |  | 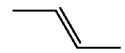 |  | $CO_2$ | 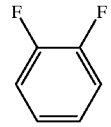 | $OC_2H_5$ |
| 9 | $C_5H_{11}$ |  | 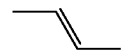 |  | $CO_2$ | 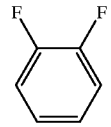 | $OCH_3$ |
| 10 | $C_5H_{11}$ |  | 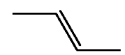 |  | $CO_2$ | 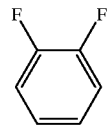 | $OC_2H_5$ |

-continued
| | | | | | | | |
|---|---|---|---|---|---|---|---|
| 11 | C$_5$H$_{11}$ |  | 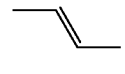 |  | CO$_2$ | 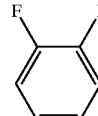 | OC$_3$H$_7$ |
| 12 | C$_5$H$_{11}$ |  | 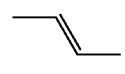 |  | CO$_2$ | 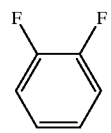 | OCH$_3$ |
| 13 | C$_5$H$_{11}$ |  | 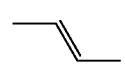 |  | CO$_2$ | 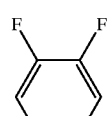 | OC$_2$H$_5$ |
| 14 | C$_5$H$_{11}$ |  | 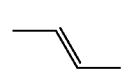 |  | CO$_2$ | 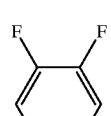 | OC$_3$H$_7$ |
| 15 | C$_3$H$_7$ |  | 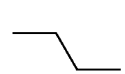 |  | CO$_2$ | 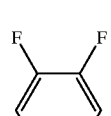 | OC$_2$H$_5$ |
| 16 | C$_3$H$_7$ |  | 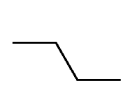 |  | CO$_2$ | 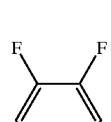 | OC$_2$H$_5$ |
| 17 | C$_3$H$_7$ |  | 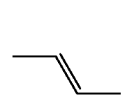 |  | CO$_2$ | 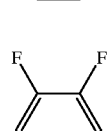 | OC$_2$H$_5$ |
| 18 | C$_3$H$_7$ |  | 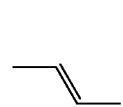 |  | CO$_2$ | 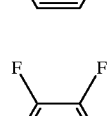 | OCH$_3$ |
| 19 | C$_3$H$_7$ |  |  |  | CO$_2$ | 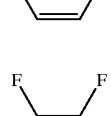 | OC$_2$H$_5$ |
| 20 | C$_3$H$_7$ |  |  |  | CO$_2$ | 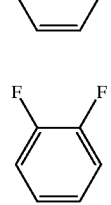 | OC$_3$H$_7$ |

-continued

| No. | R¹ | A¹ | X¹ | A² | X² | A³ | X³ | A⁴ | Y¹ |
|---|---|---|---|---|---|---|---|---|---|
| 21 | C₅H₁₁ | cyclohexyl | -CH₂CH₂- | 3-F-phenyl | CO₂ | | 3,4-diF-phenyl | | OC₂H₅ |
| 22 | C₅H₁₁ | phenyl | -CH₂CH₂- | 3-F-phenyl | CO₂ | | 3,4-diF-phenyl | | OC₂H₅ |
| 23 | C₅H₁₁ | cyclohexyl | -CH=CH- | 3-F-phenyl | CO₂ | | 3,4-diF-phenyl | | OC₂H₅ |
| 24 | C₅H₁₁ | phenyl | -CH=CH- | 3-F-phenyl | CO₂ | | 3,4-diF-phenyl | | OCH₃ |
| 25 | C₅H₁₁ | phenyl | -CH=CH- | 3-F-phenyl | CO₂ | | 3,4-diF-phenyl | | OC₂H₅ |
| 26 | C₅H₁₁ | phenyl | -CH=CH- | 3-F-phenyl | CO₂ | | 3,4-diF-phenyl | | OC₃H₇ | m = n = 1

| No. | R¹ | A¹ | X¹ | A² | X² | A³ | X³ | A⁴ | Y¹ |
|---|---|---|---|---|---|---|---|---|---|
| 27 | C₃H₇ | cyclohexyl | — | 3-F-phenyl | CO₂ | phenyl | — | 3,4-diF-phenyl | OC₂H₅ |
| 28 | C₃H₇ | cyclohexyl | — | 3-F-phenyl | CO₂ | 3,4-diF-phenyl | — | phenyl | OC₂H₅ |
| 29 | C₃H₇ | phenyl | — | 3-F-phenyl | CO₂ | phenyl | — | 3,4-diF-phenyl | OC₂H₅ |
| 30 | C₃H₇ | phenyl | — | 3-F-phenyl | CO₂ | 3,4-diF-phenyl | — | phenyl | OC₂H₅ |

-continued
| | | | | | | | | |
|---|---|---|---|---|---|---|---|---|
| 31 | C₃H₇ |  | — | 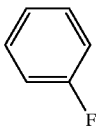 | CO₂ | 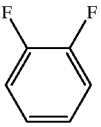 |  | OCH₃ |
| 32 | C₃H₇ |  | 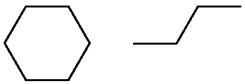 | 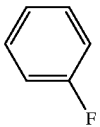 | CO₂ |  | 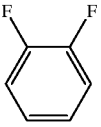 | OC₂H₅ |
| 33 | C₃H₇ |  | 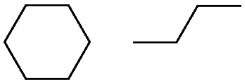 | 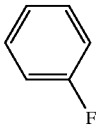 | CO₂ |  |  | OC₂H₅ |
| 34 | C₃H₇ |  | 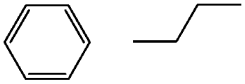 | 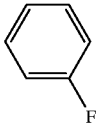 | CO₂ |  | 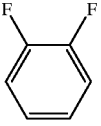 | OC₂H₅ |
| 35 | C₃H₇ |  | 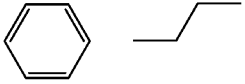 | 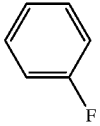 | CO₂ |  |  | OC₂H₅ |
| 36 | C₃H₇ |  | 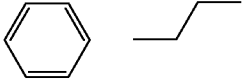 | 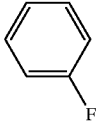 | CO₂ |  |  | OC₂H₅ |
| 37 | C₃H₇ |  | 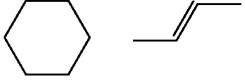 | 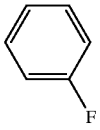 | CO₂ |  |  | OC₂H₅ |
| 38 | C₃H₇ |  | 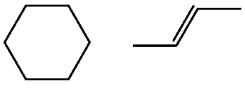 | 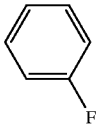 | CO₂ | 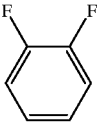 |  | OC₂H₅ |
| 39 | C₃H₇ |  | 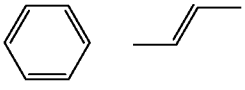 | 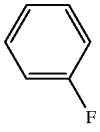 | CO₂ |  |  | OC₂H₅ |
| 40 | C₃H₇ |  | 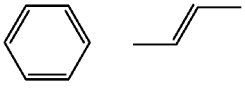 | 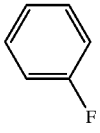 | CO₂ |  |  | OC₂H₅ |

-continued

| | | | | | | | | | |
|---|---|---|---|---|---|---|---|---|---|
| 41 | C<sub>5</sub>H<sub>11</sub> |  | 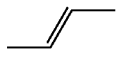 | 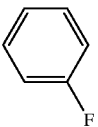 | CO<sub>2</sub> | 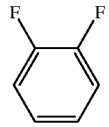 | — |  | OC<sub>3</sub>H<sub>7</sub> |
| 42 | C<sub>3</sub>H<sub>7</sub> |  | — |  | — | 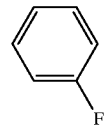 | CO<sub>2</sub> | 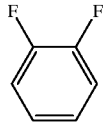 | OC<sub>2</sub>H<sub>5</sub> |
| 43 | C<sub>3</sub>H<sub>7</sub> |  | — |  | — | 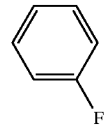 | CO<sub>2</sub> |  | OCH<sub>3</sub> |
| 44 | C<sub>5</sub>H<sub>11</sub> |  | — |  | — | 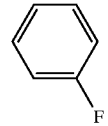 | CO<sub>2</sub> |  | OC<sub>2</sub>H<sub>5</sub> |
| 45 | C<sub>5</sub>H<sub>11</sub> |  | — |  | — | 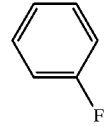 | CO<sub>2</sub> |  | OC<sub>3</sub>H<sub>7</sub> |
| 46 | C<sub>3</sub>H<sub>7</sub> |  | 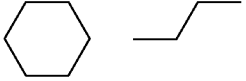 |  | — | 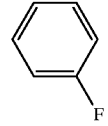 | CO<sub>2</sub> |  | OC<sub>2</sub>H<sub>5</sub> |
| 47 | C<sub>3</sub>H<sub>7</sub> |  | 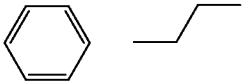 |  | — | 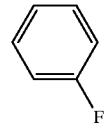 | CO<sub>2</sub> |  | OCH<sub>3</sub> |
| 48 | C<sub>5</sub>H<sub>11</sub> |  | 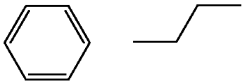 |  | — | 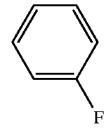 | CO<sub>2</sub> |  | OC<sub>2</sub>H<sub>5</sub> |
| 49 | C<sub>5</sub>H<sub>11</sub> |  | 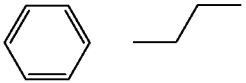 |  | — | 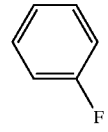 | CO<sub>2</sub> |  | OC<sub>3</sub>H<sub>7</sub> |
| 50 | C<sub>3</sub>H<sub>7</sub> |  |  |  | — |  | CO<sub>2</sub> |  | OC<sub>2</sub>H<sub>5</sub> |

-continued
| | | | | | | | | |
|---|---|---|---|---|---|---|---|---|
| 51 | C3H7 |  | 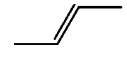 |  | — |  | CO2 | 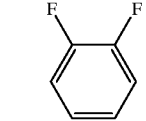 | OCH3 |
| 52 | C5H11 |  | 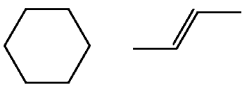 |  | — |  | CO2 | 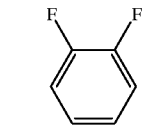 | OC2H5 |
| 53 | C5H11 |  | 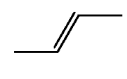 |  | — |  | CO2 | 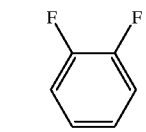 | OC3H7 |
| 54 | C3H7 |  | — |  | — |  | CO2 | 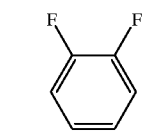 | OC2H5 |
| 55 | C3H7 |  | — | 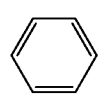 | — |  | CO2 | 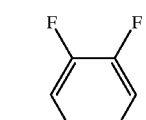 | OCH3 |
| 56 | C5H11 |  | — | 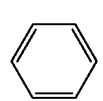 | — |  | CO2 | 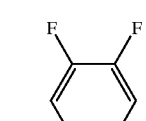 | OC2H5 |
| 57 | C5H11 |  | — | 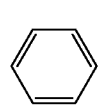 | — |  | CO2 | 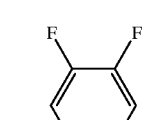 | OC3H7 |
| 58 | C3H7 |  | 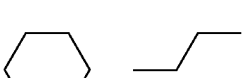 | 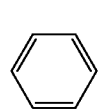 | — |  | CO2 | 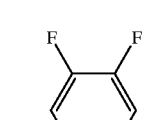 | OC2H5 |
| 59 | C3H7 |  | 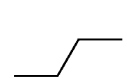 | 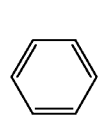 | — |  | CO2 | 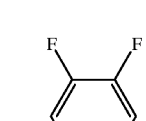 | OCH3 |
| 60 | C5H11 |  |  | 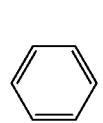 | — |  | CO2 | 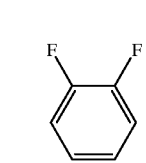 | OC2H5 |

-continued
| | | | | | | | | | |
|---|---|---|---|---|---|---|---|---|---|
| 61 | C₅H₁₁ |  | 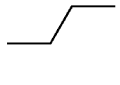 |  | — |  | CO₂ | 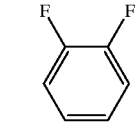 | OC₃H₇ |
| 62 | C₃H₇ |  | 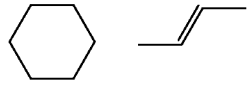 |  | — |  | CO₂ | 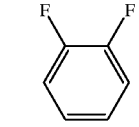 | OC₂H₅ |
| 63 | C₃H₇ |  | 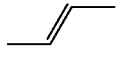 |  | — |  | CO₂ | 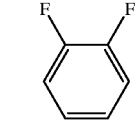 | OCH₃ |
| 64 | C₅H₁₁ |  | 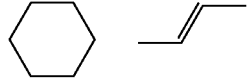 |  | — |  | CO₂ | 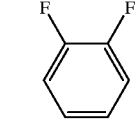 | OC₂H₅ |
| 65 | C₅H₁₁ |  | 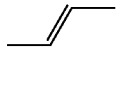 |  | — |  | CO₂ | 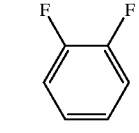 | OC₃H₇ |
| 66 | C₃H₇ |  | — |  | 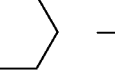 | 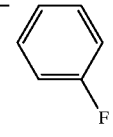 | CO₂ | 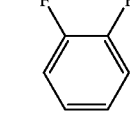 | OC₂H₅ |
| 67 | C₃H₇ |  | — |  | 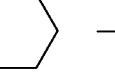 | 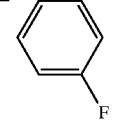 | CO₂ | 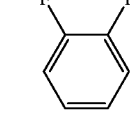 | OCH₃ |
| 68 | C₅H₁₁ |  | — |  | 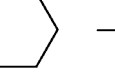 | 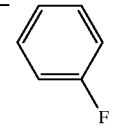 | CO₂ | 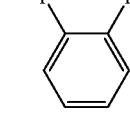 | OC₂H₅ |
| 69 | C₅H₁₁ |  | — |  | 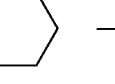 | 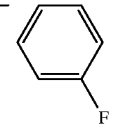 | CO₂ | 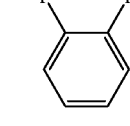 | OC₃H₇ |
| 70 | C₃H₇ |  | 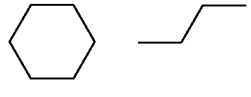 |  | 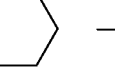 | 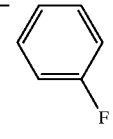 | CO₂ | 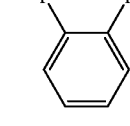 | OC₂H₅ |

-continued
| | | | | | | | | |
|---|---|---|---|---|---|---|---|---|
| 71 | C$_3$H$_7$ |  | 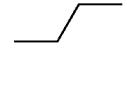 |  | 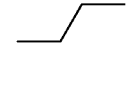 | 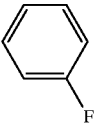 | CO$_2$ | 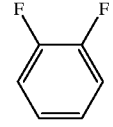 | OCH$_3$ |
| 72 | C$_5$H$_{11}$ |  | 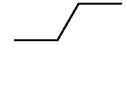 |  | 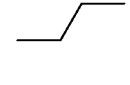 | 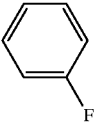 | CO$_2$ | 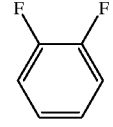 | OC$_2$H$_5$ |
| 73 | C$_5$H$_{11}$ |  | 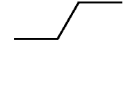 |  | 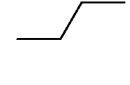 | 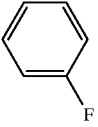 | CO$_2$ | 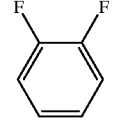 | OC$_3$H$_7$ |
| 74 | C$_3$H$_7$ |  | 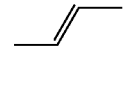 |  | 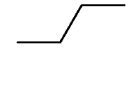 | 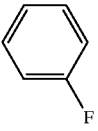 | CO$_2$ | 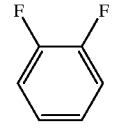 | OC$_2$H$_5$ |
| 75 | C$_3$H$_7$ |  | 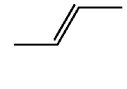 |  | 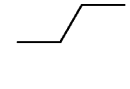 | 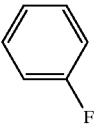 | CO$_2$ | 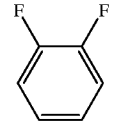 | OCH$_3$ |
| 76 | C$_5$H$_{11}$ |  | 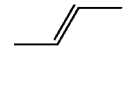 |  | 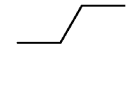 | 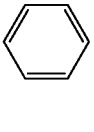 | CO$_2$ | 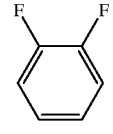 | OC$_2$H$_5$ |
| 77 | C$_5$H$_{11}$ |  | 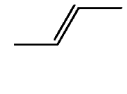 |  | 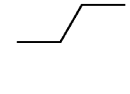 | 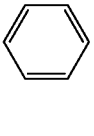 | CO$_2$ | 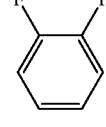 | OC$_3$H$_7$ |
| 78 | C$_3$H$_7$ |  | — |  | 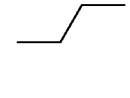 | 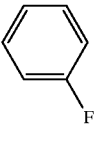 | CO$_2$ | 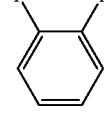 | OC$_2$H$_5$ |
| 79 | C$_3$H$_7$ |  | — |  | 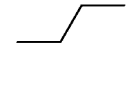 | 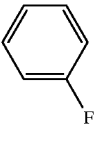 | CO$_2$ | 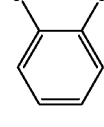 | OCH$_3$ |
| 80 | C$_5$H$_{11}$ |  | — |  | 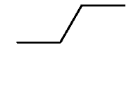 | 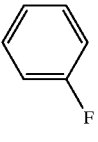 | CO$_2$ | 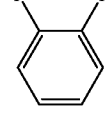 | OC$_2$H$_5$ |

-continued
| | | | | | | | | |
|---|---|---|---|---|---|---|---|---|
| 81 | $C_5H_{11}$ |  | — |  | 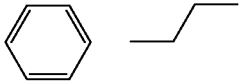 | $CO_2$ | 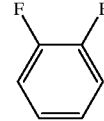 | $OC_3H_7$ |
| 82 | $C_3H_7$ |  | 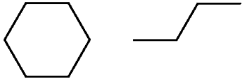 |  | 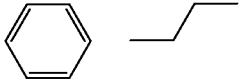 | $CO_2$ | 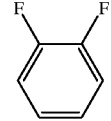 | $OC_2H_5$ |
| 83 | $C_3H_7$ |  | 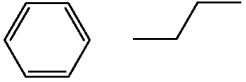 |  | 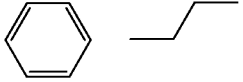 | $CO_2$ | 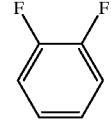 | $OCH_3$ |
| 84 | $C_5H_{11}$ |  | 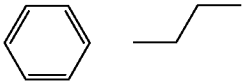 |  | 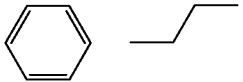 | $CO_2$ | 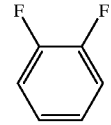 | $OC_2H_5$ |
| 85 | $C_5H_{11}$ |  | 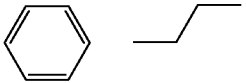 |  | 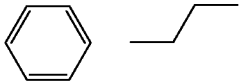 | $CO_2$ | 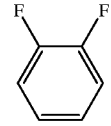 | $OC_3H_7$ |
| 86 | $C_3H_7$ |  | 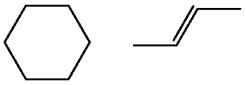 |  | 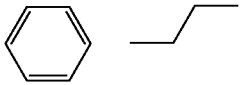 | $CO_2$ | 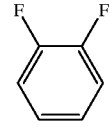 | $OC_2H_5$ |
| 87 | $C_3H_7$ |  | 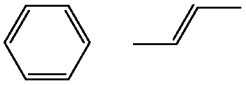 |  | 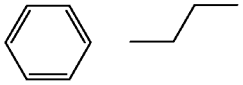 | $CO_2$ | 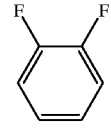 | $OCH_3$ |
| 88 | $C_5H_{11}$ |  | 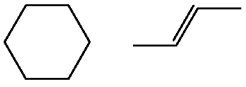 |  | 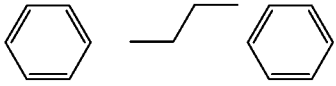 | $CO_2$ | 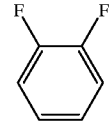 | $OC_2H_5$ |
| 89 | $C_5H_{11}$ |  | 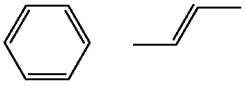 |  | 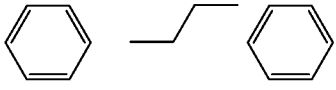 | $CO_2$ | 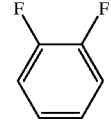 | $OC_3H_7$ |
| 90 | $C_3H_7$ |  | — |  | 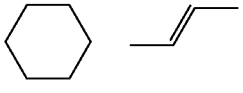 | $CO_2$ |  | $OC_2H_5$ |

-continued
| | | | | | | | | | |
|---|---|---|---|---|---|---|---|---|---|
| 91 | C_3H_7 |  | — |  | 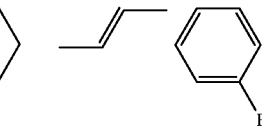 | CO_2 | 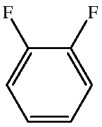 | OC_2H_5 |
| 92 | C_3H_7 |  | 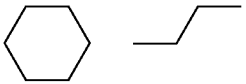 |  | 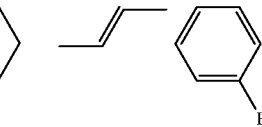 | CO_2 | 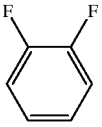 | OC_2H_5 |
| 93 | C_3H_7 |  | 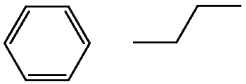 |  | 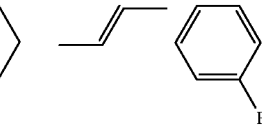 | CO_2 | 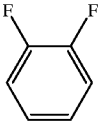 | OC_2H_5 |
| 94 | C_3H_7 |  | 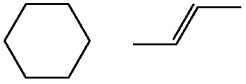 |  | 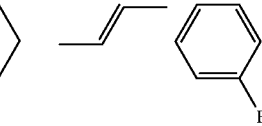 | CO_2 | 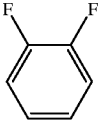 | OC_2H_5 |
| 95 | C_3H_7 |  | 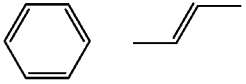 |  | 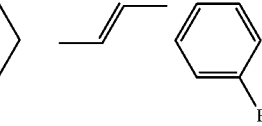 | CO_2 |  | OC_2H_5 |
| 96 | C_5H_{11} |  | 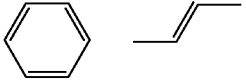 |  | 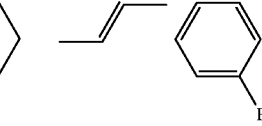 | CO_2 |  | OCH_3 |
| 97 | C_3H_7 |  | — |  | 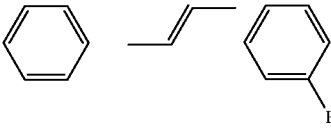 | CO_2 |  | OC_2H_5 |
| 98 | C_3H_7 |  | — |  | 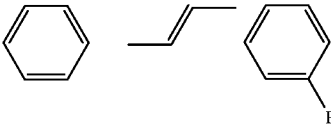 | CO_2 |  | OC_2H_5 |
| 99 | C_3H_7 |  | 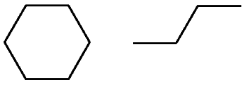 |  | 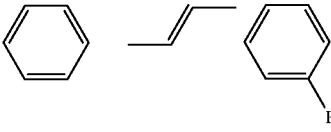 | CO_2 |  | OC_2H_5 |
| 100 | C_3H_7 |  | 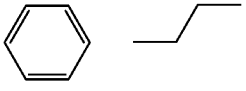 |  | 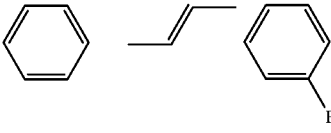 | CO_2 |  | OC_2H_5 |

-continued
| | | | | | | | | | |
|---|---|---|---|---|---|---|---|---|---|
| 101 | C_3H_7 |  | 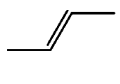 |  | 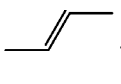 | 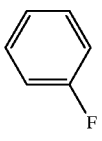 | CO_2 | 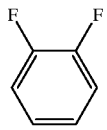 | OC_2H_5 |
| 102 | C_3H_7 |  | 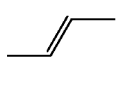 |  | 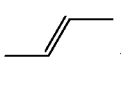 | 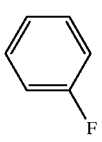 | CO_2 | 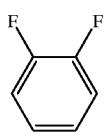 | OC_2H_5 |
| 103 | C_5H_{11} |  | 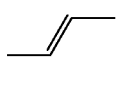 |  | 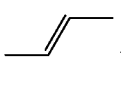 | 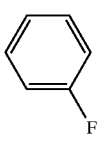 | CO_2 | 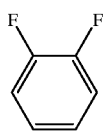 | OC_3H_7 |
| 104 | C_3H_7 |  | — |  | 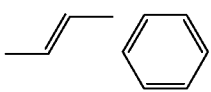 |  | CO_2 | 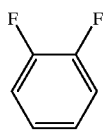 | OC_2H_5 |
| 105 | C_3H_7 |  | — |  | 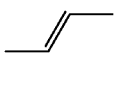 | 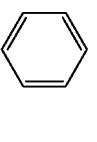 | CO_2 | 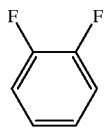 | OC_2H_5 |
| 106 | C_3H_7 |  | 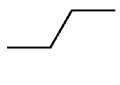 |  | 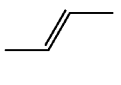 |  | CO_2 | 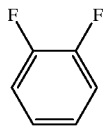 | OC_2H_5 |
| 107 | C_3H_7 |  | 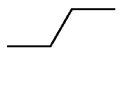 |  | 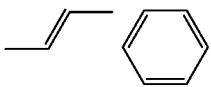 |  | CO_2 | 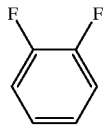 | OC_2H_5 |
| 108 | C_3H_7 |  | 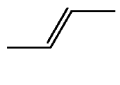 |  | 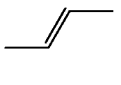 | 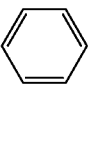 | CO_2 | 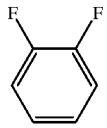 | OC_2H_5 |
| 109 | C_3H_7 |  | 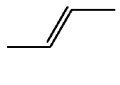 |  | 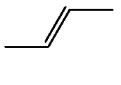 | 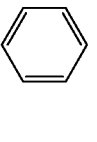 | CO_2 | 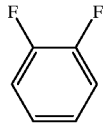 | OC_2H_5 |
| 110 | C_5H_{11} |  | 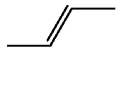 |  | 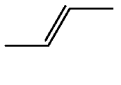 | 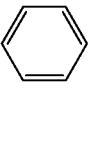 | CO_2 | 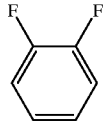 | OCH_3 |

-continued
| | | | | | | | | |
|---|---|---|---|---|---|---|---|---|
| 111 | C₃H₇ |  | — |  |  |  | CO₂ | 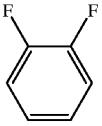 | OC₂H₅ |
| 112 | C₃H₇ |  | — |  |  |  | CO₂ | 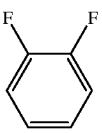 | OC₂H₅ |
| 113 | C₃H₇ |  |  |  |  |  | CO₂ | 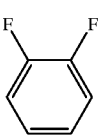 | OC₂H₅ |
| 114 | C₃H₇ |  |  |  |  |  | CO₂ | 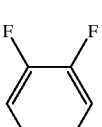 | OC₂H₅ |
| 115 | C₃H₇ |  |  |  |  |  | CO₂ | 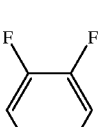 | OC₂H₅ |
| 116 | C₃H₇ |  |  |  |  |  | CO₂ | 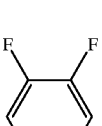 | OC₂H₅ |
| 117 | C₅H₁₁ |  |  |  |  |  | CO₂ | 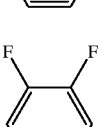 | OC₃H₇ |
| 118 | C₃H₇ |  | — |  |  |  | CO₂ | 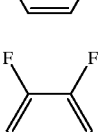 | OC₂H₅ |
| 119 | C₃H₇ |  | — |  |  |  | CO₂ | 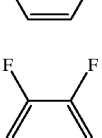 | OC₂H₅ |
| 120 | C₃H₇ |  |  |  |  |  | CO₂ | 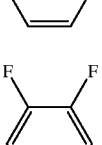 | OC₂H₅ |
| 121 | C₃H₇ |  |  |  |  |  | CO₂ | 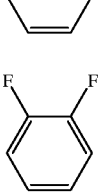 | OC₂H₅ |

-continued
| | | | | | | | | |
|---|---|---|---|---|---|---|---|---|
| 122 | C$_3$H$_7$ |  | 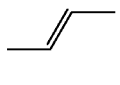 |  | 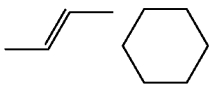 | CO$_2$ |  | OC$_2$H$_5$ |
| 123 | C$_3$H$_7$ | 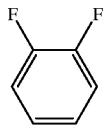 |  | 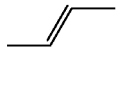 |  | CO$_2$ | 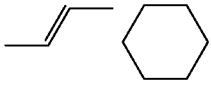 | OC$_2$H$_5$ |
| 124 | C$_5$H$_{11}$ |  | 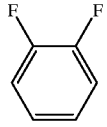 |  | 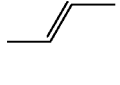 | CO$_2$ |  | OCH$_3$ |
| 125 | C$_3$H$_7$ | 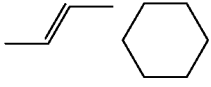 | — |  | 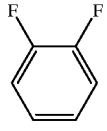 | CO$_2$ |  | OC$_2$H$_5$ |
| 126 | C$_3$H$_7$ |  | — | 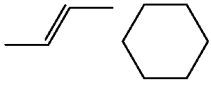 |  | CO$_2$ |  | OC$_2$H$_5$ |
| 127 | C$_3$H$_7$ |  |  | 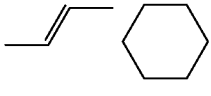 |  | CO$_2$ | 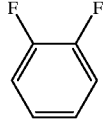 | OC$_2$H$_5$ |
| 128 | C$_3$H$_7$ |  | 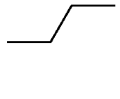 |  | 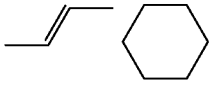 | CO$_2$ |  | OC$_2$H$_5$ |
| 129 | C$_3$H$_7$ | 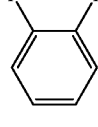 |  | 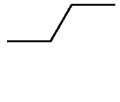 |  | CO$_2$ | 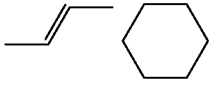 | OC$_2$H$_5$ |
| 130 | C$_3$H$_7$ |  | 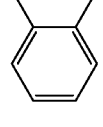 |  | 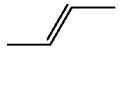 | CO$_2$ |  | OC$_2$H$_5$ |
| 131 | C$_5$H$_{11}$ | 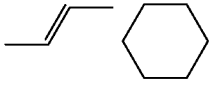 |  | 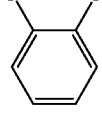 |  | CO$_2$ | 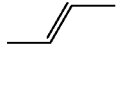 | OC$_3$H$_7$ |

-continued
| | | | m = 1, n = 0 | | | | |
|---|---|---|---|---|---|---|---|
| No. | R¹ | A¹ | X¹ | A² | X² | A⁴ | Y¹ |
| 132 | $C_3H_7$ |  | 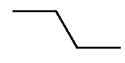 |  | $CF_2O$ | 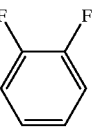 | $OC_2H_5$ |
| 133 | $C_3H_7$ |  | 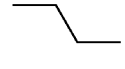 |  | $CF_2O$ |  | $OC_2H_5$ |
| 134 | $C_3H_7$ |  | 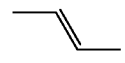 |  | $CF_2O$ |  | $OC_2H_5$ |
| 135 | $C_3H_7$ |  | 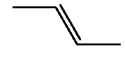 |  | $CF_2O$ |  | $OCH_3$ |
| 136 | $C_3H_7$ |  | 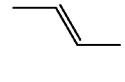 |  | $CF_2O$ |  | $OC_2H_5$ |
| 137 | $C_3H_7$ |  | 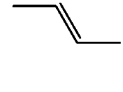 |  | $CF_2O$ |  | $OC_3H_7$ |
| 138 | $C_5H_{11}$ |  |  |  | $CF_2O$ | 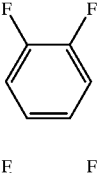 | $OC_2H_5$ |
| 139 | $C_5H_{11}$ |  |  |  | $CF_2O$ | 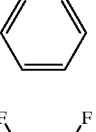 | $OC_2H_5$ |
| 140 | $C_5H_{11}$ |  |  |  | $CF_2O$ | 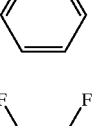 | $OC_2H_5$ |
| 141 | $C_5H_{11}$ |  |  |  | $CF_2O$ | 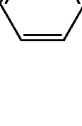 | $OCH_3$ |

-continued
| | | | | | | | |
|---|---|---|---|---|---|---|---|
| 142 | C_5H_{11} |  | 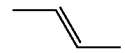 |  | CF_2O | 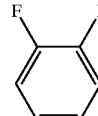 | OC_2H_5 |
| 143 | C_5H_{11} |  | 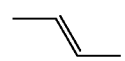 |  | CF_2O | 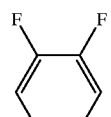 | OC_3H_7 |
| 144 | C_3H_7 |  | — |  | CF_2O | 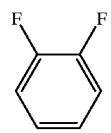 | OC_2H_5 |
| 145 | C_3H_7 |  | — |  | CF_2O | 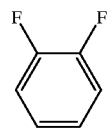 | OC_2H_5 |
| 146 | C_3H_7 |  | — |  | CF_2O | 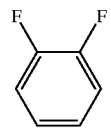 | OC_2H_5 |
| 147 | C_3H_7 |  | — |  | CF_2O | 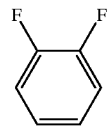 | OCH_3 |
| 148 | C_3H_7 |  | — |  | CF_2O | 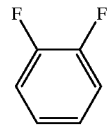 | OC_2H_5 |
| 149 | C_3H_7 |  | — |  | CF_2O | 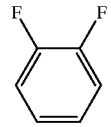 | OC_3H_7 |
| 150 | C_5H_{11} |  | — |  | CF_2O | 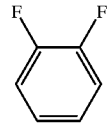 | OC_2H_5 |
| 151 | C_5H_{11} |  | — |  | CF_2O | 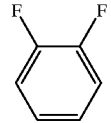 | OC_2H_5 |

-continued
| | | | | | | | |
|---|---|---|---|---|---|---|---|
| 152 | C₅H₁₁ |  | — | 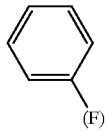(F) | CF₂O | 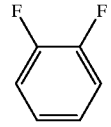 | OC₂H₅ |
| 153 | C₅H₁₁ |  | — |  | CF₂O |  | OCH₃ |
| 154 | C₅H₁₁ |  | — |  | CF₂O | 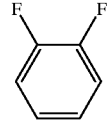 | OC₂H₅ |
| 155 | C₅H₁₁ |  | — |  | CF₂O | 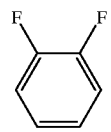 | OC₃H₇ |
| 156 | C₃H₇ |  | 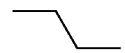 |  | CF₂O | 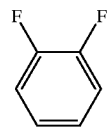 | OC₂H₅ |
| 157 | C₃H₇ |  | 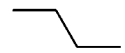 |  | CF₂O | 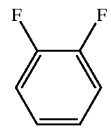 | OC₂H₅ |
| 158 | C₃H₇ |  | 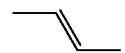 |  | CF₂O | 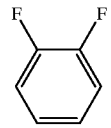 | OC₂H₅ |
| 159 | C₃H₇ |  | 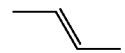 |  | CF₂O | 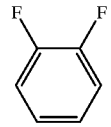 | OCH₃ |
| 160 | C₃H₇ |  | 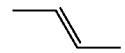 |  | CF₂O | 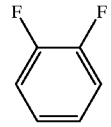 | OC₂H₅ |
| 161 | C₃H₇ |  | 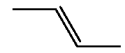 |  | CF₂O | 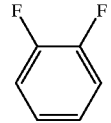 | OC₃H₇ |

-continued
| No. | R¹ | A¹ | X¹ | A² | X² | A³ | Y¹ |
|---|---|---|---|---|---|---|---|
| 162 | $C_5H_{11}$ |  | 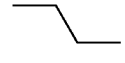 |  | $CF_2O$ | 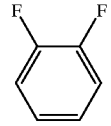 | $OC_2H_5$ |
| 163 | $C_5H_{11}$ |  | 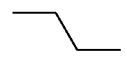 |  | $CF_2O$ | 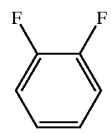 | $OC_2H_5$ |
| 164 | $C_5H_{11}$ |  | 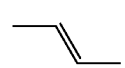 |  | $CF_2O$ | 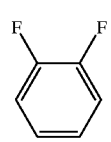 | $OC_2H_5$ |
| 165 | $C_5H_{11}$ |  | 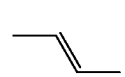 |  | $CF_2O$ | 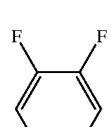 | $OC_2H_5$ |
| 166 | $C_5H_{11}$ |  | 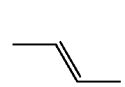 |  | $CF_2O$ | 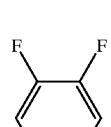 | $OC_2H_5$ |
| 167 | $C_5H_{11}$ |  | 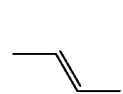 |  | $CF_2O$ | 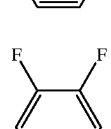 | $OC_2H_5$ |
m = n = 1
| No. | R¹ | A¹ | X¹ | A² | X² | A³ | X³ | A⁴ | Y¹ |
|---|---|---|---|---|---|---|---|---|---|
| 168 | $C_3H_7$ |  | — |  | $CF_2O$ |  | — |  | $OC_2H_5$ |
| 169 | $C_3H_7$ |  | — |  | $CF_2O$ | 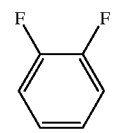 | — |  | $OC_2H_5$ |
| 170 | $C_3H_7$ |  | — |  | $CF_2O$ |  | — | 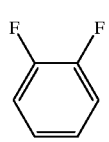 | $OC_2H_5$ |
| 171 | $C_3H_7$ |  | — |  | $CF_2O$ | 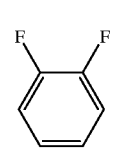 | — |  | $OC_2H_5$ |

-continued
| | | | | | | | | | |
|---|---|---|---|---|---|---|---|---|---|
| 172 | C$_5$H$_{11}$ |  | — |  | CF$_2$O | 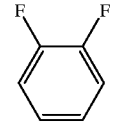 | — |  | OCH$_3$ |
| 173 | C$_3$H$_7$ |  | 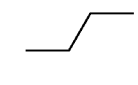 |  | CF$_2$O |  | — | 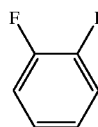 | OC$_2$H$_5$ |
| 174 | C$_3$H$_7$ |  | 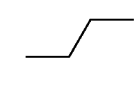 |  | CF$_2$O | 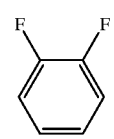 | — |  | OC$_2$H$_5$ |
| 175 | C$_3$H$_7$ |  | 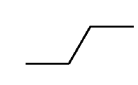 |  | CF$_2$O |  | — | 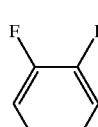 | OC$_2$H$_5$ |
| 176 | C$_3$H$_7$ |  | 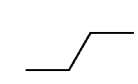 |  | CF$_2$O | 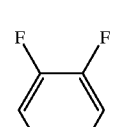 | — |  | OC$_2$H$_5$ |
| 177 | C$_5$H$_{11}$ |  | 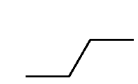 |  | CF$_2$O | 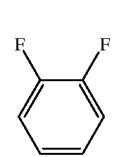 | — |  | OCH$_3$ |
| 178 | C$_3$H$_7$ |  | 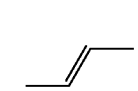 |  | CF$_2$O |  | — | 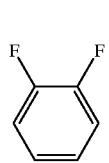 | OC$_2$H$_5$ |
| 179 | C$_3$H$_7$ |  | 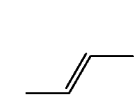 |  | CF$_2$O | 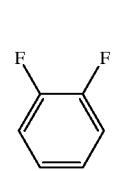 | — |  | OC$_2$H$_5$ |
| 180 | C$_3$H$_7$ |  | 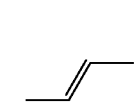 |  | CF$_2$O |  | — | 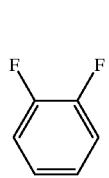 | OC$_2$H$_5$ |
| 181 | C$_3$H$_7$ |  | 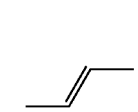 |  | CF$_2$O | 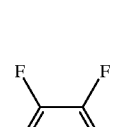 | — |  | OC$_2$H$_5$ |
| 182 | C$_5$H$_{11}$ |  | 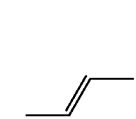 |  | CF$_2$O | 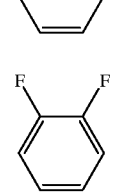 | — |  | OC$_2$H$_5$ |

-continued
| | | | | | | | |
|---|---|---|---|---|---|---|---|
| 183 | C$_3$H$_7$ |  | — |  | CF$_2$O |  | OC$_2$H$_5$ |
| 184 | C$_3$H$_7$ | 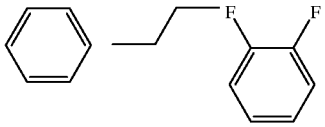 | — |  | CF$_2$O |  | OC$_2$H$_5$ |
| 185 | C$_3$H$_7$ |  | — | 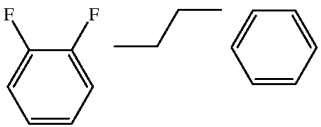 | CF$_2$O |  | OC$_2$H$_5$ |
| 186 | C$_3$H$_7$ |  | — |  | CF$_2$O | 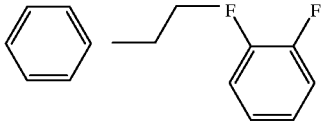 | OC$_2$H$_2$ |
| 187 | C$_3$H$_7$ |  | — |  | CF$_2$O |  | OCH$_3$ |
| 188 | C$_3$H$_7$ |  |  |  | CF$_2$O |  | OC$_2$H$_5$ |
| 189 | C$_3$H$_7$ |  |  | 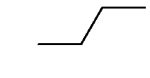 | CF$_2$O |  | OC$_2$H$_5$ |
| 190 | C$_3$H$_7$ |  | 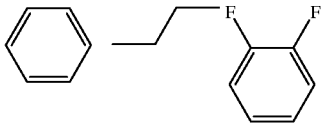 |  | CF$_2$O | 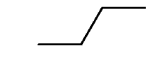 | OC$_2$H$_5$ |
| 191 | C$_3$H$_7$ |  |  |  | CF$_2$O |  | OC$_2$H$_5$ |
| 192 | C$_5$H$_{11}$ | 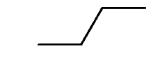 |  |  | CF$_2$O | 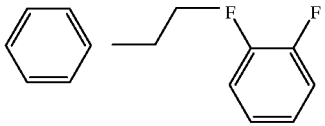 | OCH$_3$ |

-continued
| | | | | | | | | |
|---|---|---|---|---|---|---|---|---|
| 193 | $C_3H_7$ |  | 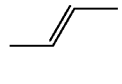 |  | $CF_2O$ |  | 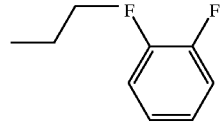 | $OC_2H_5$ |
| 194 | $C_3H_7$ |  | 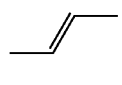 |  | $CF_2O$ | 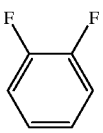 | 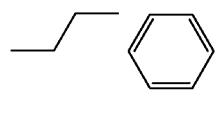 | $OC_2H_5$ |
| 195 | $C_3H_7$ |  | 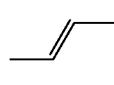 |  | $CF_2O$ |  | 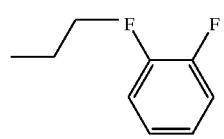 | $OC_2H_5$ |
| 196 | $C_3H_7$ |  | 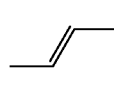 |  | $CF_2O$ | 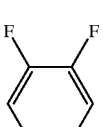 | 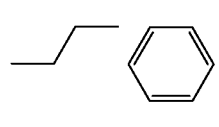 | $OC_2H_5$ |
| 197 | $C_5H_{11}$ |  | 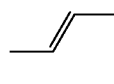 |  | $CF_2O$ |  | 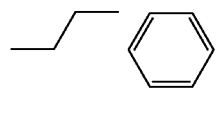 | $OC_3H_7$ |
| 198 | $C_3H_7$ |  | — |  | $CF_2O$ |  | — | $OC_2H_5$ |
| 199 | $C_3H_7$ |  | — |  | $CF_2O$ |  | — | $OC_2H_5$ |
| 200 | $C_3H_7$ | 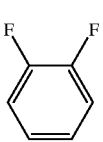 | — |  | $CF_2O$ |  | — | $OC_2H_5$ |
| 201 | $C_3H_7$ |  | — |  | $CF_2O$ | 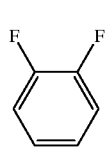 | — | $OC_2H_5$ |
| 202 | $C_3H_7$ |  | — |  | $CF_2O$ | 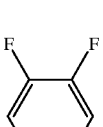 | — | $OC_2H_5$ |
| 203 | $C_3H_7$ |  |  |  | $CF_2O$ | 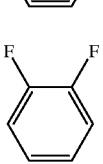 | — |  | $OC_2H_5$ |

-continued
| | | | | | | | | | |
|---|---|---|---|---|---|---|---|---|---|
| 204 | C$_3$H$_7$ |  | 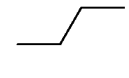 |  | CF$_2$O | 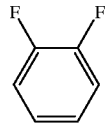 | — |  | OC$_2$H$_5$ |
| 205 | C$_3$H$_7$ |  | 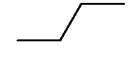 |  | CF$_2$O |  | — | 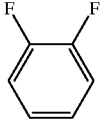 | OC$_2$H$_5$ |
| 206 | C$_3$H$_7$ |  | 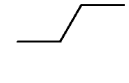 |  | CF$_2$O |  | — |  | OC$_2$H$_5$ |
| 207 | C$_5$H$_{11}$ |  | 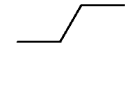 |  | CF$_2$O | 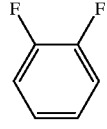 | — |  | OC$_3$H$_7$ |
| 208 | C$_3$H$_7$ |  | 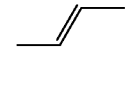 |  | CF$_2$O |  | — | 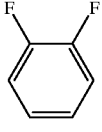 | OC$_2$H$_5$ |
| 209 | C$_3$H$_7$ |  | 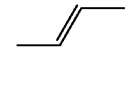 |  | CF$_2$O | 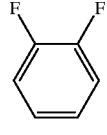 | — |  | OC$_2$H$_5$ |
| 210 | C$_3$H$_7$ |  | 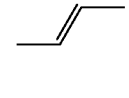 |  | CF$_2$O |  | — |  | OC$_2$H$_5$ |
| 211 | C$_3$H$_7$ |  | 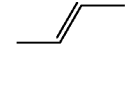 |  | CF$_2$O | 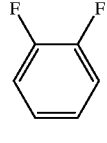 | — |  | OC$_2$H$_5$ |
| 212 | C$_5$H$_{11}$ |  | 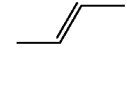 |  | CF$_2$O | 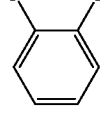 | — |  | OC$_3$H$_7$ |
| 213 | C$_3$H$_7$ |  | — |  | — |  | CF$_2$O |  | OC$_2$H$_5$ |

-continued
| | | | | | | | | |
|---|---|---|---|---|---|---|---|---|
| 214 | C₃H₇ |  | — |  | — |  | CF₂O | 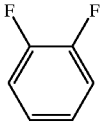 | OC₂H₅ |
| 215 | C₃H₇ |  | 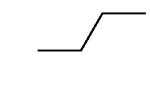 |  | — |  | CF₂O | 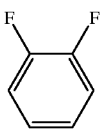 | OC₂H₅ |
| 216 | C₃H₇ |  | 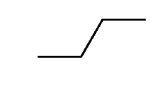 |  | — |  | CF₂O | 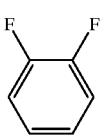 | OC₂H₅ |
| 217 | C₃H₇ |  | 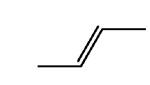 |  | — |  | CF₂O | 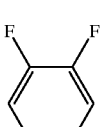 | OC₂H₅ |
| 218 | C₃H₇ |  | 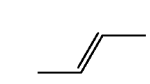 |  | — |  | CF₂O | 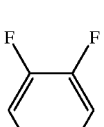 | OC₂H₅ |
| 219 | C₃H₇ |  | — |  | — |  | CF₂O | 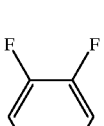 | OC₂H₅ |
| 220 | C₃H₇ |  | — |  | — |  | CF₂O | 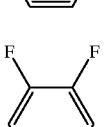 | OC₂H₅ |
| 221 | C₃H₇ |  | 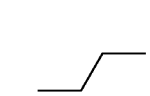 |  | — |  | CF₂O | 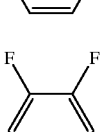 | OC₂H₅ |
| 222 | C₃H₇ |  | 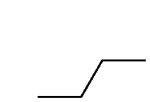 |  | — |  | CF₂O | 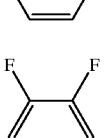 | OC₂H₅ |
| 223 | C₃H₇ |  | 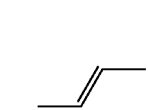 |  | — |  | CF₂O | 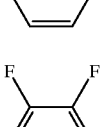 | OCH₃ |
| 224 | C₅H₁₁ |  | 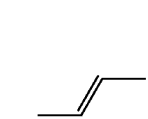 |  | — |  | CF₂O | 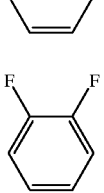 | OCH₃ |

-continued
| | | | | | | | | | |
|---|---|---|---|---|---|---|---|---|---|
| 225 | C₅H₁₁ |  |  |  | — |  | CF₂O | 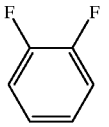 | OC₂H₅ |
| 226 | C₅H₁₁ |  |  | 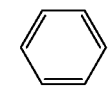 | — |  | CF₂O | 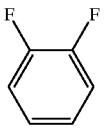 | OC₃H₇ |
| 227 | C₃H₇ |  | — |  | — | 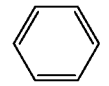 | CF₂O | 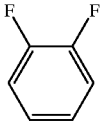 | OC₂H₅ |
| 228 | C₃H₇ |  | — |  | — |  | CF₂O | 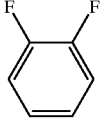 | OC₂H₅ |
| 229 | C₃H₇ |  |  |  | — |  | CF₂O | 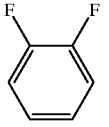 | OC₂H₅ |
| 230 | C₃H₇ |  |  |  | — | 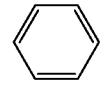 | CF₂O | 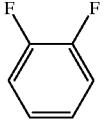 | OC₂H₅ |
| 231 | C₃H₇ |  |  | 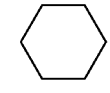 | — |  | CF₂O |  | OC₂H₅ |
| 232 | C₃H₇ |  |  | 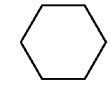 | — | 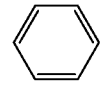 | CF₂O | 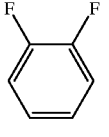 | OC₂H₅ |
| 233 | C₃H₇ |  | — | 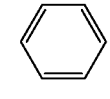 | — | 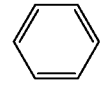 | CF₂O | 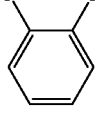 | OC₂H₅ |
| 234 | C₃H₇ |  | — | 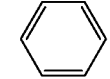 | — |  | CF₂O | 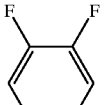 | OC₂H₅ |

-continued
| | | | | | | | | | |
|---|---|---|---|---|---|---|---|---|---|
| 235 | C₃H₇ |  |  |  | — |  | CF₂O | 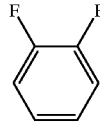 | OC₂H₅ |
| 236 | C₃H₇ |  |  |  | — |  | CF₂O | 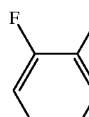 | OC₂H₅ |
| 237 | C₃H₇ |  | 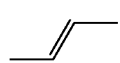 |  | — |  | CF₂O | 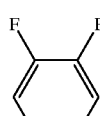 | OC₂H₅ |
| 238 | C₅H₁₁ |  | 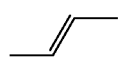 |  | — |  | CF₂O | 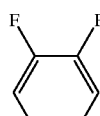 | OCH₃ |
| 239 | C₅H₁₁ |  | 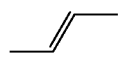 |  | — |  | CF₂O | 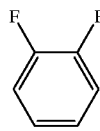 | OC₂H₅ |
| 240 | C₅H₁₁ |  | 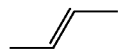 |  | — |  | CF₂O | 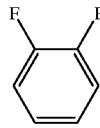 | OC₃H₇ |
| 241 | C₃H₇ |  | — |  |  |  | CF₂O | 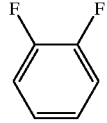 | OC₂H₅ |
| 242 | C₃H₇ |  | — |  |  |  | CF₂O |  | OC₂H₅ |
| 243 | C₃H₇ |  |  |  |  |  | CF₂O | 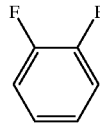 | OC₂H₅ |
| 244 | C₃H₇ |  | 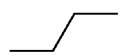 |  |  |  | CF₂O | 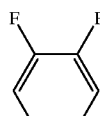 | OC₂H₅ |
| 245 | C₃H₇ |  | 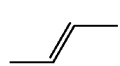 |  |  |  | CF₂O | 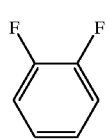 | OC₂H₅ |

-continued
| | | | | | | | | |
|---|---|---|---|---|---|---|---|---|
| 246 | C$_3$H$_7$ |  |  |  |  | CF$_2$O |  | OC$_2$H$_5$ |
| 247 | C$_3$H$_7$ |  | — |  |  | CF$_2$O |  | OC$_2$H$_5$ |
| 248 | C$_3$H$_7$ |  | — |  |  | CF$_2$O |  | OC$_2$H$_5$ |
| 249 | C$_3$H$_7$ |  |  | 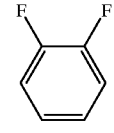 |  | CF$_2$O |  | OC$_2$H$_5$ |
| 250 | C$_3$H$_7$ |  |  |  | 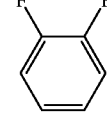 | CF$_2$O |  | OC$_2$H$_5$ |
| 251 | C$_3$H$_7$ |  |  |  |  | CF$_2$O |  | OC$_2$H$_5$ |
| 252 | C$_5$H$_{11}$ |  |  |  |  | CF$_2$O |  | OCH$_3$ |
| 253 | C$_5$H$_{11}$ | 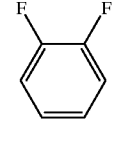 |  |  |  | CF$_2$O |  | OC$_2$H$_5$ |
| 254 | C$_5$H$_{11}$ |  | 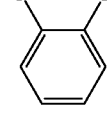 |  |  | CF$_2$O |  | OC$_3$H$_7$ |
| 255 | C$_3$H$_7$ |  | — |  | 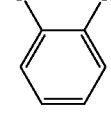 | CF$_2$O |  | OC$_2$H$_5$ |

-continued
| | | | | | | | | | |
|---|---|---|---|---|---|---|---|---|---|
| 256 | C₃H₇ |  | — |  |  |  | CF₂O | 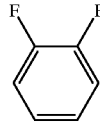 | OC₂H₅ |
| 257 | C₃H₇ |  |  |  |  |  | CF₂O | 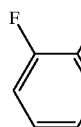 | OC₂H₅ |
| 258 | C₃H₇ |  |  |  |  |  | CF₂O | 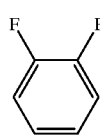 | OC₂H₅ |
| 259 | C₃H₇ |  |  |  |  |  | CF₂O | 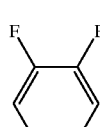 | OC₂H₅ |
| 260 | C₃H₇ |  |  |  |  |  | CF₂O | 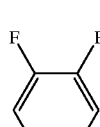 | OC₂H₅ |
| 261 | C₃H₇ |  | — |  |  |  | CF₂O | 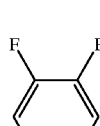 | OC₂H₅ |
| 262 | C₃H₇ |  | — |  |  |  | CF₂O | 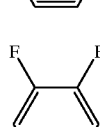 | OC₂H₅ |
| 263 | C₃H₇ |  |  |  |  |  | CF₂O | 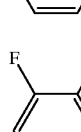 | OC₂H₅ |
| 264 | C₃H₇ |  |  |  |  |  | CF₂O | 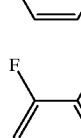 | OC₂H₅ |
| 265 | C₃H₇ |  |  |  |  |  | CF₂O | 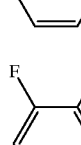 | OC₂H₅ |
| 266 | C₅H₁₁ |  |  |  |  |  | CF₂O | 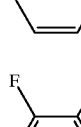 | OCH₃ |

-continued
| | | | | | | | | | |
|---|---|---|---|---|---|---|---|---|---|
| 267 | C$_5$H$_{11}$ |  | 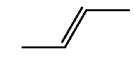 |  | 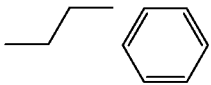 |  | CF$_2$O | 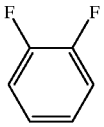 | OC$_2$H$_5$ |
| 268 | C$_5$H$_{11}$ |  | 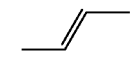 |  | 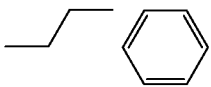 |  | CF$_2$O | 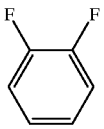 | OC$_3$H$_7$ |
| 269 | C$_3$H$_7$ |  | — |  | 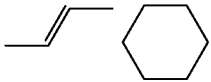 |  | CF$_2$O | 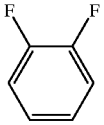 | OC$_2$H$_5$ |
| 270 | C$_3$H$_7$ |  | — |  | 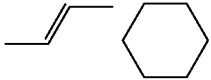 |  | CF$_2$O | 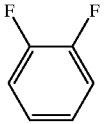 | OC$_2$H$_5$ |
| 271 | C$_3$H$_7$ |  | 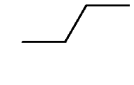 |  | 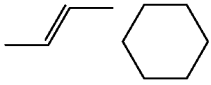 |  | CF$_2$O |  | OC$_2$H$_5$ |
| 272 | C$_3$H$_7$ |  | 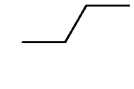 |  | 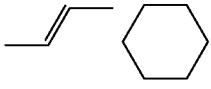 |  | CF$_2$O | 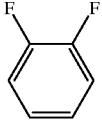 | OC$_2$H$_5$ |
| 273 | C$_3$H$_7$ |  | 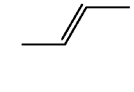 |  | 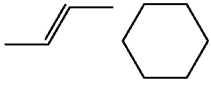 |  | CF$_2$O | 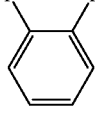 | OC$_2$H$_5$ |
| 274 | C$_3$H$_7$ |  | 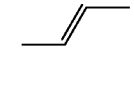 |  | 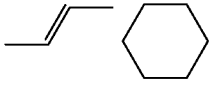 |  | CF$_2$O |  | OC$_2$H$_5$ |
| 275 | C$_3$H$_7$ |  | — |  | 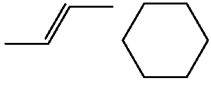 |  | CF$_2$O | 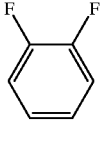 | OC$_2$H$_5$ |
| 276 | C$_3$H$_7$ |  | — |  | 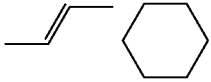 |  | CF$_2$O | 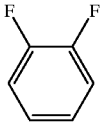 | OC$_2$H$_5$ |

-continued
| | | | | | | | | | |
|---|---|---|---|---|---|---|---|---|---|
| 277 | C₃H₇ |  | 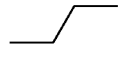 |  | 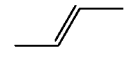 |  | CF₂O |  | OC₂H₅ |
| 278 | C₃H₇ |  | 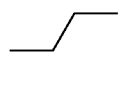 |  | 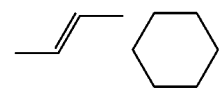 |  | CF₂O | 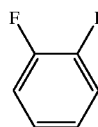 | OC₂H₅ |
| 279 | C₃H₇ |  | 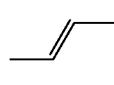 |  | 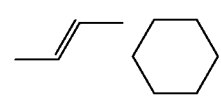 |  | CF₂O |  | OC₂H₅ |
| 280 | C₅H₁₁ |  | 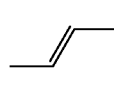 |  | 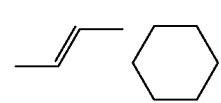 |  | CF₂O | 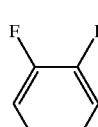 | OCH₃ |
| 281 | C₅H₁₁ |  | 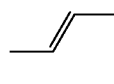 |  | 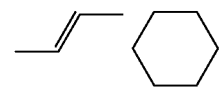 |  | CF₂O | 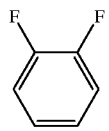 | OC₂H₅ |
| 282 | C₅H₁₁ |  | 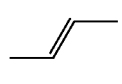 |  | 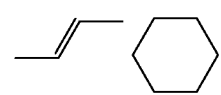 |  | CF₂O | 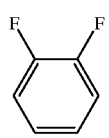 | OC₃H₇ |
| 283 | C₃H₇ |  | — |  | 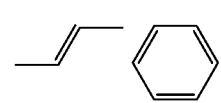 |  | CF₂O | 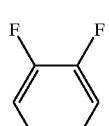 | OC₂H₅ |
| 284 | C₃H₇ |  | — |  | 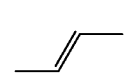 |  | CF₂O | 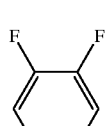 | OC₂H₅ |
| 285 | C₃H₇ |  | 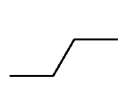 |  | 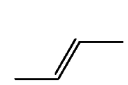 |  | CF₂O | 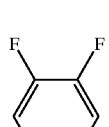 | OC₂H₅ |
| 286 | C₃H₇ |  | 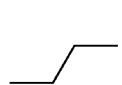 |  | 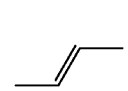 |  | CF₂O | 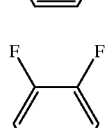 | OC₂H₅ |
| 287 | C₃H₇ |  | 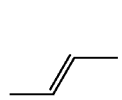 |  | 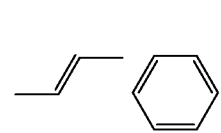 |  | CF₂O | 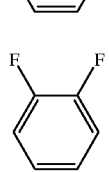 | OC₂H₅ |

-continued

| No. | R¹ | A¹ | Z¹ | A² | Z² | A³ | X¹ | A⁴ | Y¹ |
|---|---|---|---|---|---|---|---|---|---|
| 288 | C₃H₇ | phenyl | CH=CH | cyclohexyl | CH=CH | phenyl | CF₂O | 3,4-difluorophenyl | OC₂H₅ |
| 289 | C₃H₇ | cyclohexyl | — | phenyl | CH=CH | phenyl | CF₂O | 3,4-difluorophenyl | OC₂H₅ |
| 290 | C₃H₇ | phenyl | — | phenyl | CH=CH | phenyl | CF₂O | 3,4-difluorophenyl | OC₂H₅ |
| 291 | C₃H₇ | cyclohexyl | CH₂CH₂ | phenyl | CH=CH | phenyl | CF₂O | 3,4-difluorophenyl | OC₂H₅ |
| 292 | C₃H₇ | phenyl | CH₂CH₂ | phenyl | CH=CH | phenyl | CF₂O | 3,4-difluorophenyl | OC₂H₅ |
| 293 | C₃H₇ | cyclohexyl | CH=CH | phenyl | CH=CH | phenyl | CF₂O | 3,4-difluorophenyl | OC₂H₅ |
| 294 | C₅H₁₁ | phenyl | CH=CH | phenyl | CH=CH | phenyl | CF₂O | 3,4-difluorophenyl | OCH₃ |
| 295 | C₅H₁₁ | phenyl | CH₂CH₂ | phenyl | CH=CH | phenyl | CF₂O | 3,4-difluorophenyl | OC₂H₅ |
| 296 | C₅H₁₁ | phenyl | CH=CH | phenyl | CH=CH | phenyl | CF₂O | 3,4-difluorophenyl | OC₃H₇ | m = n = 0

| No. | R¹ | A¹ | X¹ | A⁴ | Y¹ |
|---|---|---|---|---|---|
| 297 | C₃H₇ | 3-fluorophenyl | COO | 3,4-difluorophenyl | OCH₃ |

-continued

| | | | | | |
|---|---|---|---|---|---|
| 298 | C$_3$H$_7$ | (phenyl-F) | COO | (difluorophenyl) | OC$_2$H$_5$ |
| 299 | C$_3$H$_7$ | (phenyl-F) | COO | (difluorophenyl) | OC$_3$H$_7$ |
| 300 | C$_5$H$_{11}$ | (phenyl-F) | COO | (difluorophenyl) | OCH$_3$ |
| 301 | C$_5$H$_{11}$ | (phenyl-F) | COO | (difluorophenyl) | OC$_2$H$_5$ |
| 302 | C$_5$H$_{11}$ | (phenyl-F) | COO | (difluorophenyl) | OC$_3$H$_7$ |
| 303 | C$_3$H$_7$ | (phenyl) | CF$_2$O | (difluorophenyl) | OC$_2$H$_5$ |
| 304 | C$_3$H$_7$ | (phenyl-F) | CF$_2$O | (difluorophenyl) | OCH$_3$ |
| 305 | C$_3$H$_7$ | (phenyl-F) | CF$_2$O | (difluorophenyl) | OC$_2$H$_5$ |
| 306 | C$_3$H$_7$ | (phenyl-F) | CF$_2$O | (difluorophenyl) | OC$_3$H$_7$ |
| 307 | C$_5$H$_{11}$ | (phenyl) | CF$_2$O | (difluorophenyl) | OC$_2$H$_5$ |

-continued

| No. | $^1R$-A$^1$-X$^1$- | | | -A$^1$-Y$^1$ |
|---|---|---|---|---|
| 308 | C$_5$H$_{11}$ | [phenyl-F] | CF$_2$O | [difluorophenyl] OCH$_3$ |
| 309 | C$_5$H$_{11}$ | [phenyl-F] | CF$_2$O | [difluorophenyl] OC$_2$H$_5$ |
| 310 | C$_5$H$_{11}$ | [phenyl-F] | CF$_2$O | [difluorophenyl] OC$_3$H$_7$ |

| No. | $^1R$-A$^1$-X$^1$- | $\left(-A^2-X^2-\right)_m$ | $\left(-A^3-X^3-\right)_n$ | -A$^1$-Y$^1$ |
|---|---|---|---|---|
| 311 | C$_3$H$_7$-[cyclohexyl]-CF$_2$O— | — | — | -[cyclohexyl]-C$_5$H$_{11}$ |
| 312 | C$_3$H$_7$-[cyclohexyl]-CF$_2$O— | — | — | -[cyclohexyl]-OC$_2$H$_5$ |
| 313 | CH$_2$=CHCH$_2$CH$_2$-[cyclohexyl]-CF$_2$O— | — | — | -[cyclohexyl]-C$_3$H$_7$ |
| 314 | C$_3$H$_7$-[cyclohexyl]-CF$_2$O— | — | — | -[phenyl]-C$_5$H$_{11}$ |
| 315 | C$_3$H$_7$-[cyclohexyl]-CF$_2$O— | — | — | -[fluorophenyl]-C$_5$H$_{11}$ |
| 316 | CH$_2$=CH-[cyclohexyl]-CF$_2$O— | — | — | -[fluorophenyl]-C$_5$H$_{11}$ |
| 317 | C$_3$H$_7$-[cyclohexyl]-CF$_2$O— | — | — | -[difluorophenyl]-C$_5$H$_{11}$ |

-continued
| | | | | |
|---|---|---|---|---|
| 318 | 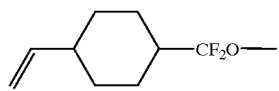 | — | — | 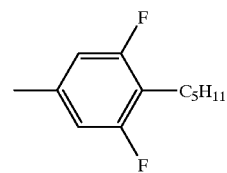 |
| 319 | 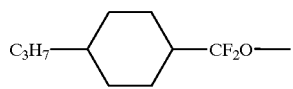 | — | — | 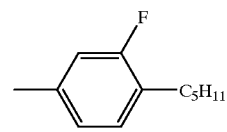 |
| 320 | 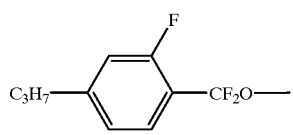 | — | — | 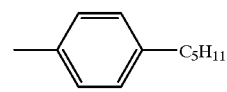 |
| 321 | 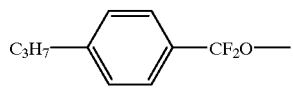 | — | — | 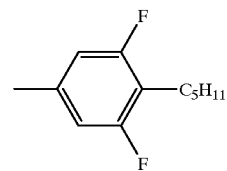 |
| 322 | 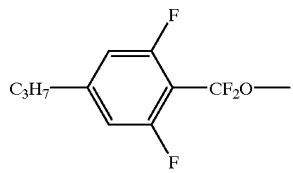 | — | — | 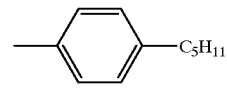 |
| 323 | 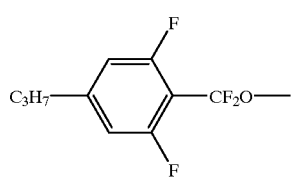 | — | — | 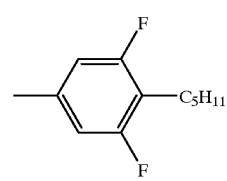 |
| 324 | 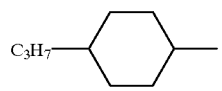 | 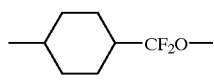 | — | 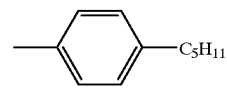 |
| 325 | 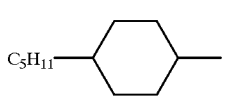 | 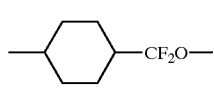 | — | 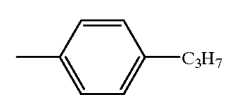 |
| 326 | 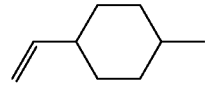 | 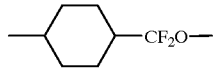 | — | 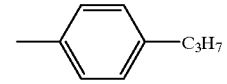 |
| 327 | 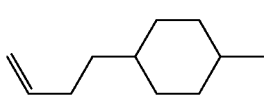 | 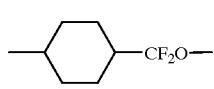 | — | 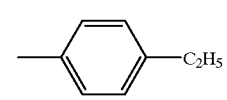 |

-continued

| No. | R¹-A¹- | -A²-X- | Z | R²-A³- |
|---|---|---|---|---|
| 328 | C₃H₇–(Cy)– | –(Cy)–CF₂O– | — | 3-F, 4-C₅H₁₁-Ph– |
| 329 | C₅H₁₁–(Cy)– | –(Cy)–CF₂O– | — | 3,5-F₂, 4-C₃H₇-Ph– |
| 330 | CH₂=CH-CH₂-CH₂–(Cy)– | –(Cy)–CF₂O– | — | 3-F, 4-C₂H₅-Ph– |
| 331 | C₃H₇–(Cy)– | –(Ph)–CF₂O– | — | C₅H₁₁-Ph– |
| 332 | C₅H₁₁–(Cy)– | –(Ph)–CF₂O– | — | C₃H₇-Ph– |
| 333 | CH₂=CH–(Cy)– | –(Ph)–CF₂O– | — | C₃H₇-Ph– |
| 334 | CH₂=CH-CH₂-CH₂–(Cy)– | –(Ph)–CF₂O– | — | C₂H₅-Ph– |
| 335 | C₃H₇–(Cy)– | –(Ph)–CF₂O– | — | 3-F, 4-C₅H₁₁-Ph– |
| 336 | C₅H₁₁–(Cy)– | –(Ph)–CF₂O– | — | 3,5-F₂, 4-C₃H₇-Ph– |
| 337 | CH₂=CH-CH₂-CH₂–(Cy)– | –(Ph)–CF₂O– | — | 3-F, 4-C₂H₅-Ph– |
| 338 | C₃H₇-(1,3-dioxane)– | –(Ph)–CF₂O– | — | C₅H₁₁-Ph– |

-continued
| | | | | |
|---|---|---|---|---|
| 339 | 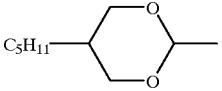 | 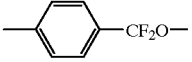 | — |  |
| 340 | 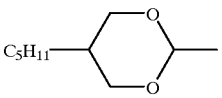 | 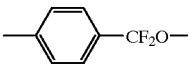 | — | 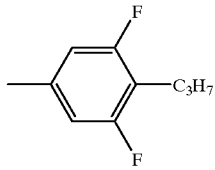 |
| 341 | 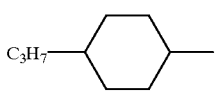 | 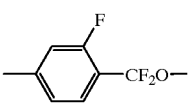 | — | 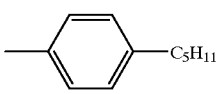 |
| 342 | 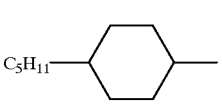 | 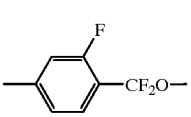 | — | 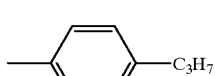 |
| 343 | 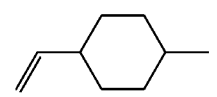 | 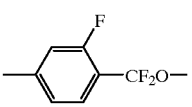 | — | 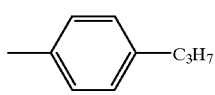 |
| 344 | 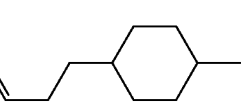 | 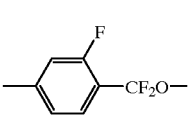 | — | 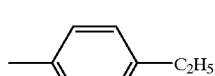 |
| 345 | 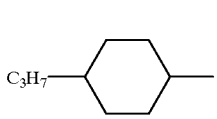 | 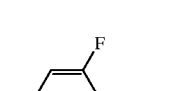 | — | 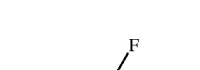 |
| 346 | 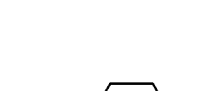 | 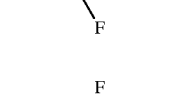 | — | 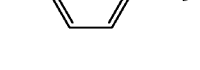 |
| 347 | 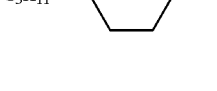 | 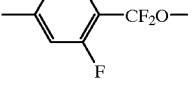 | — | 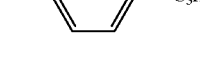 |
| 348 | 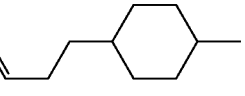 | 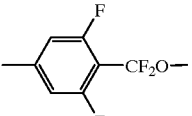 | — | 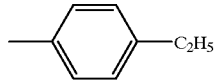 |
| 349 | 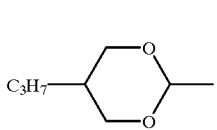 | 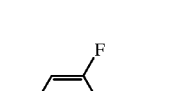 | | 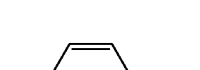 |

-continued

| | | | | |
|---|---|---|---|---|
| 350 | C5H11–[dioxane]–CH3 | –[C6H2(F)(F)]–CF2O– | — | –[C6H4]–C3H7 |
| 351 | C3H7–[cyclohexane]– | –[C6H3(F)]–CF2O– | — | –[C6H3(F)]–C5H11 |
| 352 | C5H11–[cyclohexane]– | –[C6H3(F)]–CF2O– | — | –[C6H3(F)]–C3H7 |
| 353 | CH2=CH–[cyclohexane]– | –[C6H3(F)]–CF2O– | — | –[C6H3(F)]–C3H7 |
| 354 | CH2=CH–CH2–CH2–[cyclohexane]– | –[C6H3(F)]–CF2O– | — | –[C6H3(F)]–C2H5 |
| 355 | C3H7–[cyclohexane]– | –[C6H2(F)(F)]–CF2O– | — | –[C6H3(F)]–C5H11 |
| 356 | C5H11–[cyclohexane]– | –[C6H2(F)(F)]–CF2O– | — | –[C6H2(F)(F)]–C3H7 |
| 357 | CH2=CH–CH2–CH2–[tetrahydropyran]– | –[C6H2(F)(F)]–CF2O– | — | –[C6H2(F)(F)]–C2H5 |
| 358 | C3H7–[dioxane]–CH3 | –[C6H3(F)]–CF2O– | — | –[C6H3(F)]–C5H11 |
| 359 | C5H11–[dioxane]–CH3 | –[C6H3(F)]–CF2O– | — | –[C6H3(F)]–C3H7 |

-continued

| | | | | |
|---|---|---|---|---|
| 360 | C5H11-[1,3-dioxane]-CH3 | 2,6-difluoro-4-yl-CF2O- | — | 3-fluoro-4-C3H7-phenyl |
| 361 | C3H7-Cy-CF2O- | Cy | — | 4-C5H11-phenyl |
| 362 | C5H11-Cy-CF2O- | Cy | — | 4-C3H7-phenyl |
| 363 | CH2=CH-Cy-CF2O- | Cy | — | 4-C3H7-phenyl |
| 364 | CH2=CH-CH2-CH2-Cy-CF2O- | Cy | — | 4-C2H5-phenyl |
| 365 | C3H7-Cy-CF2O- | Cy | — | 3-fluoro-4-C5H11-phenyl |
| 366 | C5H11-Cy-CF2O- | Cy | — | 3,5-difluoro-4-C3H7-phenyl |
| 367 | CH2=CH-Cy-CF2O- | Cy | — | 3-fluoro-4-C3H7-phenyl |
| 368 | CH2=CH-CH2-CH2-Cy-CF2O- | Cy | — | 3,5-difluoro-4-C2H5-phenyl |
| 369 | C3H7-Cy-CF2O- | Cy | — | 2,3-difluoro-4-OC2H5-phenyl |
| 370 | C5H11-Cy-CF2O- | Cy | — | 2,3-difluoro-4-OC2H5-phenyl |

-continued

| # | | | | |
|---|---|---|---|---|
| 371 | C3H7—[Cy]—CF2O— | —[Ph]— | — | —[Ph]—C5H11 |
| 372 | C5H11—[Cy]—CF2O— | —[Ph]— | — | —[Ph]—C3H7 |
| 373 | CH2=CH—[Cy]—CF2O— | —[Ph]— | — | —[Ph]—C3H7 |
| 374 | CH2=CH-CH2-CH2—[Cy]—CF2O— | —[Ph]— | — | —[Ph]—C2H5 |
| 375 | C3H7—[Cy]—CF2O— | —[Ph]— | — | —[Ph(3-F)]—C5H11 |
| 376 | C5H11—[Cy]—CF2O— | —[Ph]— | — | —[Ph(3,5-F2)]—C3H7 |
| 377 | CH2=CH—[Cy]—CF2O— | —[Ph]— | — | —[Ph(3-F)]—C3H7 |
| 378 | CH2=CH-CH2-CH2—[Cy]—CF2O— | —[Ph]— | — | —[Ph(3,5-F2)]—C2H5 |
| 379 | C3H7—[Cy]—CF2O— | —[Ph]— | — | —[Ph(2,3-F2)]—OC2H5 |
| 380 | C5H11—[Cy]—CF2O— | —[Ph]— | — | —[Ph(2,3-F2)]—OC2H5 |
| 381 | C3H7—[Cy]—CH2CH2— | —[Cy]—CF2O— | — | —[Ph]—C5H11 |

-continued
| | | | | |
|---|---|---|---|---|
| 382 | 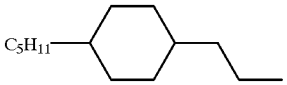 | 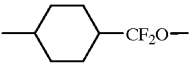 | — | 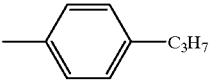 |
| 383 | 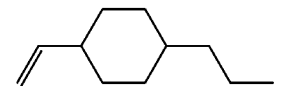 | 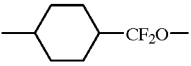 | — | 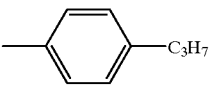 |
| 384 | 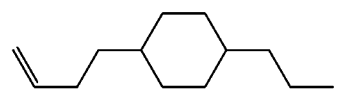 | 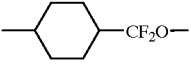 | — | 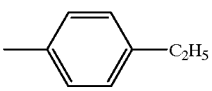 |
| 385 | 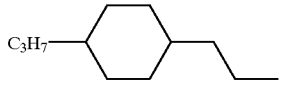 | 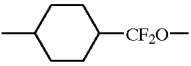 | — | 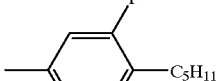 |
| 386 | 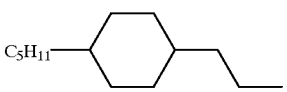 | 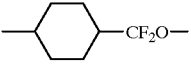 | — | 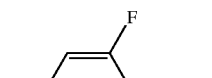 |
| 387 | 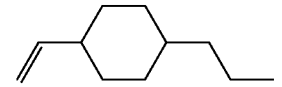 | 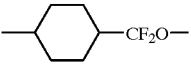 | — | 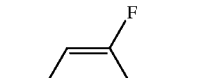 |
| 388 | 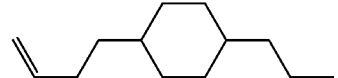 | 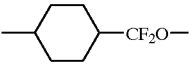 | — | 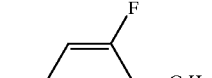 |
| 389 | 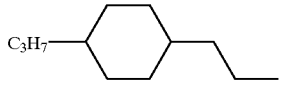 | 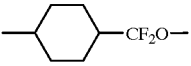 | — | 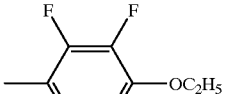 |
| 390 | 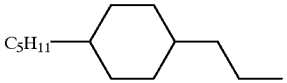 | 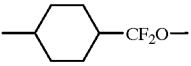 | — | 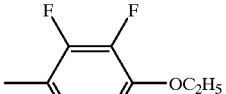 |
| 391 | 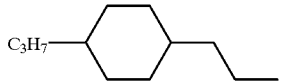 | 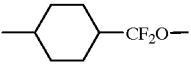 | — | 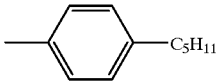 |
| 392 |  | 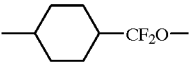 | — | 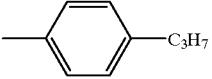 |

-continued
| | | | | |
|---|---|---|---|---|
| 393 | 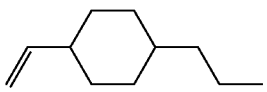 | 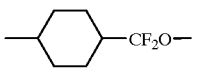 | — | 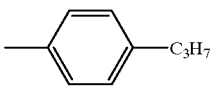 |
| 394 | 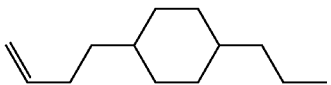 | 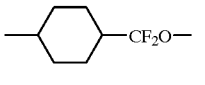 | — | 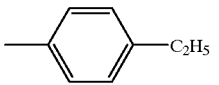 |
| 395 |  | 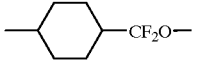 | — | 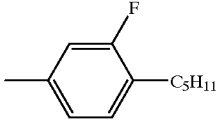 |
| 396 | 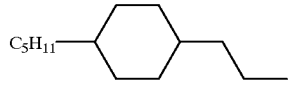 | 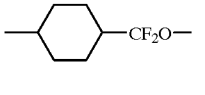 | — | 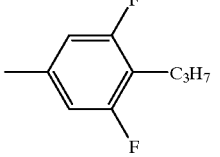 |
| 397 | 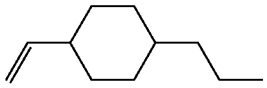 | 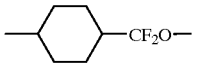 | — | 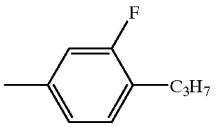 |
| 398 | 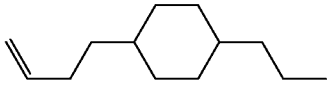 | 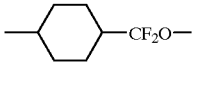 | — | 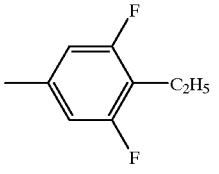 |
| 399 | 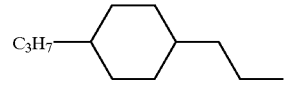 | 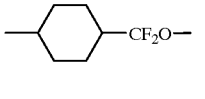 | — | 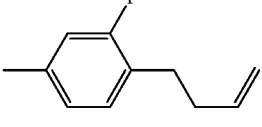 |
| 400 | 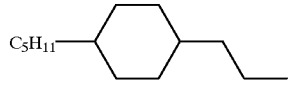 | 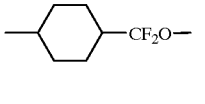 | — | 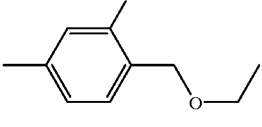 |
| 401 | 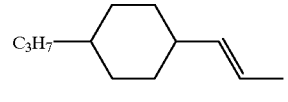 | 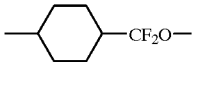 | — | 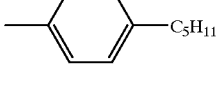 |
| 402 | 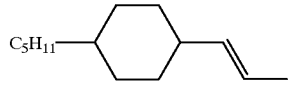 | 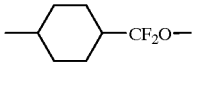 | — | 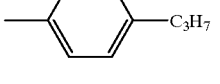 |
| 403 | 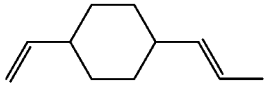 | 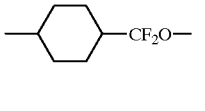 | — | 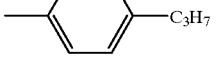 |

| | | | | |
|---|---|---|---|---|
| 404 | 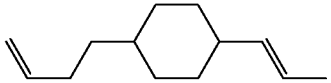 | 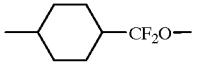 | — | 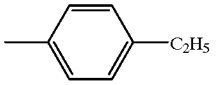 |
| 405 |  | 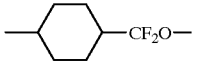 | — | 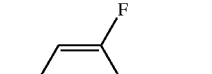 |
| 406 | 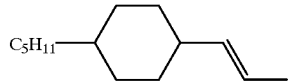 | 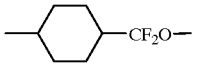 | — | 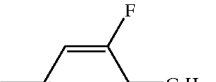 |
| 407 | 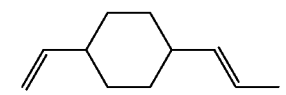 | 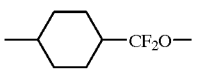 | — | 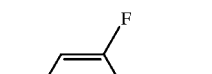 |
| 408 | 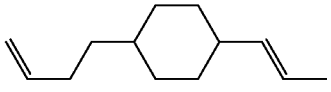 | 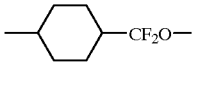 | — | 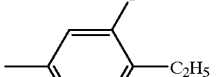 |
| 409 |  | 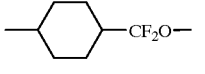 | — | 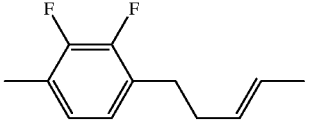 |
| 410 |  | 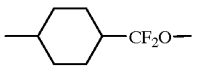 | — | 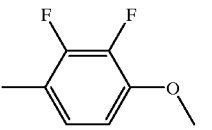 |
| 411 | 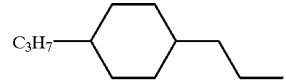 | 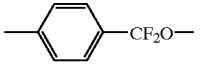 | — | 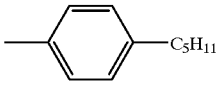 |
| 412 | 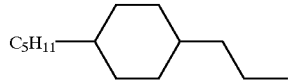 | 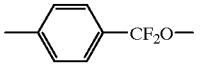 | — | 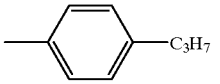 |
| 413 | 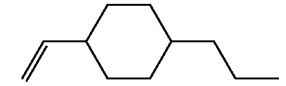 | 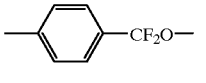 | — | 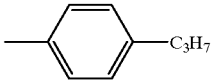 |
| 414 | 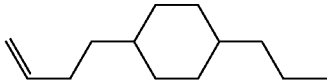 | 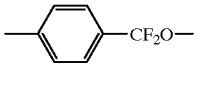 | — | 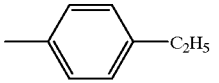 |

-continued

-continued

| | | | | |
|---|---|---|---|---|
| 425 | C₃H₇–Cy–CH₂CH₂– | –Ph(2-F,4-CF₂O–) | — | –Ph(2-F)–C₅H₁₁ |
| 426 | C₅H₁₁–Cy–CH₂CH₂– | –Ph(2,6-F₂,4-CF₂O–) | — | –Ph(2,6-F₂)–C₃H₇ |
| 427 | CH₂=CH–Cy–CH₂CH₂– | –Ph(2,6-F₂,4-CF₂O–) | — | –Ph(2-F)–C₃H₇ |
| 428 | CH₂=CHCH₂CH₂–Cy–CH₂CH₂– | –Ph(2,6-F₂,4-CF₂O–) | — | –Ph(2,6-F₂)–C₂H₅ |
| 429 | C₃H₇O–Cy–CH₂CH₂– | –Ph(2,6-F₂,4-CF₂O–) | — | –Ph(2,6-F₂)–C₂H₅ |
| 430 | C₃H₇OCH₂–Cy–CH₂CH₂– | –Ph(2,6-F₂,4-CF₂O–) | — | –Ph(2,6-F₂)–C₃H₇ |
| 431 | C₃H₇–Cy–CH=CH– | –Ph(2-F,4-CF₂O–) | — | –Ph–C₅H₁₁ |
| 432 | C₅H₁₁–Cy–CH=CH– | –Ph(2-F,4-CF₂O–) | — | –Ph–C₃H₇ |
| 433 | CH₂=CH–Cy–CH=CH– | –Ph(2-F,4-CF₂O–) | — | –Ph–C₃H₇ |
| 434 | CH₂=CHCH₂CH₂–Cy–CH=CH– | –Ph(2-F,4-CF₂O–) | — | –Ph–C₂H₅ |

-continued
| | | | | |
|---|---|---|---|---|
| 435 | 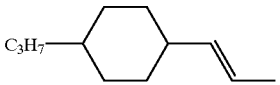 | 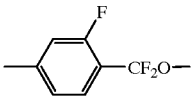 | — | 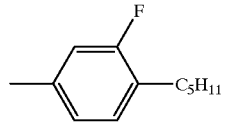 |
| 436 | 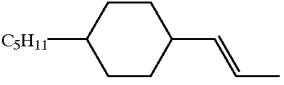 | 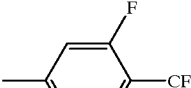 | — | 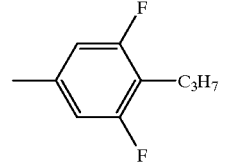 |
| 437 | 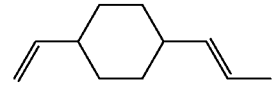 | 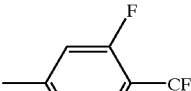 | — | 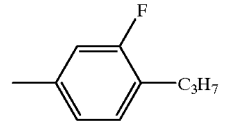 |
| 438 | 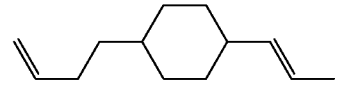 | 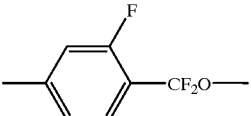 | — | 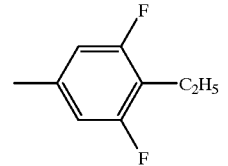 |
| 439 | 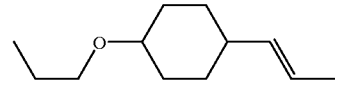 | 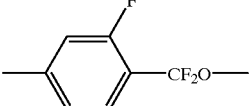 | — | 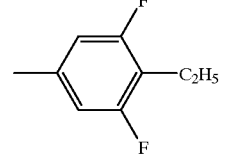 |
| 440 | 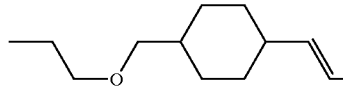 | 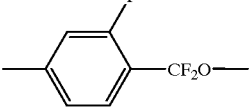 | — | 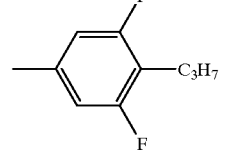 |
| 441 | 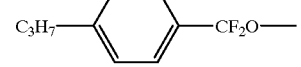 |  | — | 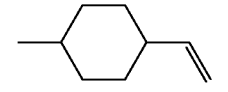 |
| 442 | 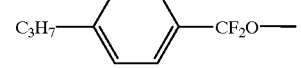 |  | — | 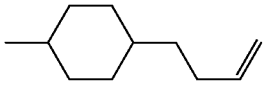 |
| 443 | 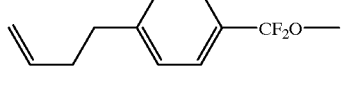 |  | — | 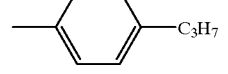 |
| 444 | 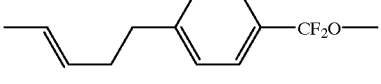 |  | — | 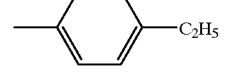 |

-continued

| # | | | | |
|---|---|---|---|---|
| 445 | C₃H₇—⟨phenyl⟩—CF₂O— | —⟨phenyl⟩— | — | —⟨3-F phenyl⟩—C₅H₁₁ |
| 446 | C₅H₁₁—⟨phenyl⟩—CF₂O— | —⟨phenyl⟩— | — | —⟨3,5-diF phenyl⟩—C₃H₇ |
| 447 | CH₂=CH-CH₂-CH₂—⟨phenyl⟩—CF₂O— | —⟨phenyl⟩— | — | —⟨3-F phenyl⟩—C₃H₇ |
| 448 | CH₃-CH=CH-CH₂—⟨phenyl⟩—CF₂O— | —⟨phenyl⟩— | — | —⟨3,5-diF phenyl⟩—C₂H₅ |
| 449 | C₃H₇—⟨phenyl⟩—CF₂O— | —⟨phenyl⟩— | — | —⟨2,3-diF phenyl⟩—OC₂H₅ |
| 450 | C₅H₁₁—⟨phenyl⟩—CF₂O— | —⟨phenyl⟩— | — | —⟨2,3-diF phenyl⟩—OC₂H₅ |
| 451 | C₃H₇—⟨phenyl⟩—CF₂O— | —⟨3-F phenyl⟩— | — | —⟨phenyl⟩—C₅H₁₁ |
| 452 | C₅H₁₁—⟨phenyl⟩—CF₂O— | —⟨3-F phenyl⟩— | — | —⟨phenyl⟩—C₃H₇ |
| 453 | CH₂=CH-CH₂-CH₂—⟨phenyl⟩—CF₂O— | —⟨3-F phenyl⟩— | — | —⟨phenyl⟩—C₃H₇ |
| 454 | CH₃-CH=CH-CH₂—⟨phenyl⟩—CF₂O— | —⟨3-F phenyl⟩— | — | —⟨phenyl⟩—C₂H₅ |

-continued

| # | | | | |
|---|---|---|---|---|
| 455 | C3H7–⟨phenyl⟩–CF2O– | F-substituted phenyl (2-F) | — | F-substituted phenyl–C5H11 |
| 456 | C5H11–⟨phenyl⟩–CF2O– | 2,3-diF phenyl | — | 2,6-diF phenyl–C3H7 |
| 457 | CH2=CH-CH2-CH2–⟨phenyl⟩–CF2O– | F phenyl | — | F phenyl–C3H7 |
| 458 | CH3-CH=CH-CH2–⟨phenyl⟩–CF2O– | F phenyl | — | 2,6-diF phenyl–C2H5 |
| 459 | C3H7–⟨phenyl⟩–CF2O– | F phenyl | — | 2,3-diF phenyl–OC2H5 |
| 460 | C5H11–⟨phenyl⟩–CF2O– | 2,3-diF phenyl | — | 2,3-diF phenyl–OC2H5 |
| 461 | C3H7–⟨2-F phenyl⟩–CF2O– | F phenyl | — | phenyl–C5H11 |
| 462 | C5H11–⟨2-F phenyl⟩–CF2O– | F phenyl | — | phenyl–C3H7 |
| 463 | CH2=CH-CH2-CH2–⟨2-F phenyl⟩–CF2O– | F phenyl | — | phenyl–C3H7 |
| 464 | CH3-CH=CH-CH2–⟨2-F phenyl⟩–CF2O– | F phenyl | — | phenyl–C2H5 |

-continued

-continued

| # | | | | |
|---|---|---|---|---|
| 476 | C5H11—Cy—CF2O— | —Ph—C≡C— | — | —Ph(2,6-F2)—C3H7 |
| 477 | CH2=CH—Cy—CF2O— | —Ph—C≡C— | — | —Ph(3-F)—C3H7 |
| 478 | CH2=CH—CH2CH2—Cy—CF2O— | —Ph—C≡C— | — | —Ph(2,6-F2)—C2H5 |
| 479 | C3H7—Cy—CF2O— | —Ph—C≡C— | — | —Ph(2,3-F2)—OC2H5 |
| 480 | C5H11—Cy—CF2O— | —Ph—C≡C— | — | —Ph(2,3-F2)—OC2H5 |
| 481 | C3H7—Cy—CF2O— | —Ph(3-F)—C≡C— | — | —Ph—C5H11 |
| 482 | C5H11—Cy—CF2O— | —Ph(3-F)—C≡C— | — | —Ph—C3H7 |
| 483 | CH2=CH—Cy—CF2O— | —Ph(3-F)—C≡C— | — | —Ph—C3H7 |
| 484 | CH2=CH—CH2CH2—Cy—CF2O— | —Ph(3-F)—C≡C— | — | —Ph—C2H5 |
| 485 | C3H7—Cy—CF2O— | —Ph(3-F)—C≡C— | — | —Ph(3-F)—C5H11 |

-continued

| | | | | |
|---|---|---|---|---|
| 486 | C5H11—◯—CF2O— | 2,3-F substituted phenyl with ethynyl | — | 3,5-F, 4-C3H7 phenyl |
| 487 | vinyl-◯—CF2O— | 2-F phenyl with ethynyl | — | 3-F, 4-C3H7 phenyl |
| 488 | allyl-◯—CF2O— | 2,3-F phenyl with ethynyl | — | 3,5-F, 4-C2H5 phenyl |
| 489 | C3H7—◯—CF2O— | 2-F phenyl with ethynyl | — | 2,3-F, 4-OC2H5 phenyl |
| 490 | C5H11—◯—CF2O— | 2,3-F phenyl with ethynyl | — | 2,3-F, 4-OC2H5 phenyl |
| 491 | C3H7—⬡—CF2O— | 2-F phenyl with ethynyl | — | 4-C5H11 phenyl |
| 492 | C5H11—⬡—CF2O— | 2-F phenyl with ethynyl | — | 4-C3H7 phenyl |
| 493 | 3-butenyl—⬡—CF2O— | 2-F phenyl with ethynyl | — | 4-C3H7 phenyl |
| 494 | 3-pentenyl—⬡—CF2O— | 2-F phenyl with ethynyl | — | 4-C2H5 phenyl |
| 495 | C3H7—⬡(diene)—CF2O— | 2-F phenyl with ethynyl | — | 3-F, 4-C5H11 phenyl |

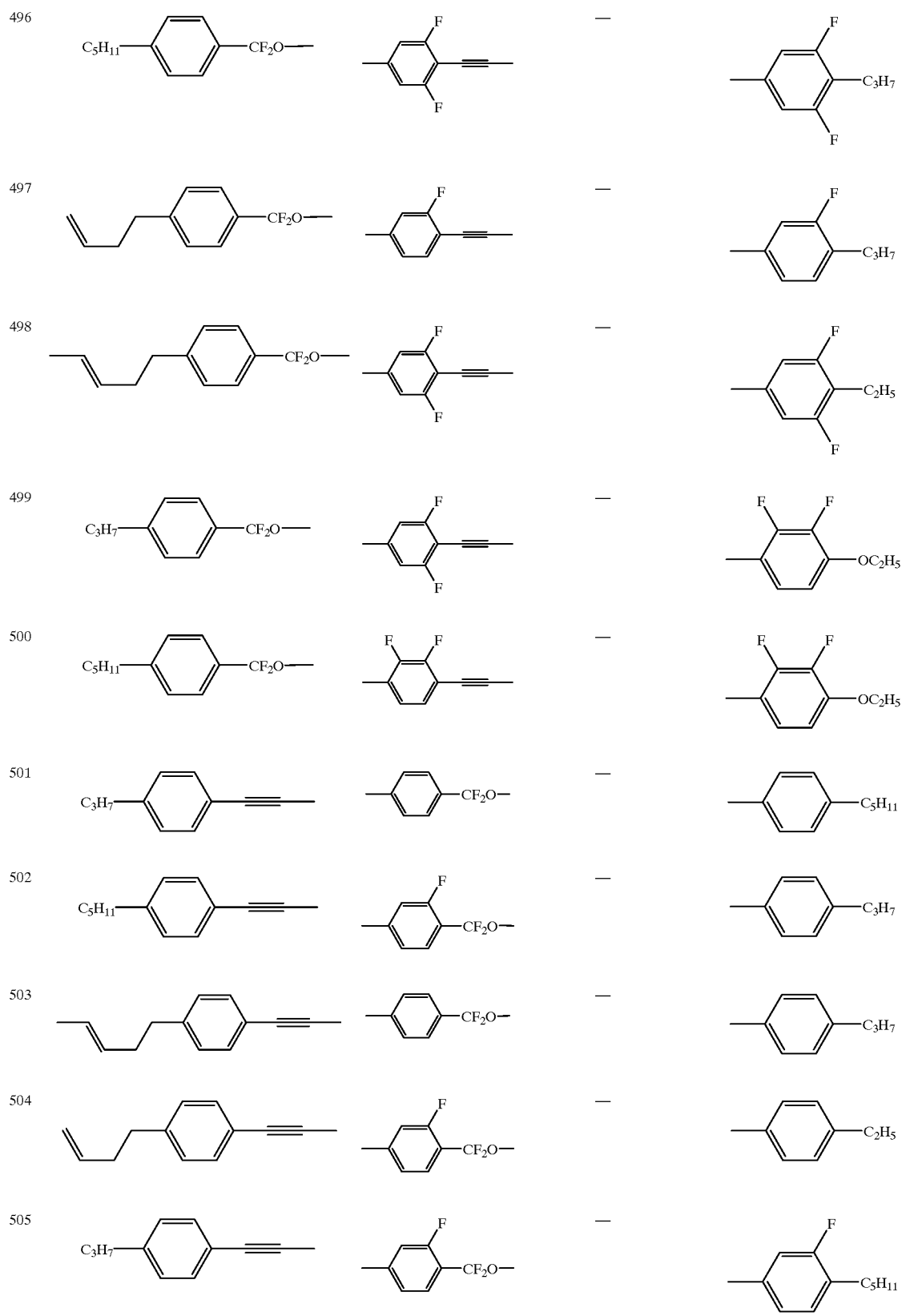

-continued

-continued

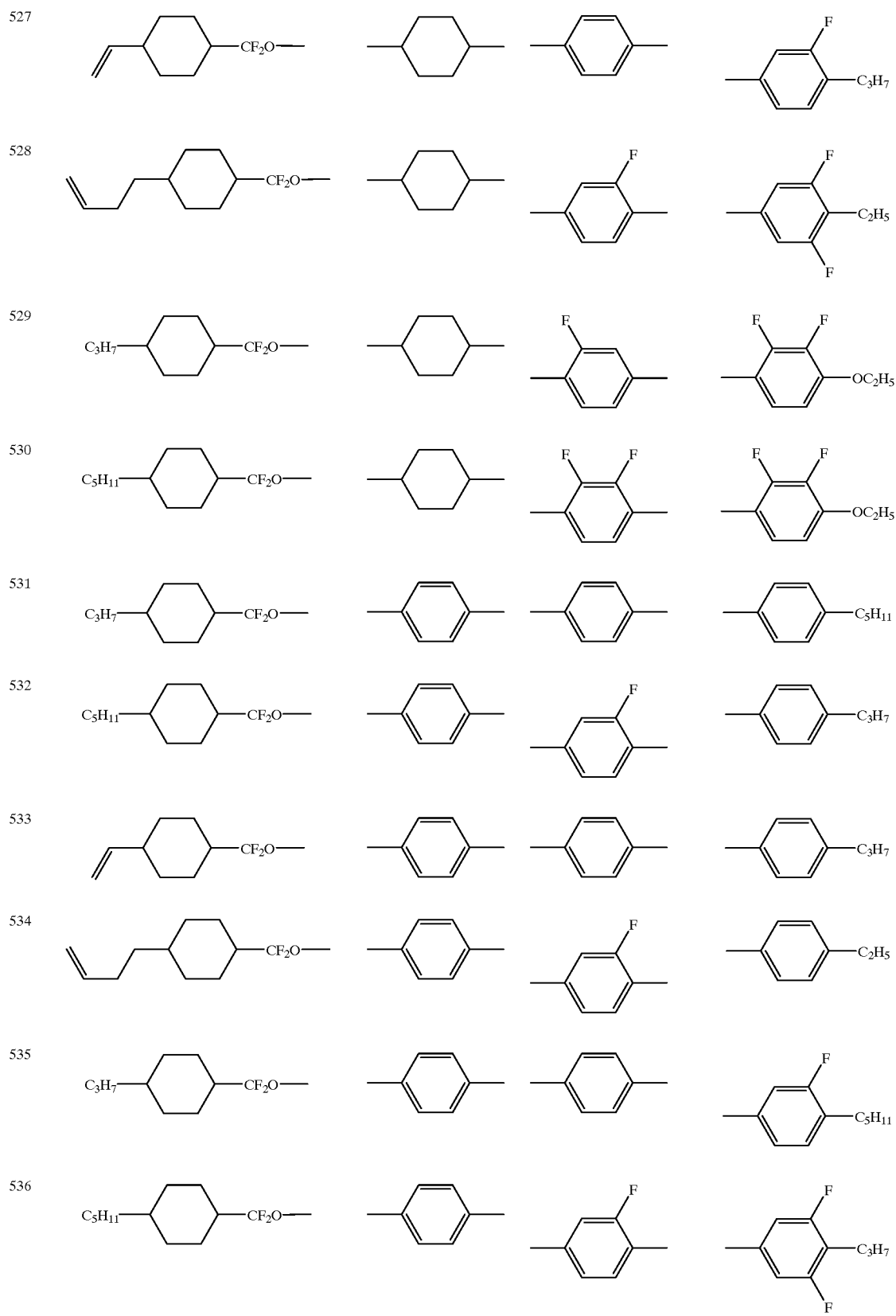

-continued
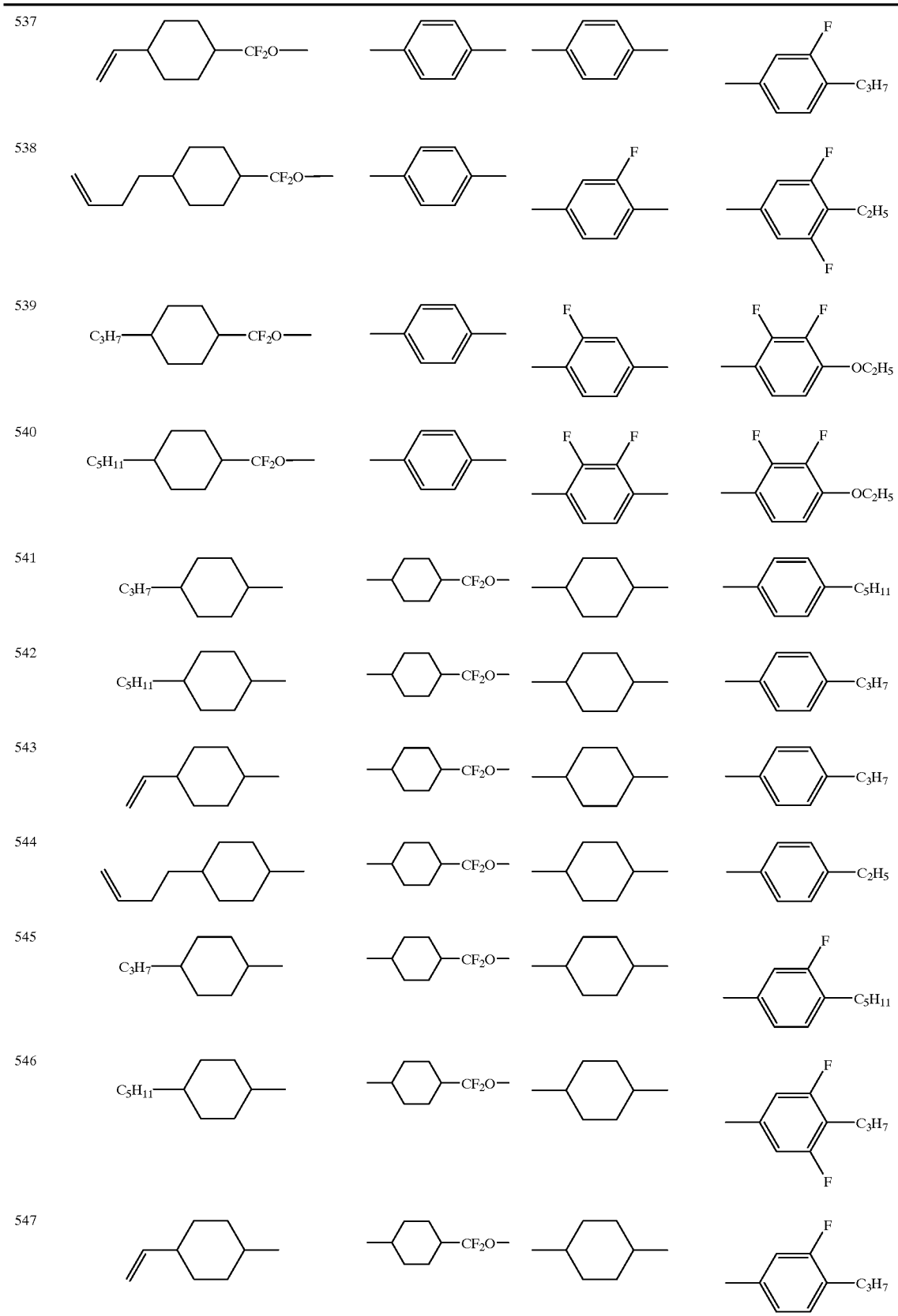

-continued
| | | | | |
|---|---|---|---|---|
| 548 | 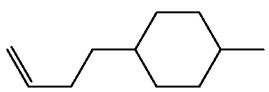 | 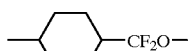 | 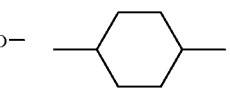 | 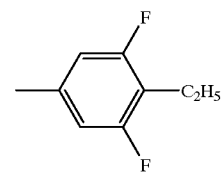 |
| 549 | 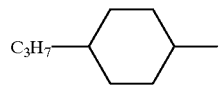 | 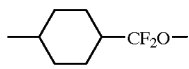 | 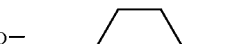 | 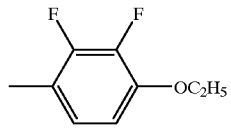 |
| 550 | 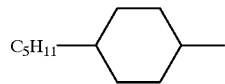 | 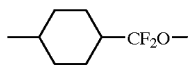 | 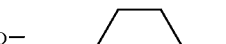 | 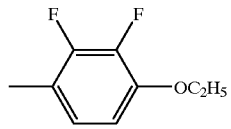 |
| 551 | 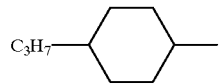 | 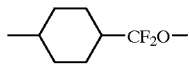 | 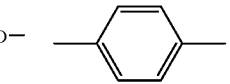 | 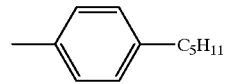 |
| 552 | 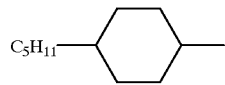 | 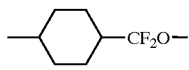 | 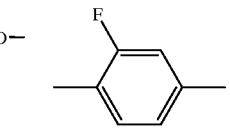 | 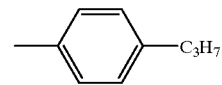 |
| 553 | 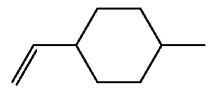 | 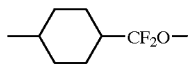 | 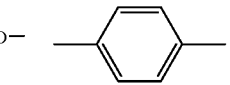 | 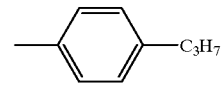 |
| 554 | 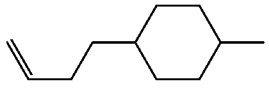 | 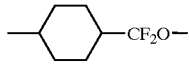 | 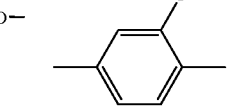 | 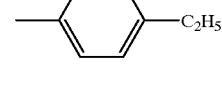 |
| 555 | 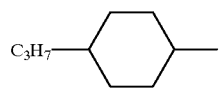 | 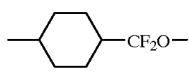 | 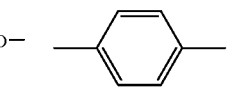 | 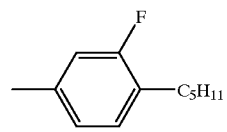 |
| 556 | 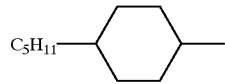 | 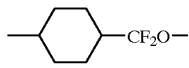 | 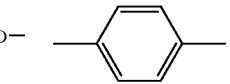 | 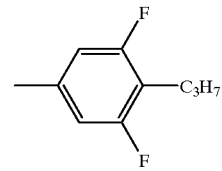 |
| 557 | 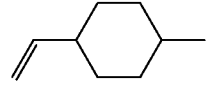 | 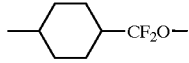 | 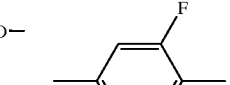 | 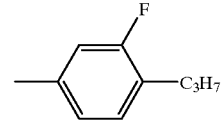 |

-continued
| | | | | |
|---|---|---|---|---|
| 558 | 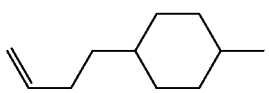 | 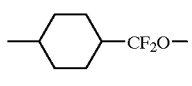 | 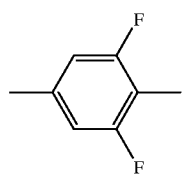 | 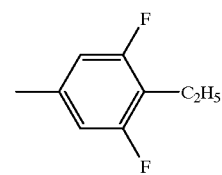 |
| 559 | 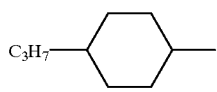 | 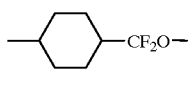 | 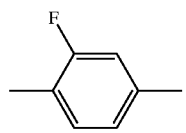 | 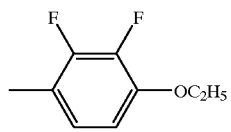 |
| 560 | 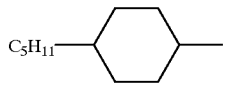 | 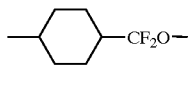 | 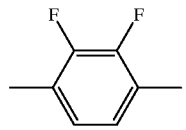 | 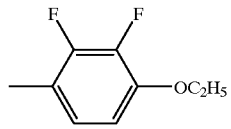 |
| 561 | 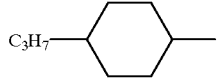 | 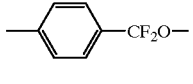 | 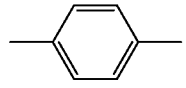 | 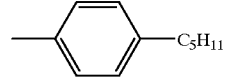 |
| 562 | 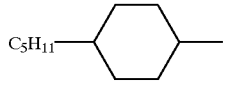 | 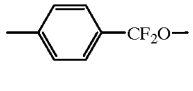 | 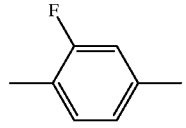 | 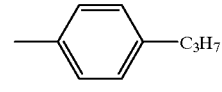 |
| 563 | 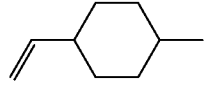 | 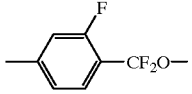 | 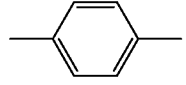 | 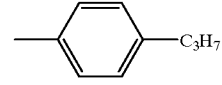 |
| 564 | 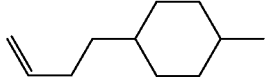 | 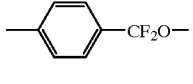 | 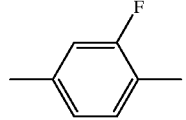 | 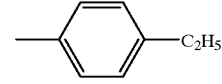 |
| 565 | 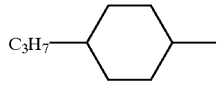 | 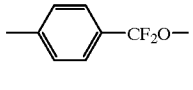 | 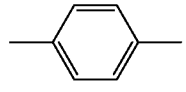 | 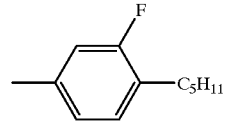 |
| 566 | 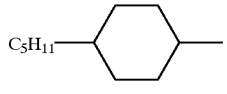 | 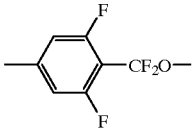 | 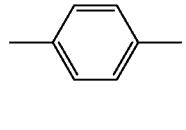 | 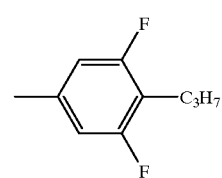 |
| 567 | 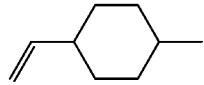 | 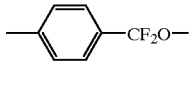 | 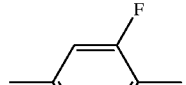 | 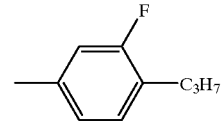 |

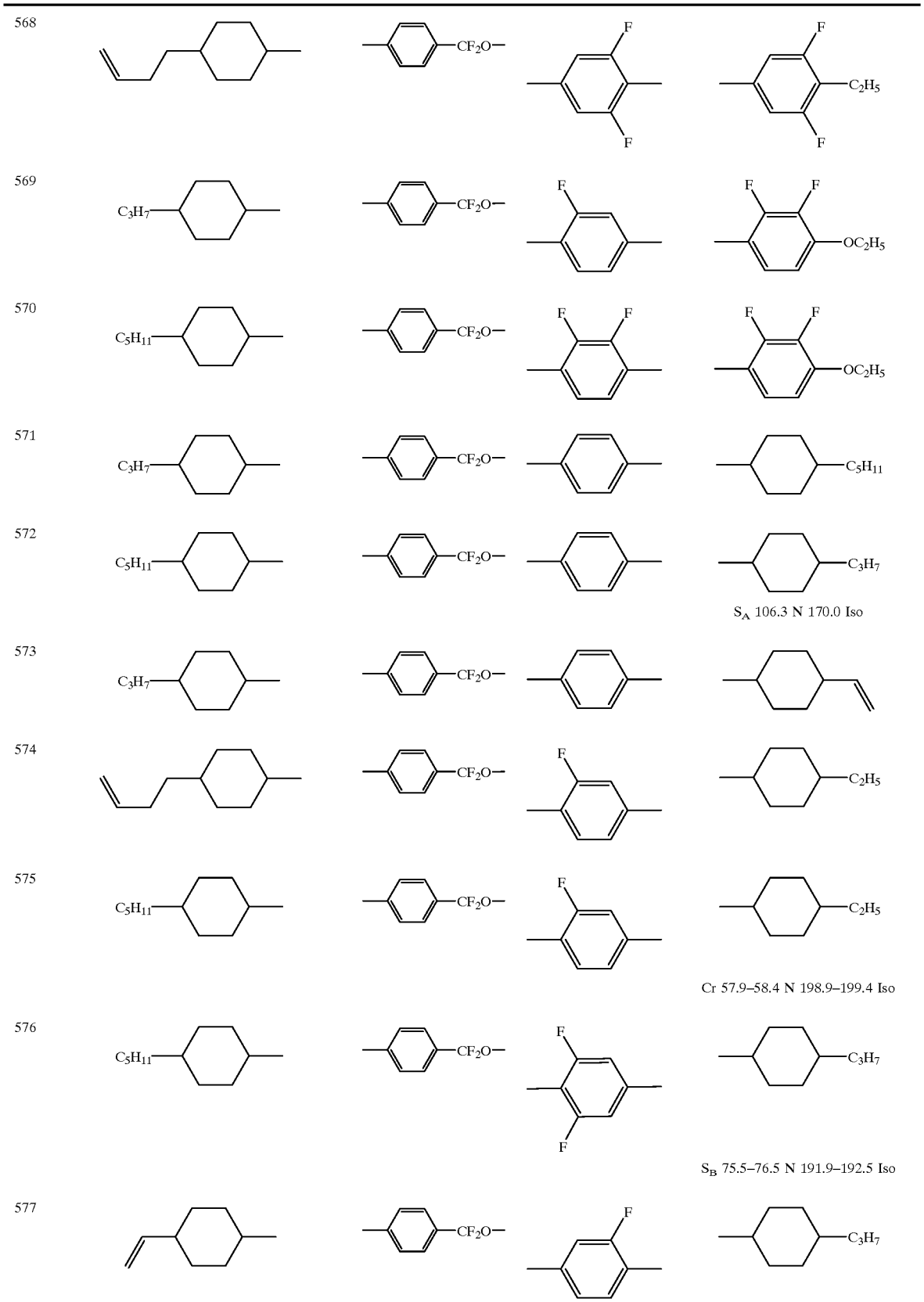

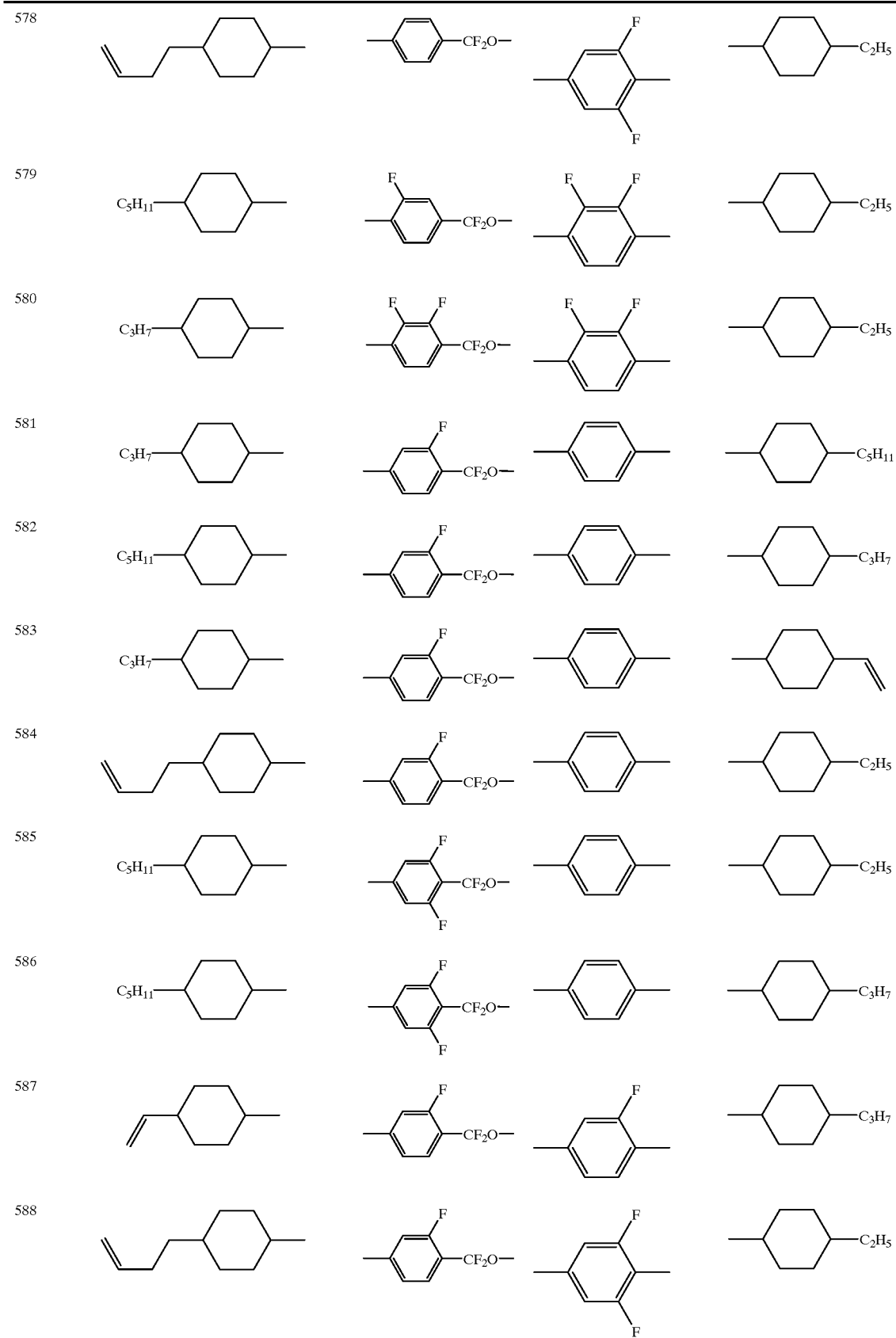

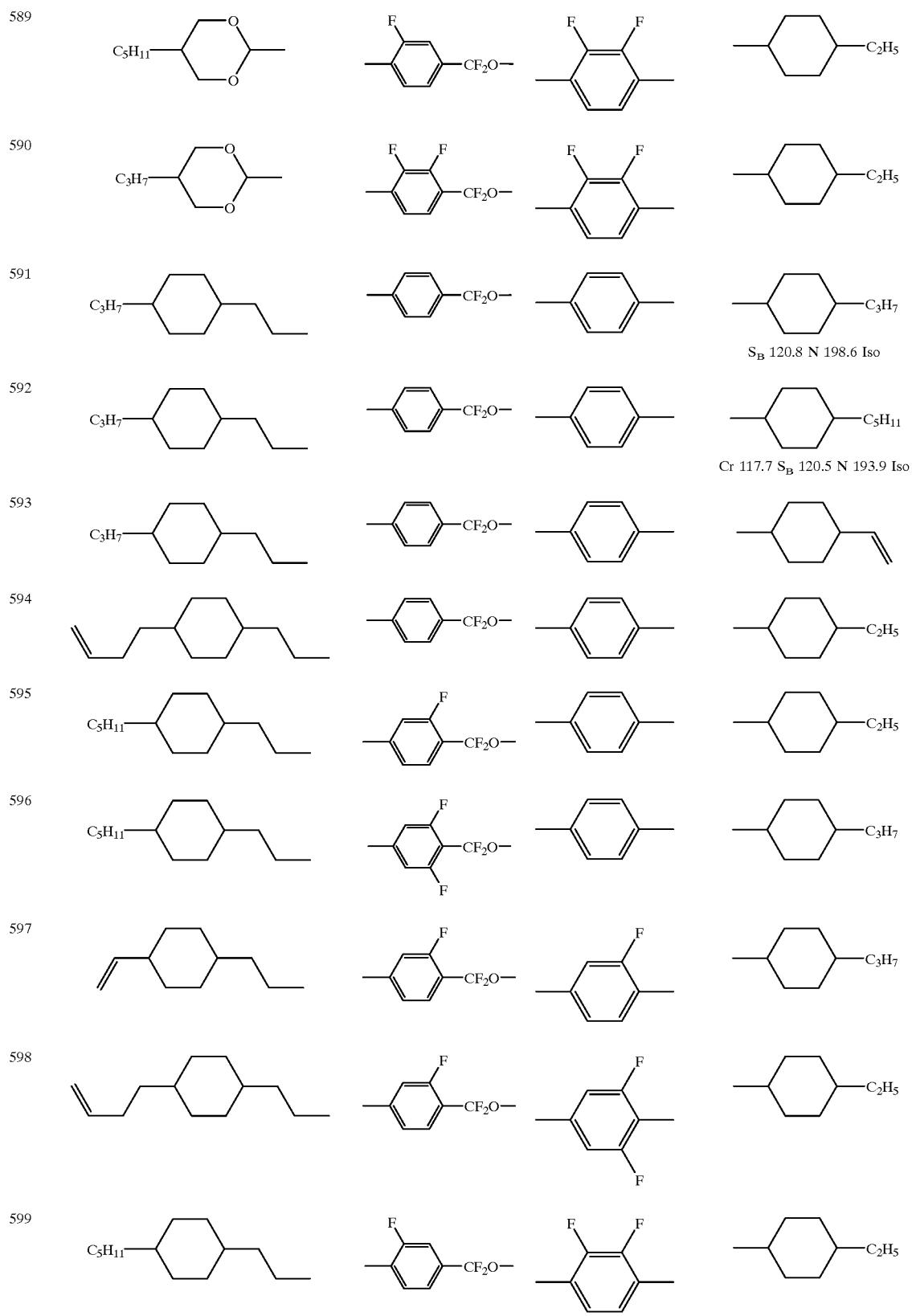
591 S$_B$ 120.8 N 198.6 Iso
592 Cr 117.7 S$_B$ 120.5 N 193.9 Iso

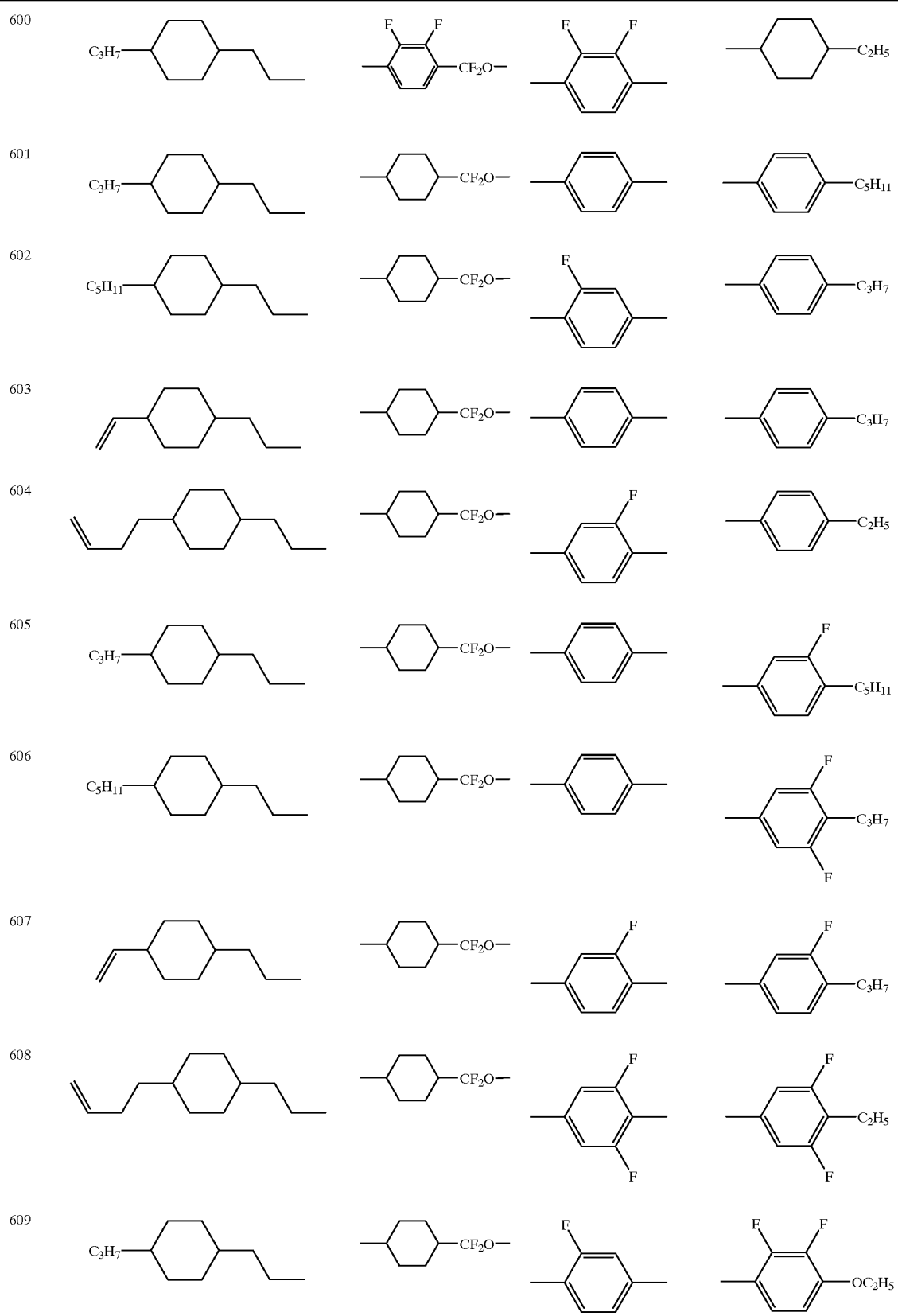

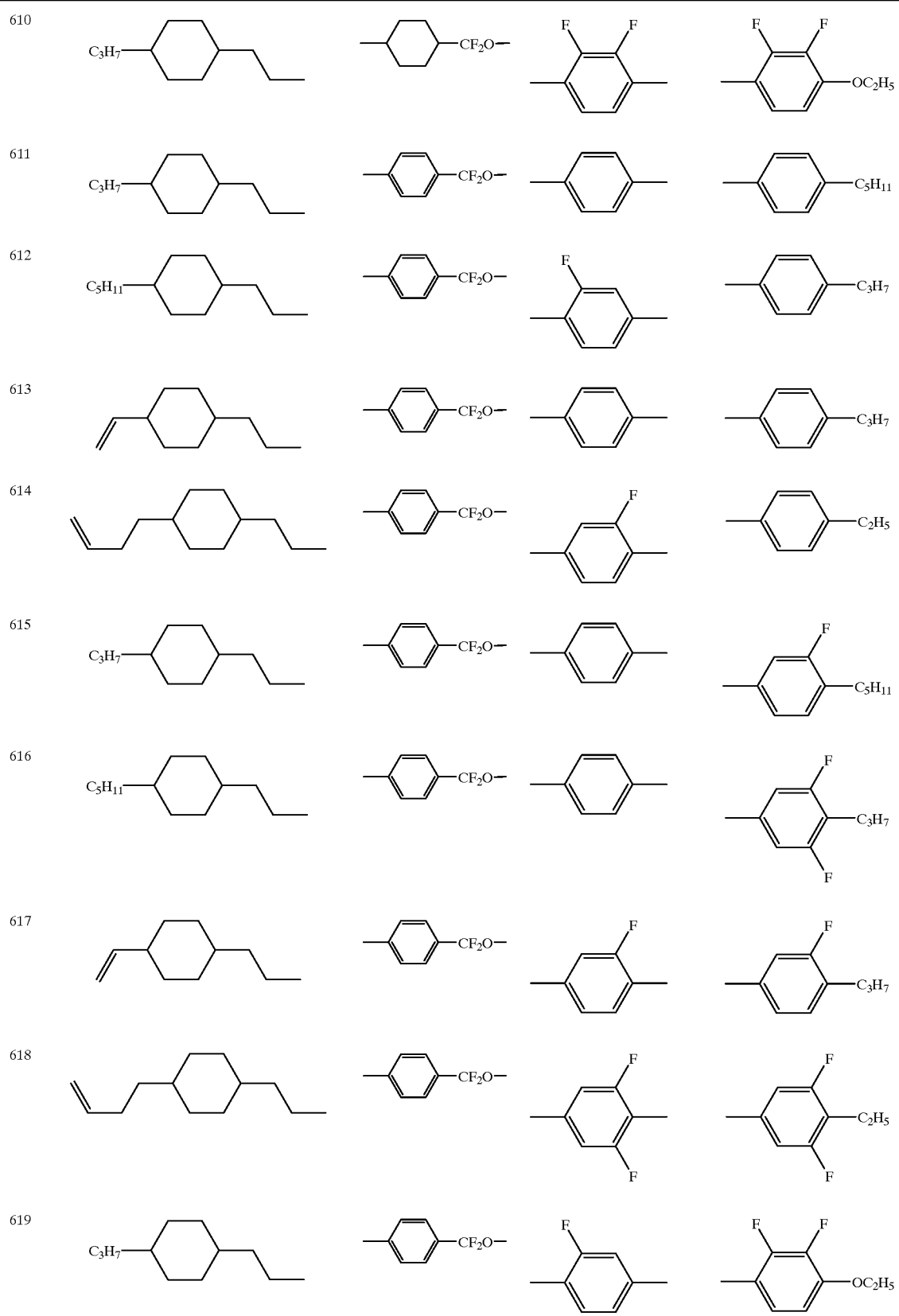

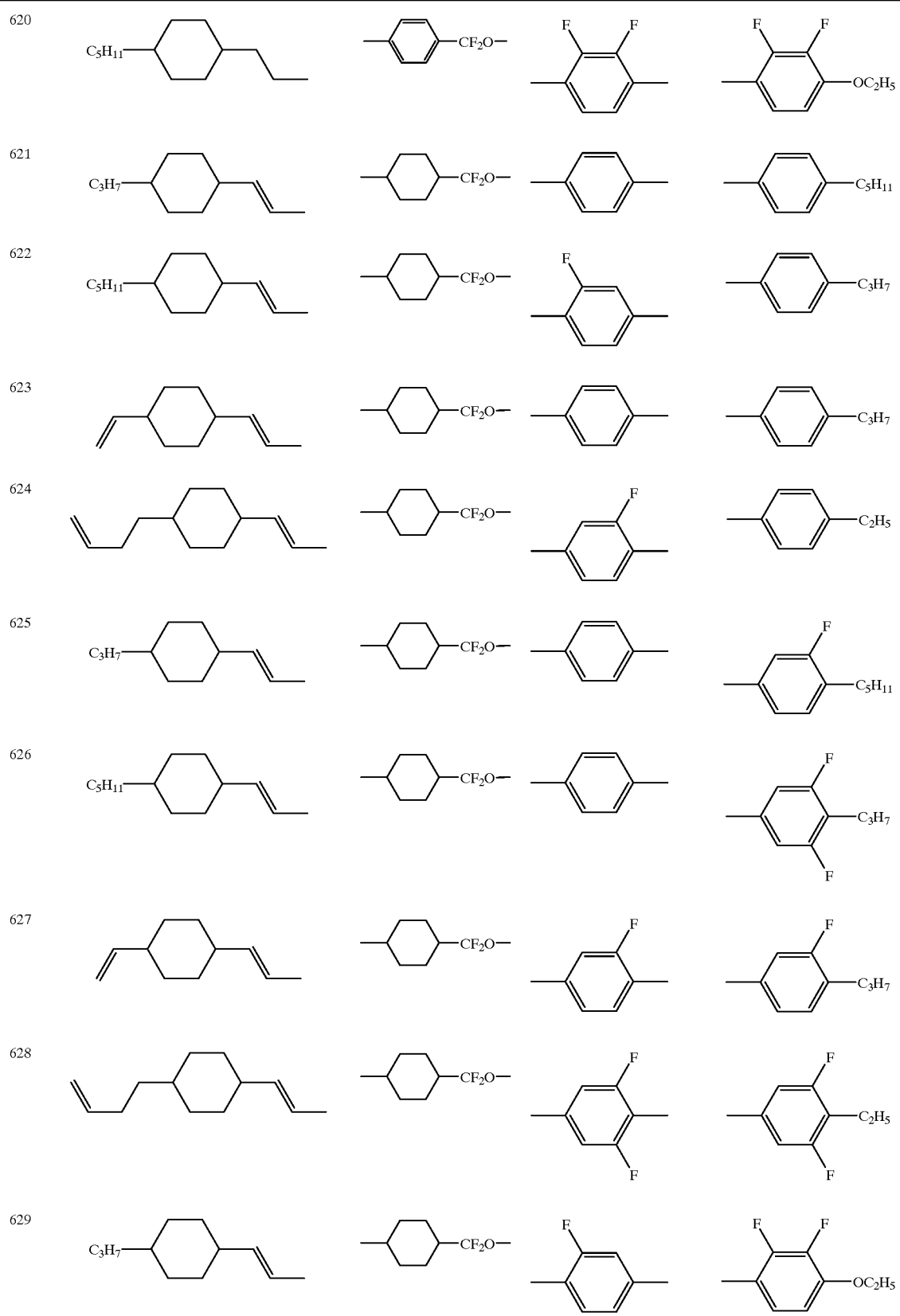

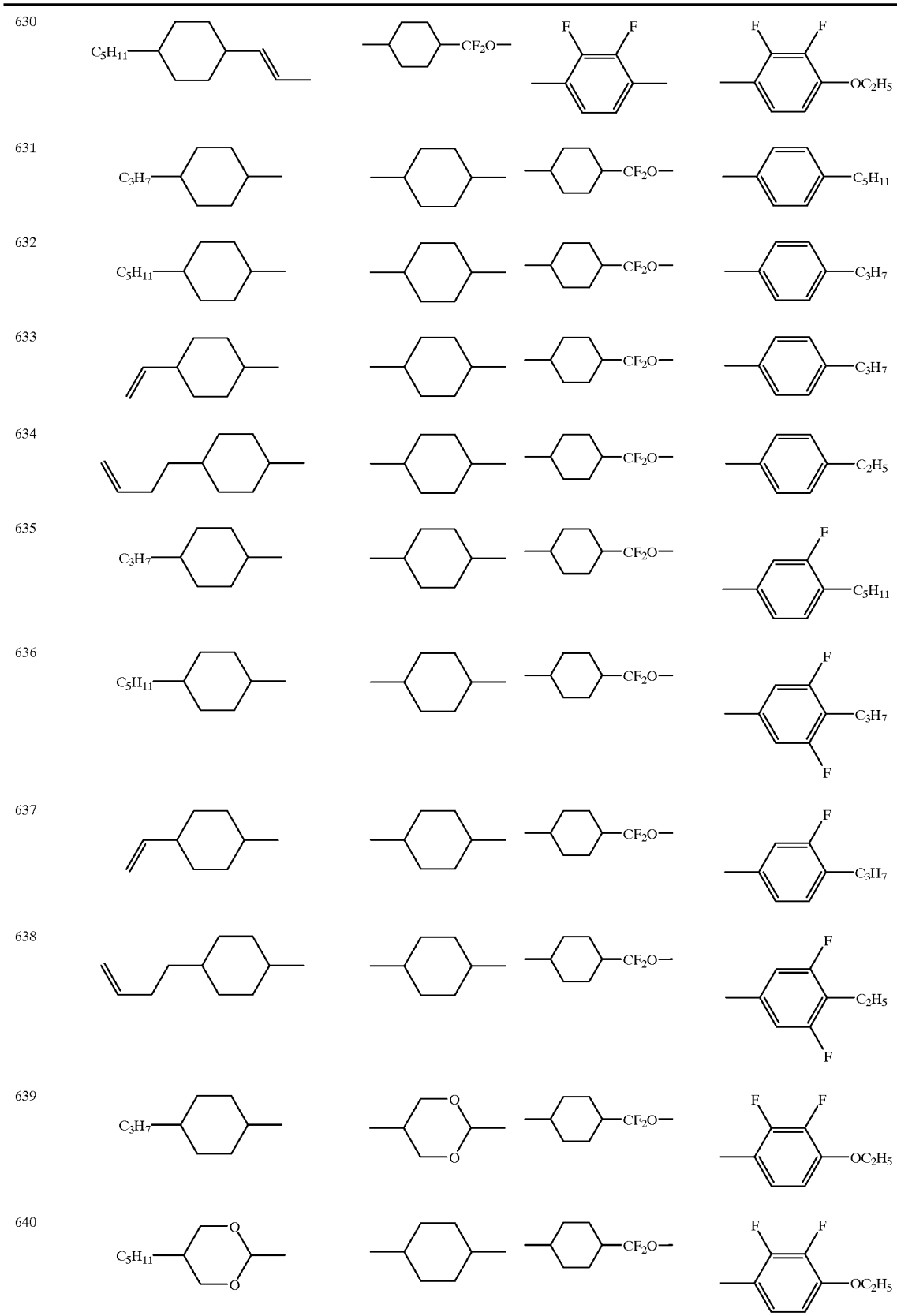

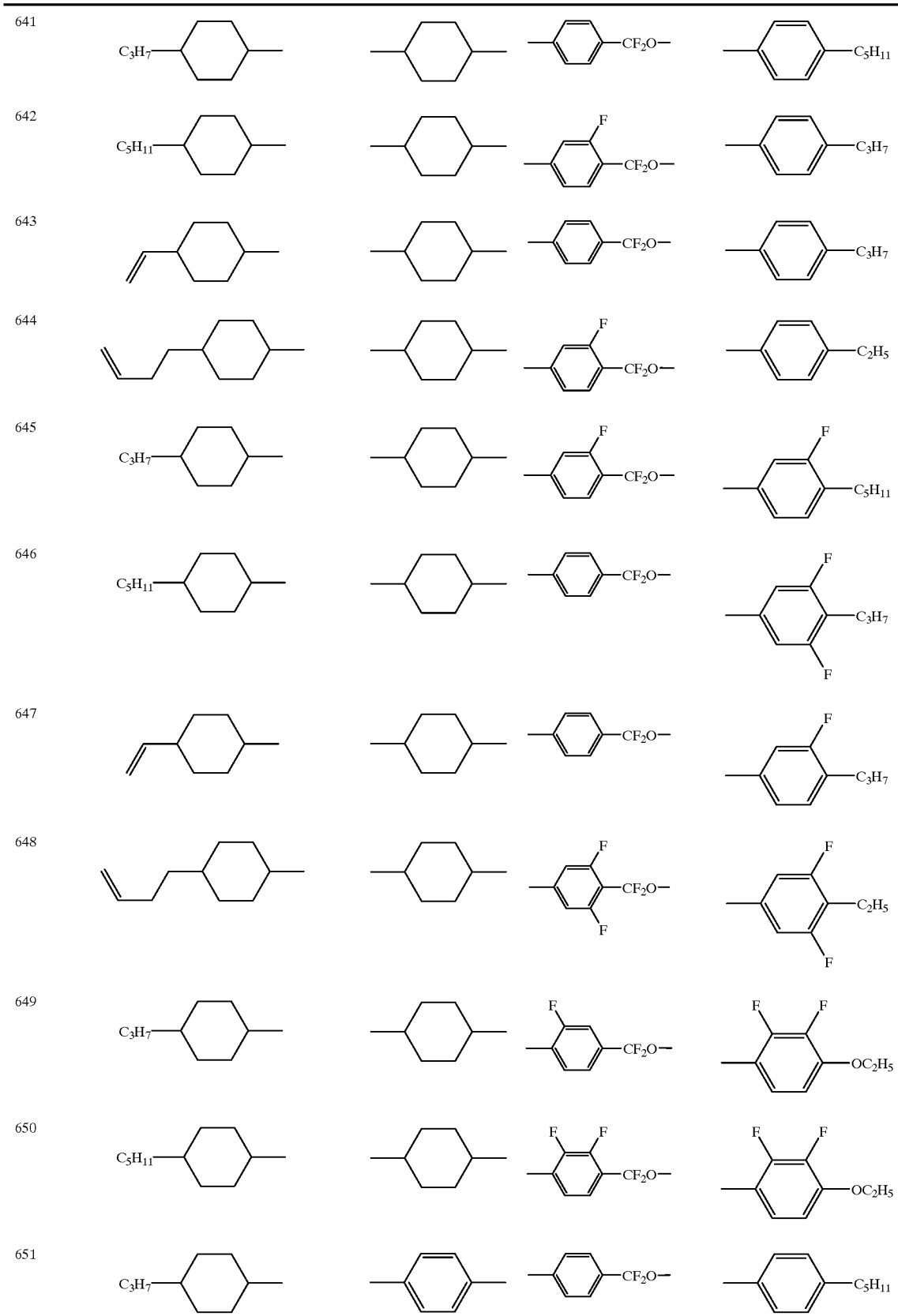

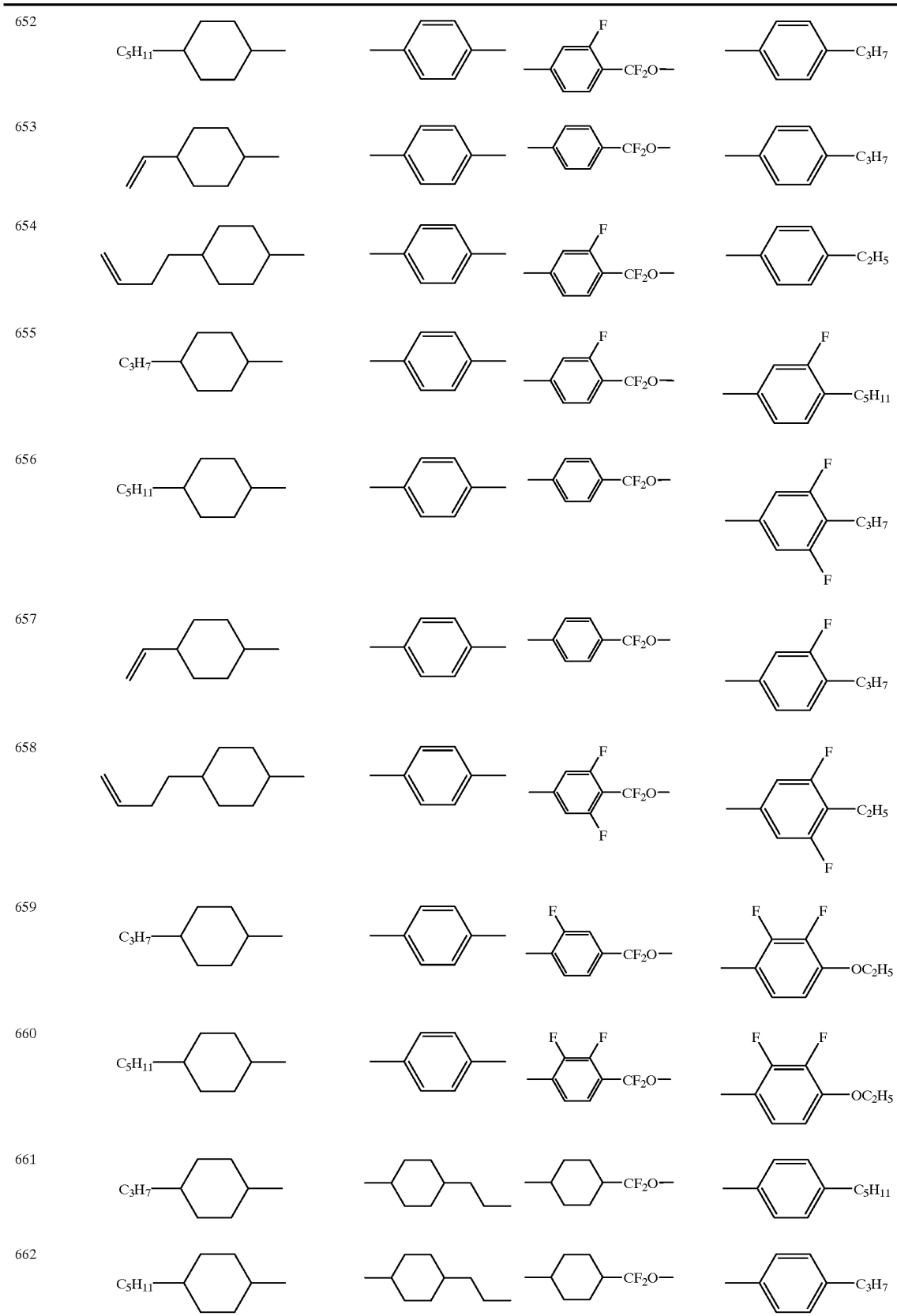

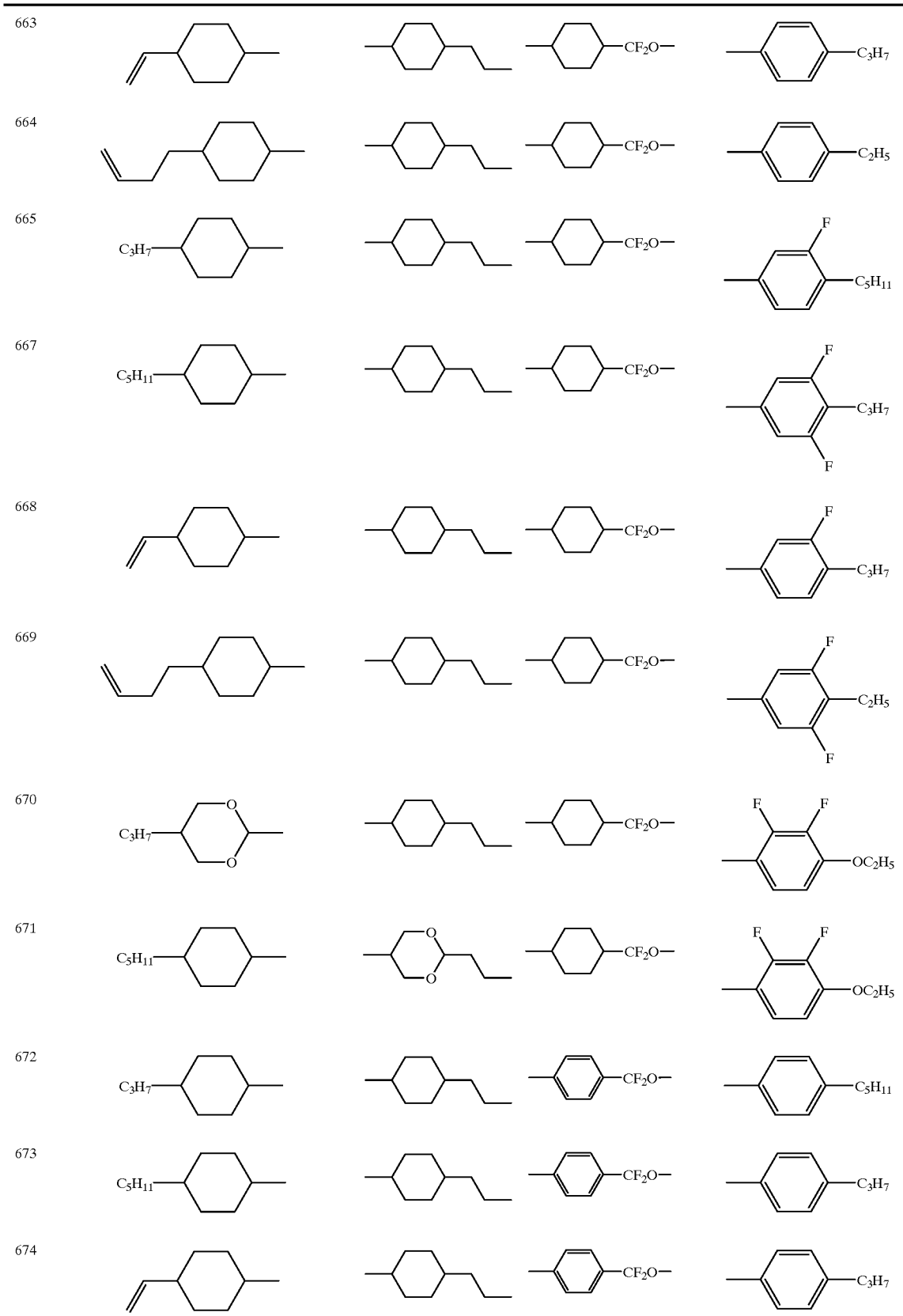

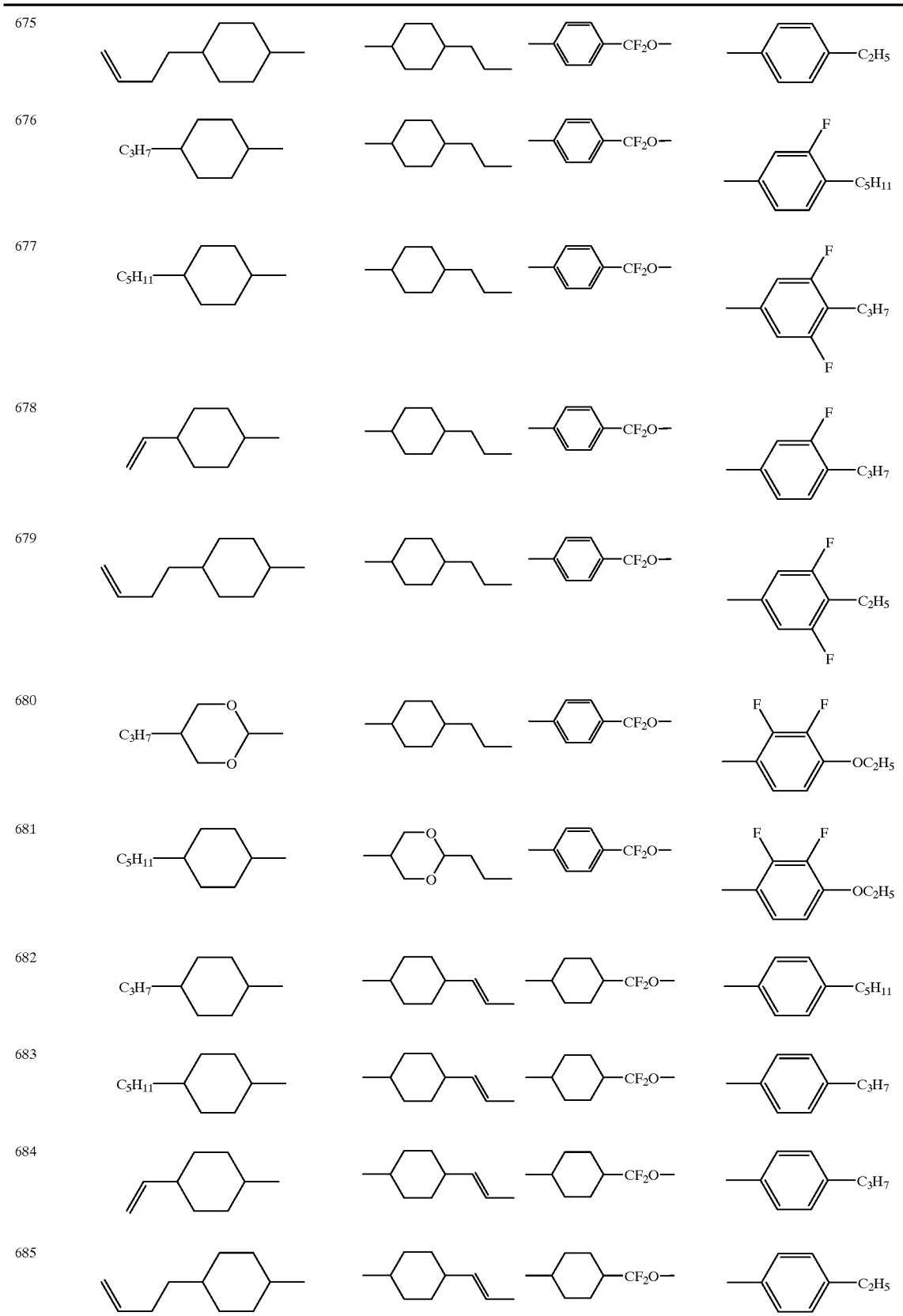

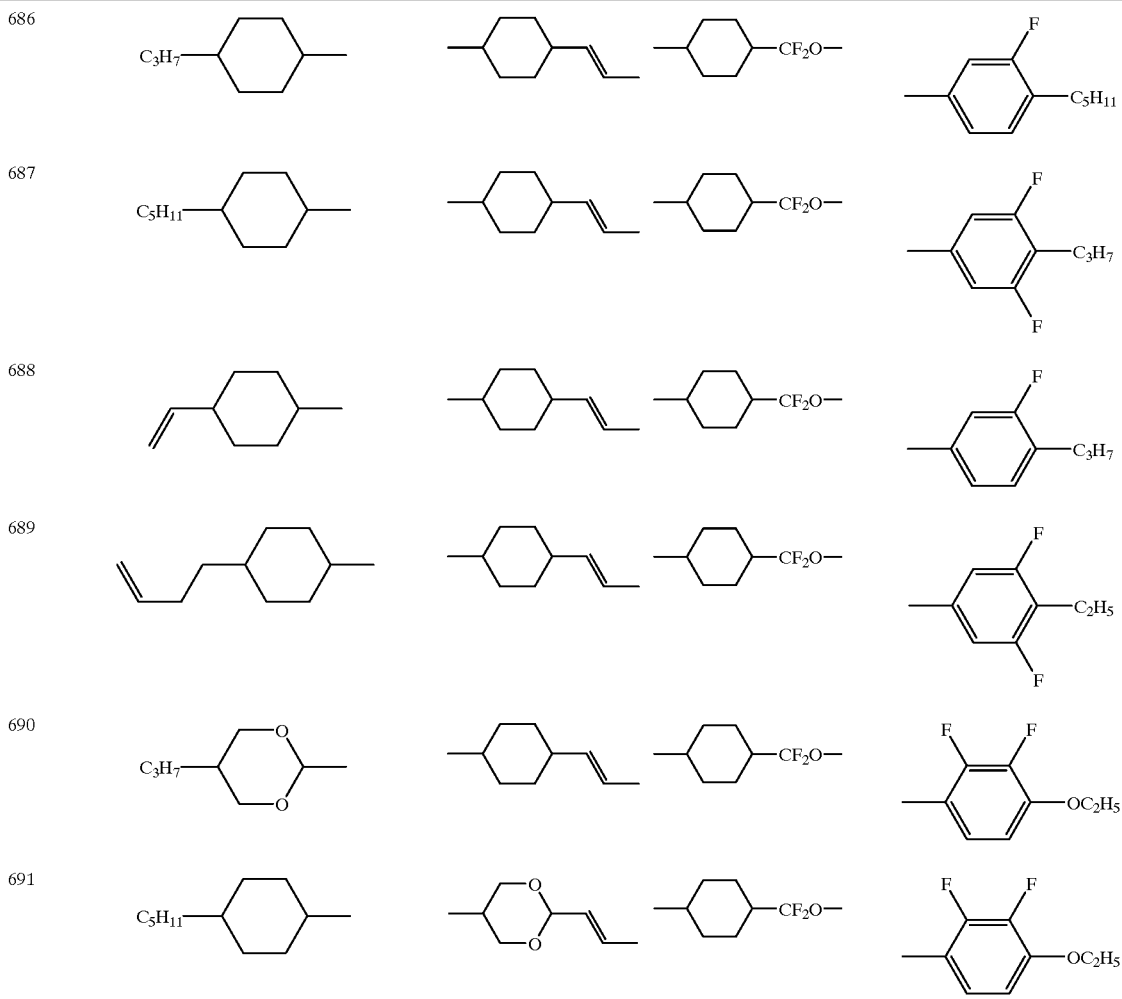

USE EXAMPLES

In the Use Examples shown below, value of dielectric anisotropy Δε was determined by using a TN cell (twisted nematic cell) having a cell thickness of 9 μm at 25° C.

EXAMPLE 9

Use Example 1

Clearing point (Cp) of a nematic liquid crystal of liquid crystal composition (hereinafter referred to as mother liquid crystal A) comprising the following compounds each in the amount shown below
4-butoxyphenyl 4-(trans-4-propylcyclohexyl) carboxybenzoate
27.6% (by weight, the same unit is applied below)
4-ethoxyphenyl 4-(trans-4-butylcyclohexyl) carboxybenzoate
20.7%
4-methoxyphenyl 4-(trans-4-pentylcyclohexyl) carboxybenzoate
20.7%
4-ethoxyphenyl 4-(trans-4-propylcyclohexyl) carboxybenzoate
17.2%
4-ethoxyphenyl 4-(trans-4-pentylcyclohexyl) carboxybenzoate
13.8%
was 74.6° C. and its Δε was 0.0.

This mother liquid crystal A in an amount of 85 parts by weight was mixed with 15 parts by weight of the 2,3-difluoro-4-ethoxyphenyl 2-fluoro-4-(2-(trans-4-propylcyclohexyl)ethyl)benzoate (Compound No. 15) obtained in Example 1, and its physical properties were determined. Value of the physical properties of the compound obtained by extrapolation from the results were as follows:
Cp: 129.4° C., Δε: −4.17

EXAMPLE 10

Use Example 2

Mother liquid crystal A in an amount of 90 parts by weight was mixed with 10 parts by weight of 2,3-difluoro-4-ethoxyphenyl 4-(2-(trans-4-pentylcyclohexyl)vinyl)cyclohexyl-carboxylate (Compound No. 7), and its physical properties were determined. Value of the physical properties of the compound obtained by extrapolation from the results were as follows:
Cp: 187.1° C., Δε: −5.67

EXAMPLE 11

Use Example 3

Mother liquid crystal A in an amount of 85 parts by weight was mixed with 15 parts by weight of the (2,3-difluoro-4ethoxyphenyl)oxy(4-(trans-4-n-pentylcyclohexyl)phenyl)difluoromethane (Compound No. 152) obtained in Example 2, and its physical properties were determined. Value of the physical properties of the compound obtained by extrapolation from the results were as follows:

Cp: 114.1IC, Δε: −4.20

EXAMPLE 12

Use Example 4

Clearing point (Cp) of a nematic liquid crystal of liquid crystal composition (hereinafter referred to as mother liquid crystal B) comprising the following compounds each in the amount shown below 4-(trans-4-propylcyclohexyl)benzonitrile 24% (by weight, the same unit is applied below)
4-(trans-4-pentylcyclohexyl)benzonitrile 36%
4-(trans-4-heptylcyclohexyl)benzonitrile 25%
4-(4-propylphenyl)benzonitrile 15% was 72.4° C. When this liquid crystal composition was filled in a TN cell (twisted nematic cell) having a cell thickness of 9 μm, its driving threshold voltage (Vth) was 1.78 V, value of dielectric anisotropy (Δε) was +11.0, value of optical anisotropy (Δn) was 0.137, and viscosity at 20° C. ($\eta_{20}$) was 27.0 mPa·s.

This mother liquid crystal B in an amount of 85 parts by weight was mixed with 15 parts by weight of the difluoro-(4-(trans-4-propylcyclohexyl)phenyloxy) (4-(trans-4-pentylcyclohexyl)phenyl)methane (Compound No. 572) obtained in Example 6, and its physical properties were determined. The results were as follows:

Cp: 90.3° C., Vth: 1.81 V, Δε: 9.9, Δn: 0.136, $\eta_{20}$: 28.4 mPa·s

Further, while this liquid crystal composition was left in a freezer at −20° C. for 25 days, separation of crystals or development of smectic phase was not noticed.

EXAMPLE 13

Use Example 5

Mother liquid crystal B in an amount of 85 parts by weight was mixed with 15 parts by weight of difluoro-(4-(trans-4-propylcyclohexyl)phenyloxy) (4-(2-(trans-4-propylcyclohexyl)ethyl)phenyl)methane (Compound No. 591), and its physical properties were determined. The results were as follows:

Cp: 87.2° C., Vth: 1.85 V, Δε: 9.9, Δn: 0.137, $\eta_{20}$: 28.2 mPa·s

Further, while this liquid crystal composition was left in a freezer at −20° C. for 25 days, separation of crystals or development of smectic phase was not noticed.

EXAMPLE 14

Use Example 6

Mother liquid crystal B in an amount of 85 parts by weight was mixed with 15 parts by weight of difluoro-(4-(trans-4-pentylcyclohexyl)phenyloxy) (4-(2-(trans-4-propylcyclohexyl)ethyl)phenyl)methane (Compound No. 592), and its physical properties were determined. The results were as follows:

Cp: 89.8° C., Vth: 1.87 V, Δε: 9.7, Δn: 0.136, $\eta_{20}$: 29.0 mPa·s

Further, while this liquid crystal composition was left in a freezer at −20° C. for 25 days, separation of crystals or development of smectic phase was not noticed.

EXAMPLE 15

Use Example 7

Physical properties of the liquid crystal composition shown in Composition Example 1 were determined. As the results, Cp was 90.2 and Δε was 6.8.

EXAMPLE 16

Use Example 8

Physical properties of the liquid crystal composition shown in Composition Example 2 were determined. As the results, Cp was 87.1 and Δε was 8.5.

EXAMPLE 17

Use Example 9

Physical properties of the liquid crystal composition shown in Composition Example 3 were determined. As the results, Cp was 94.0 and Δε was 29.8.

EXAMPLE 18

Use Example 10

Physical properties of the liquid crystal composition shown in Composition Example 4 were determined. As the results, Cp was 91.7 and Δε was 6.1.

EXAMPLE 19

Use Example 11

Physical properties of the liquid crystal composition shown in Composition Example 5 were determined. As the results, Cp was 79.4 and Δε was 7.2.

EXAMPLE 20

Use Example 12

Physical properties of the liquid crystal composition shown in Composition Example 6 were determined. As the results, Cp was 91.4 and Δε was 4.5.

EXAMPLE 21

Use Example 13

Physical properties of the liquid crystal composition shown in Composition Example 7 were determined. As the results, Cp was 87.1 and Δε was 27.9.

EXAMPLE 22

Use Example 14

Physical properties of the liquid crystal composition shown in Composition Example 8 were determined. As the results, Cp was 62.1 and Δε was 9.6.

EXAMPLE 23

Use Example 15

Physical properties of the liquid crystal composition shown in Composition Example 9 were determined. As the results, Cp was 64.1 and Δε was 6.0.

EXAMPLE 24

Use Example 16

Physical properties of the liquid crystal composition shown in Composition Example 10 were determined. As the results, Cp was 100.7 and Δε was 7.5.

EXAMPLE 25

Use Example 17

Physical properties of the liquid crystal composition shown in Composition Example 11 were determined. As the results, Cp was 96.6 and AΔε was 6.4.

EXAMPLE 26

Use Example 18

Physical properties of the liquid crystal composition shown in Composition Example 12 were determined. As the results, Cp was 79.8 and Δε was 6.2.

EXAMPLE 27

Use Example 19

Physical properties of the liquid crystal composition shown in Composition Example 13 were determined. As the results, Cp was 94.5 and Δε was 3.8.

EXAMPLE 28

Use Example 20

Physical properties of the liquid crystal composition shown in Composition Example 14 were determined. As the results, Cp was 99.8 and Δε was 4.6.

EXAMPLE 29

Use Example 21

Physical properties of the liquid crystal composition shown in Composition Example 15 were determined. As the results, Cp was 88.5 and Δε was 2.9.

EXAMPLE 30

Use Example 22

Physical properties of the liquid crystal composition shown in Composition Example 16 were determined. As the results, Cp was 86.5 and Δε was 5.4.

EXAMPLE 31

Use Example 23

Physical properties of the liquid crystal composition shown in Composition Example 17 were determined. As the results, Cp was 73.8 and Δε was 8.4.

EXAMPLE 32

Use Example 24

Physical properties of the liquid crystal composition shown in Composition Example 18 were determined. As the results, Cp was 76.8 and Δε was 12.6.

EXAMPLE 33

Use Example 25

Physical properties of the liquid crystal composition shown in Composition Example 19 were determined. As the results, Cp was 97.0 and Δε was 8.1.

EXAMPLE 34

Use Example 26

Physical properties of the liquid crystal composition shown in Composition Example 20 were determined. As the results, Cp was 83.1 and Δε was 4.1.

EXAMPLE 35

Use Example 27

Physical properties of the liquid crystal composition shown in Composition Example 21 were determined. AS the results, Cp was 82.4 and AΔε was −1.8.

EXAMPLE 36

Use Example 28

Physical properties of the liquid crystal composition shown in Composition Example 22 were determined. As the results, Cp was 77.3 and Δε was −2.1.

EXAMPLE 37

Use Example 29

Physical properties of the liquid crystal composition shown in Composition Example 23 were determined. As the results, Cp was 78.8 and Δε was −3.0.

In addition to the Examples shown above, the following Examples (Use Examples) can be shown. In the following Examples, compounds are designated by using symbols according to the definitions shown in Table 1 described above, and $T_{NI}$ indicates clearing point, η: viscosity, Δn: optical anisotropy value, Δε: dielectric anisotropy value, $V_{th}$: threshold voltage, and P: pitch.

EXAMPLE 38

Use Example 30

| | |
|---|---|
| 5-HBCF2OBH-3 | 3.0% |
| 2-HB(F)OCF2BH | 3.0% |
| 1V2-BEB(F,F)—C | 5.0% |
| 3-HB—C | 25.0% |
| 1-BTB-3 | 5.0% |
| 2-BTB-1 | 10.0% |
| 3-HH-4 | 11.0% |
| 3-HHB-1 | 5.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

$T_{NI}$ = 92.4 (° C.)
η = 16.0 (mPa.s)
Δn = 0.162
Δε = 7.0
$V_{th}$ = 2.12 (V)

Pitch of a liquid crystal composition prepared by adding 0.8 part by weight of optically active compound CM 33 to 100 parts by weight of the liquid crystal composition described above was as follows:

P=11 μm

EXAMPLE 39

Use Example 31

| | |
|---|---|
| 3-H2BCF2OBH-5 | 5.0% |
| 3-HB(F,F)OCF2BH-5 | 5.0% |
| 2O1-BEB(F)—C | 5.0% |
| 3O1-BEB(F)—C | 15.0% |
| 4O1-BEB(F)—C | 13.0% |
| 5O1-BEB(F)—C | 13.0% |
| 2-HHB(F)—C | 15.0% |
| 3-HHB(F)—C | 5.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB—O1 | 4.0% |

$T_{NI}$ = 92.9 (° C.)
$\eta$ = 86.0 (mPa.s)
$\Delta n$ = 0.146
$\Delta\epsilon$ = 29.7
$V_{th}$ = 0.90 (V)

EXAMPLE 40

Use Example 32

| | |
|---|---|
| 3-H2BCF2OBH-5 | 4.0% |
| 3-HB(F,F)OCF2BH-5 | 4.0% |
| 2-BEB—C | 12.0% |
| 3-BEB—C | 4.0% |
| 4-BEB—C | 6.0% |
| 3-HB—C | 28.0% |
| 3-HEB—O4 | 12.0% |
| 4-HEB—O2 | 8.0% |
| 5-HEB—O1 | 4.0% |
| 3-HEB—O2 | 6.0% |
| 5-HEB—O2 | 5.0% |
| 3-HHB-1 | 3.0% |
| 3-HHB—O1 | 4.0% |

$T_{NI}$ = 67.8 (° C.)
$\eta$ = 28.2 (mPa.s)
$\Delta n$ = 0.115
$\Delta\epsilon$ = 10.0
$V_{th}$ = 1.35 (V)

EXAMPLE 41

Use Example 33

| | |
|---|---|
| 5-HBCF2OBH-3 | 3.0% |
| 3-H2BCF2OBH-3 | 3.0% |
| 7-HB(F)—F | 5.0% |
| 5-H2B(F)—F | 5.0% |
| 3-HB—O2 | 10.0% |
| 3-HH-4 | 5.0% |
| 2-HHB(F)—F | 10.0% |
| 3-HHB(F)—F | 10.0% |
| 5-HHB(F)—F | 10.0% |
| 3-H2HB(F)—F | 5.0% |
| 2-HBB(F)—F | 3.0% |
| 3-HBB(F)—F | 3.0% |
| 5-HBB(F)—F | 6.0% |
| 2-H2BB(F)—F | 5.0% |
| 3-H2BB(F)—F | 6.0% |
| 3-HHB-1 | 2.0% |
| 3-HHB—O1 | 5.0% |
| 3-HHB-3 | 4.0% |

$T_{NI}$ = 90.6 (° C.)
$\eta$ = 19.4 (mPa.s)
$\Delta n$ = 0.093
$\Delta\epsilon$ = 3.2
$V_{th}$ = 2.67 (V)

EXAMPLE 42

Use Example 34

| | |
|---|---|
| 3-H2BCF2OBH-3 | 4.0% |
| 2-HB(F)OCF2BH-5 | 3.0% |
| 5-HVHEB(2F,3F)—O2 | 3.0% |
| 7-HB(F,F)—F | 3.0% |
| 3-HB—O2 | 7.0% |
| 2-HHB(F)—F | 10.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 6.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |

$T_{NI}$ = 93.0 (° C.)
$\eta$ = 24.1 (mPa.s)
$\Delta n$ = 0.113
$\Delta\epsilon$ = 5.8
$V_{th}$ = 1.99 (V)

EXAMPLE 43

Use Example 35

| | |
|---|---|
| 5-HBCF2OBH-3 | 3.0% |
| 3-H2BCF2OBH-5 | 3.0% |
| 3-HB(F,F)OCF2BH-5 | 3.0% |
| 7-HB(F,F)—F | 4.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 10.0% |
| 5-HH2B(F,F)—F | 6.0% |
| 3-HBB(F,F)—F | 12.0% |
| 5-HBB(F,F)—F | 12.0% |

$T_{NI}$ = 81.4 (° C.)
$\eta$ = 28.8 (mPa.s)
$\Delta n$ = 0.079
$\Delta\epsilon$ = 8.2
$V_{th}$ = 1.61 (V)

EXAMPLE 44

Use Example 36

| | |
|---|---|
| 2-HB(F)OCF2BH-5 | 4.0% |
| 3-HB(F,F)OCF2BH-5 | 4.0% |
| 3-HB—CL | 10.0% |
| 5-HB—CL | 4.0% |
| 7-HB—CL | 4.0% |
| 1O1-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |

$T_{NI}$ = 90.5 (° C.)
$\eta$ = 22.9 (mPa.s)
$\Delta n$ = 0.128
$\Delta \epsilon$ = 4.7
$V_{th}$ = 2.37 (V)

EXAMPLE 45

Use Example 37

| | |
|---|---|
| 5-HBCF2OB(2F,3F)—O2 | 15.0% |
| 3-HEB—O4 | 24.0% |
| 4-HEB—O2 | 17.0% |
| 5-HEB—O1 | 17.0% |
| 3-HEB—O2 | 15.0% |
| 5-HEB—O2 | 12.0% |

$T_{NI}$ = 80.1 (° C.)
$\eta$ = 23.2 (mPa.s)
$\Delta n$ = 0.092
$\Delta \epsilon$ = −1.8

EXAMPLE 46

Use Example 38

| | |
|---|---|
| 3-H2B(F)EB(2F,3F)—O2 | 15.0% |
| 3-HEB—O4 | 24.0% |
| 4-HEB—O2 | 17.0% |
| 5-HEB—O1 | 17.0% |
| 3-HEB—O2 | 15.0% |
| 5-HEB—O2 | 12.0% |

$T_{NI}$ = 82.4 (° C.)
$\eta$ = 29.1 (mPa.s)
$\Delta n$ = 0.093

EXAMPLE 47

Use Example 39

| | |
|---|---|
| 3-H2B(F)EB(2F,3F)—O2 | 5.0% |
| 5-HVHEB(2F,3F)—O2 | 5.0% |
| 3-HH-2 | 5.0% |
| 3-HH-4 | 6.0% |
| 3-HH—O1 | 4.0% |
| 3-HH—O3 | 5.0% |
| 5-HH—O1 | 4.0% |
| 3-HB(2F,3F)—O2 | 12.0% |
| 5-HB(2F,3F)—O2 | 11.0% |
| 3-HHB(2F,3F)—O2 | 4.0% |
| 5-HHB(2F,3F)—O2 | 15.0% |
| 3-HHB(2F,3F)-2 | 24.0% |

$T_{NI}$ = 84.6 (° C.)
$\Delta n$ = 0.083
$\Delta \epsilon$ = −3.9

EXAMPLE 48

Use Example 40

| | |
|---|---|
| 5-HVHEB(2F,3F)—O2 | 5.0% |
| 3-HH-5 | 5.0% |
| 3-HH-4 | 5.0% |
| 3-HH—O1 | 6.0% |
| 3-HH—O3 | 6.0% |
| 3-HB—O1 | 5.0% |
| 3-HB—O2 | 5.0% |
| 3-HB(2F,3F)—O2 | 10.0% |
| 5-HB(2F,3F)—O2 | 10.0% |
| 3-HHB(2F,3F)—O2 | 12.0% |
| 5-HHB(2F,3F)—O2 | 8.0% |
| 3-HHB(2F,3F)-2 | 4.0% |
| 2-HHB(2F,3F)-1 | 4.0% |
| 3-HHEH-3 | 5.0% |
| 3-HHEH-5 | 5.0% |
| 4-HHEH-3 | 5.0% |

$T_{NI}$ = 85.5 (° C.)
$\Delta n$ = 0.079
$\Delta \epsilon$ = −3.4

EXAMPLE 49

Use Example 41

| | |
|---|---|
| 3-h2B(F)EB(2F,3F)—O2 | 5.0% |
| 5-HBCF2OB(2F,3F)—O2 | 5.0% |
| 3-BB(2F,3F)—O2 | 12.0% |
| 3-BB(2F,3F)—O4 | 10.0% |
| 5-BB(2F,3F)—O4 | 10.0% |
| 2-BB(2F,3F)B-3 | 25.0% |
| 3-BB(2F,3F)B-5 | 13.0% |
| 5-BB(2F,3F)B-5 | 14.0% |
| 5-BB(2F,3F)B-7 | 6.0% |

$T_{NI}$ = 72.5 (° C.)
$\Delta n$ = 0.188
$\Delta \epsilon$ = −3.6

EXAMPLE 50

Use Example 42

| | |
|---|---|
| 5-HBCF2OBH-3 | 3.0% |
| 3-H2B(F)EB(2F,3F)—O2 | 4.0% |
| 5-HVHEB(2F,3F)—O2 | 4.0% |
| 5-HBCF2OB(2F,3F)—O2 | 4.0% |
| 3-BB(2F,3F)—O2 | 10.0% |
| 5-BB-5 | 9.0% |
| 5-BB—O6 | 9.0% |
| 5-BB—O8 | 8.0% |
| 1-BEB-5 | 6.0 & |

-continued

| | |
|---|---|
| 3-BEB-5 | 6.0 & |
| 5-BEB-5 | 3.0 & |
| 3-HEB—O2 | 20.0% |
| 5-BBB(2F,3F)-7 | 9.0% |
| 3-H2BB(2F)-5 | 5.0% |

$T_{NI}$ = 79.1 (° C.)
$\Delta n$ = 0.145
$\Delta \epsilon$ = −3.1

EXAMPLE 51

Use Example 43

| | |
|---|---|
| 3-H2BCF2OBH-5 | 3.0% |
| 3-H2B(F)EB(2F,3F)—O2 | 9.0% |
| 5-HVHEB(2F,3F)—O2 | 9.0% |
| 5-HBCF2OB(2F,3F)—O2 | 9.0% |
| 3-HB—O1 | 15.0% |
| 3-HB—O2 | 6.0% |
| 3-HEB(2F,3F)—O2 | 9.0% |
| 4-HEB(2F,3F)—O2 | 9.0% |
| 5-HEB(2F,3F)—O2 | 4.0% |
| 2-BB2B—O2 | 6.0% |
| 1-B2BB(2F)-5 | 7.0% |
| 5-B(3F)BB—O2 | 7.0% |
| 3-BB(2F,3F)B-3 | 7.0% |

$T_{NI}$ = 84.5 (° C.)
$\Delta n$ = 0.145
$\eta$ = 32.0 (mPa.s)

EXAMPLE 52

Use Example 44

| | |
|---|---|
| 5-HVHEB(2F,3F)—O2 | 3.0% |
| 5-HBCF2OB(2F,3F)—O2 | 3.0% |
| 3-HB—O1 | 9.0% |
| 3-HB—O2 | 9.0% |
| 3-HB—O4 | 9.0% |
| 2-BTB—O1 | 5.0% |
| 1-BTB—O2 | 5.0% |
| 3-BTB(2F,3F)—O2 | 13.0% |
| 5-BTB(2F,3F)—O2 | 13.0% |
| 3-B(2F,3F)TB(2F,3F)—O4 | 4.0% |
| 5-B(2F,3F)TB(2F,3F)—O4 | 4.0% |
| 3-HBTB—O1 | 5.0% |
| 3-HBTB—O3 | 5.0% |
| 3-HHB(2F,3F)—O2 | 6.0% |
| 5-HBB(2F,3F)—O2 | 4.0% |
| 5-BPr(F)—O2 | 3.0% |

$T_{NI}$ = 82.4 (° C.)
$\Delta n$ = 0.210

EXAMPLE 53

Use Example 45

| | |
|---|---|
| 3-H2B(F)EB(2F,3F)—O2 | 5.0% |
| 5-HBCF2OB(2F,3F)—O2 | 5.0% |
| 3-HB—O2 | 10.0% |
| 5-HB-3 | 8.0% |
| 5-BB(2F,3F)—O2 | 10.0% |
| 3-HB(2F,3F)—O2 | 10.0% |
| 5-HB(2F,3F)—O2 | 8.0% |

-continued

| | |
|---|---|
| 3-HHB(2F,3F)—O2 | 7.0% |
| 5-HHB(2F,3F)—O2 | 4.0% |
| 5-HHB(2F,3F)-1O1 | 4.0% |
| 2-HHB(2F,3F)-1 | 5.0% |
| 3-HBB-2 | 6.0% |
| 3-BB(2F,3F)B-3 | 8.0% |
| 5-B2BB(2F,3F0B—O2 | 10.0% |

$T_{NI}$ = 69.9 (° C.)
$\Delta n$ = 0.143
$\Delta \epsilon$ = −3.9

EXAMPLE 54

Use Example 46

| | |
|---|---|
| 3-H2B(F)EB(2F,3F)—O2 | 3.0% |
| 5-HVHEB(2F,3F)—O2 | 3.0% |
| 5-HBCF2OB(2F,3F)—O2 | 3.0% |
| 3-HB—O2 | 20.0% |
| 1O1-HH-3 | 6.0% |
| 1O1-HH-5 | 5.0% |
| 3-HH—EMe | 12.0% |
| 4-HEB—O1 | 9.0% |
| 4-HEB—O2 | 7.0% |
| 5-HEB—O1 | 8.0% |
| 3-HHB-1 | 3.0% |
| 4-HEB(2CN, 3CN)—O4 | 3.0% |
| 6-HEB(2CN, 3CN)—O4 | 3.0% |
| 3-HEB(2CN, 3CN)—O5 | 4.0% |
| 4-HEB(2CN, 3CN)—O5 | 3.0% |
| 5-HEB(2CN, 3CN)—O5 | 2.0% |
| 2-HBEB(2CN, 3CN)—O2 | 2.0% |
| 4-HBEB(2CN, 3CN)—O4 | 4.0% |

$T_{NI}$ = 63.9 (° C.)
$\Delta n$ = 0.073
$\eta$ = 43.3 (mPa.s)
$\Delta \epsilon$ = −5.7

EXAMPLE 55

Use Example 47

| | |
|---|---|
| 3-H2B(F)EB(2F,3F)—O2 | 5.0% |
| 1V2-BEB(F,F)—C | 5.0% |
| 3-HB—C | 20.0% |
| V2-HB—C | 6.0% |
| 1-BTB-3 | 5.0% |
| 2-BTB-1 | 10.0% |
| 1O1-HH-3 | 3.0% |
| 3-HH-4 | 11.0% |
| 3-HHB-1 | 11.0% |
| 3-HHB-3 | 3.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HHB—C | 3.0% |

$T_{NI}$ = 88.1 (° C.)
$\eta$ = 17.9 (mPa.s)
$\Delta n$ = 0.156
$\Delta \epsilon$ = 7.1
$V_{th}$ = 2.09 (V)

Pitch of a liquid crystal composition prepared by adding 0.8 part by weight of optically active compound CM 33 to 100 parts by weight of the liquid crystal composition described above was as follows:

P=11.0 μm

EXAMPLE 56

Use Example 48

| | |
|---|---|
| 3-H2B(F)EB(2F,3F)—O2 | 5.0% |
| 5-HVHEB(2F,3F)—O2 | 5.0% |
| 5-PyB—F | 4.0% |
| 3-PyB(F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 3.0% |
| 2-H2BTB-2 | 4.0% |
| 2-H2BTB-3 | 4.0% |
| 3-H2BTB-2 | 5.0% |
| 3-H2BTB-3 | 5.0% |
| 3-H2BTB-4 | 5.0% |

$T_{NI}$ = 94.3 (° C.)
$\eta$ 39.7 (mPa.s)
$\Delta n$ = 0.197
$\Delta\epsilon$ = 6.6
$V_{th}$ = 2.23 (V)

EXAMPLE 57

Use Example 49

| | |
|---|---|
| 3-H2B(F)EB(2F,3F)—O2 | 3.0% |
| 5-HVHEB(2F,3F)—O2 | 3.0% |
| 5-HBCF2OB(2F,3F)—O2 | 3.0% |
| 2O1-BEB(F)—C | 5.0% |
| 3O1-BEB(F)—C | 12.0% |
| 5O1-BEB(F)—C | 4.0% |
| 1V2-BEB(F,F)—C | 10.0% |
| 3-HEB—O4 | 4.0% |
| 3-HH—EMe | 6.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F,F)—C | 2.0% |
| 3-HHB—F | 4.0% |
| 3-HHB—O1 | 4.0% |
| 3-HEBEB—F | 2.0% |
| 3-HEBEB-1 | 2.0% |
| 3-HHB(F)—C | 4.0% |

$T_{NI}$ = 78.3 (° C,)
$\eta$ = 40.6 (mPa.s)
$\Delta n$ = 0.116
$\Delta\epsilon$ = 24.3
$V_{th}$ = 0.95 (V)

EXAMPLE 58

Use Example 50

| | |
|---|---|
| 3-H2B(F)EB(2F,3F)—O2 | 3.0% |
| 5-HBCF2OB(2F,3F)—O2 | 3.0% |
| 7-HB(F)—F | 5.0% |
| 5-H2B(F)—F | 5.0% |
| 3-HB—O2 | 10.0% |
| 3-HH-4 | 5.0% |
| 2-HHB(F)—F | 10.0% |
| 3-HHB(F)—F | 10.0% |
| 5-HHB(F)—F | 10.0% |
| 3-H2HB(F)—F | 5.0% |
| 2-HBB(F)—F | 3.0% |
| 3-HBB(F)—F | 3.0% |
| 5-HBB(F)—F | 6.0% |
| 2-H2BB(F)—F | 5.0% |
| 3-H2BB(F)—F | 6.0% |
| 3-HHB-1 | 2.0% |
| 3-HHB—O1 | 5.0% |
| 3-HHB-3 | 4.0% |

$T_{NI}$ = 85.2 (° C.)
$\eta$ = 25.9 (mPa.s)
$\Delta n$ = 0.093
$\Delta\epsilon$ = 3.4
$V_{th}$ = 2.62 (V)

Pitch of a liquid crystal composition prepared by adding 0.3 part by weight of optically active compound CN to 100 parts by weight of the liquid crystal composition described above was as follows:

P=75 $\mu$m

EXAMPLE 59

Use Example 51

| | |
|---|---|
| 5-HVHEB(2F,3F)—O2 | 5.0% |
| 3-HB—CL | 10.0% |
| 5-HB—CL | 4.0% |
| 7-HB—CL | 4.0% |
| 1O1-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 3.0% |
| 3-H2HB(F)—CL | 4.0% |
| 3-HBB(F,F)—F | 10.0% |
| 5-H2BB(F,F)—F | 9.0% |
| 3-HB(F)—VB-2 | 4.0% |
| 3-H2BTB-2 | 4.0% |

$T_{NI}$ = 91.2 (° C.)
$\eta$ = 20.8 (mPa.s)
$\Delta n$ = 0.128
$\Delta\epsilon$ = 4.8
$V_{th}$ = 2.35 (V)

EXAMPLE 60

Use Example 52

| | |
|---|---|
| 3-H2BCF2OBH-3 | 2.0% |
| 3-H2B(F)EB(2F,3F)—O2 | 4.0% |
| 5-HBCF2OB(2F,3F)—O2 | 4.0% |
| 5-HB—F | 12.0% |
| 6-HB—F | 9.0% |

-continued

| | |
|---|---|
| 7-HB—F | 7.0% |
| 2-HHB—OCF3 | 2.0% |
| 3-HHB—OCF3 | 7.0% |
| 4-HHB—OCF3 | 7.0% |
| 3-HH2B—OCF3 | 4.0% |
| 5-HH2B—OCF3 | 4.0% |
| 3-HHB(F,F)—OCF3 | 5.0% |
| 3-HBB(F)—F | 10.0% |
| 3-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |

$T_{NI}$ = 87.2 (° C.)
$\eta$ = 18.6 (mPa.s)
$\Delta n$ = 0.096
$\Delta\epsilon$ = 4.6
$V_{th}$ = 2.37 (V)

EXAMPLE 61

Use Example 53

| | |
|---|---|
| 3-H2B(F)EB(2F,3F)—O2 | 5.0% |
| 5-HVHEB(2F,3F)—O2 | 5.0% |
| 5HBCF2OB(2F,3F)—O2 | 5.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 3-H2BB(F)—F | 9.0% |
| 3-HBB(F,F)—F | 25.0% |
| 5-HBB(F,F)—F | 19.0% |
| 1O1-HBBH-4 | 2.0% |
| 1O1-HBBH-5 | 2.0% |

$T_{NI}$ = 94.7 (° C.)
$\eta$ = 31.6 (mPa.s)
$\Delta n$ = 0.131
$\Delta\epsilon$ = 7.0
$V_{th}$ = 1.95 (V)

COMPARATIVE EXAMPLES 1 AND 2

As compounds to be compared with ones of the present invention, compound (c-1) described in Japanese Patent Publication No. Sho 62-39136 (R=$C_3H_7$, R'=$CH_3$) and compound (d-1) described in Japanese patent Publication No. Sho 62-46527 (R=$C_5H_{11}$, R'=$C_3H_7$, X=Y=H) were synthesized according to a preparation method described in each of the patent publications.

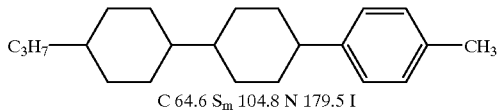

(c-1)

C 64.6 $S_m$ 104.8 N 179.5 I

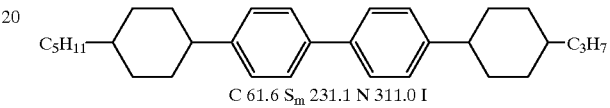

(d-1)

C 61.6 $S_m$ 231.1 N 311.0 I

Mother liquid crystal B in an amount of 85 parts by weight and 15 parts by weight of compound (c-1), and 85 parts by weight of mother liquid crystal B and 15 parts by weight of compound (d-1) were mixed, respectively, to prepare two liquid crystal compositions, and the physical properties of the liquid crystal compositions were determined. Further, liquid crystal compositions thus prepared were left in separate freezers each kept at −20° C., and miscibility was judged by counting the number of days lapsed from the day when the compositions were put in the freezer until the day when crystals separated (or smectic phase developed) in the liquid crystal compositions. These results are shown in Table 2 together with the results in Example 12 (Use Example 4) (numeral shown in the parentheses indicate the value of physical properties of each of the compounds obtained by extrapolation from the mother liquid crystal).

TABLE 2

| | | Cp (° C.) | Δε | $\eta_{20}$ (mPa·s) | Vth (V) | Miscibil.[*1] |
|---|---|---|---|---|---|---|
| | Mother liquid crystal B | 72.4 | 11.0 | 27.5 | 1.78 | >25 |
| Com. Ex. 1 | 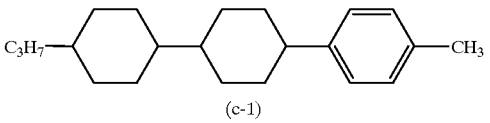 (c-1) | 85.6 (159.7) | 9.6 (2.3) | 26.8 (28.5) | 1.96 — | >25 |
| Com. Ex. 2 | 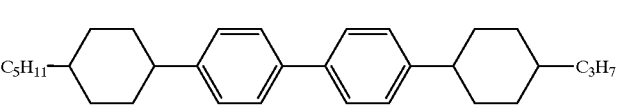 (d-1) | 100.8 (261.7) | 9.5 (1.0) | 31.8 (59.0) | 2.02 — | 15 |

TABLE 2-continued

| | | Cp (° C.) | Δε | η₂₀ (mPa·s) | Vth (V) | Miscibil.[*1] |
|---|---|---|---|---|---|---|
| Ex. 12 | 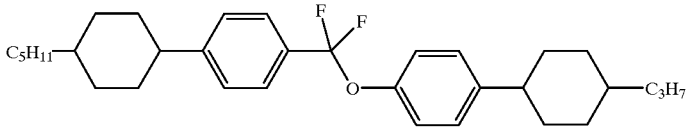<br>Compound No.572 | 90.3 (191.7) | 9.9 (3.7) | 28.4 (33.5) | 1.81 — | >25 |

[*1]Miscibility: Number of days lapsed from the day when the liquid crystal composition was left in a freezer at −20° C. until the day when crystals (solid such as smectic phase) separated.

In Comparative Example 1, whereas viscosity of the liquid crystal composition lowered compared with mother liquid crystal B, threshold voltage raised by 0.18 V. In Comparative Example 2, whereas it is demonstrated that comparative compound (d-1) was remarkable than compound (c-1) in the effect of raising clearing point, viscosity of liquid crystal composition was higher than mother liquid crystal B, and as to the threshold voltage, its value raised by as large as 0.24 V. In such a way, although compounds (c-1) and (d-1) have a respective merit, they have a defect that threshold voltage becomes high, and thereby it can be understood that the compounds can not be used for liquid crystal compositions for low voltage driving. In contrast to the comparative compounds, a compound of the present invention (Compound No. 572, Example 12) has an intermediate ability between compound (c-1) and compound (d-1) in the effect of raising clearing point; exhibits such a low viscosity as that of three rings compound (c-1) despite of having a four rings structure; and to our surprise, exhibits almost the same threshold voltage as mother liquid crystal B. That is, this compound can raise clearing point by nearly 20° C. by adding to mother liquid crystal B with hardly affecting threshold voltage.

Four rings compound (d-1) is very strong in smectogenecity, and development of its smectic phase was confirmed in a freezer at −20° C. in 15 days. In contrast to compound (d-1), separation of crystals was not noticed over 25 days with the compound of the present invention and the present compound was confirmed to have considerably excellent miscibility at low temperatures.

COMPARATIVE EXAMPLE 3

Mother liquid crystal B in an amount of 85 parts by weight was mixed with 15 parts by weight of compound (c-1) to prepare a liquid crystal composition and its physical properties were determined. The results are shown in Table 3 together with the results in Example 9 (Use Example 1) to Example 11 (Use Example 3).

TABLE 3

| | | Cp (° C.) | Δε |
|---|---|---|---|
| | Mother liquid crystal A | 74.6 | 0.0 |
| Com. Ex. 3 | 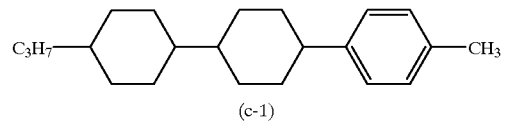<br>(c-1) | 160.7 | 1.4 |
| Ex. 9 | 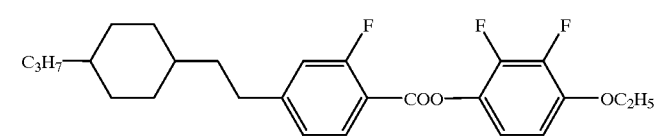<br>Compound No. 15 | 129.4 | −4.17 |
| Ex. 10 | 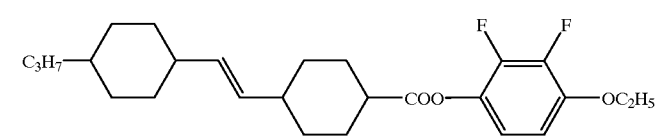 | 187.1 | −5.67 |

TABLE 3-continued

| | Cp (° C.) | Δε |
|---|---|---|
| Ex. 11 | 114.1 | −4.20 |

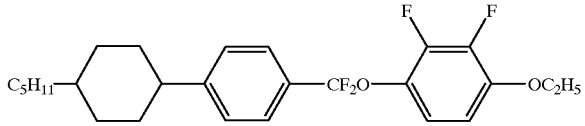

Compound No. 152

In the value of negative dielectric anisotropy which is considered to be important in IPS driving, whereas the dielectric anisotropy value obtained by extrapolation with the compound (c-1) was 1.4, the value of the compound of Examples 9, 10, and 11 exhibited remarkably as large negative value as −4.17, −5.67, and −4.20, respectively. Further, whereas the clearing point obtained by extrapolation with compound (c-1) was 160.6, that of the compound of Examples 9, 10, and 11 were such closely resembled values as 129.4° C., 187.1° C., and 114.4° C., respectively.

As described above, the liquid crystalline compounds of the present invention are very effective in largely reducing dielectric anisotropy value and have characteristics which can sufficiently cope with IPS driving.

Industrial Applicability

As will be clear from the Examples and Comparative Examples described above, the liquid crystalline compounds of the present invention are excellent in an overall balance of 1) effect of raising clearing point of liquid crystal compositions, 2) effect of lowering viscosity of liquid crystal compositions, and 3) effect of not lowering dielectric anisotropy (raising threshold voltage) of liquid crystal compositions;

have a low viscosity and negative large dielectric anisotropy; and have very useful characteristics which can not be found in known liquid crystalline compounds.

What is claimed is:

1. A liquid crystalline compound expressed by the general formula (1)

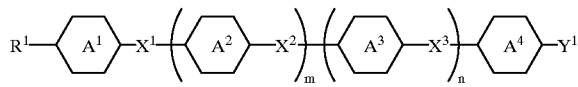

(1)

wherein $R^1$ and $Y^1$ represent an alkyl group having 1 to 20 carbon atoms one or more non-adjacent methylene groups in the alkyl group may be replaced by oxygen atom, sulfur atom, or vinylene group;

$X^1$, $X^2$, and $X^3$ independently represent single bond, 1,2-ethylene group, vinylene group, —COO—, —CF$_2$O—, or —OCF$_2$— provided that at least one of $X^1$, $X^2$, and $X^3$ represents —CF$_2$O— or —OCF$_2$—;

ring $A^1$, ring $A^2$, ring $A^3$, and ring $A^4$ independently represent trans-1,4-cyclohexylene group CH$_2$ group on which ring may be replaced by oxygen atom, or 1,4-phenylene group one or more hydrogen atoms of which may be replaced by fluorine atom or chlorine atom; and m and n are independently 0 or 1;

provided that at least one ring among $A^1$, ring $A^2$, ring $A^3$, and ring $A^4$ represents 1,4-phenylene group at least one hydrogen atom in which group is replaced by fluorine atom or chlorine atom; and when m=n=0, and $X^1$ represents —CF$_2$O or —OCF$_2$, then ring $A^1$ or ring $A^4$ represents trans-1,4-cyclohexylene group;

when m+n≧1 and at least two among $X^1$, $X^2$, and $X^3$ are bonding groups selected from —CF$_2$O— or —OCF$_2$—, then at least one of rings which bond directly to the carbon atom in the —CF$_2$O— or —OCF$_2$— is trans-1,4-cyclohexylene group.

2. The liquid crystalline compound according to claim 1 wherein m=n=0 in the general formula (1).

3. The liquid crystalline compound according to claim 1 wherein m=1, n=0, and $X^1$ or $X^2$ is —CF$_2$O— or —OCF$_2$— in the general formula (1).

4. The liquid crystalline compound according to claim 3 wherein both $R^1$ and $Y^1$ are an alkyl group in the general formula (1).

5. The liquid crystalline compound according to claim 3 wherein at least one of $R^1$ and $Y^1$ is an alkenyl group in the general formula (1).

6. The liquid crystalline compound according to claim 3 wherein $X^1$ is single bond, $X^2$ is —CF$_2$O— or —OCF$_2$—, both ring $A^1$ and ring $A^2$ are 1,4-cyclohexylene group, and ring $A^4$ is 1,4-phenylene group at least one hydrogen atom of which is replaced by fluorine atom or chlorine atom in the general formula (1).

7. The liquid crystalline compound according to claim 1 wherein m=n=1, and $X^1$, $X^2$, or $X^3$ is -CF$_2$O— or OCF$_2$— in the general formula (1).

8. The liquid crystalline compound according to claim 7 wherein at least one of $R^1$ and $Y^1$ is an alkenyl group in the general formula (1).

9. The liquid crystalline compound according to claim 7 wherein $R^1$ and $Y^1$ are an alkyl group, both ring $A^1$ and ring $A^4$ are 1,4-cyclohexylene group, any one of ring $A^2$ and ring $A^3$ is 1,4-phenylene group at least one hydrogen atom of which may be replaced by fluorine atom or chlorine atom and the other is 1,4-phenylene group at least one hydrogen atom of which is replaced by fluorine atom or chlorine atom, $X^2$ is —CF$_2$O— or —OCF$_2$—, and both $X^1$ and $X^3$ are single bond in the general formula (1).

10. The liquid crystalline compound according to claim 7 wherein $R^1$ and $Y^1$ are an alkyl group, both ring $A^1$ and ring $A^4$ are 1,4-cyclohexylene group, any one of ring $A^2$ and ring $A^3$ is 1,4-phenylene group at least one hydrogen atom of which may be replaced by fluorine atom or chlorine atom and the other is 1,4-phenylene group at least one hydrogen atom of which is replaced by fluorine atom or chlorine atom, $X^2$ is —CF$_2$O— or —OCF$_2$—, and any one of $X^1$ and $X^3$ are single bond and the other is 1,2-ethylene group in the general formula (1).

11. A liquid crystal composition comprising at least two components at least one of which is a liquid crystalline compound expressed by the general formula (1) according to claim 1.

12. A liquid crystal composition comprising, as a first component, at least one liquid crystalline compound defined in any one of claims 1–10, and, as a second component, at least one compound selected from the group consisting of the compounds expressed by any one of the general formulas (2), (3), and (4)

(2)

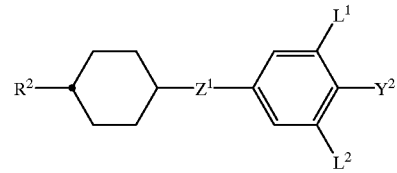

(3)

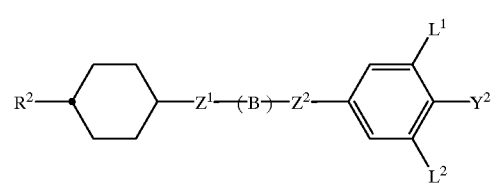

(4)

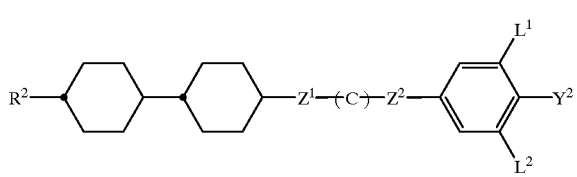

wherein $R^2$ represents an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

$Y^2$ represents fluorine atom, chlorine atom, —OCF$_3$, —OCF$_2$H, —CF$_3$, —CF$_2$H, —CFH$_2$OCF$_2$CF$_2$H, or —OCF$_2$CFHCF$_3$;

$L^1$ and $L^2$ independently represent hydrogen atom or fluorine atom;

$Z^1$ and $Z^2$ independently represent 1,2-ethylene group, vinylene group, 1,4-butylene group, —COO—, —CF$_2$O—, —OCF$_2$—, or single bond;

ring B represents trans-1,4-cyclohexylene or 1,3-dioxane-2,5-diyl, or 1,4-phenylene group hydrogen atom of which may be replaced by fluorine atom; and ring C represents trans-1,4-cyclohexylene, or 1,4-phenylene group hydrogen atom of which may be replaced by fluorine atom.

13. A liquid crystal composition comprising, as a first component, at least one liquid crystalline compound defined in any one of claims 1–10, and, as a second component, at least one compound selected from the group consisting of the compounds expressed by the general formula (5) or (6)

(5)

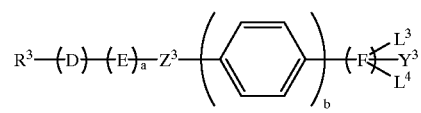

(6)

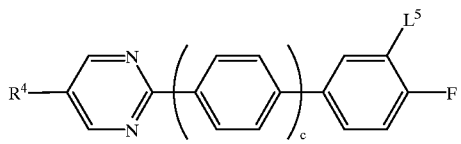

wherein $R^3$ and $R^4$ independently represent an alkyl group having 1 to 10 carbon atoms one or more non-adjacent methylene groups in the alkyl group may be replaced by oxygen atom or vinylene group, and any hydrogen atom in the alkyl group may be replaced by fluorine atom;

$Y^3$ represents CN group or —C≡C—CN;

ring D represents trans-1,4-cyclohexylene, 1,4-phenylene, pyrimidine-2,5-diyl, or 1,3-dioxane-2,5-diyl group;

ring E represents trans-1,4-cyclohexylene, 1,4-phenylene group hydrogen atom of which may be replaced by fluorine atom, or pyrimidine-2,5-diyl group;

ring F represents trans-1,4-cyclohexylene or 1,4-phenylene group;

$Z^3$ represents 1,2-ethylene group, —COO—, or single bond;

$L^3$, $L^4$, and $L^5$ independently represent hydrogen atom or fluorine atom; and a, b, and c are independently 0 or 1.

14. A liquid crystal composition comprising, as a first component, at least one liquid crystalline compound defined in any one of claims 1–10, and, as a second component, at least one compound selected from the group consisting of the compounds expressed by any one of the general formulas (10), (11), and (12)

(10)

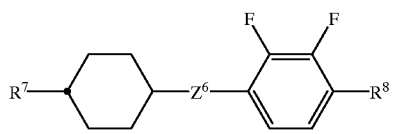

(11)

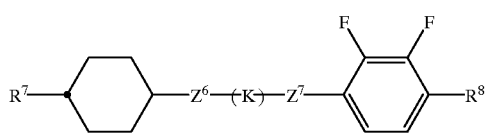

(12)

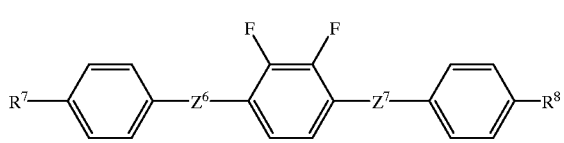

wherein $R^7$ and $R^8$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring K represents trans-1,4-cyclohexylene or 1,4-phenylene group; and $Z^6$ and $Z^7$ independently represent —CH$_2$CH$_2$—, —CH$_2$O—, or single bond.

15. A liquid crystal composition comprising one or more optically active compounds in addition to the liquid crystal composition defined in claim 11.

16. A liquid crystal display device comprising the liquid crystal composition defined in claim 11.

17. A liquid crystal composition comprising, as a first component, at least one liquid crystalline compound defined in any one of claims 1–10, and as a second component, at least one compound selected from the group consisting of the compounds expressed by any one of the general formulas (7), (8), and (9)

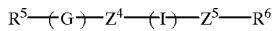
(7)

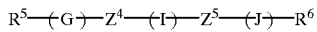
(8)

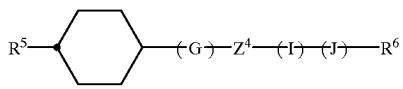
(9)

wherein $R^5$ and $R^6$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring G, ring I, and ring J independently represent trans-, 1,4-cyclohexylene or pyrimidine-2,5-diyl, or 1,4-phenylene group at least one hydrogen atom of which may be replaced by fluorine atom; and $Z^4$ and $Z^5$ independently represent —C≡C—, —COO—, —CH$_2$CH$_2$—, CH=CH—, or single bond.

18. A liquid crystal composition comprising, as a first component, at least one liquid crystalline compound defined in any one of claims 1–10, as a second component, at least one compound selected from the group consisting of the compounds expressed by any one of the general formulas (7), (8), and (9)

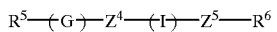
(7)

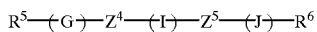
(8)

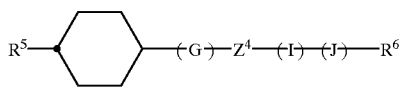
(9)

wherein $R^5$ and $R^6$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring G, ring I, and ring J independently represent trans-1,4-cyclohexylene, pyrimidine-2,5-diyl, or 1,4-phenylene group at least one hydrogen atom of which may be replaced by fluorine atom; and $Z^4$ and $Z^5$ independently represent —C≡C—, —COO—, —CH$_2$CH$_2$—, —CH=CH—, or single bond;

and as a third component, at least one compound selected from the group consisting of the compounds expressed by any one of the general formulas (10), (11), and (12)

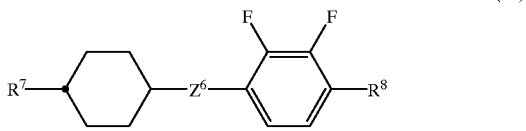
(10)

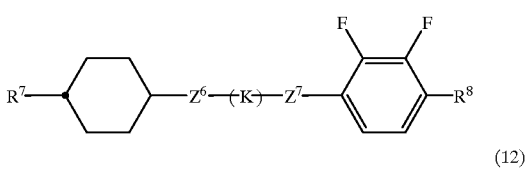
(11)

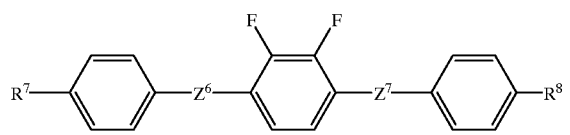
(12)

wherein $R^7$ and $R^8$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring K represents trans-1,4-cyclohexylene or 1,4-phenylene group; and $Z^6$ and $Z^7$ independently represent —CH$_2$CH$_2$—, —CH$_2$O—, or single bond.

19. A liquid crystal composition comprising, as a first component, at least one liquid crystalline compound defined in any one of claims 1–10, as a second component, at least one compound selected from the group consisting of the compounds expressed by any one of the general formulas (2), (3), and (4)

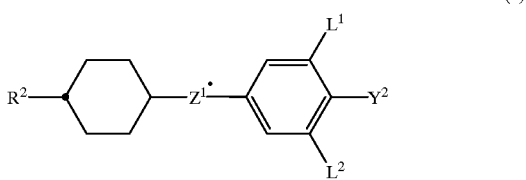
(2)

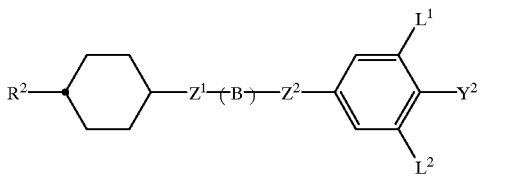
(3)

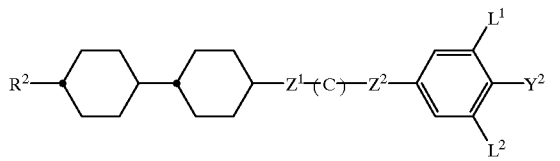
(4)

wherein $R^2$ represents an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

$Y^2$ represents fluorine atom, chlorine atom, —$OCF_3$, —$OCF_2H$, —$CF_3$, —$CF_2H$, —$CFH_2OCF_2CF_2H$, or —$OCF_2CFHCF_3$;

$L^1$ and $L^2$ independently represent hydrogen atom or fluorine atom;

$Z^1$ and $Z^2$ independently represent 1,2-ethylene group, vinylene group, 1,4-butylene group, —COO—, —$CF_2O$—, —$OCF_2$—, or single bond;

ring B represents trans-1,4-cyclohexylene or 1,3-dioxane-2,5-diyl, or 1,4-phenylene group hydrogen atom of which may be replaced by fluorine atom; and ring C represents trans-1,4-cyclohexylene, or 1,4-phenylene group hydrogen atom of which may be replaced by fluorine atom, and as a third component, at least one compound selected from the group consisting of the compounds expressed by any one of the general formulas (7), (8), and (9)

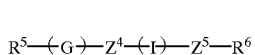

(7)

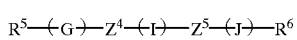

(8)

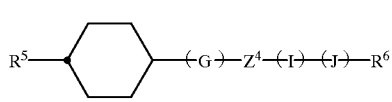

(9)

wherein $R^5$ and $R^6$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring G, ring I, and ring J independently represent trans-1,4-cyclohexylene, pyrimidine-2,5-diyl, or 1,4-phenylene group at least one hydrogen atom of which may be replaced by fluorine atom;

$Z^4$ and Zr independently represent —C≡C—, —COO—, —$CH_2CH_2$—, —CH=CH—, or single bond.

20. A liquid crystal composition comprising, as a first component, at least one liquid crystalline compound defined in any one of claims 1–10, as a second component, at least one compound selected from the group consisting of the compounds expressed by the general formula (5) or (6)

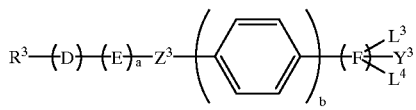

(5)

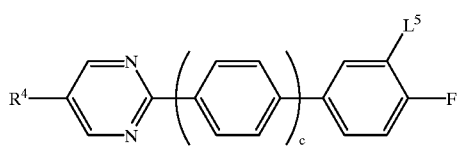

(6)

wherein $R^3$ and $R^4$ independently represent an alkyl group having 1 to 10 carbon atoms one or more non-adjacent methylene groups in the alkyl group may be replaced by oxygen atom or vinylene group, and any hydrogen atom in the alkyl group may be replaced by fluorine atom;

$Y^3$ represents CN group or —C≡C—CN;

ring D represents trans-1,4-cyclohexylene, 1,4-phenylene, pyrimidine-2,5-diyl, or 1,3-dioxane-2,5-diyl group;

ring E represents trans-1,4-cyclohexylene, 1,4-phenylene group hydrogen atom of which may be replaced by fluorine atom, or pyrimidine-2,5-diyl group;

ring F represents trans-1,4-cyclohexylene or 1,4-phenylene group;

$Z^3$ represents 1,2-ethylene group, —COO—, or single bond;

$L^3$, $L^4$, and $L^5$ independently represent hydrogen atom or fluorine atom; and a, b, and c are independently 0 or 1, and as a third component, at least one compound selected from the group consisting of the compounds expressed by any one of the general formulas (7), (8), and (9)

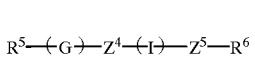

(7)

(8)

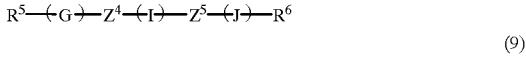

(9)

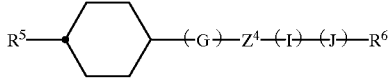

wherein $R^5$ and $R^6$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring G, ring I, and ring J independently represent trans-1,4-cyclohexylene, pyrimidine-2,5-diyl, or 1,4-phenylene group at least one hydrogen atom of which may be replaced by fluorine atom; and $Z^4$ and $Z^5$ independently represent —C≡C—, —COO—, —$CH_2CH_2$—, —CH=CH—, or single bond.

21. A liquid crystal composition comprising, as a first component, at least one liquid crystalline compound defined in any one of claims 1–10, as a second component, at least one compound selected from the group consisting of the compounds expressed by any one of the general formulas (2), (3), and (4)

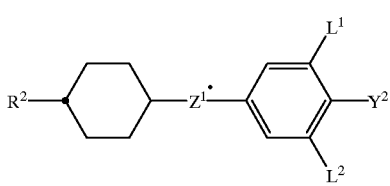

(2)

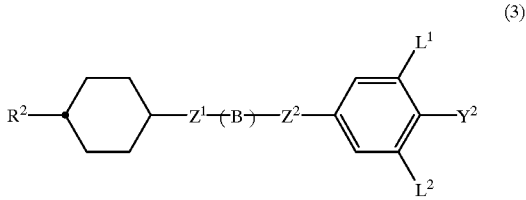

(3)

(4)

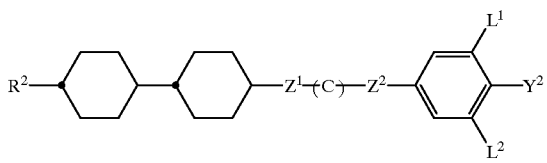

wherein $R^2$ represents an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

$Y^2$ represents fluorine atom, chlorine atom, —OCF$_3$, —OCF$_2$H, —CF$_3$, —CF$_2$H, —CFH$_2$OCF$_2$CF$_2$H, or —OCF$_2$CFHCF$_3$;

$L^1$ and $L^2$ independently represent hydrogen atom or fluorine atom;

$Z^1$ and $Z^2$ independently represent 1,2-ethylene group, vinylene group, 1,4-butylene group, —COO—, —CF$_2$O—, —OCF$_2$—, or single bond;

ring B represents trans-1,4-cyclohexylene or 1,3-dioxane-2,5-diyl, or 1,4-phenylene group hydrogen atom of which may be replaced by fluorine atom; and ring C represents trans-1,4-cyclohexylene, or 1,4-phenylene group hydrogen atom of which may be replaced by fluorine atom, as a third component, at least one compound selected from the group consisting of the compounds expressed by the general formula (5) or (6)

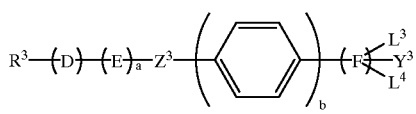 (5)

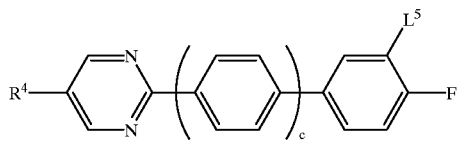 (6)

wherein $R^3$ and $R^4$ independently represent an alkyl group having 1 to 10 carbon atoms one or more non-adjacent methylene groups in the alkyl group may be replaced by oxygen atom or vinylene group, and any hydrogen atom in the alkyl group may be replaced by fluorine atom;

$Y^3$ represents CN group or —C≡C—CN;

ring D represents trans-1,4-cyclohexylene, 1,4-phenylene, pyrimidine-2,5-diyl, or 1,3-dioxane-2,5-diyl group;

ring E represents trans-1,4-cyclohexylene, 1,4-phenylene group hydrogen atom of which may be replaced by fluorine atom, or pyrimidine-2,5-diyl group;

ring F represents trans-1,4-cyclohexylene or 1,4-phenylene group;

$Z^3$ represents 1,2-ethylene group, —COO—, or single bond;

$L^3$, $L^4$, and $L^5$ independently represent hydrogen atom or fluorine atom;

a, b, and c are independently 0 or 1, and as a fourth component, at least one compound selected from the group consisting of the compounds expressed by any one of the general formulas (7), (8), and (9)

 (7)

 (8)

 (9)

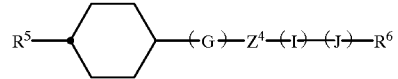

wherein $R^5$ and $R^6$ independently represent an alkyl group having 1 to 10 carbon atoms one or more non-adjacent methylene groups in the alkyl group may be replaced by oxygen atom or —CH=CH—, and any hydrogen atom in the alkyl group may be replaced by fluorine atom;

ring G, ring 1, and ring J independently represent trans-1,4-cyclohexylene, pyrimidine-2,5-diyl, or 1,4-phenylene group at least one hydrogen atom of which may be replaced by fluorine atom; and $Z^4$ and $Z^5$ independently represent —C≡C—, —COO—, —CH$_2$CH$_2$—, —CH=CH—, or single bond.

* * * * *